(12) United States Patent
Fruehauf et al.

(10) Patent No.: US 9,714,426 B2
(45) Date of Patent: Jul. 25, 2017

(54) BACTERIA MEDIATED GENE SILENCING

(71) Applicant: Marina Biotech, Inc., Bothell, WA (US)

(72) Inventors: Johannes Fruehauf, Newton, MA (US); Moreshwar B. Vaze, Bedford, MA (US); Floyd Stephen Laroux, Jr., Brookline, MA (US); Noel Joy Sauer, Attleboro, MA (US)

(73) Assignee: Marina Biotech, Inc., City of Industry, CA (US)

( * ) Notice: Subject to any disclaimer, the term of this patent is extended or adjusted under 35 U.S.C. 154(b) by 0 days.

(21) Appl. No.: 14/658,176

(22) Filed: Mar. 14, 2015

(65) Prior Publication Data

US 2015/0184167 A1    Jul. 2, 2015

Related U.S. Application Data

(63) Continuation of application No. 12/632,985, filed on Dec. 8, 2009, now Pat. No. 9,012,213, which is a continuation of application No. 12/157,969, filed on Jun. 13, 2008, now abandoned.

(60) Provisional application No. 61/010,028, filed on Jan. 4, 2008, provisional application No. 60/934,751, filed on Jun. 15, 2007.

(51) Int. Cl.
| | |
|---|---|
| *C07H 21/02* | (2006.01) |
| *C07H 21/04* | (2006.01) |
| *C12N 15/63* | (2006.01) |
| *C12N 15/11* | (2006.01) |
| *C12N 15/113* | (2010.01) |

(52) U.S. Cl.
CPC ............ *C12N 15/63* (2013.01); *C12N 15/111* (2013.01); *C12N 15/113* (2013.01); *C12N 15/1131* (2013.01); *C12N 15/1135* (2013.01); *C12N 15/1136* (2013.01); *C12N 2310/111* (2013.01); *C12N 2310/14* (2013.01); *C12N 2320/30* (2013.01); *C12N 2320/32* (2013.01)

(58) Field of Classification Search
CPC .......................... C12N 2310/11; C12N 15/113
See application file for complete search history.

*Primary Examiner* — Amy Bowman
(74) *Attorney, Agent, or Firm* — Eckman Law Group

(57) ABSTRACT

Methods are described for the delivery of one or more small interfering RNAs (siRNAs) to a eukaryotic cell using a bacterium or BTP. Methods are also described for using this bacterium to regulate gene expression in eukaryotic cells using RNA interference, and methods for treating viral diseases and disorders. The bacterium or BTP includes one or more siRNAs or one or more DNA molecules encoding one or more siRNAs. Vectors are also described for use with the bacteria of the invention for causing RNA interference in eukaryotic cells.

9 Claims, 18 Drawing Sheets

SEQUENCE LISTING

<160> NUMBER OF SEQ ID NOS: 563

<210> SEQ ID NO 1
<211> LENGTH: 18
<212> TYPE: DNA
<213> ORGANISM: Escherichia coli

<400> SEQUENCE: 1
taatacgact cactatag                                                18

<210> SEQ ID NO 2
<211> LENGTH: 53
<212> TYPE: DNA
<213> ORGANISM: Escherichia coli

<400> SEQUENCE: 2
taaccaggct ttacacttta tgcttccggc tcgtataatg tgtggaagga tcc         53

<210> SEQ ID NO 3
<211> LENGTH: 47
<212> TYPE: DNA
<213> ORGANISM: Escherichia coli

<400> SEQUENCE: 3
taaccaggct ttacacttta tgcttccggc tcgtataatg tgtggaa                47

<210> SEQ ID NO 4
<211> LENGTH: 53
<212> TYPE: DNA
<213> ORGANISM: Escherichia coli

<400> SEQUENCE: 4
taaaattcaa aaatttattt gctttcagga aaattttttct gtataataga ttc        53

<210> SEQ ID NO 5
<211> LENGTH: 32

```
<212> TYPE: DNA
<213> ORGANISM: Escherichia coli

<400> SEQUENCE: 5
taattgatac tttatgcttt tttctgtata at                                32

<210> SEQ ID NO 6
<211> LENGTH: 100
<212> TYPE: DNA
<213> ORGANISM: Escherichia coli

<400> SEQUENCE: 6
aagctttcag tcgcgtaatg cttaggcaca ggattgattt gtcgcaatga ttgacacgat    60
tccgcttgac actgcgtaag ttttgtgtta taatggatcc                         100

<210> SEQ ID NO 7
<211> LENGTH: 100
<212> TYPE: DNA
<213> ORGANISM: Escherichia coli

<400> SEQUENCE: 7
aagcttaagg agagacaact taaagagact taaaagatta atttaaaatt tatcaaaaag    60
agtattgact taaagtctaa cctataggat acttggatcc                         100

<210> SEQ ID NO 8
<211> LENGTH: 77
<212> TYPE: DNA
<213> ORGANISM: Escherichia coli

<400> SEQUENCE: 8
aagctttgtg tggaattgtg agcggataac aattccacac attgacactt tatgcttccg    60
gctcgtataa tggatcc                                                  77

<210> SEQ ID NO 9
<211> LENGTH: 75
<212> TYPE: DNA
<213> ORGANISM: Escherichia coli

<400> SEQUENCE: 9
aagcttggaa aatttttttt aaaaaagtca tgtgtggaat tgtgagcgga taacaattcc    60
acatataatg gatcc                                                    75

<210> SEQ ID NO 10
<211> LENGTH: 1285
<212> TYPE: DNA
<213> ORGANISM: Escherichia coli

<400> SEQUENCE: 10
gacttcatat acccaagctt taaaaaaaaa atccttagct ttcgctaagg atctccgtca    60
agccgtcaat tgtctgattc gttaccaatt atgacaactt gacggctaca tcattcactt   120
tttcttcaca accggcacga aactcgctcg ggctggcccc ggtgcatttt ttaaatactc   180
gcgagaaata gagttgatcg tcaaaaccaa cattgcgacc gacggtggcg ataggcatcc   240
gggtagtgct caaaagcagc ttcgcctgac taatgcgttg gtcctcgcgc cagcttaaga   300
cgctaatccc taactgctgg cggaaaagat gtgacagacg cgacggcgac aagcaaacat   360
gctgtgcgac gctggcgata tcaaaattgc tgtctgccag gtgatcgctg atgtactgac   420
aagcctcgcg tacccgatta tccatcggtg gatggagcga ctcgttaatc gcttccatgc   480
```

```
gccgcagtaa caattgctca agcagattta tcgccagcag ctccgaatag cgcccttccc    540
cttgcccggc gttaatgatt tgcccaaaca ggtcgctgaa atgcggctgg tgcgcttcat    600
ccgggcgaaa gaaacccgta ttggcaaata ttgacggcca gttaagccat tcatgccagt    660
aggcgcgcgg acgaaagtaa acccactggt gataccattc gcgagcctcc ggatgacgac    720
cgtagtgatg aatctctcct ggcgggaaca gcaaaatatc acccggtcgg cagacaaatt    780
ctcgtccctg atttttcacc accccctgac cgcgaatggt gagattgaga atataacctt    840
tcattcccag cggtcggtcg ataaaaaaat cgagataacc gttggcctca atcggcgtta    900
aacccgccac cagatgggcg ttaaacgagt atcccggcag caggggatca ttttgcgctt    960
cagccatact tttcatactc ccaccattca gagaagaaac caattgtcca tattgcatca   1020
gacattgccg tcactgcgtc ttttactggc tcttctcgct aacccaaccg gtaaccccgc   1080
ttattaaaag cattctgtaa caaagcggga ccaaagccat gacaaaaacg cgtaacaaaa   1140
gtgtctataa tcacggcaga aaagtccaca ttgattattt gcacggcgtc acactttgct   1200
atgccatagc attttatcc ataagattag cggatcctac ctgacgcttt ttatcgcaac   1260
tctctactgt agatctatct gcgat                                        1285
```

<210> SEQ ID NO 11
<211> LENGTH: 59
<212> TYPE: DNA
<213> ORGANISM: Escherichia coli

<400> SEQUENCE: 11

```
taaaattcaa aaatttattt gctttcagga aaatttttct gtataataga ttcggatcc    59
```

<210> SEQ ID NO 12
<211> LENGTH: 38
<212> TYPE: DNA
<213> ORGANISM: Escherichia coli

<400> SEQUENCE: 12

```
taattgatac tttatgcttt tttctgtata atggatcc                            38
```

<210> SEQ ID NO 13
<211> LENGTH: 47
<212> TYPE: DNA
<213> ORGANISM: Escherichia coli

<400> SEQUENCE: 13

```
tagcataacc ccttggggcc tctaaacggg tcttgagggg tttttg                  47
```

<210> SEQ ID NO 14
<211> LENGTH: 49
<212> TYPE: DNA
<213> ORGANISM: Escherichia coli

<400> SEQUENCE: 14

```
ttgtcacgtg agcggataac aatttcacac aggaaacaga attcttaat               49
```

<210> SEQ ID NO 15
<211> LENGTH: 43
<212> TYPE: DNA
<213> ORGANISM: Escherichia coli

<400> SEQUENCE: 15

```
ttgtcacaaa ccccgccacc ggcggggttt ttttctgctt aat                     43
```

```
<210> SEQ ID NO 16
<211> LENGTH: 65
<212> TYPE: DNA
<213> ORGANISM: Escherichia coli

<400> SEQUENCE: 16
ttgtcacaat ctatggtgt atgcatttat ttgcatacat tcaatcaatt ggatcctgca      60
ttaat                                                                 65

<210> SEQ ID NO 17
<211> LENGTH: 42
<212> TYPE: DNA
<213> ORGANISM: Escherichia coli

<400> SEQUENCE: 17
gtgagcggat aacaatttca cacaggaaac agaattctta at                        42

<210> SEQ ID NO 18
<211> LENGTH: 36
<212> TYPE: DNA
<213> ORGANISM: Escherichia coli

<400> SEQUENCE: 18 aaacccgcc accggcgggg ttttttctg cttaat                                 36

<210> SEQ ID NO 19
<211> LENGTH: 58
<212> TYPE: DNA
<213> ORGANISM: Escherichia coli

<400> SEQUENCE: 19
aattctatgg tgtatgcatt tatttgcata cattcaatca attggatcct gcattaat       58

<210> SEQ ID NO 20
<211> LENGTH: 86
<212> TYPE: DNA
<213> ORGANISM: Escherichia coli

<400> SEQUENCE: 20
aattcggggc tatagctcag ctgggagagc gcttgcatct aatgcaagag gtcagcggtt      60
cgatcccgct agctccacc actgca                                           86

<210> SEQ ID NO 21
<211> LENGTH: 83
<212> TYPE: DNA
<213> ORGANISM: Escherichia coli

<400> SEQUENCE: 21
aattcgcccg gatagctcag tcggtagagc aggggattct aaatcccgt gtccttggtt       60 cgattccgag tccgggcact gca                                             83

<210> SEQ ID NO 22
<211> LENGTH: 876
<212> TYPE: DNA
<213> ORGANISM: Escherichia coli

<400> SEQUENCE: 22
atgaccagta gctatctgca ttagccggag taggatccgg tcattttctc aataggaccc      60
gtggcgcttc actggtacgg cctgatgtat ctggtgggtt tcattttgc aatgtggctg      120 gcaacacgac gggcgaatcg tccgggcagc ggctggacca aaaatgaagt tgaaaactta    180
```

```
ctctatgcgg gcttcctcgg cgtcttcctc gggggacgta ttggttatgt tctgttctac    240
aatttcccgc agtttatggc cgatccgctg tatctgttcc gtgtctggga cggcggcatg    300
tctttccacg gcggcctgat tggcgttatc gtggtgatga ttatcttcgc ccgccgtact    360
aaacgttcct tcttccaggt ctctgatttt atcgcaccac tcattccgtt tggtcttggt    420
gccgggcgtc tgggcaactt tattaacggt gaattgtggg gccgcgttga cccgaacttc    480
ccgtttgcca tgctgttccc tggctcccgt acagaagata ttttgctgct gcaaaccaac    540
ccgcagtggc aatccatttt cgacacttac ggtgtgctgc cgcgccaccc atcacagctt    600
tacgagctgc tgctggaagg tgtggtgctg tttattatcc tcaacctgta tattcgtaaa    660
ccacgcccaa tgggagctgt ctcaggtttg ttcctgattg gttacggcgc gtttcgcatc    720
attgttgagt ttttccgcca gcccgacgcg cagtttaccg tgcctgggt gcagtacatc     780 agcatggggc aaattctttc catcccgatg attgtcgcgg gtgtgatcat gatggtctgg    840
gcatatcgtc gcagcccaca gcaacacgtt cctga                              876
```

<210> SEQ ID NO 23
<211> LENGTH: 1260
<212> TYPE: DNA
<213> ORGANISM: Escherichia coli

<400> SEQUENCE: 23

```
atggataaat tcgtgttca ggggccaacg aagctccagg gcgaagtcac aatttccggc      60
gctaaaaatt agtagctgcc tatcctttt gccgcactac tggcggaaga accggtagag    120
atccagaacg tcccgaaact gaaagacgtc gatacatcaa tgaagctgct aagccagctg    180
ggtgcgaaag tagaacgtaa tggttctgtg catattgatg cccgcgacgt taatgtattc    240 tgcgcaccctt acgatctggt taaaaccatg cgtgcttcta tctgggcgct ggggccgctg    300
gtagcgcgct ttggtcaggg gcaagtttca ctacctggcg gttgtacgat cggtgcgcgt    360
ccggttgatc tacacatttc tggcctcgaa caattaggcg cgaccatcaa actgaagaa     420 ggttacgtta agcttccgt cgatggtcgt ttgaaaggtg cacatatcgt gatggataaa    480
gtcagcgttg gcgcaacggt gaccatcatg tgtgctgcaa ccctggcgga aggcaccacg    540
attattgaaa acgcagcgcg tgaaccggaa atcgtcgata ccgcgaactt cctgattacg    600
ctgggtgcga aaattagcgg tcagggcacc gatcgtatcg tcatcgaagg tgtgaacgt    660 ttaggcggcg gtgtctatcg cgttctgccg gatcgtatcg aaaccggtac tttcctggtg    720
gcggcggcga tttctcgcgg caaaattatc tgccgtaacg cgcagccaga tactctcgac    780
gccgtgctgg cgaaactgcg tgacgctgga gcggacatcg aagtcggcga agactggatt    840
agcctggata tgcatggcaa acgtccgaag gctgttaacg tacgtaccgc gccgcatccg    900
gcattcccga ccgatatgca ggcccagttc acgctgttga acctggtggc agaagggacc    960
gggtttatca ccgaaacggt cttgaaaac cgctttatgc atgtgccaga gctgagccgt   1020
atgggcgcgc acgccgaaat cgaaagcaat accgttattt gtcacggtgt tgaaaaactt   1080
tctggcgcac aggttatggc aaccgatctg cgtgcatcag caagcctggt gctggctggc   1140
tgtattgcgg aagggacgac ggtggttgat cgtatttatc acatcgatcg tggctacgaa   1200
cgcattgaag acaaactgcg cgctttaggt gcaaatattg agcgtgtgaa aggcgaataa   1260
```

<210> SEQ ID NO 24
<211> LENGTH: 1297
<212> TYPE: DNA
<213> ORGANISM: Escherichia coli

<400> SEQUENCE: 24

```
gccaggcgac tgtcttcaat attacagccg caactactga catgacgggt gatggtgttc      60
acaattccag ggcgatcggc acccaacgca gtgatcacca gataatgttg cgatgacagt     120
gtcaaactgg ttattccttt aagggtgag ttgttcttaa ggaaagcata aaaaaaacat      180
gcatacaaca atcagaacgg ttctgtctgc ttgcttttaa tgccatacca aacgtaccat     240
tgagacactt gtttgcacag aggatggccc atgttcacgg gaagtattgt cgcgattgtt     300
actccgatgg atgaaaaagg taatgtctgt cgggctagct tgaaaaaact gattgattat     360
catgtcgcca gcggtacttc ggcgatcgtt tctgttggca ccactggcga gtccgctacc     420
ttaaatcatg acgaacatgc tgatgtggtg atgatgacgc tggatctggc tgatgggcgc     480
attccggtaa ttgccgggac cggcgctaac gctactgcgg aagccattag cctgacgcag     540
cgcttcaatg acagtggtat cgtcggctgc ctgacggtaa ccccttacta caatcgtccg     600
tcgcaagaag gtttgtatca gcatttcaaa gccatcgctg agcatactga cctgccgcaa     660
attctgtata atgtgccgtc ccgtactggc tgcgatctgc tcccggaaac ggtgggccgt     720
ctggcgaaag taaaaatat tatcggaatc aaagaggcaa cagggaactt aacgcgtgta     780
aaccagatca aagagctggt ttcagatgat tttgttctgc tgagcggcga tgatgcgagc     840
gcgctggact tcatgcaatt ggggcggtcat ggggttattt ccgttacggc taacgtcgca     900
gcgcgtgata tggcccagat gtgcaaactg gcagcagaag ggcattttgc cgaggcacgc     960
gttattaatc agcgtctgat gccattacac aacaaactat tgtcgaacc caatccaatc    1020
ccggtgaaat gggcatgtaa ggaactgggt cttgtggcga ccgatacgct gcgcctgcca    1080
atgacaccaa tcaccgacag tggtcgtgag acggtcagag cggcgcttaa gcatgccggt    1140
ttgctgtaaa gtttagggag atttgatggc ttactctgtt caaaagtcgc gcctggcaaa    1200
ggttgcgggt gtttcgcttg ttttattact cgctgcctgt agttctgact cacgctataa    1260
gcgtcaggtc agtggtgatg aagcctacct ggaagcg                             1297
```

<210> SEQ ID NO 25
<211> LENGTH: 99
<212> TYPE: DNA
<213> ORGANISM: Escherichia coli

<400> SEQUENCE: 25

```
catggcgccg cttctttgag cgaacgatca aaataagtg gcgccccatc aaaaaaatat       60
tctcaacata aaaaactttg tgtaatactt gtaacgctg                             99
```

<210> SEQ ID NO 26
<211> LENGTH: 63
<212> TYPE: DNA
<213> ORGANISM: Escherichia coli

<400> SEQUENCE: 26

```
catggcgccc catcaaaaaa atattctcaa cataaaaaac tttgtgtaat acttgtaacg       60
ctg                                                                    63
```

<210> SEQ ID NO 27
<211> LENGTH: 32
<212> TYPE: DNA
<213> ORGANISM: Escherichia coli

<400> SEQUENCE: 27

```
gatccttagc gaaagctaag gattttttt ac                              32

<210> SEQ ID NO 28
<211> LENGTH: 32
<212> TYPE: DNA
<213> ORGANISM: Escherichia coli

<400> SEQUENCE: 28
gatccttagc gaaagctaag gattttttt tt                              32

<210> SEQ ID NO 29
<211> LENGTH: 720
<212> TYPE: DNA
<213> ORGANISM: Escherichia coli

<400> SEQUENCE: 29
atgcaagaga actacaagat tctggtggtc gatgacgaca tgcgcctgcg tgcgctgctg    60
gaacgttatc tcaccgaaca aggcttccag gttcgaagcg tcgctaatgc agaacagatg   120
gatcgcctgc tgactcgtga atctttccat cttatggtac tggatttaat gttacctggt   180
gaagatggct tgtcgatttg ccgacgtctt cgtagtcaga gcaacccgat gccgatcatt   240
atggtgacgg cgaaagggga agaagtggac cgtatcgtag gcctggagat tggcgctgac   300
gactacattc aaaaccgtt taacccgcgt gaactgctgg cccgtatccg tgcggtgctg   360
cgtcgtcagg cgaacgaact gccaggcgca ccgtcacagg aagaggcggt aattgctttc   420
ggtaagttca aacttaacct cggtacgcgc gaaatgttcc gcgaagacga gccgatgccg   480
ctcaccagcg gtgagtttgc ggtactgaag gcactggtca gccatcgcg tgagccgctc   540 tcccgcgata agctgatgaa ccttgcccgt ggtcgtgaat attccgcaat ggaacgctcc   600
atcgacgtgc agatttcgcg tctgcgccgc atggtggaag aagatccagc gcatccgcgt   660
tacattcaga ccgtctgggg tctgggctac gtctttgtac cggacggctc taaagcatga   720

<210> SEQ ID NO 30
<211> LENGTH: 672
<212> TYPE: DNA
<213> ORGANISM: Escherichia coli

<400> SEQUENCE: 30
atgcgcgtac tggttgttga agacaatgcg ttgttacgtc accaccttaa agttcagatt    60
caggatgctg gtcatcaggt cgatgacgca gaagatgcca agaagccga ttattatctc   120 aatgaacata taccggatat tgcgattgtc gatctcggat tgccagacga ggacggtctg   180
tcactgattc gccgctggcg tagcaacgat gtttcactgc cgattctggt attaaccgcc   240
cgtgaaagct ggcaggacaa agtcgaagta ttaagtgccg gtgctgatga ttatgtgact   300
aaaccgtttc atattgaaga ggtgatggcg cgaatgcagg cattaatgcg gcgtaatagc   360
ggtctggctt cacaggtcat ttcgctcccc ccgtttcagg ttgatctctc tcgccgtgaa   420
ttatctatta atgacgaagt gatcaaactg accgcgttcg aatacactat tatgaaaacg   480
ttgatacgca ataatggcaa agtggtcagc aaagattcgt taatgctcca actctatccg   540
gatgcggagc tgcgggaaag ccataccatt gatgtactga tggacgtct gcgcaaaaaa   600 attcaggcac aatatcccca agaagtgatt accaccgttc gcggccaggg ctatctgttc   660
gaattgcgct ga                                                        672

<210> SEQ ID NO 31
<211> LENGTH: 390
```

<212> TYPE: DNA
<213> ORGANISM: Escherichia coli

<400> SEQUENCE: 31

```
gatcatcctg ttacggaata ttacattgca acatttacgc gcaaaaacta atccgcattc    60
ttattgcgga ttagttttttt cttagctaat agcacaattt tcatactatt ttttggcatt   120
ctggatgtct gaaagaagat tttgtgccag gtcgataaag tttccatcag aaacaaaatt   180
tccgtttagt taatttaaat ataaggaaat catataaata gattaaaatt gctgtaaata   240
tcatcacgtc tctatggaaa tatgacggtg ttcacaaagt tccttaaatt ttacttttgg   300
ttacatattt tttcttttg aaaccaaatc tttatctttg tagcactttc acggtagcga   360
aacgttagtt tgaatggaaa gatgcctgca                                    390
```

<210> SEQ ID NO 32
<211> LENGTH: 198
<212> TYPE: DNA
<213> ORGANISM: Escherichia coli

<400> SEQUENCE: 32

```
tttaaaaaag ttccgtaaaa ttcatatttt gaaacatcta tgtagataac tgtaacatct    60
taaaagtttt agtatcatat tcgtgttgga ttattctgta tttttgcgga gaatggactt   120
gccgactggt taatgagggt taaccagtaa gcagtggcat aaaaaagcaa taaaggcata   180
taacagaggg ttaataac                                                 198
```

<210> SEQ ID NO 33
<211> LENGTH: 200
<212> TYPE: DNA
<213> ORGANISM: Escherichia coli

<400> SEQUENCE: 33

```
agtgattcca ttttttaccc ttctgttttt ttgaccttaa gtctccgcat cttagcacat    60
cgttcatcca gagcgtgatt tctgccgagc gtgatcagat cggcatttct ttaatctttt   120
gtttgcatat ttttaacaca aaatacacac ttcgactcat ctggtacgac cagatcacct   180
tgcggattca ggagactgac                                               200
```

<210> SEQ ID NO 34
<211> LENGTH: 200
<212> TYPE: DNA
<213> ORGANISM: Escherichia coli

<400> SEQUENCE: 34

```
gagctatcac gatggttgat gagctgaaat aaacctcgta tcagtgccgg atggcgatgc    60
tgtccggcct gcttattaag attatccgct ttttattttt tcactttacc tcccctcccc   120
gctggtttat ttaatgttta cccccataac cacataatcg cgttacacta ttttaataat   180
taagacaggg agaaataaaa                                               200
```

<210> SEQ ID NO 35
<211> LENGTH: 238
<212> TYPE: DNA
<213> ORGANISM: Escherichia coli

<400> SEQUENCE: 35

```
gcttcaacac gctcgcgggt gagctggctc acgccgcttt cgttattcag cacccgggaa    60
actgtagatt tccccacgcc gcttaagcgc gcgatatctt tgatggtcag ccgattttgc   120
```

```
atcctgttgt cctgtaacgt gttgtttaat tatttgagcc taacgttacc cgtgcattca    180
gcaatgggta agtctggtt tatcgttggt ttagttgtca gcaggtatta tatcgcca      238
```

<210> SEQ ID NO 36
<211> LENGTH: 73
<212> TYPE: DNA
<213> ORGANISM: Escherichia coli

<400> SEQUENCE: 36

```
gagctgttga caattaatca tcgaactagt taactagtac gcaagttcac gtaaaaggg    60 tatctagaat tct                                                      73
```

<210> SEQ ID NO 37
<211> LENGTH: 1353
<212> TYPE: DNA
<213> ORGANISM: Escherichia coli

<400> SEQUENCE: 37

```
atgaggcgat tgcgcttctc gccacgaagt tcatttgccc gtacgttatt gctcatcgtc    60
accttgctgt tcgccagcct ggtgacgact tatctggtgg tgctgaactt cgcgattttg    120
ccgagcctcc agcagtttaa taaagtcctc gcgtacgaag tgcgtatgtt gatgaccgac    180
aaactgcaac tggaggacgg cacgcagttg ttgtgcctc cgctttccg tcgggagatc      240 taccgtgagc tggggatctc tctctactcc aacgaggctg ccgaagaggc aggtctgcgt    300
tgggcgcaac actatgaatt cttaagccat cagatggcgc agcaactggg cggcccgacg    360
gaagtgcgcg ttgaggtcaa caaaagttcg cctgtcgtct ggctgaaaac ctggctgtcg    420
cccaatatct gggtacgcgt gccgctgacc gaaattcatc agggcgattt ctctccgctg    480
ttccgctata cgctggcgat tatgctattg gcgataggcg gggcgtggct gtttattcgt    540
atccagaacc gaccgttggt cgatctcgaa cacgcagcct tgcaggttgg taagggatt    600 attccgccgc cgctgcgtga gtatggcgct tcggaggtgc gttccgttac ccgtgccttt    660
aaccatatgg cggctggtgt taagcaactg gcggatgacc gcacgctgct gatggcgggg    720
gtaagtcacg acttgcgcac gccgctgacg cgtattcgcc tggcgactga gatgatgagc    780
gagcaggatg gctatctggc agaatcgatc aataaagata tcgaagagtg caacgccatc    840
attgagcagt ttatcgacta cctgcgcacc gggcaggaga tgccgatgga aatggcggat    900
cttaatgcag tactcggtga ggtgattgct gccgaaagtg gctatgagcg ggaaattgaa    960
accgcgcttt accccggcag cattgaagtg aaaatgcacc cgctgtcgat caaacgcgcg    1020
gtggcgaata tggtggtcaa cgccgcccgt tatggcaatg gctggatcaa agtcagcagc    1080
ggaacggagc cgaatcgcgc ctggttccag gtggaagatg acggtccggg aattgcgccg    1140
gaacaacgta agcacctgtt ccagccgttt gtccgcggcg acagtgcgcg caccattagc    1200
ggcacgggat tagggctggc aattgtgcag cgtatcgtgg ataaccataa cgggatgctg    1260
gagcttggca ccagcgagcg gggcgggctt tccattcgcg cctggctgcc agtgccggta    1320
acgcgggcgc agggcacgac aaaagaaggg taa                                 1353
```

<210> SEQ ID NO 38
<211> LENGTH: 1461
<212> TYPE: DNA
<213> ORGANISM: Escherichia coli

<400> SEQUENCE: 38

```
atgaaaaaat tactgcgtct tttttttccg ctctcgctgc gggtacgttt tctgttggca    60
```

```
acggcagcgg tagtactggt gctttcgctt gcctacggaa tggtcgcgct gatcggttat        120
agcgtcagtt tcgataaaac tacgtttcgg ctgttacgtg gcgagagcaa tctgttctat        180
acccttgcga agtgggaaaa caataagttg catgtcgagt tacccgaaaa tatcgacaag        240
caaagcccca ccatgacgct aatttatgat gagaacgggc agcttttatg ggcgcaacgt        300
gacgtgccct ggctgatgaa gatgatccag cctgactggc tgaaatcgaa tggttttcat        360
gaaattgaag cggatgttaa cgataccagc ctcttgctga gtggagatca ttcgatacag        420
caacagttgc aggaagtgcg ggaagatgat gacgacgcgg agatgaccca ctcggtggca        480
gtaaacgtct acccggcaac atcgcggatg ccaaaattaa ccattgtggt ggtggatacc        540
attccggtgg agctaaaaag ttcctatatg gtctggagct ggtttatcta tgtgctctca        600
gccaatctgc tgttagtgat cccgctgctg tgggtcgccg cctggtggag tttacgcccc        660
atcgaagccc tggcaaaaga agtccgcgaa ctggaagaac ataaccgcga attgctcaat        720
ccagccacaa cgcgagaact gaccagtctg gtacgaaacc tgaaccgatt gttaaaaagt        780
gaacgcgaac gttacgacaa ataccgtacg acgctcaccg acctgaccca tagtctgaaa        840
acgccactgg cggtgctgca aagtacgctg cgttctctgc gtagtgaaaa gatgagcgtc        900
agtgatgctg agccggtaat gctggagcaa atcagccgca tttcacagca aattggctac        960
tacctgcatc gtgccagtat gcgcggcggg acattgctca gccgcgagct gcatccggtc       1020
gccccactgc tggacaatct cacctcagcg ctgaacaaag tgtatcaacg caaaggggtc       1080
aatatctctc tcgatatttc gccagagatc agctttgtcg gtgagcagaa cgattttgtc       1140
gaggtgatgg gcaacgtgct ggataatgcc tgtaaatatt gcctcgagtt tgtcgaaatt       1200
tctgcaaggc aaaccgacga gcatctctat attgtggtcg aggatgatgg ccccggtatt       1260
ccattaagca agcgagaggt cattttcgac cgtggtcaac gggttgatac tttacgccct       1320
gggcaaggtg tagggctggc ggtagcccgc gaaatcaccg agcaatatga gggtaaaatc       1380
gtcgccggag agagcatgct gggcggtgcg cggatggagg tgattttttgg tcgccagcat       1440 tctgcgccga aagatgaata a                                                 1461
```

<210> SEQ ID NO 39
<211> LENGTH: 490
<212> TYPE: DNA
<213> ORGANISM: Homo sapiens

<400> SEQUENCE: 39

```
ctatagaaga cctgggacag aggactgctg tctgccctct ctggtcaccc tgcctagcta         60
gaggatctgt gaccccagcc atgaggaccc tcgccatcct tgctgccatt ctcctggtgg        120
ccctgcaggc ccaggctgag ccactccagg caagagctga tgaggttgct gcagcccgg         180 agcagattgc agcggacatc ccagaagtgg ttgtttccct tgcatgggac gaaagcttgg        240
ctccaaagca tccaggctca aggaaaaaca tggcctgcta ttgcagaata ccagcgtgca        300
ttgcaggaga acgtcgctat ggaacctgca tctaccaggg aagactctgg gcattctgct        360
gctgagcttg cagaaaaaga aaatgagct caaaatttgc tttgagagct acagggaatt        420
gctattactc ctgtaccttc tgctcaattt cctttcctca tcccaaataa atgccttggt        480
acaagaaaag                                                              490
```

<210> SEQ ID NO 40
<211> LENGTH: 487
<212> TYPE: DNA

<213> ORGANISM: Homo sapiens

<400> SEQUENCE: 40

```
ccttgctata gaagacctgg gacagaggac tgctgtctgc cctctctggt caccctgcct      60
agctagagga tctgtgaccc cagccatgag gaccctcgcc atccttgctg ccattctcct    120
ggtggccctg caggcccagg ctgagccact ccaggcaaga gctgatgagg ttgctgcagc    180
cccggagcag attgcagcgg acatcccaga agtggttgtt tcccttgcat gggacgaaag    240
cttggctcca aagcatccag gctcaaggaa aaacatggac tgctattgca gaataccagc    300
gtgcattgca ggagaacgtc gctatggaac ctgcatctac cagggaagac tctgggcatt    360
ctgctgctga gcttgcagaa aagaaaaat gagctcaaaa tttgctttga gagctacagg     420
gaattgctat tactcctgta ccttctgctc aatttccttt cctcatctca aataaatgcc    480
ttgttac                                                              487
```

<210> SEQ ID NO 41
<211> LENGTH: 542
<212> TYPE: DNA
<213> ORGANISM: Homo sapiens

<400> SEQUENCE: 41

```
gtctgccctc tctgctcgcc ctgcctagct tgaggatctg tcaccccagc catgaggatt      60
atcgccctcc tcgctgctat tctcttggta gccctccagg tccgggcagg cccactccag    120
gcaagaggtg atgaggctcc aggccaggag cagcgtgggc cagaagacca ggacatatct    180
atttcctttg catgggataa aagctctgct cttcaggttt caggctcaac aaggggcatg    240
gtctgctctt gcagattagt attctgccgg cgaacagaac ttcgtgttgg gaactgcctc    300
attggtggtg tgagtttcac atactgctgc acgcgtgtcg attaacgttc tgctgtccaa    360
gagaatgtca tgctgggaac gccatcatcg gtggtgttag cttcacatgc ttctgcagct    420
gagcttgcag aatagagaaa aatgagctca taatttgctt tgagagctac aggaaatggt    480
tgtttctcct atactttgtc cttaacatct ttcttgatcc taaatatata tctcgtaaca    540
ag                                                                   542
```

<210> SEQ ID NO 42
<211> LENGTH: 449
<212> TYPE: DNA
<213> ORGANISM: Homo sapiens

<400> SEQUENCE: 42

```
atatccactc ctgctctccc tcctgcaggt gaccccagcc atgaggacca tcgccatcct      60
tgctgccatt ctcctggtgg ccctgcaggc ccaggctgag tcactccagg aaagagctga    120
tgaggctaca acccagaagc agtctgggga agacaaccag gaccttgcta tctcctttgc    180
aggaaatgga ctctctgctc ttagaacctc aggttctcag gcaagagcca cctgctattg    240
ccgaaccggc cgttgtgcta cccgtgagtc cctctccggg gtgtgtgaaa tcagtggccg    300
cctctacaga ctctgctgtc gctgagcttc ctagatagaa accaaagcag tgcaagattc    360
agttcaaggt cctgaaaaaa gaaaaacatt ttactctgtg taccttgtgt ctttctaaat    420
ttctctctcc aaaataaagt tcaagcatt                                      449
```

<210> SEQ ID NO 43
<211> LENGTH: 475
<212> TYPE: DNA
<213> ORGANISM: Homo sapiens

```
<400> SEQUENCE: 43
acacatctgc tcctgctctc tctcctccag cgaccctagc catgagaacc ctcaccatcc     60
tcactgctgt tctcctcgtg gccctccagg ccaaggctga gccactccaa gctgaggatg    120
atccactgca ggcaaaagct tatgaggctg atgcccagga gcagcgtggg gcaaatgacc    180
aggactttgc cgtctccttt gcagaggatg caagctcaag tcttagagct ttgggctcaa    240
caagggcttt cacttgccat tgcagaaggt cctgttattc aacagaatat tcctatggga    300
cctgcactgt catgggtatt aaccacagat tctgctgcct ctgagggatg agaacagaga    360
gaaatatatt cataatttac tttatgacct agaaggaaac tgtcgtgtgt cccatacatt    420
gccatcaact ttgtttcctc atctcaaata aagtcctttc agcaaaaaaa aaaaa         475

<210> SEQ ID NO 44
<211> LENGTH: 484
<212> TYPE: DNA
<213> ORGANISM: Homo sapiens

<400> SEQUENCE: 44
tcccttcagt tccgtcgacg aggttgtgca atccaccagt cttataaata cagtgacgct     60
ccagcctctg gaagcctctg tcagctcagc ctccaaagga gccagcgtct ccccagttcc    120
tgaaatcctg ggtgttgcct gccagtcgcc atgagaactt cctaccttct gctgtttact    180
ctctgcttac ttttgtctga gatggcctca ggtggtaact ttctcacagg ccttggccac    240
agatctgatc attacaattg cgtcagcagt ggagggcaat gtctctattc tgcctgcccg    300
atctttacca aaattcaagg cacctgttac agagggaagg ccaagtgctg caagtgagct    360
gggagtgacc agaagaaatg acgcagaagt gaaatgaact ttttataagc attcttttaa    420
taaaggaaaa ttgcttttga agtataccta ctttgggcca aaaaaaaaaa aaaaaaaaaa    480
aaaa                                                                 484

<210> SEQ ID NO 45
<211> LENGTH: 337
<212> TYPE: DNA
<213> ORGANISM: Homo sapiens

<400> SEQUENCE: 45
tgagtctcag cgtggggtga agcctagcag ctatgaggat ccattatctt ctgtttgctt     60
tgctcttcct gttttggtg cctgtcccag gtcatggagg aatcataaac acattacaga    120
aatattattg cagagtcaga ggcggccggt gtgctgtgct cagctgcctt ccaaggagg    180 aacagatcgg caagtgctcg acgcgtggcc gaaaatgctg ccgaagaaag aaataaaaac    240
cctgaaacat gacgagagtg ttgtaaagtg tggaaatgcc ttcttaaagt ttataaaagt    300
aaaatcaaat tacatttttt tttcaaaaaa aaaaaaa                             337

<210> SEQ ID NO 46
<211> LENGTH: 336
<212> TYPE: DNA
<213> ORGANISM: Homo sapiens

<400> SEQUENCE: 46
agactcagct cctggtgaag ctcccagcca tcagccatga gggtcttgta tctcctcttc     60
tcgttcctct tcatattcct gatgcctctt ccaggtgttt ttggtggtat aggcgatcct    120
gttacctgcc ttaagagtgg agccatatgt catccagtct tttgccctag aaggtataaa    180
```

| | |
|---|---|
| caaattggca cctgtggtct ccctggaaca aaatgctgca aaaagccatg aggaggccaa | 240 |
| gaagctgctg tggctgatgc ggattcagaa agggctccct catcagagac gtgcgacatg | 300 |
| taaaccaaat taaactatgg tgtccaaaga tacgca | 336 |

<210> SEQ ID NO 47
<211> LENGTH: 691
<212> TYPE: DNA
<213> ORGANISM: Homo sapiens

<400> SEQUENCE: 47

| | |
|---|---|
| atggagaccc agagagccag cctgtgcctg gggcgctggt cactgtggct tctgctgctg | 60 |
| gcactcgtgg tgccctcggc cagcgcccag ccctcagct acagggaggc cgtgcttcgt | 120 |
| gctgtggatc gcctcaacga gcagtcctcg gaagctaatc tctaccgcct cctggagctg | 180 |
| gaccagccgc ccaaggccga cgaggacccg ggcaccccga aacctgtgag cttcacggtg | 240 |
| aaggagactg tgtgtcccag gccgacccgg cagcccccgg agctgtgtga cttcaaggag | 300 |
| aacgggcggg tgaaacagtg tgtggggaca gtcaccctgg atcagatcaa ggaccccgctc | 360 |
| gacatcacct gcaatgaggt tcaaggtgtc aggggaggtc gcctgtgcta ttgtaggcgt | 420 |
| aggttctgcg tctgtgtcgg acgaggatga cggttgcgac ggcaggcttt ccctccccca | 480 |
| attttcccgg ggccaggttt ccgtccccca attttccgc ctccaccttt ccggcccgca | 540 |
| ccattcggtc caccaaggtt ccctggtaga cggtgaagga tttgcaggca actcacccag | 600 |
| aaggcctttc ggtacattaa atcccagca aggagaccta agcatctgct ttgcccaggc | 660 |
| ccgcatctgt caaataaatt cttgtgaaac c | 691 |

<210> SEQ ID NO 48
<211> LENGTH: 691
<212> TYPE: DNA
<213> ORGANISM: Homo sapiens

<400> SEQUENCE: 48

| | |
|---|---|
| atggagaccc agagagccag cctgtgcctg gggcgctggt cactgtggct tctgctgctg | 60 |
| gcactcgtgg tgccctcggc cagcgcccag ccctcagct acagggaggc cgtgcttcgt | 120 |
| gctgtggatc gcctcaacga gcagtcctcg gaagctaatc tctaccgcct cctggagctg | 180 |
| gaccagccgc ccaaggccga cgaggacccg ggcaccccga aacctgtgag cttcacggtg | 240 |
| aaggagactg tgtgtcccag gccgacccgg cagcccccgg agctgtgtga cttcaaggag | 300 |
| aacgggcggg tgaaacagtg tgtggggaca gtcaccctgg atcagatcaa ggaccccgctc | 360 |
| gacatcacct gcaatgaggt tcaaggtgtc aggggaggtg gcctgtgcta ttgtaggcgt | 420 |
| aggttctgcg tctgtgtcgg acgaggatga cggttgcgac ggcaggcttt ccctccccca | 480 |
| attttcccgg ggccaggttt ccgtccccca attttccgc ctccaccttt ccggcccgca | 540 |
| ccattcggtc caccaaggtt ccctggtaga cggtgaagga tttgcaggca actcacccag | 600 |
| aaggcctttc ggtacattaa atcccagca aggagaccta agcatctgct ttgcccaggc | 660 |
| ccgcatctgt caaataaatt cttgtgaaac c | 691 |

<210> SEQ ID NO 49
<211> LENGTH: 691
<212> TYPE: DNA
<213> ORGANISM: Homo sapiens

<400> SEQUENCE: 49

| | |
|---|---|
| atggagaccc agagagccag cctgtgcctg gggcgctggt cactgtggct tctgctgctg | 60 |

-continued

```
gcactcgtgg tgccctcggc cagcgcccag gccctcagct acaggaggc cgtgcttcgt    120 gctgtggatc gcctcaacga gcagtcctcg gaagctaatc tctaccgcct cctggagctg    180
gaccagccgc ccaaggccga cgaggacccg ggcaccccga aacctgtgag cttcacggtg    240
aaggagactg tgtgtcccag gccgacccgg cagcccccgg agctgtgtga cttcaaggag    300
aacgggcggg tgaaacagtg tgtggggaca gtcaccctgg atcagatcaa ggacccgctc    360
gacatcacct gcaatgaggt tcaaggtgtc aggggaggtc gcctgtgcta ttgtaggggt    420
tggatctgct tctgtgtcgg acgaggatga cggttgcgac ggcaggcttt ccctccccca    480
attttcccgg ggccaggttt ccgtccccca attttccgc ctccacctt ccggccgca    540 ccattcggtc caccaaggtt ccctggtaga cggtgaagga tttgcaggca actcacccag    600
aaggcctttc ggcacattaa atcccagca aggagaccta agcatctgct ttgcccaggc    660
ccgcatctgt caaataaatt cttgtgaaac c                                    691
```

<210> SEQ ID NO 50
<211> LENGTH: 55
<212> TYPE: DNA
<213> ORGANISM: Artificial Sequence
<220> FEATURE:
<223> OTHER INFORMATION: Construct containing an HPV target sequence,
      a hairpin sequence and BamH1 and SalI restriction sites.

<400> SEQUENCE: 50

```
gatcctaggt atttgaattt gcatttcaag agaatgcaaa ttcaaatacc ttttg          55
```

<210> SEQ ID NO 51
<211> LENGTH: 55
<212> TYPE: DNA
<213> ORGANISM: Artificial Sequence
<220> FEATURE:
<223> OTHER INFORMATION: Construct containing an HPV target sequence,
      a hairpin sequence and BamH1 and SalI restriction sites. Sequence
      given in 3' to 5' orientation.

<400> SEQUENCE: 51

```
gatccataaa cttaaacgta aagttctctt acgtttaagt ttatggaaaa cagct          55
```

<210> SEQ ID NO 52
<211> LENGTH: 21
<212> TYPE: DNA
<213> ORGANISM: Homo sapiens

<400> SEQUENCE: 52

```
agccaatggc ttggaatgag a                                               21
```

<210> SEQ ID NO 53
<211> LENGTH: 21
<212> TYPE: DNA
<213> ORGANISM: Homo sapiens

<400> SEQUENCE: 53

```
atcagctggc ctggtttgat a                                               21
```

<210> SEQ ID NO 54
<211> LENGTH: 21
<212> TYPE: DNA
<213> ORGANISM: Homo sapiens

<400> SEQUENCE: 54

```
ctgtgaactt gctcaggaca a                                               21
```

<210> SEQ ID NO 55
<211> LENGTH: 21
<212> TYPE: DNA
<213> ORGANISM: Homo sapiens

<400> SEQUENCE: 55
agcaatcagc tggcctggtt t                                              21

<210> SEQ ID NO 56
<211> LENGTH: 21
<212> TYPE: DNA
<213> ORGANISM: Homo sapiens

<400> SEQUENCE: 56
cctctgtgaa cttgctcagg a                                              21

<210> SEQ ID NO 57
<211> LENGTH: 21
<212> TYPE: DNA
<213> ORGANISM: Homo sapiens

<400> SEQUENCE: 57
ttccgaatgt ctgaggacaa g                                              21

<210> SEQ ID NO 58
<211> LENGTH: 21
<212> TYPE: DNA
<213> ORGANISM: Homo sapiens

<400> SEQUENCE: 58
ccaatggctt ggaatgagac t                                              21

<210> SEQ ID NO 59
<211> LENGTH: 21
<212> TYPE: DNA
<213> ORGANISM: Homo sapiens

<400> SEQUENCE: 59
ggtgctgact atccagttga t                                              21

<210> SEQ ID NO 60
<211> LENGTH: 21
<212> TYPE: DNA
<213> ORGANISM: Homo sapiens

<400> SEQUENCE: 60
caatcagctg gcctggtttg a                                              21

<210> SEQ ID NO 61
<211> LENGTH: 21
<212> TYPE: DNA
<213> ORGANISM: Homo sapiens

<400> SEQUENCE: 61
caccctggtg ctgactatcc a                                              21

<210> SEQ ID NO 62
<211> LENGTH: 21
<212> TYPE: DNA
<213> ORGANISM: Homo sapiens

<400> SEQUENCE: 62

-continued

```
caccaccctg gtgctgacta t                                              21

<210> SEQ ID NO 63
<211> LENGTH: 21
<212> TYPE: DNA
<213> ORGANISM: Homo sapiens

<400> SEQUENCE: 63
tgctttattc tcccattgaa a                                              21

<210> SEQ ID NO 64
<211> LENGTH: 21
<212> TYPE: DNA
<213> ORGANISM: Homo sapiens

<400> SEQUENCE: 64
ctggtgctga ctatccagtt g                                              21

<210> SEQ ID NO 65
<211> LENGTH: 21
<212> TYPE: DNA
<213> ORGANISM: Homo sapiens

<400> SEQUENCE: 65
tctgtgctct tcgtcatctg a                                              21

<210> SEQ ID NO 66
<211> LENGTH: 21
<212> TYPE: DNA
<213> ORGANISM: Homo sapiens

<400> SEQUENCE: 66
tgccatctgt gctcttcgtc a                                              21

<210> SEQ ID NO 67
<211> LENGTH: 21
<212> TYPE: DNA
<213> ORGANISM: Homo sapiens

<400> SEQUENCE: 67
tggtgctgac tatccagttg a                                              21

<210> SEQ ID NO 68
<211> LENGTH: 21
<212> TYPE: DNA
<213> ORGANISM: Homo sapiens

<400> SEQUENCE: 68
cctggtgctg actatccagt t                                              21

<210> SEQ ID NO 69
<211> LENGTH: 21
<212> TYPE: DNA
<213> ORGANISM: Homo sapiens

<400> SEQUENCE: 69
accctggtgc tgactatcca g                                              21

<210> SEQ ID NO 70
<211> LENGTH: 21
<212> TYPE: DNA
<213> ORGANISM: Homo sapiens

<400> SEQUENCE: 70
```
gagcctgcca tctgtgctct t                                        21

<210> SEQ ID NO 71
<211> LENGTH: 21
<212> TYPE: DNA
<213> ORGANISM: Homo sapiens

<400> SEQUENCE: 71
ctggtttgat actgacctgt a                                        21

<210> SEQ ID NO 72
<211> LENGTH: 21
<212> TYPE: DNA
<213> ORGANISM: Homo sapiens

<400> SEQUENCE: 72
tggtttgata ctgacctgta a                                        21

<210> SEQ ID NO 73
<211> LENGTH: 21
<212> TYPE: DNA
<213> ORGANISM: Homo sapiens

<400> SEQUENCE: 73
tcgaggagta acaatacaaa t                                        21

<210> SEQ ID NO 74
<211> LENGTH: 21
<212> TYPE: DNA
<213> ORGANISM: Homo sapiens

<400> SEQUENCE: 74
accatgcaga atacaaatga t                                        21

<210> SEQ ID NO 75
<211> LENGTH: 21
<212> TYPE: DNA
<213> ORGANISM: Homo sapiens

<400> SEQUENCE: 75
aggagtaaca atacaaatgg a                                        21

<210> SEQ ID NO 76
<211> LENGTH: 21
<212> TYPE: DNA
<213> ORGANISM: Homo sapiens

<400> SEQUENCE: 76
gtcgaggagt aacaatacaa a                                        21

<210> SEQ ID NO 77
<211> LENGTH: 21
<212> TYPE: DNA
<213> ORGANISM: Homo sapiens

<400> SEQUENCE: 77
ttgttgtaac ctgctgtgat a                                        21

<210> SEQ ID NO 78
<211> LENGTH: 21
<212> TYPE: DNA
<213> ORGANISM: Homo sapiens

<400> SEQUENCE: 78
gagtaatggt gtagaacact a                                              21

<210> SEQ ID NO 79
<211> LENGTH: 21
<212> TYPE: DNA
<213> ORGANISM: Homo sapiens

<400> SEQUENCE: 79
agtaatggtg tagaacacta a                                              21

<210> SEQ ID NO 80
<211> LENGTH: 21
<212> TYPE: DNA
<213> ORGANISM: Homo sapiens

<400> SEQUENCE: 80
cacactaacc aagctgagtt t                                              21

<210> SEQ ID NO 81
<211> LENGTH: 21
<212> TYPE: DNA
<213> ORGANISM: Homo sapiens

<400> SEQUENCE: 81
tttggtcgag gagtaacaat a                                              21

<210> SEQ ID NO 82
<211> LENGTH: 21
<212> TYPE: DNA
<213> ORGANISM: Homo sapiens

<400> SEQUENCE: 82
taccattcca ttgtttgtgc a                                              21

<210> SEQ ID NO 83
<211> LENGTH: 21
<212> TYPE: DNA
<213> ORGANISM: Homo sapiens

<400> SEQUENCE: 83
tagggtaaat cagtaagagg t                                              21

<210> SEQ ID NO 84
<211> LENGTH: 21
<212> TYPE: DNA
<213> ORGANISM: Homo sapiens

<400> SEQUENCE: 84
ctaaccaagc tgagtttcct a                                              21

<210> SEQ ID NO 85
<211> LENGTH: 21
<212> TYPE: DNA
<213> ORGANISM: Homo sapiens

<400> SEQUENCE: 85
tggtcgagga gtaacaatac a                                              21

<210> SEQ ID NO 86
<211> LENGTH: 21
<212> TYPE: DNA
<213> ORGANISM: Homo sapiens

```
<400> SEQUENCE: 86
ctggcctggt tgatactga c                                              21

<210> SEQ ID NO 87
<211> LENGTH: 21
<212> TYPE: DNA
<213> ORGANISM: Homo sapiens

<400> SEQUENCE: 87
taacctcact tgcaataatt a                                             21

<210> SEQ ID NO 88
<211> LENGTH: 21
<212> TYPE: DNA
<213> ORGANISM: Homo sapiens

<400> SEQUENCE: 88
atcccactgg cctctgataa a                                             21

<210> SEQ ID NO 89
<211> LENGTH: 21
<212> TYPE: DNA
<213> ORGANISM: Homo sapiens

<400> SEQUENCE: 89
gaccacaagc agagtgctga a                                             21

<210> SEQ ID NO 90
<211> LENGTH: 21
<212> TYPE: DNA
<213> ORGANISM: Homo sapiens

<400> SEQUENCE: 90
cacaagcaga gtgctgaagg t                                             21

<210> SEQ ID NO 91
<211> LENGTH: 21
<212> TYPE: DNA
<213> ORGANISM: Homo sapiens

<400> SEQUENCE: 91
ctaacctcac ttgcaataat t                                             21

<210> SEQ ID NO 92
<211> LENGTH: 19
<212> TYPE: DNA
<213> ORGANISM: Homo sapiens

<400> SEQUENCE: 92
agctgatatt gatggacag                                                19

<210> SEQ ID NO 93
<211> LENGTH: 23
<212> TYPE: DNA
<213> ORGANISM: Human papillomavirus

<400> SEQUENCE: 93
cggtgccaga aaccgttgaa tcc                                           23

<210> SEQ ID NO 94
<211> LENGTH: 23
<212> TYPE: DNA
```

```
<213> ORGANISM: Human papillomavirus

<400> SEQUENCE: 94
cactgcaaga catagaaata acc                                          23

<210> SEQ ID NO 95
<211> LENGTH: 23
<212> TYPE: DNA
<213> ORGANISM: Human papillomavirus

<400> SEQUENCE: 95
aggtgcctgc ggtgccagaa acc                                          23

<210> SEQ ID NO 96
<211> LENGTH: 23
<212> TYPE: DNA
<213> ORGANISM: Human papillomavirus

<400> SEQUENCE: 96
gcggtgccag aaaccgttga atc                                          23

<210> SEQ ID NO 97
<211> LENGTH: 23
<212> TYPE: DNA
<213> ORGANISM: Human papillomavirus

<400> SEQUENCE: 97
tcactgcaag acatagaaat aac                                          23

<210> SEQ ID NO 98
<211> LENGTH: 23
<212> TYPE: DNA
<213> ORGANISM: Human papillomavirus

<400> SEQUENCE: 98
cccatgctgc atgccataaa tgt                                          23

<210> SEQ ID NO 99
<211> LENGTH: 23
<212> TYPE: DNA
<213> ORGANISM: Human papillomavirus

<400> SEQUENCE: 99
atgctgcatg ccataaatgt ata                                          23

<210> SEQ ID NO 100
<211> LENGTH: 23
<212> TYPE: DNA
<213> ORGANISM: Human papillomavirus

<400> SEQUENCE: 100
gtggtgtata gagacagtat acc                                          23

<210> SEQ ID NO 101
<211> LENGTH: 23
<212> TYPE: DNA
<213> ORGANISM: Human papillomavirus

<400> SEQUENCE: 101
gcgcgctttg aggatccaac acg                                          23

<210> SEQ ID NO 102
<211> LENGTH: 23
```

```
<212> TYPE: DNA
<213> ORGANISM: Human papillomavirus

<400> SEQUENCE: 102
ctgcggtgcc agaaaccgtt gaa                                              23

<210> SEQ ID NO 103
<211> LENGTH: 23
<212> TYPE: DNA
<213> ORGANISM: Human papillomavirus

<400> SEQUENCE: 103
ccccatgctg catgccataa atg                                              23

<210> SEQ ID NO 104
<211> LENGTH: 23
<212> TYPE: DNA
<213> ORGANISM: Human papillomavirus

<400> SEQUENCE: 104
accccatgct gcatgccata aat                                              23

<210> SEQ ID NO 105
<211> LENGTH: 23
<212> TYPE: DNA
<213> ORGANISM: Human papillomavirus

<400> SEQUENCE: 105
aacactgggt tatacaattt att                                              23

<210> SEQ ID NO 106
<211> LENGTH: 23
<212> TYPE: DNA
<213> ORGANISM: Human papillomavirus

<400> SEQUENCE: 106
acgacgcaga gaaacacaag tat                                              23

<210> SEQ ID NO 107
<211> LENGTH: 23
<212> TYPE: DNA
<213> ORGANISM: Human papillomavirus

<400> SEQUENCE: 107
aaggtgcctg cggtgccaga aac                                              23

<210> SEQ ID NO 108
<211> LENGTH: 23
<212> TYPE: DNA
<213> ORGANISM: Human papillomavirus

<400> SEQUENCE: 108
ggtgcctgcg gtgccagaaa ccg                                              23

<210> SEQ ID NO 109
<211> LENGTH: 23
<212> TYPE: DNA
<213> ORGANISM: Human papillomavirus

<400> SEQUENCE: 109
catgctgcat gccataaatg tat                                              23

<210> SEQ ID NO 110
```

<211> LENGTH: 23
<212> TYPE: DNA
<213> ORGANISM: Homo sapiens

<400> SEQUENCE: 110
gacgcagaga aacacaagta taa                                          23

<210> SEQ ID NO 111
<211> LENGTH: 23
<212> TYPE: DNA
<213> ORGANISM: Human papillomavirus

<400> SEQUENCE: 111
ttcactgcaa gacatagaaa taa                                          23

<210> SEQ ID NO 112
<211> LENGTH: 23
<212> TYPE: DNA
<213> ORGANISM: Human papillomavirus

<400> SEQUENCE: 112
ggtgccagaa accgttgaat cca                                          23

<210> SEQ ID NO 113
<211> LENGTH: 23
<212> TYPE: DNA
<213> ORGANISM: Human papillomavirus

<400> SEQUENCE: 113
tggcgcgctt tgaggatcca aca                                          23

<210> SEQ ID NO 114
<211> LENGTH: 23
<212> TYPE: DNA
<213> ORGANISM: Human papillomavirus

<400> SEQUENCE: 114
tgtggtgtat agagacagta tac                                          23

<210> SEQ ID NO 115
<211> LENGTH: 23
<212> TYPE: DNA
<213> ORGANISM: Human papillomavirus

<400> SEQUENCE: 115
gtgcctgcgg tgccagaaac cgt                                          23

<210> SEQ ID NO 116
<211> LENGTH: 23
<212> TYPE: DNA
<213> ORGANISM: Human papillomavirus

<400> SEQUENCE: 116
ctgcatgcca taaatgtata gat                                          23

<210> SEQ ID NO 117
<211> LENGTH: 23
<212> TYPE: DNA
<213> ORGANISM: Human papillomavirus

<400> SEQUENCE: 117
gactccaacg acgcagagaa aca                                          23

```
<210> SEQ ID NO 118
<211> LENGTH: 23
<212> TYPE: DNA
<213> ORGANISM: Human papillomavirus

<400> SEQUENCE: 118
ctgggcacta tagaggccag tgc                                              23

<210> SEQ ID NO 119
<211> LENGTH: 23
<212> TYPE: DNA
<213> ORGANISM: Human papillomavirus

<400> SEQUENCE: 119
tgctgcatgc cataaatgta tag                                              23

<210> SEQ ID NO 120
<211> LENGTH: 23
<212> TYPE: DNA
<213> ORGANISM: Human papillomavirus

<400> SEQUENCE: 120
gtgccagaaa ccgttgaatc cag                                              23

<210> SEQ ID NO 121
<211> LENGTH: 23
<212> TYPE: DNA
<213> ORGANISM: Human papillomavirus

<400> SEQUENCE: 121
ttacagaggt atttgaattt gca                                              23

<210> SEQ ID NO 122
<211> LENGTH: 23
<212> TYPE: DNA
<213> ORGANISM: Human papillomavirus

<400> SEQUENCE: 122
gaggccagtg ccattcgtgc tgc                                              23

<210> SEQ ID NO 123
<211> LENGTH: 23
<212> TYPE: DNA
<213> ORGANISM: Human papillomavirus

<400> SEQUENCE: 123
attccggttg accttctatg tca                                              23

<210> SEQ ID NO 124
<211> LENGTH: 23
<212> TYPE: DNA
<213> ORGANISM: Human papillomavirus

<400> SEQUENCE: 124
gatggagtta atcatcaaca ttt                                              23

<210> SEQ ID NO 125
<211> LENGTH: 23
<212> TYPE: DNA
<213> ORGANISM: Human papillomavirus

<400> SEQUENCE: 125
aagccagaat tgagctagta gta                                              23
```

```
<210> SEQ ID NO 126
<211> LENGTH: 23
<212> TYPE: DNA
<213> ORGANISM: Human papillomavirus

<400> SEQUENCE: 126
catggaccta aggcaacatt gca                                             23

<210> SEQ ID NO 127
<211> LENGTH: 23
<212> TYPE: DNA
<213> ORGANISM: Human papillomavirus

<400> SEQUENCE: 127
aaccacaacg tcacacaatg ttg                                             23

<210> SEQ ID NO 128
<211> LENGTH: 23
<212> TYPE: DNA
<213> ORGANISM: Human papillomavirus

<400> SEQUENCE: 128
atggacctaa ggcaacattg caa                                             23

<210> SEQ ID NO 129
<211> LENGTH: 23
<212> TYPE: DNA
<213> ORGANISM: Human papillomavirus

<400> SEQUENCE: 129
taagcgactc agaggaagaa aac                                             23

<210> SEQ ID NO 130
<211> LENGTH: 23
<212> TYPE: DNA
<213> ORGANISM: Human papillomavirus

<400> SEQUENCE: 130
gaagccagaa ttgagctagt agt                                             23

<210> SEQ ID NO 131
<211> LENGTH: 23
<212> TYPE: DNA
<213> ORGANISM: Human papillomavirus

<400> SEQUENCE: 131
gagccgaacc acaacgtcac aca                                             23

<210> SEQ ID NO 132
<211> LENGTH: 23
<212> TYPE: DNA
<213> ORGANISM: Human papillomavirus

<400> SEQUENCE: 132
acgtcacaca atgttgtgta tgt                                             23

<210> SEQ ID NO 133
<211> LENGTH: 23
<212> TYPE: DNA
<213> ORGANISM: Human papillomavirus

<400> SEQUENCE: 133
gaaccacaac gtcacacaat gtt                                             23
```

<210> SEQ ID NO 134
<211> LENGTH: 23
<212> TYPE: DNA
<213> ORGANISM: Human papillomavirus

<400> SEQUENCE: 134
aggcaacatt gcaagacatt gta                                              23

<210> SEQ ID NO 135
<211> LENGTH: 23
<212> TYPE: DNA
<213> ORGANISM: Human papillomavirus

<400> SEQUENCE: 135
aagacattgt attgcattta gag                                              23

<210> SEQ ID NO 136
<211> LENGTH: 23
<212> TYPE: DNA
<213> ORGANISM: Human papillomavirus

<400> SEQUENCE: 136
taaggcaaca ttgcaagaca ttg                                              23

<210> SEQ ID NO 137
<211> LENGTH: 23
<212> TYPE: DNA
<213> ORGANISM: Human papillomavirus

<400> SEQUENCE: 137
ccagcccgac gagccgaacc aca                                              23

<210> SEQ ID NO 138
<211> LENGTH: 23
<212> TYPE: DNA
<213> ORGANISM: Human papillomavirus

<400> SEQUENCE: 138
aagctcagca gacgaccttc gag                                              23

<210> SEQ ID NO 139
<211> LENGTH: 23
<212> TYPE: DNA
<213> ORGANISM: Human papillomavirus

<400> SEQUENCE: 139
gcccgacgag ccgaaccaca acg                                              23

<210> SEQ ID NO 140
<211> LENGTH: 23
<212> TYPE: DNA
<213> ORGANISM: Human papillomavirus

<400> SEQUENCE: 140
ttccggttga ccttctatgt cac                                              23

<210> SEQ ID NO 141
<211> LENGTH: 23
<212> TYPE: DNA
<213> ORGANISM: Human papillomavirus

<400> SEQUENCE: 141
tgcatggacc taaggcaaca ttg                                                23

<210> SEQ ID NO 142
<211> LENGTH: 23
<212> TYPE: DNA
<213> ORGANISM: Human papillomavirus

<400> SEQUENCE: 142
ttccagcagc tgtttctgaa cac                                                23

<210> SEQ ID NO 143
<211> LENGTH: 23
<212> TYPE: DNA
<213> ORGANISM: Human papillomavirus

<400> SEQUENCE: 143
aacaccctgt cctttgtgtg tcc                                                23

<210> SEQ ID NO 144
<211> LENGTH: 23
<212> TYPE: DNA
<213> ORGANISM: Human papillomavirus

<400> SEQUENCE: 144
cttctatgtc acgagcaatt aag                                                23

<210> SEQ ID NO 145
<211> LENGTH: 23
<212> TYPE: DNA
<213> ORGANISM: Human papillomavirus

<400> SEQUENCE: 145
acgagccgaa ccacaacgtc aca                                                23

<210> SEQ ID NO 146
<211> LENGTH: 23
<212> TYPE: DNA
<213> ORGANISM: Human papillomavirus

<400> SEQUENCE: 146
ttgagctagt agtagaaagc tca                                                23

<210> SEQ ID NO 147
<211> LENGTH: 23
<212> TYPE: DNA
<213> ORGANISM: Human papillomavirus

<400> SEQUENCE: 147
cagcagacga ccttcgagca ttc                                                23

<210> SEQ ID NO 148
<211> LENGTH: 23
<212> TYPE: DNA
<213> ORGANISM: Human papillomavirus

<400> SEQUENCE: 148
agccagaatt gagctagtag tag                                                23

<210> SEQ ID NO 149
<211> LENGTH: 23
<212> TYPE: DNA
<213> ORGANISM: Human papillomavirus

<400> SEQUENCE: 149

-continued

```
gtcacacaat gttgtgtatg tgt                                           23

<210> SEQ ID NO 150
<211> LENGTH: 23
<212> TYPE: DNA
<213> ORGANISM: Human papillomavirus

<400> SEQUENCE: 150
ccgacgagcc gaaccacaac gtc                                           23

<210> SEQ ID NO 151
<211> LENGTH: 23
<212> TYPE: DNA
<213> ORGANISM: Human papillomavirus

<400> SEQUENCE: 151
aattccggtt gaccttctat gtc                                           23

<210> SEQ ID NO 152
<211> LENGTH: 23
<212> TYPE: DNA
<213> ORGANISM: Human papillomavirus

<400> SEQUENCE: 152
attccagcag ctgtttctga aca                                           23

<210> SEQ ID NO 153
<211> LENGTH: 19
<212> TYPE: DNA
<213> ORGANISM: Human papillomavirus

<400> SEQUENCE: 153
taggtatttg aatttgcat                                                19

<210> SEQ ID NO 154
<211> LENGTH: 19
<212> TYPE: DNA
<213> ORGANISM: Human papillomavirus

<400> SEQUENCE: 154
gaggtatttg aatttgcat                                                19

<210> SEQ ID NO 155
<211> LENGTH: 20
<212> TYPE: DNA
<213> ORGANISM: Homo sapiens

<400> SEQUENCE: 155
atgttgtctg gacaagcact                                               20

<210> SEQ ID NO 156
<211> LENGTH: 19
<212> TYPE: DNA
<213> ORGANISM: Homo sapiens

<400> SEQUENCE: 156
gttggagctg ttggcgtag                                                19

<210> SEQ ID NO 157
<211> LENGTH: 21
<212> TYPE: DNA
<213> ORGANISM: Homo sapiens
```

<400> SEQUENCE: 157
ctcctggaac tcatctttct a                                              21

<210> SEQ ID NO 158
<211> LENGTH: 21
<212> TYPE: DNA
<213> ORGANISM: Homo sapiens

<400> SEQUENCE: 158
gctctcctgc ttccggaaga g                                              21

<210> SEQ ID NO 159
<211> LENGTH: 21
<212> TYPE: DNA
<213> ORGANISM: Homo sapiens

<400> SEQUENCE: 159
ctccacgact ctggaaacta t                                              21

<210> SEQ ID NO 160
<211> LENGTH: 21
<212> TYPE: DNA
<213> ORGANISM: Homo sapiens

<400> SEQUENCE: 160
cagaagttct cctgccagtt a                                              21

<210> SEQ ID NO 161
<211> LENGTH: 21
<212> TYPE: DNA
<213> ORGANISM: Homo sapiens

<400> SEQUENCE: 161
ccggaagaca atgccactgt t                                              21

<210> SEQ ID NO 162
<211> LENGTH: 21
<212> TYPE: DNA
<213> ORGANISM: Homo sapiens

<400> SEQUENCE: 162
ctgaacggtc aaagacattc a                                              21

<210> SEQ ID NO 163
<211> LENGTH: 21
<212> TYPE: DNA
<213> ORGANISM: Homo sapiens

<400> SEQUENCE: 163
cacaacatgg atggtcaagg a                                              21

<210> SEQ ID NO 164
<211> LENGTH: 21
<212> TYPE: DNA
<213> ORGANISM: Homo sapiens

<400> SEQUENCE: 164
atgcaggcac ttactactaa t                                              21

<210> SEQ ID NO 165
<211> LENGTH: 21
<212> TYPE: DNA
<213> ORGANISM: Homo sapiens

```
<400> SEQUENCE: 165
atcgggctga acggtcaaag a                                              21

<210> SEQ ID NO 166
<211> LENGTH: 21
<212> TYPE: DNA
<213> ORGANISM: Homo sapiens

<400> SEQUENCE: 166
agctctcctg cttccggaag a                                              21

<210> SEQ ID NO 167
<211> LENGTH: 21
<212> TYPE: DNA
<213> ORGANISM: Homo sapiens

<400> SEQUENCE: 167
cagctctcct gcttccggaa g                                              21

<210> SEQ ID NO 168
<211> LENGTH: 21
<212> TYPE: DNA
<213> ORGANISM: Homo sapiens

<400> SEQUENCE: 168
caggcactta ctactaataa a                                              21

<210> SEQ ID NO 169
<211> LENGTH: 21
<212> TYPE: DNA
<213> ORGANISM: Homo sapiens

<400> SEQUENCE: 169
cacttgctgg tggatgttcc c                                              21

<210> SEQ ID NO 170
<211> LENGTH: 21
<212> TYPE: DNA
<213> ORGANISM: Homo sapiens

<400> SEQUENCE: 170
aacggtcaaa gacattcaca a                                              21

<210> SEQ ID NO 171
<211> LENGTH: 21
<212> TYPE: DNA
<213> ORGANISM: Homo sapiens

<400> SEQUENCE: 171
tgcacaagct gcaccctcag g                                              21

<210> SEQ ID NO 172
<211> LENGTH: 21
<212> TYPE: DNA
<213> ORGANISM: Mouse

<400> SEQUENCE: 172
atcctggagg gtgacaaagt a                                              21

<210> SEQ ID NO 173
<211> LENGTH: 21
<212> TYPE: DNA
```

<213> ORGANISM: Mouse

<400> SEQUENCE: 173
tgggtctgac aataccgtaa a        21

<210> SEQ ID NO 174
<211> LENGTH: 21
<212> TYPE: DNA
<213> ORGANISM: Mouse

<400> SEQUENCE: 174
aacgaagcgt ttcacagctt a        21

<210> SEQ ID NO 175
<211> LENGTH: 21
<212> TYPE: DNA
<213> ORGANISM: Mouse

<400> SEQUENCE: 175
ccgctgtttc ctataacaga a        21

<210> SEQ ID NO 176
<211> LENGTH: 21
<212> TYPE: DNA
<213> ORGANISM: Mouse

<400> SEQUENCE: 176
acgaagcgtt tcacagctta a        21

<210> SEQ ID NO 177
<211> LENGTH: 21
<212> TYPE: DNA
<213> ORGANISM: Mouse

<400> SEQUENCE: 177
ctgctgtgaa agggaaattt a        21

<210> SEQ ID NO 178
<211> LENGTH: 21
<212> TYPE: DNA
<213> ORGANISM: Mouse

<400> SEQUENCE: 178
aaccttgtgg tatcagccat a        21

<210> SEQ ID NO 179
<211> LENGTH: 21
<212> TYPE: DNA
<213> ORGANISM: Mouse

<400> SEQUENCE: 179
cacagtgtgg tgcttagatt a        21

<210> SEQ ID NO 180
<211> LENGTH: 21
<212> TYPE: DNA
<213> ORGANISM: Mouse

<400> SEQUENCE: 180
cagcttcgat accgacctgt a        21

<210> SEQ ID NO 181
<211> LENGTH: 21

```
<212> TYPE: DNA
<213> ORGANISM: Mouse

<400> SEQUENCE: 181
cagtgtggtg cttagattaa a                                              21

<210> SEQ ID NO 182
<211> LENGTH: 21
<212> TYPE: DNA
<213> ORGANISM: Mouse

<400> SEQUENCE: 182
cccggcagga atcctctgga a                                              21

<210> SEQ ID NO 183
<211> LENGTH: 21
<212> TYPE: DNA
<213> ORGANISM: Mouse

<400> SEQUENCE: 183
cccgctgttt cctataacag a                                              21

<210> SEQ ID NO 184
<211> LENGTH: 21
<212> TYPE: DNA
<213> ORGANISM: Mouse

<400> SEQUENCE: 184
aaccacgagg atcagtacga a                                              21

<210> SEQ ID NO 185
<211> LENGTH: 21
<212> TYPE: DNA
<213> ORGANISM: Mouse

<400> SEQUENCE: 185
acctgccgtc ttactgaact a                                              21

<210> SEQ ID NO 186
<211> LENGTH: 21
<212> TYPE: DNA
<213> ORGANISM: Mouse

<400> SEQUENCE: 186
accacgagga tcagtacgaa a                                              21

<210> SEQ ID NO 187
<211> LENGTH: 21
<212> TYPE: DNA
<213> ORGANISM: Mouse

<400> SEQUENCE: 187
acagcttgtg atgactgaat a                                              21

<210> SEQ ID NO 188
<211> LENGTH: 21
<212> TYPE: DNA
<213> ORGANISM: Mouse

<400> SEQUENCE: 188
aggatcagta cgaaagttct a                                              21

<210> SEQ ID NO 189
```

```
<211> LENGTH: 21
<212> TYPE: DNA
<213> ORGANISM: Mouse

<400> SEQUENCE: 189
aacccgctgt ttcctataac a                                              21

<210> SEQ ID NO 190
<211> LENGTH: 21
<212> TYPE: DNA
<213> ORGANISM: Mouse

<400> SEQUENCE: 190
cagtacgaaa gttctacaga a                                              21

<210> SEQ ID NO 191
<211> LENGTH: 21
<212> TYPE: DNA
<213> ORGANISM: Mouse

<400> SEQUENCE: 191
tacgcgagtg acaatttctc a                                              21

<210> SEQ ID NO 192
<211> LENGTH: 21
<212> TYPE: DNA
<213> ORGANISM: Mouse

<400> SEQUENCE: 192
acgaaagttc tacagaagca a                                              21

<210> SEQ ID NO 193
<211> LENGTH: 21
<212> TYPE: DNA
<213> ORGANISM: Mouse

<400> SEQUENCE: 193
caggcactta ctactaataa a                                              21

<210> SEQ ID NO 194
<211> LENGTH: 21
<212> TYPE: DNA
<213> ORGANISM: Mouse

<400> SEQUENCE: 194
cacttgctgg tggatgttcc c                                              21

<210> SEQ ID NO 195
<211> LENGTH: 21
<212> TYPE: DNA
<213> ORGANISM: Mouse

<400> SEQUENCE: 195
aacggtcaaa gacattcaca a                                              21

<210> SEQ ID NO 196
<211> LENGTH: 21
<212> TYPE: DNA
<213> ORGANISM: Mouse

<400> SEQUENCE: 196
tgcacaagct gcaccctcag g                                              21
```

```
<210> SEQ ID NO 197
<211> LENGTH: 21
<212> TYPE: DNA
<213> ORGANISM: Homo sapiens

<400> SEQUENCE: 197
taagagagtc ataaacctta a                                              21

<210> SEQ ID NO 198
<211> LENGTH: 21
<212> TYPE: DNA
<213> ORGANISM: Homo sapiens

<400> SEQUENCE: 198
aacaaggtcc aagataccta a                                              21

<210> SEQ ID NO 199
<211> LENGTH: 21
<212> TYPE: DNA
<213> ORGANISM: Homo sapiens

<400> SEQUENCE: 199
aagattgaac ctgcagacca a                                              21

<210> SEQ ID NO 200
<211> LENGTH: 21
<212> TYPE: DNA
<213> ORGANISM: Homo sapiens

<400> SEQUENCE: 200
aagagatttc aagagattta a                                              21

<210> SEQ ID NO 201
<211> LENGTH: 21
<212> TYPE: DNA
<213> ORGANISM: Homo sapiens

<400> SEQUENCE: 201
aagcgcaaag tagaaactga a                                              21

<210> SEQ ID NO 202
<211> LENGTH: 21
<212> TYPE: DNA
<213> ORGANISM: Homo sapiens

<400> SEQUENCE: 202
tagcatcatc tgattgtgat a                                              21

<210> SEQ ID NO 203
<211> LENGTH: 21
<212> TYPE: DNA
<213> ORGANISM: Homo sapiens

<400> SEQUENCE: 203
taagataata atatatgttt a                                              21

<210> SEQ ID NO 204
<211> LENGTH: 21
<212> TYPE: DNA
<213> ORGANISM: Homo sapiens

<400> SEQUENCE: 204
atggtcagca tcgatcaatt a                                              21
```

<210> SEQ ID NO 205
<211> LENGTH: 21
<212> TYPE: DNA
<213> ORGANISM: Homo sapiens

<400> SEQUENCE: 205
ttgcctgaat aatgaattta a                                              21

<210> SEQ ID NO 206
<211> LENGTH: 21
<212> TYPE: DNA
<213> ORGANISM: Homo sapiens

<400> SEQUENCE: 206
atctgtgatg ctaataagga a                                              21

<210> SEQ ID NO 207
<211> LENGTH: 21
<212> TYPE: DNA
<213> ORGANISM: Homo sapiens

<400> SEQUENCE: 207
aacaaactat ttcttatata t                                              21

<210> SEQ ID NO 208
<211> LENGTH: 21
<212> TYPE: DNA
<213> ORGANISM: Homo sapiens

<400> SEQUENCE: 208
aacatttatc aatcagtata a                                              21

<210> SEQ ID NO 209
<211> LENGTH: 21
<212> TYPE: DNA
<213> ORGANISM: Homo sapiens

<400> SEQUENCE: 209
atcaatcagt ataattctgt a                                              21

<210> SEQ ID NO 210
<211> LENGTH: 21
<212> TYPE: DNA
<213> ORGANISM: Homo sapiens

<400> SEQUENCE: 210
aaggtatcag ttgcaataat a                                              21

<210> SEQ ID NO 211
<211> LENGTH: 21
<212> TYPE: DNA
<213> ORGANISM: Mouse

<400> SEQUENCE: 211
cggatcctac ggaagttatg g                                              21

<210> SEQ ID NO 212
<211> LENGTH: 21
<212> TYPE: DNA
<213> ORGANISM: Mouse

<400> SEQUENCE: 212
gaccatgttc catgtttctt t                                              21

<210> SEQ ID NO 213
<211> LENGTH: 21
<212> TYPE: DNA
<213> ORGANISM: Mouse

<400> SEQUENCE: 213
aacctaaatg acctttatta a                                          21

<210> SEQ ID NO 214
<211> LENGTH: 21
<212> TYPE: DNA
<213> ORGANISM: Mouse

<400> SEQUENCE: 214
caggagacta ggaccctata a                                          21

<210> SEQ ID NO 215
<211> LENGTH: 21
<212> TYPE: DNA
<213> ORGANISM: Mouse

<400> SEQUENCE: 215
tagggtctta ttcgtatcta a                                          21

<210> SEQ ID NO 216
<211> LENGTH: 21
<212> TYPE: DNA
<213> ORGANISM: Mouse

<400> SEQUENCE: 216
atgagccaat atgcttaatt a                                          21

<210> SEQ ID NO 217
<211> LENGTH: 21
<212> TYPE: DNA
<213> ORGANISM: Mouse

<400> SEQUENCE: 217
gccaatatgc ttaattagaa a                                          21

<210> SEQ ID NO 218
<211> LENGTH: 21
<212> TYPE: DNA
<213> ORGANISM: Mouse

<400> SEQUENCE: 218
cagcatcgat gaattggaca a                                          21

<210> SEQ ID NO 219
<211> LENGTH: 21
<212> TYPE: DNA
<213> ORGANISM: Mouse

<400> SEQUENCE: 219
ttgcctgaat aatgaattta a                                          21

<210> SEQ ID NO 220
<211> LENGTH: 21
<212> TYPE: DNA
<213> ORGANISM: Mouse

<400> SEQUENCE: 220

-continued ctgatagtaa ttgcccgaat a                                              21

<210> SEQ ID NO 221
<211> LENGTH: 21
<212> TYPE: DNA
<213> ORGANISM: Mouse

<400> SEQUENCE: 221
aagggtttgc ttgtactgaa t                                              21

<210> SEQ ID NO 222
<211> LENGTH: 21
<212> TYPE: DNA
<213> ORGANISM: Mouse

<400> SEQUENCE: 222
aacatgtatg tgatgataca a                                              21

<210> SEQ ID NO 223
<211> LENGTH: 21
<212> TYPE: DNA
<213> ORGANISM: Mouse

<400> SEQUENCE: 223
ttgcaacatg taataattta a                                              21

<210> SEQ ID NO 224
<211> LENGTH: 21
<212> TYPE: DNA
<213> ORGANISM: Mouse

<400> SEQUENCE: 224
aagagactac tgagagaaat a                                              21

<210> SEQ ID NO 225
<211> LENGTH: 21
<212> TYPE: DNA
<213> ORGANISM: Mouse

<400> SEQUENCE: 225
aagaatctac tggttcatat a                                              21

<210> SEQ ID NO 226
<211> LENGTH: 21
<212> TYPE: DNA
<213> ORGANISM: Mouse

<400> SEQUENCE: 226
tgccgtcagc atatacatat a                                              21

<210> SEQ ID NO 227
<211> LENGTH: 21
<212> TYPE: DNA
<213> ORGANISM: Mouse

<400> SEQUENCE: 227
agggctcacg gtgatggata a                                              21

<210> SEQ ID NO 228
<211> LENGTH: 21
<212> TYPE: DNA
<213> ORGANISM: Homo sapiens

<400> SEQUENCE: 228
cgcctcccgc agaccatgtt c                    21

<210> SEQ ID NO 229
<211> LENGTH: 21
<212> TYPE: DNA
<213> ORGANISM: Homo sapiens

<400> SEQUENCE: 229
tccgtgctgc tcgcaagttg a                    21

<210> SEQ ID NO 230
<211> LENGTH: 21
<212> TYPE: DNA
<213> ORGANISM: Homo sapiens

<400> SEQUENCE: 230
gcctcccgca gaccatgttc c                    21

<210> SEQ ID NO 231
<211> LENGTH: 21
<212> TYPE: DNA
<213> ORGANISM: Homo sapiens

<400> SEQUENCE: 231
cctcccgcag accatgttcc a                    21

<210> SEQ ID NO 232
<211> LENGTH: 21
<212> TYPE: DNA
<213> ORGANISM: Homo sapiens

<400> SEQUENCE: 232
ctcccgcaga ccatgttcca t                    21

<210> SEQ ID NO 233
<211> LENGTH: 21
<212> TYPE: DNA
<213> ORGANISM: Homo sapiens

<400> SEQUENCE: 233
tcccgcagac catgttccat g                    21

<210> SEQ ID NO 234
<211> LENGTH: 21
<212> TYPE: DNA
<213> ORGANISM: Homo sapiens

<400> SEQUENCE: 234
cccgcagacc atgttccatg t                    21

<210> SEQ ID NO 235
<211> LENGTH: 21
<212> TYPE: DNA
<213> ORGANISM: Homo sapiens

<400> SEQUENCE: 235
ccgcagacca tgttccatgt t                    21

<210> SEQ ID NO 236
<211> LENGTH: 21
<212> TYPE: DNA
<213> ORGANISM: Homo sapiens

```
<400> SEQUENCE: 236
cgcagaccat gttccatgtt t                                              21

<210> SEQ ID NO 237
<211> LENGTH: 21
<212> TYPE: DNA
<213> ORGANISM: Homo sapiens

<400> SEQUENCE: 237
gcagaccatg ttccatgttt c                                              21

<210> SEQ ID NO 238
<211> LENGTH: 21
<212> TYPE: DNA
<213> ORGANISM: Homo sapiens

<400> SEQUENCE: 238
cagaccatgt tccatgtttc t                                              21

<210> SEQ ID NO 239
<211> LENGTH: 21
<212> TYPE: DNA
<213> ORGANISM: Homo sapiens

<400> SEQUENCE: 239
agaccatgtt ccatgtttct t                                              21

<210> SEQ ID NO 240
<211> LENGTH: 21
<212> TYPE: DNA
<213> ORGANISM: Homo sapiens

<400> SEQUENCE: 240
aacctgatcc tccacatatt a                                              21

<210> SEQ ID NO 241
<211> LENGTH: 21
<212> TYPE: DNA
<213> ORGANISM: Homo sapiens

<400> SEQUENCE: 241
cctgatcctc cacatattaa a                                              21

<210> SEQ ID NO 242
<211> LENGTH: 21
<212> TYPE: DNA
<213> ORGANISM: Homo sapiens

<400> SEQUENCE: 242
agaaatgttt ggagaccaga a                                              21

<210> SEQ ID NO 243
<211> LENGTH: 21
<212> TYPE: DNA
<213> ORGANISM: Homo sapiens

<400> SEQUENCE: 243
caaataatgg tcaaggataa t                                              21

<210> SEQ ID NO 244
<211> LENGTH: 21
<212> TYPE: DNA
<213> ORGANISM: Homo sapiens
```

<400> SEQUENCE: 244
ttcctgatcc tggcaagatt t                                              21

<210> SEQ ID NO 245
<211> LENGTH: 21
<212> TYPE: DNA
<213> ORGANISM: Homo sapiens

<400> SEQUENCE: 245
taaagaaatg tttggagacc a                                              21

<210> SEQ ID NO 246
<211> LENGTH: 21
<212> TYPE: DNA
<213> ORGANISM: Homo sapiens

<400> SEQUENCE: 246
atgtttggag accagaatga t                                              21

<210> SEQ ID NO 247
<211> LENGTH: 21
<212> TYPE: DNA
<213> ORGANISM: Homo sapiens

<400> SEQUENCE: 247
ctccaattcc tgatcctggc a                                              21

<210> SEQ ID NO 248
<211> LENGTH: 21
<212> TYPE: DNA
<213> ORGANISM: Mouse

<400> SEQUENCE: 248
caagaagact ctaatgatgt a                                              21

<210> SEQ ID NO 249
<211> LENGTH: 21
<212> TYPE: DNA
<213> ORGANISM: Mouse

<400> SEQUENCE: 249
cacagtcaga gtaagagtca a                                              21

<210> SEQ ID NO 250
<211> LENGTH: 21
<212> TYPE: DNA
<213> ORGANISM: Mouse

<400> SEQUENCE: 250
acccagggta tcatagttct a                                              21

<210> SEQ ID NO 251
<211> LENGTH: 21
<212> TYPE: DNA
<213> ORGANISM: Mouse

<400> SEQUENCE: 251
ctgctttgaa atttccagaa a                                              21

<210> SEQ ID NO 252
<211> LENGTH: 21
<212> TYPE: DNA

<213> ORGANISM: Mouse

<400> SEQUENCE: 252
atcatagttc taagaatgaa a    21

<210> SEQ ID NO 253
<211> LENGTH: 21
<212> TYPE: DNA
<213> ORGANISM: Mouse

<400> SEQUENCE: 253
aaggcttaag atcattatat t    21

<210> SEQ ID NO 254
<211> LENGTH: 21
<212> TYPE: DNA
<213> ORGANISM: Mouse

<400> SEQUENCE: 254
aactacttat aagaaagtaa a    21

<210> SEQ ID NO 255
<211> LENGTH: 21
<212> TYPE: DNA
<213> ORGANISM: Mouse

<400> SEQUENCE: 255
cacagaacat ctagcaaaca a    21

<210> SEQ ID NO 256
<211> LENGTH: 21
<212> TYPE: DNA
<213> ORGANISM: Mouse

<400> SEQUENCE: 256
ctcgttcttg ttcaatccta a    21

<210> SEQ ID NO 257
<211> LENGTH: 21
<212> TYPE: DNA
<213> ORGANISM: Mouse

<400> SEQUENCE: 257
aacttgtagg ttcacatatt a    21

<210> SEQ ID NO 258
<211> LENGTH: 21
<212> TYPE: DNA
<213> ORGANISM: Mouse

<400> SEQUENCE: 258
aaccatttct gcaaatttaa a    21

<210> SEQ ID NO 259
<211> LENGTH: 21
<212> TYPE: DNA
<213> ORGANISM: Mouse

<400> SEQUENCE: 259
ctcagtgtag tgccaatgaa a    21

<210> SEQ ID NO 260
<211> LENGTH: 21

-continued

```
<212> TYPE: DNA
<213> ORGANISM: Mouse

<400> SEQUENCE: 260
caggccttag ggactcataa a                                              21

<210> SEQ ID NO 261
<211> LENGTH: 21
<212> TYPE: DNA
<213> ORGANISM: Mouse

<400> SEQUENCE: 261
aagtatgaca tctatgagaa a                                              21

<210> SEQ ID NO 262
<211> LENGTH: 21
<212> TYPE: DNA
<213> ORGANISM: Mouse

<400> SEQUENCE: 262
gtggaggtca ataatactca a                                              21

<210> SEQ ID NO 263
<211> LENGTH: 21
<212> TYPE: DNA
<213> ORGANISM: Mouse

<400> SEQUENCE: 263
cagagtatag gtaaggagca a                                              21

<210> SEQ ID NO 264
<211> LENGTH: 21
<212> TYPE: DNA
<213> ORGANISM: Homo sapiens

<400> SEQUENCE: 264
ttgaatgacc aagttctctt c                                              21

<210> SEQ ID NO 265
<211> LENGTH: 21
<212> TYPE: DNA
<213> ORGANISM: Mouse

<400> SEQUENCE: 265
ctctctgtga aggatagtaa a                                              21

<210> SEQ ID NO 266
<211> LENGTH: 21
<212> TYPE: DNA
<213> ORGANISM: Mouse

<400> SEQUENCE: 266
ccgcagtaat acggaatata a                                              21

<210> SEQ ID NO 267
<211> LENGTH: 21
<212> TYPE: DNA
<213> ORGANISM: Mouse

<400> SEQUENCE: 267
caaggaaatg atgtttattg a                                              21

<210> SEQ ID NO 268
```

```
<211> LENGTH: 21
<212> TYPE: DNA
<213> ORGANISM: Mouse

<400> SEQUENCE: 268
cagactgata atatacatgt a                                              21

<210> SEQ ID NO 269
<211> LENGTH: 21
<212> TYPE: DNA
<213> ORGANISM: Mouse

<400> SEQUENCE: 269
ttggccgact tcactgtaca a                                              21

<210> SEQ ID NO 270
<211> LENGTH: 21
<212> TYPE: DNA
<213> ORGANISM: Mouse

<400> SEQUENCE: 270
ccagaccaga ctgataatat a                                              21

<210> SEQ ID NO 271
<211> LENGTH: 21
<212> TYPE: DNA
<213> ORGANISM: Mouse

<400> SEQUENCE: 271
aagatggagt ttgaatcttc a                                              21

<210> SEQ ID NO 272
<211> LENGTH: 21
<212> TYPE: DNA
<213> ORGANISM: Mouse

<400> SEQUENCE: 272
acgctttact ttatacctga a                                              21

<210> SEQ ID NO 273
<211> LENGTH: 21
<212> TYPE: DNA
<213> ORGANISM: Mouse

<400> SEQUENCE: 273
tacaaccgca gtaatacgga a                                              21

<210> SEQ ID NO 274
<211> LENGTH: 21
<212> TYPE: DNA
<213> ORGANISM: Mouse

<400> SEQUENCE: 274
ctgcatgatt tatagagtaa a                                              21

<210> SEQ ID NO 275
<211> LENGTH: 21
<212> TYPE: DNA
<213> ORGANISM: Mouse

<400> SEQUENCE: 275
cccgaggctg catgatttat a                                              21
```

```
<210> SEQ ID NO 276
<211> LENGTH: 21
<212> TYPE: DNA
<213> ORGANISM: Mouse

<400> SEQUENCE: 276
cacgctttac tttatacctg a                                              21

<210> SEQ ID NO 277
<211> LENGTH: 21
<212> TYPE: DNA
<213> ORGANISM: Mouse

<400> SEQUENCE: 277
cgcctgtatt tccataacag a                                              21

<210> SEQ ID NO 278
<211> LENGTH: 21
<212> TYPE: DNA
<213> ORGANISM: Mouse

<400> SEQUENCE: 278
cgcagtaata cggaatataa a                                              21

<210> SEQ ID NO 279
<211> LENGTH: 21
<212> TYPE: DNA
<213> ORGANISM: Mouse

<400> SEQUENCE: 279
tacatgtaca aagacagtga a                                              21

<210> SEQ ID NO 280
<211> LENGTH: 21
<212> TYPE: DNA
<213> ORGANISM: Mouse

<400> SEQUENCE: 280
caggcctgac atcttctgca a                                              21

<210> SEQ ID NO 281
<211> LENGTH: 21
<212> TYPE: DNA
<213> ORGANISM: Mouse

<400> SEQUENCE: 281
ttcgaggata tgactgatat t                                              21

<210> SEQ ID NO 282
<211> LENGTH: 21
<212> TYPE: DNA
<213> ORGANISM: Mouse

<400> SEQUENCE: 282
ctgtatttcc ataacagaat a                                              21

<210> SEQ ID NO 283
<211> LENGTH: 21
<212> TYPE: DNA
<213> ORGANISM: Mouse

<400> SEQUENCE: 283
gaggatatga ctgatattga t                                              21
```

<210> SEQ ID NO 284
<211> LENGTH: 21
<212> TYPE: DNA
<213> ORGANISM: Mouse

<400> SEQUENCE: 284
caagttctct tcgttgacaa a                                             21

<210> SEQ ID NO 285
<211> LENGTH: 21
<212> TYPE: DNA
<213> ORGANISM: Mouse

<400> SEQUENCE: 285
cactaactta catcaaagtt a                                             21

<210> SEQ ID NO 286
<211> LENGTH: 21
<212> TYPE: DNA
<213> ORGANISM: Mouse

<400> SEQUENCE: 286
accgcagtaa tacggaatat a                                             21

<210> SEQ ID NO 287
<211> LENGTH: 21
<212> TYPE: DNA
<213> ORGANISM: Mouse

<400> SEQUENCE: 287
ctctcactaa cttacatcaa a                                             21

<210> SEQ ID NO 288
<211> LENGTH: 21
<212> TYPE: DNA
<213> ORGANISM: Homo sapiens

<400> SEQUENCE: 288
atcatctttc acacaaagaa a                                             21

<210> SEQ ID NO 289
<211> LENGTH: 21
<212> TYPE: DNA
<213> ORGANISM: Homo sapiens

<400> SEQUENCE: 289
aacagacttg ggtgaaatat a                                             21

<210> SEQ ID NO 290
<211> LENGTH: 21
<212> TYPE: DNA
<213> ORGANISM: Homo sapiens

<400> SEQUENCE: 290
atggaattgg acatagccca a                                             21

<210> SEQ ID NO 291
<211> LENGTH: 21
<212> TYPE: DNA
<213> ORGANISM: Homo sapiens

<400> SEQUENCE: 291
gagggtttag tgcttatcta a                                             21

<210> SEQ ID NO 292
<211> LENGTH: 21
<212> TYPE: DNA
<213> ORGANISM: Homo sapiens

<400> SEQUENCE: 292
ctcactggac ttgtccaatt a                                              21

<210> SEQ ID NO 293
<211> LENGTH: 21
<212> TYPE: DNA
<213> ORGANISM: Homo sapiens

<400> SEQUENCE: 293
atcatagttt gctttgttta a                                              21

<210> SEQ ID NO 294
<211> LENGTH: 21
<212> TYPE: DNA
<213> ORGANISM: Homo sapiens

<400> SEQUENCE: 294
ttgtttaagc atcacattaa a                                              21

<210> SEQ ID NO 295
<211> LENGTH: 21
<212> TYPE: DNA
<213> ORGANISM: Homo sapiens

<400> SEQUENCE: 295
aagcatcaca ttaaagttaa a                                              21

<210> SEQ ID NO 296
<211> LENGTH: 21
<212> TYPE: DNA
<213> ORGANISM: Homo sapiens

<400> SEQUENCE: 296
cccaaagaac tgggtactca a                                              21

<210> SEQ ID NO 297
<211> LENGTH: 21
<212> TYPE: DNA
<213> ORGANISM: Homo sapiens

<400> SEQUENCE: 297
cacattaaag ttaaactgta t                                              21

<210> SEQ ID NO 298
<211> LENGTH: 21
<212> TYPE: DNA
<213> ORGANISM: Homo sapiens

<400> SEQUENCE: 298
cagatctgtt ctttgagcta a                                              21

<210> SEQ ID NO 299
<211> LENGTH: 21
<212> TYPE: DNA
<213> ORGANISM: Homo sapiens

<400> SEQUENCE: 299
ttggtttagt gcaaagtata a    21

<210> SEQ ID NO 300
<211> LENGTH: 21
<212> TYPE: DNA
<213> ORGANISM: Homo sapiens

<400> SEQUENCE: 300
cagaccgtat tcttcatcct a    21

<210> SEQ ID NO 301
<211> LENGTH: 21
<212> TYPE: DNA
<213> ORGANISM: Homo sapiens

<400> SEQUENCE: 301
aacattaata agacaaatat t    21

<210> SEQ ID NO 302
<211> LENGTH: 21
<212> TYPE: DNA
<213> ORGANISM: Homo sapiens

<400> SEQUENCE: 302
gaccgtattc ttcatcctaa a    21

<210> SEQ ID NO 303
<211> LENGTH: 21
<212> TYPE: DNA
<213> ORGANISM: Mouse

<400> SEQUENCE: 303
aagcttgtga cattaatgct a    21

<210> SEQ ID NO 304
<211> LENGTH: 21
<212> TYPE: DNA
<213> ORGANISM: Mouse

<400> SEQUENCE: 304
caataagcta ttgtaaagat a    21

<210> SEQ ID NO 305
<211> LENGTH: 21
<212> TYPE: DNA
<213> ORGANISM: Mouse

<400> SEQUENCE: 305
atcatctttc acacgaagaa a    21

<210> SEQ ID NO 306
<211> LENGTH: 21
<212> TYPE: DNA
<213> ORGANISM: Mouse

<400> SEQUENCE: 306
agctattgta aagatattta a    21

<210> SEQ ID NO 307
<211> LENGTH: 21
<212> TYPE: DNA
<213> ORGANISM: Mouse

<400> SEQUENCE: 307
cagcctaaga gtcaagaaga t                                        21

<210> SEQ ID NO 308
<211> LENGTH: 21
<212> TYPE: DNA
<213> ORGANISM: Mouse

<400> SEQUENCE: 308
cccagtggac ttgtcaatgg a                                        21

<210> SEQ ID NO 309
<211> LENGTH: 21
<212> TYPE: DNA
<213> ORGANISM: Mouse

<400> SEQUENCE: 309
atgaagttga ttcatattgc a                                        21

<210> SEQ ID NO 310
<211> LENGTH: 21
<212> TYPE: DNA
<213> ORGANISM: Mouse

<400> SEQUENCE: 310
aagttgattc atattgcatc a                                        21

<210> SEQ ID NO 311
<211> LENGTH: 21
<212> TYPE: DNA
<213> ORGANISM: Mouse

<400> SEQUENCE: 311
tcacattaga gttaagttgt a                                        21

<210> SEQ ID NO 312
<211> LENGTH: 21
<212> TYPE: DNA
<213> ORGANISM: Mouse

<400> SEQUENCE: 312
cacattagag ttaagttgta t                                        21

<210> SEQ ID NO 313
<211> LENGTH: 21
<212> TYPE: DNA
<213> ORGANISM: Mouse

<400> SEQUENCE: 313
tatgttattt atagatctga a                                        21

<210> SEQ ID NO 314
<211> LENGTH: 21
<212> TYPE: DNA
<213> ORGANISM: Mouse

<400> SEQUENCE: 314
atgtttagct atttaatgtt a                                        21

<210> SEQ ID NO 315
<211> LENGTH: 21
<212> TYPE: DNA
<213> ORGANISM: Mouse

```
<400> SEQUENCE: 315
ttagtggaag gattaatatt a                                              21

<210> SEQ ID NO 316
<211> LENGTH: 21
<212> TYPE: DNA
<213> ORGANISM: Mouse

<400> SEQUENCE: 316
acccagcact gagtacatca a                                              21

<210> SEQ ID NO 317
<211> LENGTH: 21
<212> TYPE: DNA
<213> ORGANISM: Mouse

<400> SEQUENCE: 317
tatgtttaag ggaatagttt a                                              21

<210> SEQ ID NO 318
<211> LENGTH: 21
<212> TYPE: DNA
<213> ORGANISM: Homo sapiens

<400> SEQUENCE: 318
atgaagttga ttcatattgc a                                              21

<210> SEQ ID NO 319
<211> LENGTH: 21
<212> TYPE: DNA
<213> ORGANISM: Homo sapiens

<400> SEQUENCE: 319
tgaagttgat tcatattgca t                                              21

<210> SEQ ID NO 320
<211> LENGTH: 21
<212> TYPE: DNA
<213> ORGANISM: Homo sapiens

<400> SEQUENCE: 320
gaagttgatt catattgcat c                                              21

<210> SEQ ID NO 321
<211> LENGTH: 21
<212> TYPE: DNA
<213> ORGANISM: Homo sapiens

<400> SEQUENCE: 321
aagttgattc atattgcatc a                                              21

<210> SEQ ID NO 322
<211> LENGTH: 21
<212> TYPE: DNA
<213> ORGANISM: Homo sapiens

<400> SEQUENCE: 322
agttgattca tattgcatca t                                              21

<210> SEQ ID NO 323
<211> LENGTH: 21
<212> TYPE: DNA
<213> ORGANISM: Homo sapiens
```

```
<400> SEQUENCE: 323
gttgattcat attgcatcat a                                              21

<210> SEQ ID NO 324
<211> LENGTH: 21
<212> TYPE: DNA
<213> ORGANISM: Homo sapiens

<400> SEQUENCE: 324
ttgattcata ttgcatcata g                                              21

<210> SEQ ID NO 325
<211> LENGTH: 21
<212> TYPE: DNA
<213> ORGANISM: Homo sapiens

<400> SEQUENCE: 325
tgattcatat tgcatcatag t                                              21

<210> SEQ ID NO 326
<211> LENGTH: 21
<212> TYPE: DNA
<213> ORGANISM: Homo sapiens

<400> SEQUENCE: 326
tcaatgctat catctttcac a                                              21

<210> SEQ ID NO 327
<211> LENGTH: 21
<212> TYPE: DNA
<213> ORGANISM: Homo sapiens

<400> SEQUENCE: 327
caatgctatc atctttcaca c                                              21

<210> SEQ ID NO 328
<211> LENGTH: 21
<212> TYPE: DNA
<213> ORGANISM: Homo sapiens

<400> SEQUENCE: 328
taatgaagtt gattcatatt g                                              21

<210> SEQ ID NO 329
<211> LENGTH: 21
<212> TYPE: DNA
<213> ORGANISM: Homo sapiens

<400> SEQUENCE: 329
aatgaagttg attcatattg c                                              21

<210> SEQ ID NO 330
<211> LENGTH: 21
<212> TYPE: DNA
<213> ORGANISM: Homo sapiens

<400> SEQUENCE: 330
agcatgaaat ttgagattgg a                                              21

<210> SEQ ID NO 331
<211> LENGTH: 21
<212> TYPE: DNA
```

<213> ORGANISM: Homo sapiens

<400> SEQUENCE: 331
tacagagcct ctgaaagacc a                                          21

<210> SEQ ID NO 332
<211> LENGTH: 21
<212> TYPE: DNA
<213> ORGANISM: Homo sapiens

<400> SEQUENCE: 332
cactacagag cctctgaaag a                                          21

<210> SEQ ID NO 333
<211> LENGTH: 21
<212> TYPE: DNA
<213> ORGANISM: Homo sapiens

<400> SEQUENCE: 333
ctgacagcat gaaatttgag a                                          21

<210> SEQ ID NO 334
<211> LENGTH: 21
<212> TYPE: DNA
<213> ORGANISM: Homo sapiens

<400> SEQUENCE: 334
atctctgtgg tgggcatgag a                                          21

<210> SEQ ID NO 335
<211> LENGTH: 21
<212> TYPE: DNA
<213> ORGANISM: Homo sapiens

<400> SEQUENCE: 335
catgaaattt gagattggag a                                          21

<210> SEQ ID NO 336
<211> LENGTH: 21
<212> TYPE: DNA
<213> ORGANISM: Homo sapiens

<400> SEQUENCE: 336
tctggctgag gttggctctt a                                          21

<210> SEQ ID NO 337
<211> LENGTH: 21
<212> TYPE: DNA
<213> ORGANISM: Homo sapiens

<400> SEQUENCE: 337
gtgggctaca tcctaggcct t                                          21

<210> SEQ ID NO 338
<211> LENGTH: 21
<212> TYPE: DNA
<213> ORGANISM: Mouse

<400> SEQUENCE: 338
cagcttcctg ctaaaccaca a                                          21

<210> SEQ ID NO 339
<211> LENGTH: 21

<212> TYPE: DNA
<213> ORGANISM: Mouse

<400> SEQUENCE: 339
caagagtgag ttcaactcat a                                              21

<210> SEQ ID NO 340
<211> LENGTH: 21
<212> TYPE: DNA
<213> ORGANISM: Mouse

<400> SEQUENCE: 340
ctggttcctg acagcatgaa a                                              21

<210> SEQ ID NO 341
<211> LENGTH: 21
<212> TYPE: DNA
<213> ORGANISM: Mouse

<400> SEQUENCE: 341
tggctgggac tatatatata a                                              21

<210> SEQ ID NO 342
<211> LENGTH: 21
<212> TYPE: DNA
<213> ORGANISM: Mouse

<400> SEQUENCE: 342
gagggcaatt gctatatctt a                                              21

<210> SEQ ID NO 343
<211> LENGTH: 21
<212> TYPE: DNA
<213> ORGANISM: Mouse

<400> SEQUENCE: 343
cagcagccaa acgacaagca a                                              21

<210> SEQ ID NO 344
<211> LENGTH: 21
<212> TYPE: DNA
<213> ORGANISM: Mouse

<400> SEQUENCE: 344
caagggtttc cttaaggaca a                                              21

<210> SEQ ID NO 345
<211> LENGTH: 21
<212> TYPE: DNA
<213> ORGANISM: Mouse

<400> SEQUENCE: 345
cagatacttg taaggaggaa a                                              21

<210> SEQ ID NO 346
<211> LENGTH: 21
<212> TYPE: DNA
<213> ORGANISM: Mouse

<400> SEQUENCE: 346
aagaaatgga ttagtcagta a                                              21

<210> SEQ ID NO 347

```
<211> LENGTH: 21
<212> TYPE: DNA
<213> ORGANISM: Mouse

<400> SEQUENCE: 347
aaggaaagca caagaagcca a                                         21

<210> SEQ ID NO 348
<211> LENGTH: 21
<212> TYPE: DNA
<213> ORGANISM: Mouse

<400> SEQUENCE: 348
ctggctgagg ttggctctta a                                         21

<210> SEQ ID NO 349
<211> LENGTH: 21
<212> TYPE: DNA
<213> ORGANISM: Mouse

<400> SEQUENCE: 349
aacctgggat ctaaagaaac a                                         21

<210> SEQ ID NO 350
<211> LENGTH: 21
<212> TYPE: DNA
<213> ORGANISM: Mouse

<400> SEQUENCE: 350
aagggcttgg gtatcaaaga a                                         21

<210> SEQ ID NO 351
<211> LENGTH: 21
<212> TYPE: DNA
<213> ORGANISM: Mouse

<400> SEQUENCE: 351
caggctccga agatacttct a                                         21

<210> SEQ ID NO 352
<211> LENGTH: 21
<212> TYPE: DNA
<213> ORGANISM: Mouse

<400> SEQUENCE: 352
cccaatatat aaattgccta a                                         21

<210> SEQ ID NO 353
<211> LENGTH: 21
<212> TYPE: DNA
<213> ORGANISM: Mouse

<400> SEQUENCE: 353
ctgacccagc ttcctgctaa a                                         21

<210> SEQ ID NO 354
<211> LENGTH: 21
<212> TYPE: DNA
<213> ORGANISM: Homo sapiens

<400> SEQUENCE: 354
acccacatca tctacagctt t                                         21
```

<210> SEQ ID NO 355
<211> LENGTH: 21
<212> TYPE: DNA
<213> ORGANISM: Homo sapiens

<400> SEQUENCE: 355
catcatctac agctttgcca a                                              21

<210> SEQ ID NO 356
<211> LENGTH: 21
<212> TYPE: DNA
<213> ORGANISM: Homo sapiens

<400> SEQUENCE: 356
cagctggtcc cagtaccggg a                                              21

<210> SEQ ID NO 357
<211> LENGTH: 21
<212> TYPE: DNA
<213> ORGANISM: Homo sapiens

<400> SEQUENCE: 357
caccaaggag gcagggaccc t                                              21

<210> SEQ ID NO 358
<211> LENGTH: 21
<212> TYPE: DNA
<213> ORGANISM: Homo sapiens

<400> SEQUENCE: 358
ccggttcacc aaggaggcag g                                              21

<210> SEQ ID NO 359
<211> LENGTH: 21
<212> TYPE: DNA
<213> ORGANISM: Homo sapiens

<400> SEQUENCE: 359
agctggtccc agtaccggga a                                              21

<210> SEQ ID NO 360
<211> LENGTH: 21
<212> TYPE: DNA
<213> ORGANISM: Homo sapiens

<400> SEQUENCE: 360
caggccggtt caccaaggag g                                              21

<210> SEQ ID NO 361
<211> LENGTH: 21
<212> TYPE: DNA
<213> ORGANISM: Homo sapiens

<400> SEQUENCE: 361
ggccggttca ccaaggaggc a                                              21

<210> SEQ ID NO 362
<211> LENGTH: 21
<212> TYPE: DNA
<213> ORGANISM: Mouse

<400> SEQUENCE: 362
taggtttgac agatacagca a                                              21

```
<210> SEQ ID NO 363
<211> LENGTH: 21
<212> TYPE: DNA
<213> ORGANISM: Mouse

<400> SEQUENCE: 363
aaccctgtta aggaatgcaa a                                             21

<210> SEQ ID NO 364
<211> LENGTH: 21
<212> TYPE: DNA
<213> ORGANISM: Mouse

<400> SEQUENCE: 364
atcaagtagg caaatatctt a                                             21

<210> SEQ ID NO 365
<211> LENGTH: 21
<212> TYPE: DNA
<213> ORGANISM: Mouse

<400> SEQUENCE: 365
cgcagctttg tcagcaggaa a                                             21

<210> SEQ ID NO 366
<211> LENGTH: 21
<212> TYPE: DNA
<213> ORGANISM: Mouse

<400> SEQUENCE: 366
ttggatcaag taggcaaata t                                             21

<210> SEQ ID NO 367
<211> LENGTH: 21
<212> TYPE: DNA
<213> ORGANISM: Mouse

<400> SEQUENCE: 367
ttgagggacc atactaatta t                                             21

<210> SEQ ID NO 368
<211> LENGTH: 21
<212> TYPE: DNA
<213> ORGANISM: Mouse

<400> SEQUENCE: 368
gaggacaagg agagtgtcaa a                                             21

<210> SEQ ID NO 369
<211> LENGTH: 21
<212> TYPE: DNA
<213> ORGANISM: Mouse

<400> SEQUENCE: 369
tgcgtacaag ctggtctgct a                                             21

<210> SEQ ID NO 370
<211> LENGTH: 21
<212> TYPE: DNA
<213> ORGANISM: Mouse

<400> SEQUENCE: 370
caggagttta atctcttgca a                                             21
```

```
<210> SEQ ID NO 371
<211> LENGTH: 21
<212> TYPE: DNA
<213> ORGANISM: Mouse

<400> SEQUENCE: 371
atcaaggaac tgaatgcgga a                                              21

<210> SEQ ID NO 372
<211> LENGTH: 21
<212> TYPE: DNA
<213> ORGANISM: Mouse

<400> SEQUENCE: 372
caccctgatc aaggaactga a                                              21

<210> SEQ ID NO 373
<211> LENGTH: 21
<212> TYPE: DNA
<213> ORGANISM: Mouse

<400> SEQUENCE: 373
cacttggatc aagtaggcaa a                                              21

<210> SEQ ID NO 374
<211> LENGTH: 21
<212> TYPE: DNA
<213> ORGANISM: Mouse

<400> SEQUENCE: 374
caggattgag ggaccatact a                                              21

<210> SEQ ID NO 375
<211> LENGTH: 21
<212> TYPE: DNA
<213> ORGANISM: Mouse

<400> SEQUENCE: 375
aactatgaca agctgaataa a                                              21

<210> SEQ ID NO 376
<211> LENGTH: 21
<212> TYPE: DNA
<213> ORGANISM: Mouse

<400> SEQUENCE: 376
atgcaaattc tcagactcta a                                              21

<210> SEQ ID NO 377
<211> LENGTH: 21
<212> TYPE: DNA
<213> ORGANISM: Mouse

<400> SEQUENCE: 377
atccttccct taggaactta a                                              21

<210> SEQ ID NO 378
<211> LENGTH: 79
<212> TYPE: DNA
<213> ORGANISM: Escherichia coli

<400> SEQUENCE: 378
```

```
gacttcatat acccaagctt ggaaaatttt ttttaaaaaa gtcttgacac tttatgcttc      60
cggctcgtat aatggatcc                                                  79

<210> SEQ ID NO 379
<211> LENGTH: 23
<212> TYPE: DNA
<213> ORGANISM: Escherichia coli

<400> SEQUENCE: 379
ggaaaatttt ttttaaaaaa gtc                                             23

<210> SEQ ID NO 380
<211> LENGTH: 65
<212> TYPE: DNA
<213> ORGANISM: Artificial Sequence
<220> FEATURE:
<223> OTHER INFORMATION: Hairpin sequence which contains BamHI and SalI
      restriction sites.

<400> SEQUENCE: 380
ggatccagga gtaacaatac aaatggattc aagagatcca tttgtattgt tactcctttg     60
tcgac                                                                 65

<210> SEQ ID NO 381
<211> LENGTH: 21
<212> TYPE: DNA
<213> ORGANISM: Human papillomavirus

<400> SEQUENCE: 381
ctgatctgtg cacggaactg a                                               21

<210> SEQ ID NO 382
<211> LENGTH: 25
<212> TYPE: DNA
<213> ORGANISM: Human papillomavirus

<400> SEQUENCE: 382
tgtctaagtt tttctgctgg attca                                           25

<210> SEQ ID NO 383
<211> LENGTH: 25
<212> TYPE: DNA
<213> ORGANISM: Human papillomavirus

<400> SEQUENCE: 383
ttggaactta cagaggtgcc tgcgc                                           25

<210> SEQ ID NO 384
<211> LENGTH: 61
<212> TYPE: DNA
<213> ORGANISM: Artificial Sequence
<220> FEATURE:
<223> OTHER INFORMATION: HPV shRNA

<400> SEQUENCE: 384
ggatcctagg tatttgaatt tgcatttcaa gagaatgcaa attcaaatac cttttgtcga     60
c                                                                     61

<210> SEQ ID NO 385
<211> LENGTH: 61
<212> TYPE: DNA
<213> ORGANISM: Artificial Sequence
<220> FEATURE:
```

<223> OTHER INFORMATION: HPV shRNA

<400> SEQUENCE: 385
gtcgacaaaa ggtatttgaa tttgcattct cttgaaatgc aaattcaaat acctaggatc    60
c                                                                    61

<210> SEQ ID NO 386
<211> LENGTH: 61
<212> TYPE: DNA
<213> ORGANISM: Artificial Sequence
<220> FEATURE:
<223> OTHER INFORMATION: HPV shRNA

<400> SEQUENCE: 386
ggatcctcag aaaaacttag acaccttcaa gagaggtgtc taagttttc tgtttgtcga     60
c                                                                    61

<210> SEQ ID NO 387
<211> LENGTH: 61
<212> TYPE: DNA
<213> ORGANISM: Artificial Sequence
<220> FEATURE:
<223> OTHER INFORMATION: HPV shRNA

<400> SEQUENCE: 387
gtcgacaaac agaaaaactt agacacctct cttgaaggtg tctaagtttt tctgaggatc    60
c                                                                    61

<210> SEQ ID NO 388
<211> LENGTH: 9
<212> TYPE: DNA
<213> ORGANISM: Artificial Sequence
<220> FEATURE:
<223> OTHER INFORMATION: Loop Sequence

<400> SEQUENCE: 388 ttcaagaga                                                             9

<210> SEQ ID NO 389
<211> LENGTH: 55
<212> TYPE: DNA
<213> ORGANISM: Artificial Sequence
<220> FEATURE:
<223> OTHER INFORMATION: HPV shRNA

<400> SEQUENCE: 389
gatcctaggt atttgaattt gcatttcaag agaatgcaaa ttcaaatacc ttttg          55

<210> SEQ ID NO 390
<211> LENGTH: 55
<212> TYPE: DNA
<213> ORGANISM: Artificial Sequence
<220> FEATURE:
<223> OTHER INFORMATION: HPV shRNA, sequence written in 3' to 5'
      orientation

<400> SEQUENCE: 390
gatccataaa cttaaacgta aagttctctt acgtttaagt ttatggaaaa cagct          55

<210> SEQ ID NO 391
<211> LENGTH: 21
<212> TYPE: DNA
<213> ORGANISM: Artificial Sequence
<220> FEATURE:

<223> OTHER INFORMATION: siRNA sense strand

<400> SEQUENCE: 391
gcuugugaca uuaaugcuat t                                              21

<210> SEQ ID NO 392
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 392
uagcauuaau gucacaagct t                                              21

<210> SEQ ID NO 393
<211> LENGTH: 21
<212> TYPE: DNA
<213> ORGANISM: Artificial Sequence
<220> FEATURE:
<223> OTHER INFORMATION: siRNA sense strand

<400> SEQUENCE: 393
auaagcuauu guaaagauat t                                              21

<210> SEQ ID NO 394
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 394
uaucuuuaca auagcuuaut g                                              21

<210> SEQ ID NO 395
<211> LENGTH: 21
<212> TYPE: DNA
<213> ORGANISM: Artificial Sequence
<220> FEATURE:
<223> OTHER INFORMATION: siRNA sense strand

<400> SEQUENCE: 395
caucuuucac acgaagaaat t                                              21

<210> SEQ ID NO 396
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 396
uuucuucgug ugaaagauga t                                              21

<210> SEQ ID NO 397
<211> LENGTH: 21
<212> TYPE: DNA
<213> ORGANISM: Artificial Sequence
<220> FEATURE:
<223> OTHER INFORMATION: siRNA sense strand

<400> SEQUENCE: 397
cuauuguaaa gauauuuaat t                                              21

```
<210> SEQ ID NO 398
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 398
uuaaauaucu uuacaauagc t                                              21

<210> SEQ ID NO 399
<211> LENGTH: 21
<212> TYPE: DNA
<213> ORGANISM: Artificial Sequence
<220> FEATURE:
<223> OTHER INFORMATION: siRNA sense strand

<400> SEQUENCE: 399
gccuaagagu caagaagaut t                                              21

<210> SEQ ID NO 400
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 400
aucuucuuga cucuuaggct g                                              21

<210> SEQ ID NO 401
<211> LENGTH: 21
<212> TYPE: DNA
<213> ORGANISM: Artificial Sequence
<220> FEATURE:
<223> OTHER INFORMATION: siRNA sense strand

<400> SEQUENCE: 401
caguggacuu gucaauggat t                                              21

<210> SEQ ID NO 402
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 402
uccauugaca aguccacugg g                                              21

<210> SEQ ID NO 403
<211> LENGTH: 21
<212> TYPE: DNA
<213> ORGANISM: Artificial Sequence
<220> FEATURE:
<223> OTHER INFORMATION: siRNA sense strand

<400> SEQUENCE: 403
gaaguugauu cauauugcat t                                              21

<210> SEQ ID NO 404
<211> LENGTH: 21
<212> TYPE: DNA
<213> ORGANISM: Artificial Sequence
<220> FEATURE:
<223> OTHER INFORMATION: siRNA antisense strand
```

```
<400> SEQUENCE: 404
ugcaauauga aucaacuuca t                                              21

<210> SEQ ID NO 405
<211> LENGTH: 21
<212> TYPE: DNA
<213> ORGANISM: Artificial Sequence
<220> FEATURE:
<223> OTHER INFORMATION: siRNA sense strand

<400> SEQUENCE: 405
guugauucau auugcaucat t                                              21

<210> SEQ ID NO 406
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 406
ugaugcaaua ugaaucaact t                                              21

<210> SEQ ID NO 407
<211> LENGTH: 21
<212> TYPE: DNA
<213> ORGANISM: Artificial Sequence
<220> FEATURE:
<223> OTHER INFORMATION: siRNA sense strand

<400> SEQUENCE: 407
acauuagagu uaaguuguat t                                              21

<210> SEQ ID NO 408
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 408
uacaacuuaa cucuaaugug a                                              21

<210> SEQ ID NO 409
<211> LENGTH: 21
<212> TYPE: DNA
<213> ORGANISM: Artificial Sequence
<220> FEATURE:
<223> OTHER INFORMATION: siRNA sense strand

<400> SEQUENCE: 409
cauuagaguu aaguuguaut t                                              21

<210> SEQ ID NO 410
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 410
auacaacuua acucuaaugt g                                              21

<210> SEQ ID NO 411
<211> LENGTH: 21
```

```
<212> TYPE: DNA
<213> ORGANISM: Artificial Sequence
<220> FEATURE:
<223> OTHER INFORMATION: siRNA sense strand

<400> SEQUENCE: 411
uguuauuuau agaucugaat t                                              21

<210> SEQ ID NO 412
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 412
uucagaucua uaaauaacat a                                              21

<210> SEQ ID NO 413
<211> LENGTH: 21
<212> TYPE: DNA
<213> ORGANISM: Artificial Sequence
<220> FEATURE:
<223> OTHER INFORMATION: siRNA sense strand

<400> SEQUENCE: 413
guuuagcuau uuaauguuat t                                              21

<210> SEQ ID NO 414
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 414
uaacauuaaa uagcuaaaca t                                              21

<210> SEQ ID NO 415
<211> LENGTH: 21
<212> TYPE: DNA
<213> ORGANISM: Artificial Sequence
<220> FEATURE:
<223> OTHER INFORMATION: siRNA sense strand

<400> SEQUENCE: 415
aguggaagga uuaauauuat t                                              21

<210> SEQ ID NO 416
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 416
uaauauuaau ccuuccacua a                                              21

<210> SEQ ID NO 417
<211> LENGTH: 21
<212> TYPE: DNA
<213> ORGANISM: Artificial Sequence
<220> FEATURE:
<223> OTHER INFORMATION: siRNA sense strand

<400> SEQUENCE: 417
```
ccagcacuga guacaucaat t                                              21

<210> SEQ ID NO 418
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 418
uugauguacu cagugcuggg t                                              21

<210> SEQ ID NO 419
<211> LENGTH: 21
<212> TYPE: DNA
<213> ORGANISM: Artificial Sequence
<220> FEATURE:
<223> OTHER INFORMATION: siRNA sense strand

<400> SEQUENCE: 419
uguuuaaggg aauaguuuat t                                              21

<210> SEQ ID NO 420
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 420
uaaacuauuc ccuuaaacat a                                              21

<210> SEQ ID NO 421
<211> LENGTH: 21
<212> TYPE: DNA
<213> ORGANISM: Artificial Sequence
<220> FEATURE:
<223> OTHER INFORMATION: siRNA sense strand

<400> SEQUENCE: 421
gcugggacua uauauauaat t                                              21

<210> SEQ ID NO 422
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 422
uuauauauau agucccagcc a                                              21

<210> SEQ ID NO 423
<211> LENGTH: 21
<212> TYPE: DNA
<213> ORGANISM: Artificial Sequence
<220> FEATURE:
<223> OTHER INFORMATION: siRNA sense strand

<400> SEQUENCE: 423
gggcaauugc uauaucuuat t                                              21

<210> SEQ ID NO 424
<211> LENGTH: 21
<212> TYPE: DNA
<213> ORGANISM: Artificial Sequence

```
<220> FEATURE:
<223> OTHER INFORMATION: siRNA antisense strand

<400> SEQUENCE: 424
uaagauauag caauugccct c                                              21

<210> SEQ ID NO 425
<211> LENGTH: 21
<212> TYPE: DNA
<213> ORGANISM: Artificial Sequence
<220> FEATURE:
<223> OTHER INFORMATION: siRNA sense strand

<400> SEQUENCE: 425
gcagccaaac gacaagcaat t                                              21

<210> SEQ ID NO 426
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 426
uugcuugucg uuuggcugct g                                              21

<210> SEQ ID NO 427
<211> LENGTH: 21
<212> TYPE: DNA
<213> ORGANISM: Artificial Sequence
<220> FEATURE:
<223> OTHER INFORMATION: siRNA sense strand

<400> SEQUENCE: 427
aggguuuccu uaaggacaat t                                              21

<210> SEQ ID NO 428
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 428
uuguccuuaa ggaaacccut g                                              21

<210> SEQ ID NO 429
<211> LENGTH: 21
<212> TYPE: DNA
<213> ORGANISM: Artificial Sequence
<220> FEATURE:
<223> OTHER INFORMATION: siRNA sense strand

<400> SEQUENCE: 429
gaaauggauu agucaguaat t                                              21

<210> SEQ ID NO 430
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 430
uuacugacua auccauuuct t                                              21
```

```
<210> SEQ ID NO 431
<211> LENGTH: 21
<212> TYPE: DNA
<213> ORGANISM: Artificial Sequence
<220> FEATURE:
<223> OTHER INFORMATION: siRNA sense strand

<400> SEQUENCE: 431
ggcuccgaag auacuucuat t                                              21

<210> SEQ ID NO 432
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 432
uagaaguauc uucggagcct g                                              21

<210> SEQ ID NO 433
<211> LENGTH: 21
<212> TYPE: DNA
<213> ORGANISM: Artificial Sequence
<220> FEATURE:
<223> OTHER INFORMATION: siRNA sense strand

<400> SEQUENCE: 433
ccuggagggu gacaaaguat t                                              21

<210> SEQ ID NO 434
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 434
uacuuuguca cccuccagga t                                              21

<210> SEQ ID NO 435
<211> LENGTH: 21
<212> TYPE: DNA
<213> ORGANISM: Artificial Sequence
<220> FEATURE:
<223> OTHER INFORMATION: siRNA sense strand

<400> SEQUENCE: 435
ggucugacaa uaccguaaat t                                              21

<210> SEQ ID NO 436
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 436
uuuacgguau ugucagaccc a                                              21

<210> SEQ ID NO 437
<211> LENGTH: 21
<212> TYPE: DNA
<213> ORGANISM: Artificial Sequence
<220> FEATURE:
<223> OTHER INFORMATION: siRNA sense strand
```

<400> SEQUENCE: 437
gcuguuuccu auaacagaat t                                              21

<210> SEQ ID NO 438
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 438
uucuguuaua ggaaacagcg g                                              21

<210> SEQ ID NO 439
<211> LENGTH: 21
<212> TYPE: DNA
<213> ORGANISM: Artificial Sequence
<220> FEATURE:
<223> OTHER INFORMATION: siRNA sense strand

<400> SEQUENCE: 439
gcugugaaag ggaaauuuat t                                              21

<210> SEQ ID NO 440
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 440
uaaauuuccc uuucacagca g                                              21

<210> SEQ ID NO 441
<211> LENGTH: 21
<212> TYPE: DNA
<213> ORGANISM: Artificial Sequence
<220> FEATURE:
<223> OTHER INFORMATION: siRNA sense strand

<400> SEQUENCE: 441 ccuguggua ucagccauat t                                               21

<210> SEQ ID NO 442
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 442
uauggcugau accacaaggt t                                              21

<210> SEQ ID NO 443
<211> LENGTH: 21
<212> TYPE: DNA
<213> ORGANISM: Artificial Sequence
<220> FEATURE:
<223> OTHER INFORMATION: siRNA sense strand

<400> SEQUENCE: 443
gcuucgauac cgaccuguat t                                              21

<210> SEQ ID NO 444

```
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 444
uacaggucgg uaucgaagct g                                              21

<210> SEQ ID NO 445
<211> LENGTH: 21
<212> TYPE: DNA
<213> ORGANISM: Artificial Sequence
<220> FEATURE:
<223> OTHER INFORMATION: siRNA sense strand

<400> SEQUENCE: 445
cggcaggaau ccucuggaat t                                              21

<210> SEQ ID NO 446
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 446
uuccagagga uuccugccgg g                                              21

<210> SEQ ID NO 447
<211> LENGTH: 21
<212> TYPE: DNA
<213> ORGANISM: Artificial Sequence
<220> FEATURE:
<223> OTHER INFORMATION: siRNA sense strand

<400> SEQUENCE: 447
ccacgaggau caguacgaat t                                              21

<210> SEQ ID NO 448
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 448
uucguacuga uccucguggt t                                              21

<210> SEQ ID NO 449
<211> LENGTH: 21
<212> TYPE: DNA
<213> ORGANISM: Artificial Sequence
<220> FEATURE:
<223> OTHER INFORMATION: siRNA sense strand

<400> SEQUENCE: 449
cacgaggauc aguacgaaat t                                              21

<210> SEQ ID NO 450
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 450
```
uuucguacug auccucgugg t         21

<210> SEQ ID NO 451
<211> LENGTH: 21
<212> TYPE: DNA
<213> ORGANISM: Artificial Sequence
<220> FEATURE:
<223> OTHER INFORMATION: siRNA sense strand

<400> SEQUENCE: 451
gaucaguacg aaaguucuat t         21

<210> SEQ ID NO 452
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 452
uagaacuuuc guacugaucc t         21

<210> SEQ ID NO 453
<211> LENGTH: 21
<212> TYPE: DNA
<213> ORGANISM: Artificial Sequence
<220> FEATURE:
<223> OTHER INFORMATION: siRNA sense strand

<400> SEQUENCE: 453
guacgaaagu ucuacagaat t         21

<210> SEQ ID NO 454
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 454
uucuguagaa cuuucguact g         21

<210> SEQ ID NO 455
<211> LENGTH: 21
<212> TYPE: DNA
<213> ORGANISM: Artificial Sequence
<220> FEATURE:
<223> OTHER INFORMATION: siRNA sense strand

<400> SEQUENCE: 455
gaaaguucua cagaagcaat t         21

<210> SEQ ID NO 456
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 456
uugcuucugu agaacuuucg t         21

<210> SEQ ID NO 457
<211> LENGTH: 21
<212> TYPE: DNA

```
<213> ORGANISM: Artificial Sequence
<220> FEATURE:
<223> OTHER INFORMATION: siRNA sense strand

<400> SEQUENCE: 457
gggucugaca auaccguaat t                                              21

<210> SEQ ID NO 458
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 458
uuacgguauu gucagaccca g                                              21

<210> SEQ ID NO 459
<211> LENGTH: 21
<212> TYPE: DNA
<213> ORGANISM: Artificial Sequence
<220> FEATURE:
<223> OTHER INFORMATION: siRNA sense strand

<400> SEQUENCE: 459
agaagacucu aaugauguat t                                              21

<210> SEQ ID NO 460
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 460
uacaucauua gagucuucut g                                              21

<210> SEQ ID NO 461
<211> LENGTH: 21
<212> TYPE: DNA
<213> ORGANISM: Artificial Sequence
<220> FEATURE:
<223> OTHER INFORMATION: siRNA sense strand

<400> SEQUENCE: 461
cagucagagu aagagucaat t                                              21

<210> SEQ ID NO 462
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 462
uugacucuua cucugacugt g                                              21

<210> SEQ ID NO 463
<211> LENGTH: 21
<212> TYPE: DNA
<213> ORGANISM: Artificial Sequence
<220> FEATURE:
<223> OTHER INFORMATION: siRNA sense strand

<400> SEQUENCE: 463
cagaacaucu agcaaacaat t                                              21
```

<210> SEQ ID NO 464
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 464
uuguuugcua gauguucugt g                                             21

<210> SEQ ID NO 465
<211> LENGTH: 21
<212> TYPE: DNA
<213> ORGANISM: Artificial Sequence
<220> FEATURE:
<223> OTHER INFORMATION: siRNA sense strand

<400> SEQUENCE: 465
cuuguagguu cacauauuat t                                             21

<210> SEQ ID NO 466
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 466
uaauauguga accuacaagt t                                             21

<210> SEQ ID NO 467
<211> LENGTH: 21
<212> TYPE: DNA
<213> ORGANISM: Artificial Sequence
<220> FEATURE:
<223> OTHER INFORMATION: siRNA sense strand

<400> SEQUENCE: 467
caguguagug ccaaugaaat t                                             21

<210> SEQ ID NO 468
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 468
uuucauuggc acuacacuga g                                             21

<210> SEQ ID NO 469
<211> LENGTH: 21
<212> TYPE: DNA
<213> ORGANISM: Artificial Sequence
<220> FEATURE:
<223> OTHER INFORMATION: siRNA sense strand

<400> SEQUENCE: 469
guaugacauc uaugagaaat t                                             21

<210> SEQ ID NO 470
<211> LENGTH: 21
<212> TYPE: DNA
<213> ORGANISM: Artificial Sequence
<220> FEATURE:

```
<223> OTHER INFORMATION: siRNA antisense strand

<400> SEQUENCE: 470
uuucucauag augucauact t                                              21

<210> SEQ ID NO 471
<211> LENGTH: 21
<212> TYPE: DNA
<213> ORGANISM: Artificial Sequence
<220> FEATURE:
<223> OTHER INFORMATION: siRNA sense strand

<400> SEQUENCE: 471
aggaaaugau guuuauugat t                                              21

<210> SEQ ID NO 472
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 472
ucaauaaaca ucauuuccut g                                              21

<210> SEQ ID NO 473
<211> LENGTH: 21
<212> TYPE: DNA
<213> ORGANISM: Artificial Sequence
<220> FEATURE:
<223> OTHER INFORMATION: siRNA sense strand

<400> SEQUENCE: 473
ggccgacuuc acuguacaat t                                              21

<210> SEQ ID NO 474
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 474
uuguacagug aagucggcca a                                              21

<210> SEQ ID NO 475
<211> LENGTH: 21
<212> TYPE: DNA
<213> ORGANISM: Artificial Sequence
<220> FEATURE:
<223> OTHER INFORMATION: siRNA sense strand

<400> SEQUENCE: 475
gauggaguuu gaaucuucat t                                              21

<210> SEQ ID NO 476
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 476
ugaagauuca aacuccauct t                                              21
```

```
<210> SEQ ID NO 477
<211> LENGTH: 21
<212> TYPE: DNA
<213> ORGANISM: Artificial Sequence
<220> FEATURE:
<223> OTHER INFORMATION: siRNA sense strand

<400> SEQUENCE: 477
caaccgcagu aauacggaat t                                              21

<210> SEQ ID NO 478
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 478
uuccguauua cugcgguugt a                                              21

<210> SEQ ID NO 479
<211> LENGTH: 21
<212> TYPE: DNA
<213> ORGANISM: Artificial Sequence
<220> FEATURE:
<223> OTHER INFORMATION: siRNA sense strand

<400> SEQUENCE: 479
cgaggcugca ugauuuauat t                                              21

<210> SEQ ID NO 480
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 480
uauaaaucau gcagccucgg g                                              21

<210> SEQ ID NO 481
<211> LENGTH: 21
<212> TYPE: DNA
<213> ORGANISM: Artificial Sequence
<220> FEATURE:
<223> OTHER INFORMATION: siRNA sense strand

<400> SEQUENCE: 481
ccuguauuuc cauaacagat t                                              21

<210> SEQ ID NO 482
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 482
ucuguuaugg aaauacaggc g                                              21

<210> SEQ ID NO 483
<211> LENGTH: 21
<212> TYPE: DNA
<213> ORGANISM: Artificial Sequence
<220> FEATURE:
<223> OTHER INFORMATION: siRNA sense strand
```

```
<400> SEQUENCE: 483
cauguacaaa gacagugaat t                                              21

<210> SEQ ID NO 484
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 484
uucacugucu uuguacaugt a                                              21

<210> SEQ ID NO 485
<211> LENGTH: 21
<212> TYPE: DNA
<213> ORGANISM: Artificial Sequence
<220> FEATURE:
<223> OTHER INFORMATION: siRNA sense strand

<400> SEQUENCE: 485
cgaggauaug acugauauut t                                              21

<210> SEQ ID NO 486
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 486
aauaucaguc auauccucga a                                              21

<210> SEQ ID NO 487
<211> LENGTH: 21
<212> TYPE: DNA
<213> ORGANISM: Artificial Sequence
<220> FEATURE:
<223> OTHER INFORMATION: siRNA sense strand

<400> SEQUENCE: 487
ggauaugacu gauauugaut t                                              21

<210> SEQ ID NO 488
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 488
aucaauauca gucauaucct c                                              21

<210> SEQ ID NO 489
<211> LENGTH: 21
<212> TYPE: DNA
<213> ORGANISM: Artificial Sequence
<220> FEATURE:
<223> OTHER INFORMATION: siRNA sense strand

<400> SEQUENCE: 489
cuaacuuaca ucaaaguuat t                                              21

<210> SEQ ID NO 490
<211> LENGTH: 21
```

```
<212> TYPE: DNA
<213> ORGANISM: Artificial Sequence
<220> FEATURE:
<223> OTHER INFORMATION: siRNA antisense strand

<400> SEQUENCE: 490
uaacuuugau guaaguuagt g                                              21

<210> SEQ ID NO 491
<211> LENGTH: 21
<212> TYPE: DNA
<213> ORGANISM: Artificial Sequence
<220> FEATURE:
<223> OTHER INFORMATION: siRNA sense strand

<400> SEQUENCE: 491
cucacuaacu uacaucaaat t                                              21

<210> SEQ ID NO 492
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 492
uuugauguaa guuagugaga g                                              21

<210> SEQ ID NO 493
<211> LENGTH: 21
<212> TYPE: DNA
<213> ORGANISM: Artificial Sequence
<220> FEATURE:
<223> OTHER INFORMATION: siRNA sense strand

<400> SEQUENCE: 493
gauccuacgg aaguuauggt t                                              21

<210> SEQ ID NO 494
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 494
ccauaacuuc cguaggaucc g                                              21

<210> SEQ ID NO 495
<211> LENGTH: 21
<212> TYPE: DNA
<213> ORGANISM: Artificial Sequence
<220> FEATURE:
<223> OTHER INFORMATION: siRNA sense strand

<400> SEQUENCE: 495
ccauguucca uguuucuuut t                                              21

<210> SEQ ID NO 496
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 496
```

```
aaagaaacau ggaacauggt c                                              21
```

<210> SEQ ID NO 497
<211> LENGTH: 21
<212> TYPE: DNA
<213> ORGANISM: Artificial Sequence
<220> FEATURE:
<223> OTHER INFORMATION: siRNA sense strand

<400> SEQUENCE: 497

```
ccucccgcag accauguuct t                                              21
```

<210> SEQ ID NO 498
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 498

```
gaacaugguc ugcgggaggc g                                              21
```

<210> SEQ ID NO 499
<211> LENGTH: 21
<212> TYPE: DNA
<213> ORGANISM: Artificial Sequence
<220> FEATURE:
<223> OTHER INFORMATION: siRNA sense strand

<400> SEQUENCE: 499

```
cucccgcaga ccauguucct t                                              21
```

<210> SEQ ID NO 500
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 500

```
ggaacauggu cugcgggagg c                                              21
```

<210> SEQ ID NO 501
<211> LENGTH: 21
<212> TYPE: DNA
<213> ORGANISM: Artificial Sequence
<220> FEATURE:
<223> OTHER INFORMATION: siRNA sense strand

<400> SEQUENCE: 501

```
ucccgcagac cauguuccat t                                              21
```

<210> SEQ ID NO 502
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 502

```
uggaacaugg ucugcgggag g                                              21
```

<210> SEQ ID NO 503
<211> LENGTH: 21
<212> TYPE: DNA
<213> ORGANISM: Artificial Sequence

```
<220> FEATURE:
<223> OTHER INFORMATION: siRNA sense strand

<400> SEQUENCE: 503
cccgcagacc auguccaut t                                                 21

<210> SEQ ID NO 504
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 504
auggaacaug gucugcggga g                                                21

<210> SEQ ID NO 505
<211> LENGTH: 21
<212> TYPE: DNA
<213> ORGANISM: Artificial Sequence
<220> FEATURE:
<223> OTHER INFORMATION: siRNA sense strand

<400> SEQUENCE: 505
ccgcagacca uguccaugt t                                                 21

<210> SEQ ID NO 506
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 506
cauggaacau ggucugcggg a                                                21

<210> SEQ ID NO 507
<211> LENGTH: 21
<212> TYPE: DNA
<213> ORGANISM: Artificial Sequence
<220> FEATURE:
<223> OTHER INFORMATION: siRNA sense strand

<400> SEQUENCE: 507
cgcagaccau guccaugut t                                                 21

<210> SEQ ID NO 508
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 508
acauggaaca uggucugcgg g                                                21

<210> SEQ ID NO 509
<211> LENGTH: 21
<212> TYPE: DNA
<213> ORGANISM: Artificial Sequence
<220> FEATURE:
<223> OTHER INFORMATION: siRNA sense strand

<400> SEQUENCE: 509
agaccauguu ccauguuuct t                                                21
```

<210> SEQ ID NO 510
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 510
gaaacaugga acauggucug c                                              21

<210> SEQ ID NO 511
<211> LENGTH: 21
<212> TYPE: DNA
<213> ORGANISM: Artificial Sequence
<220> FEATURE:
<223> OTHER INFORMATION: siRNA sense strand

<400> SEQUENCE: 511
accauguucc auguuucuut t                                              21

<210> SEQ ID NO 512
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 512
aagaaacaug gaacaugguc t                                              21

<210> SEQ ID NO 513
<211> LENGTH: 21
<212> TYPE: DNA
<213> ORGANISM: Artificial Sequence
<220> FEATURE:
<223> OTHER INFORMATION: siRNA sense strand

<400> SEQUENCE: 513
ccacaucauc uacagcuuut t                                              21

<210> SEQ ID NO 514
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 514
aaagcuguag augauguggg t                                              21

<210> SEQ ID NO 515
<211> LENGTH: 21
<212> TYPE: DNA
<213> ORGANISM: Artificial Sequence
<220> FEATURE:
<223> OTHER INFORMATION: siRNA sense strand

<400> SEQUENCE: 515
gguuugacag auacagcaat t                                              21

<210> SEQ ID NO 516
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 516
uugcuguauc ugucaaacct a                                              21

<210> SEQ ID NO 517
<211> LENGTH: 21
<212> TYPE: DNA
<213> ORGANISM: Artificial Sequence
<220> FEATURE:
<223> OTHER INFORMATION: siRNA sense strand

<400> SEQUENCE: 517
ucaucuacag cuuugccaat t                                              21

<210> SEQ ID NO 518
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 518
uuggcaaagc uguagaugat g                                              21

<210> SEQ ID NO 519
<211> LENGTH: 21
<212> TYPE: DNA
<213> ORGANISM: Artificial Sequence
<220> FEATURE:
<223> OTHER INFORMATION: siRNA sense strand

<400> SEQUENCE: 519
cccuguuaag gaaugcaaat t                                              21

<210> SEQ ID NO 520
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 520
uuugcauucc uuaacagggt t                                              21

<210> SEQ ID NO 521
<211> LENGTH: 21
<212> TYPE: DNA
<213> ORGANISM: Artificial Sequence
<220> FEATURE:
<223> OTHER INFORMATION: siRNA sense strand

<400> SEQUENCE: 521
caaguaggca aauaucuuat t                                              21

<210> SEQ ID NO 522
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 522
uaagauauuu gccuacuuga t                                              21

<210> SEQ ID NO 523

```
<211> LENGTH: 21
<212> TYPE: DNA
<213> ORGANISM: Artificial Sequence
<220> FEATURE:
<223> OTHER INFORMATION: siRNA sense strand

<400> SEQUENCE: 523
cagcuuuguc agcaggaaat t                                              21

<210> SEQ ID NO 524
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 524
uuuccugcug acaaagcugc g                                              21

<210> SEQ ID NO 525
<211> LENGTH: 21
<212> TYPE: DNA
<213> ORGANISM: Artificial Sequence
<220> FEATURE:
<223> OTHER INFORMATION: siRNA sense strand

<400> SEQUENCE: 525
gguucaccaa ggaggcaggt t                                              21

<210> SEQ ID NO 526
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 526
ccugccuccu uggugaaccg g                                              21

<210> SEQ ID NO 527
<211> LENGTH: 21
<212> TYPE: DNA
<213> ORGANISM: Artificial Sequence
<220> FEATURE:
<223> OTHER INFORMATION: siRNA sense strand

<400> SEQUENCE: 527
ggaucaagua ggcaaauaut t                                              21

<210> SEQ ID NO 528
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 528
auauuugccu acuugaucca a                                              21

<210> SEQ ID NO 529
<211> LENGTH: 21
<212> TYPE: DNA
<213> ORGANISM: Artificial Sequence
<220> FEATURE:
<223> OTHER INFORMATION: siRNA sense strand

<400> SEQUENCE: 529
```
gagggaccau acuaauuaut t                                          21

<210> SEQ ID NO 530
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 530
auaauuagua uggucccuca a                                          21

<210> SEQ ID NO 531
<211> LENGTH: 21
<212> TYPE: DNA
<213> ORGANISM: Artificial Sequence
<220> FEATURE:
<223> OTHER INFORMATION: siRNA sense strand

<400> SEQUENCE: 531
ggccgguuca ccaaggaggt t                                          21

<210> SEQ ID NO 532
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 532
ccuccuuggu gaaccggcct g                                          21

<210> SEQ ID NO 533
<211> LENGTH: 21
<212> TYPE: DNA
<213> ORGANISM: Artificial Sequence
<220> FEATURE:
<223> OTHER INFORMATION: siRNA sense strand

<400> SEQUENCE: 533
ggacaaggag agugucaaat t                                          21

<210> SEQ ID NO 534
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 534
uuugacacuc uccuugucct c                                          21

<210> SEQ ID NO 535
<211> LENGTH: 21
<212> TYPE: DNA
<213> ORGANISM: Artificial Sequence
<220> FEATURE:
<223> OTHER INFORMATION: siRNA sense strand

<400> SEQUENCE: 535
ccgguucacc aaggaggcat t                                          21

<210> SEQ ID NO 536
<211> LENGTH: 21
<212> TYPE: DNA

```
<213> ORGANISM: Artificial Sequence
<220> FEATURE:
<223> OTHER INFORMATION: siRNA antisense strand

<400> SEQUENCE: 536
ugccuccuug gugaaccggc c                                              21

<210> SEQ ID NO 537
<211> LENGTH: 21
<212> TYPE: DNA
<213> ORGANISM: Artificial Sequence
<220> FEATURE:
<223> OTHER INFORMATION: siRNA sense strand

<400> SEQUENCE: 537
cguacaagcu ggucugcuat t                                              21

<210> SEQ ID NO 538
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 538
uagcagacca gcuuguacgc a                                              21

<210> SEQ ID NO 539
<211> LENGTH: 21
<212> TYPE: DNA
<213> ORGANISM: Artificial Sequence
<220> FEATURE:
<223> OTHER INFORMATION: siRNA sense strand

<400> SEQUENCE: 539
ggaguuuaau cucuugcaat t                                              21

<210> SEQ ID NO 540
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 540
uugcaagaga uuaaacucct g                                              21

<210> SEQ ID NO 541
<211> LENGTH: 21
<212> TYPE: DNA
<213> ORGANISM: Artificial Sequence
<220> FEATURE:
<223> OTHER INFORMATION: siRNA sense strand

<400> SEQUENCE: 541
caaggaacug aaugcggaat t                                              21

<210> SEQ ID NO 542
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 542
uuccgcauuc aguuccuuga t                                              21
```

<210> SEQ ID NO 543
<211> LENGTH: 21
<212> TYPE: DNA
<213> ORGANISM: Artificial Sequence
<220> FEATURE:
<223> OTHER INFORMATION: siRNA sense strand

<400> SEQUENCE: 543
cccugaucaa ggaacugaat t                                        21

<210> SEQ ID NO 544
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 544
uucaguuccu ugaucagggt g                                        21

<210> SEQ ID NO 545
<211> LENGTH: 21
<212> TYPE: DNA
<213> ORGANISM: Artificial Sequence
<220> FEATURE:
<223> OTHER INFORMATION: siRNA sense strand

<400> SEQUENCE: 545
cuuggaucaa guaggcaaat t                                        21

<210> SEQ ID NO 546
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 546
uuugccuacu ugauccaagt g                                        21

<210> SEQ ID NO 547
<211> LENGTH: 21
<212> TYPE: DNA
<213> ORGANISM: Artificial Sequence
<220> FEATURE:
<223> OTHER INFORMATION: siRNA sense strand

<400> SEQUENCE: 547
ggauugaggg accauacuat t                                        21

<210> SEQ ID NO 548
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 548
uaguaugguc ccucaaucct g                                        21

<210> SEQ ID NO 549
<211> LENGTH: 21
<212> TYPE: DNA
<213> ORGANISM: Artificial Sequence
<220> FEATURE:

<223> OTHER INFORMATION: siRNA sense strand

<400> SEQUENCE: 549
gcaaauucuc agacucuaat t                                         21

<210> SEQ ID NO 550
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 550
uuagagucug agaauuugca t                                         21

<210> SEQ ID NO 551
<211> LENGTH: 21
<212> TYPE: DNA
<213> ORGANISM: Artificial Sequence
<220> FEATURE:
<223> OTHER INFORMATION: siRNA sense strand

<400> SEQUENCE: 551
ccuucccuua ggaacuuaat t                                         21

<210> SEQ ID NO 552
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 552
uuaaguuccu aagggaagga t                                         21

<210> SEQ ID NO 553
<211> LENGTH: 100
<212> TYPE: DNA
<213> ORGANISM: Artificial Sequence
<220> FEATURE:
<223> OTHER INFORMATION: OHBOT Oligonucleotide

<400> SEQUENCE: 553
gacttcatat acccaagctt ggaaaatttt ttttaaaaaa gtcttgacac tttatgcttc    60
cggctcgtat aatggatcca ggagtaacaa tacaaatgga                        100

<210> SEQ ID NO 554
<211> LENGTH: 100
<212> TYPE: DNA
<213> ORGANISM: Artificial Sequence
<220> FEATURE:
<223> OTHER INFORMATION: OHBOT Oligonucleotide

<400> SEQUENCE: 554
ttcaagagat ccatttgtat tgttactcct ttttttttt gtcgacgatc cttagcgaaa    60
gctaaggatt ttttttttac tcgagcggat tactacatac                        100

<210> SEQ ID NO 555
<211> LENGTH: 70
<212> TYPE: DNA
<213> ORGANISM: Artificial Sequence
<220> FEATURE:
<223> OTHER INFORMATION: OHBOT Oligonucleotide

<400> SEQUENCE: 555

```
gtatgtagta atccgctcga gtaaaaaaaa aatccttagc tttcgctaag gatcgtcgac    60
aaaaaaaaaa                                                          70

<210> SEQ ID NO 556
<211> LENGTH: 60
<212> TYPE: DNA
<213> ORGANISM: Artificial Sequence
<220> FEATURE:
<223> OTHER INFORMATION: OHBOT Oligonucleotide

<400> SEQUENCE: 556
aggagtaaca atacaaatgg atctcttgaa tccatttgta ttgttactcc tggatccatt    60

<210> SEQ ID NO 557
<211> LENGTH: 70
<212> TYPE: DNA
<213> ORGANISM: Artificial Sequence
<220> FEATURE:
<223> OTHER INFORMATION: OHBOT Oligonucleotide

<400> SEQUENCE: 557
atacgagccg gaagcataaa gtgtcaagac ttttttaaaa aaaattttcc aagcttgggt    60
atatgaagtc                                                          70

<210> SEQ ID NO 558
<211> LENGTH: 8884
<212> TYPE: DNA
<213> ORGANISM: Artificial Sequence
<220> FEATURE:
<223> OTHER INFORMATION: pKSII-inv-hly

<400> SEQUENCE: 558
ctaaattgta agcgttaata ttttgttaaa attcgcgtta aattttttgtt aaatcagctc    60 atttttttaac caataggccg aaatcggcaa aatcccttat aaatcaaaag aatagaccga   120
gatagggttg agtgttgttc cagtttggaa caagagtcca ctattaaaga acgtggactc   180
caacgtcaaa gggcgaaaaa ccgtctatca gggcgatggc ccactacgtg aaccatcacc   240
ctaatcaagt tttttggggt cgaggtgccg taaagcacta aatcggaacc ctaaagggag   300
cccccgattt agagcttgac ggggaaagcc ggcgaacgtg gcgagaaagg aagggaagaa   360
agcgaaagga gcgggcgcta gggcgctggc aagtgtagcg gtcacgctgc gcgtaaccac   420
cacacccgcc gcgcttaatg cgccgctaca gggcgcgtcc cattcgccat tcaggctgcg   480
caactgttgg gaagggcgat cggtgcgggc ctcttcgcta ttacgccagc tggcgaaagg   540
gggatgtgct gcaaggcgat taagttgggt aacgccaggg ttttcccagt cacgacgttg   600
taaaacgacg gccagtgagc gcgcgtaata cgactcacta tagggcgaat tggagctcca   660
ccgcggtggc ggccgctcta gaactagtgg atccccgggg ctgcagctgg gccgtaagat   720
cggcatttaa tcgcgacaat ccttttaaaa aaacagcgcc gctcaattaa cctgagcggc   780
gttgttcttc tggacgtttg ctacttatgg ggcgagtcta ggattgccgg actcccattc   840
gcgccccaaa taatcagctc attaaactgt tcttattgct atctgttatc tggttatatt   900
gacagcgcac agagcgggaa cgccaagtat gcaggccctg gttgcagtgc gcctgtgtcc   960
atattcatgg tttcaaaatc cgtgctggtc tttttgaccc aatattcacc agattgccaa  1020
tcagaactat acgcggtcaa gctccccac tcgccccaca atgtcccgtc aggcgcacgc  1080
gttccgttgg ttgcacgtga ggattcaaga accgcagaca tatctgaacc ttggcattgt  1140
```

```
ctgctggcct cgagactgga taccagcgat ctgccgccat cgtatatcca ccgatttggg    1200
tagaaccgat aactcaccga ataacttggg aattttttac ttttcgccgt cacagccact    1260
tcgctatagg tttggtaggt aatcgtcacc tgaccctgat cgttaaccga tacattgggt    1320
gtgaatgacg acgaccactc atactgagta ttattagcaa catcgttatc catctgtaac    1380
tggaatgtgg cgttttttaaa gatcgttttc gggaacccctt tatccgtagc gaaattttgc    1440
ccgttaacca gaataccggt cagcgtaggt accgggaata gggatatttt tttctgcaat    1500
gtactcagta tcagggtatc aacctgcggc gtgattgtga catcaccgac actattccca    1560
accaccgtcg cggtatagct atctggctgc tcggtaatgg ggctaatact caccggcaca    1620
ccgttttgag taaaactcaa gccctgcatc ccactgataa aatggccatt cttatcgaca    1680
gggacaaagg ataatgtgga actcatcgtg ccatcagcca agatatccgg tgtggagacg    1740
gtgaaactgg agcggccagc atctggaata ggatctgccg tgaaattaac cgtcacactc    1800
ggcacactga acgcagcccc atccactttc accgttactg ttgctacccc caacgtggta    1860
ctggtcaatg gtgcgctata agtgccgtca ttgtgatccg tgataacgcc catattgcct    1920
aaggttgtgt caaaagccac attcgcgcca gcctgcgggt ccccataggt atccttcaac    1980
tccaacgtga tggttgaagc cattagacca tcagcgatga tagatgtcgg taccgcagcc    2040
agagtggatt tatccgccgc gatagtaccc ttaacaaagt gggtatcaac actttgccgt    2100
tgcccctcca cttctgctgt gactaccgtc acgccatctg tcgtattggt taatgcaatg    2160
cgcgcgacgc catttgcatc tgtcttttcc gtgatttat tcggtagcgc accattattg    2220
gtggttatca ccacctcctg cccggctaag ggtttccct caaatcagc aacggtgaac    2280 tcaacggtga ttgcagtttt cccattagcc ggtgcgccat caccaatgac ggccgccgtt    2340
aatgtcaact gaggctgctg aacggtgacg ctcaatgtga atgagttaga tcggtttcct    2400
tggtgatcaa ccgcgagcgc actaagcgaa taaaagttgg ctgtcaggtc gtccgttacc    2460
cgactcactt gtgctgtgcg tttataaggc ggtaaaacca agttgaattg tgtggtactc    2520
agtggtgtta atgtgccgcc agcggcaatc agttcggcat cactccagac aatttccctt    2580
acagcagatg cccccttgtac ttgtgcgttc acctgataaa cctgacccgg caggccggag    2640
atagttgctg gcgataatgt cagtttaacc acctgctgtt tctgatactc caacacgata    2700
ttattgttac gatcgacaag gttatagcgg ctctccgcca gtagacgtgt tcctgccacc    2760
gctgaagggc taagttgcga ctgaaaactc tcgcccaggc gatagttcat ttggaggttc    2820
cactgtgttt catgcttact gcttttcccc atacgctgat ctaccccgac agtgagtaga    2880
ggcacggggg tgtaattgat cccggcagtc acggcataag ggttgcgttg cagattatct    2940
ttaccaaata aagcaacacg ctcaccggtg tattgctcat acatcaactt ccccccccagt    3000 tgtgggagtg caggtaaata agcattcgcg cgcaaatccc ccccagtggc tgggcgctct    3060
ttatagtcgg agaaatcacg cgacgagtgc catccattga ggcgaaaata cccattggca    3120
gccaactgta aataatcggt ccaggcctcg gcaccaagac cgatacggtg gttgtggccg    3180
gtcaaatcat tatcataaaa agtattaagt ccgtacagcc aaccgttctc caatgtacgt    3240
atcccgacgc caaggttaag tgtgttgcgg ctgtctttat tgcgaatacc taactgacta    3300
aaaaagagga atgaagcaga gtcataccaa ggagccagcc aatcaagaga gctttctttt    3360
agcgaaaaat ttttgtcaaa attcagatta acttgagccg taccgaatcg atttaaccac    3420
tgtttgattt cttgattaac cgcatcgccc accattgagt gagcaacatc agatgccctg    3480
cctgatgcag ctaacctggc cccggtgctt atcatcttat tcaccgcttc agtctcctgc    3540
```

```
tccttattgg cgcgatctat tattgcagca tttctttctg tatccgatgc ggaaaaggga    3600
ttgattgaac tctccatttc attattagga tggagatttt caaatgcaga tgaagagaca    3660
gaataaggct ggacctgttg cggtgcgtta gcatcatatt tttctgaagc cccagccatg    3720
aacattccac atatcaaaaa gatacaaata actattcgtg aaataatatt aaatgaaatt    3780
attttattaa aatacataga cattcccgca ttccttatca agagaaactc actgattggc    3840
tggaaaacca tcataattta aatgaaataa agcatacctg tcatacgtca aactgcatgt    3900
gcgttggctg tgctcaacaa cttgagttat ttgaggtata actggccaca acgagcatt    3960 tgaaatcacc ttgaccatta attaaagatg caatagttga aagtgaaact tgttttctaa    4020
tttagtaaag acattaagag gatagcactt ttttaaaaaa ccagactggg cagattaaaa    4080
atattcaaaa tatataataa aacagtctat accatacagc gatagaattg atttattgta    4140
actaagcagg tgagaatatc aaaaaaaaca aaaatacaaa atgaactatt atcatataaa    4200
taatatcaat tagaataagc cccttcatt tgatgttgtc agttgtctgc tgcggttttt    4260
atttctactt tcagtctgaa gtgttactcc gcaatatccg cattaatcct gatggttgcc    4320
ttgatgactg caggaattcg atccctcctt tgattagtat attcctatct aaagtgact    4380 tttatgttga ggcattaaca tttgttaacg acgataaagg gacagcagga ctagaataaa    4440
gctataaagc aagcatataa tattgcgttt catctttaga agcgaatttc gccaatatta    4500
taattatcaa agagaggggg tggcaaacgg tatttggcat tattaggtta aaaaatgtag    4560
aaggagagtg aaacccatga aaaaaataat gctagttttt attacactta tattagttag    4620
tctaccaatt gcgcaacaaa ctgaagcaaa ggatgcatct gcattcaata agaaaaattc    4680
aatttcatcc atggcaccac cagcatctcc gcctgcaagt cctaagacgc caatcgaaaa    4740
gaaacacgcg gatgaaatcg ataagtatat acaaggattg gattacaata aaaacaatgt    4800
attagtatac cacggagatg cagtgacaaa tgtgccgcca agaaaaggtt acaaagatgg    4860
aaatgaatat attgttgtgg agaaaaagaa gaaatccatc aatcaaaata tgcagacat    4920 tcaagttgtg aatgcaattt cgagcctaac ctatccaggt gctctcgtaa agcgaattc    4980 ggaattagta gaaaatcaac cagatgttct ccctgtaaaa cgtgattcat taacactcag    5040
cattgatttg ccaggtatga ctaatcaaga caataaaatc gttgtaaaaa atgccactaa    5100
atcaaacgtt aacaacgcag taatacatt agtggaaaga tggaatgaaa atatatgctca    5160 agcttatcca aatgtaagtg caaaaattga ttatgatgac gaaatggctt acagtgaatc    5220
acaattaatt gcgaaatttg gtacagcatt taaagctgta aataatagct tgaatgtaaa    5280
cttcggcgca atcagtgaag ggaaaatgca agaagaagtc attagtttta aacaaattta    5340
ctataacgtg aatgttaatg aacctacaag accttccaga tttttcggca aagctgttac    5400
taaagagcag ttgcaagcgc ttggagtgaa tgcagaaaat cctcctgcat atatctcaag    5460
tgtggcgtat ggccgtcaag tttatttgaa attatcaact aattcccata gtactaaagt    5520
aaaagctgct tttgatgctg ccgtaagcgg aaaatctgtc tcaggtgatg tagaactaac    5580
aaatatcatc aaaaattctt ccttcaaagc cgtaatttac ggaggttccg caaaagatga    5640
agttcaaatc atcgacggca acctcggaga cttacgcgat atttgaaaa aaggcgctac    5700 ttttaatcga gaaacaccag gagttcccat tgcttataca acaaacttcc taaaagacaa    5760
tgaattagct gttattaaaa acaactcaga atatattgaa acaacttcaa aagcttatac    5820
agatggaaaa attaacatcg atcactctgg aggatacgtt gctcaattca acatttcttg    5880
```

```
ggatgaagta aattatgatc ctgaaggtaa cgaaattgtt caacataaaa actggagcga    5940
aaacaataaa agcaagctag ctcatttcac atcgtccatc tatttgccag gtaacgcgag    6000
aaatattaat gtttacgcta agaatgcac tggtttagct tgggaatggt ggagaacggt    6060
aattgatgac cggaacttac cacttgtgaa aaatagaaat atctccatct ggggcaccac    6120
gctttatccg aaatatagta ataaagtaga taatccaatc gaataattgt aaaagtaata    6180
aaaaattaag aataaaaccg cttaacacac acgaaaaaat aagcttgttt tgcactcttc    6240
gtaaattatt ttgtgaagaa tgtagaaaca ggcttatttt ttaattttt tagaagaatt    6300 aacaaatgta aaagaatatc tgactgttta tccatataat ataagcatat cccaaagttt    6360
aagccaccta tagtttctac tgcaaaacgt ataatttagt tcccacatat actaaaaaac    6420
gtgtccttaa ctctctctgt cagattagtt gtaggtggct taaacttagt tttacgaatt    6480
aaaaaggagc ggtgaaatga aaagtaaact tatttgtatc atcatggtaa tagcttttca    6540
ggctcatttc actatgacgg taaaagcaga ttctgtcggg gaagaaaaac ttcaaaataa    6600
tacacaagcc aaaaagaccc ctgctgattt aaaagcttat caagcttatc gataccgtcg    6660
acctcgaggg ggggcccggt acccagcttt tgttcccttt agtgagggtt aattgcgcgc    6720
ttggcgtaat catggtcata gctgtttcct gtgtgaaatt gttatccgct cacaattcca    6780
cacaacatac gagccggaag cataaagtgt aaagcctggg gtgcctaatg agtgagctaa    6840
ctcacattaa ttgcgttgcg ctcactgccc gctttccagt cgggaaacct gtcgtgccag    6900
ctgcattaat gaatcggcca acgcgcgggg agaggcggtt tgcgtattgg gcgctcttcc    6960
gcttcctcgc tcactgactc gctgcgctcg gtcgttcggc tgcggcgagc ggtatcagct    7020
cactcaaagg cggtaatacg gttatccaca gaatcagggg ataacgcagg aaagaacatg    7080
tgagcaaaag gccagcaaaa ggccaggaac cgtaaaaagg ccgcgttgct ggcgtttttc    7140
cataggctcc gcccccctga cgagcatcac aaaaatcgac gctcaagtca gaggtggcga    7200
aacccgacag gactataaag ataccaggcg tttccccctg gaagctccct cgtgcgctct    7260
cctgttccga ccctgccgct taccggatac ctgtccgcct ttctcccttc gggaagcgtg    7320
gcgctttctc atagctcacg ctgtaggtat ctcagttcgg tgtaggtcgt tcgctccaag    7380
ctgggctgtg tgcacgaacc ccccgttcag cccgaccgct gcgccttatc cggtaactat    7440
cgtcttgagt ccaacccggt aagacacgac ttatcgccac tggcagcagc cactggtaac    7500
aggattagca gagcgaggta tgtaggcggt gctacagagt tcttgaagtg gtggcctaac    7560
tacggctaca ctagaaggac agtatttggt atctgcgctc tgctgaagcc agttaccttc    7620
ggaaaaagag ttggtagctc ttgatccggc aaacaaacca ccgctggtag cggtggtttt    7680
tttgtttgca agcagcagat tacgcgcaga aaaaaaggat ctcaagaaga tcctttgatc    7740
ttttctacgg ggtctgacgc tcagtggaac gaaaactcac gttaagggat tttggtcatg    7800
agattatcaa aaaggatctt cacctagatc cttttaaatt aaaaatgaag ttttaaatca    7860
atctaaagta tatatgagta aacttggtct gacagttacc aatgcttaat cagtgaggca    7920
cctatctcag cgatctgtct atttcgttca tccatagttg cctgactccc cgtcgtgtag    7980
ataactacga tacgggaggg cttaccatct ggccccagtg ctgcaatgat accgcgagac    8040
ccacgctcac cggctccaga tttatcagca ataaaccagc cagccggaag ggccgagcgc    8100
agaagtggtc ctgcaacttt atccgcctcc atccagtcta ttaattgttg ccgggaagct    8160
agagtaagta gttcgccagt taatagtttg cgcaacgttg ttgccattgc tacaggcatc    8220
gtggtgtcac gctcgtcgtt tggtatggct tcattcagct ccggttccca acgatcaagg    8280
```

```
cgagttacat gatcccccat gttgtgcaaa aaagcggtta gctccttcgg tcctccgatc    8340
gttgtcagaa gtaagttggc cgcagtgtta tcactcatgg ttatggcagc actgcataat    8400
tctcttactg tcatgccatc cgtaagatgc ttttctgtga ctggtgagta ctcaaccaag    8460
tcattctgag aatagtgtat gcggcgaccg agttgctctt gcccggcgtc aatacgggat    8520
aataccgcgc cacatagcag aactttaaaa gtgctcatca ttggaaaacg ttcttcgggg    8580
cgaaaactct caaggatctt accgctgttg agatccagtt cgatgtaacc cactcgtgca    8640
cccaactgat cttcagcatc ttttactttc accagcgttt ctgggtgagc aaaaacagga    8700
aggcaaaatg ccgcaaaaaa gggaataagg gcgacacgga aatgttgaat actcatactc    8760
ttcctttttc aatattattg aagcatttat caggttatt gtctcatgag cggatacata    8820
tttgaatgta tttagaaaaa taaacaaata ggggttccgc gcacatttcc ccgaaaagtg    8880
ccac                                                                 8884
```

<210> SEQ ID NO 559
<211> LENGTH: 8538
<212> TYPE: DNA
<213> ORGANISM: Artificial Sequence
<220> FEATURE:
<223> OTHER INFORMATION: pMBV40

<400> SEQUENCE: 559

```
tcgcgcgttt cggtgatgac ggtgaaaacc tctgacacat gcagctcccg gagacggtca      60
cagcttgtct gtaagcggat gccgggagca gacaagcccg tcaggcgcg tcagcgggtg     120 ttggcgggtg tcggggctgg cttaactatg cggcatcaga gcagattgta ctgagagtgc    180
accatatcga cggtatcgat aagcttgata agcttttaaa tcagcagggg tcttttggc    240 ttgtgtatta ttttgaagtt tttcttcccc gacagaatct gcttttaccg tcatagtgaa    300
atgagcctga aaagctatta ccatgatgat acaaataagt ttactttca tttcaccgct    360 ccttttaat tcgtaaaact aagtttaagc cacctacaac taatctgaca gagagagtta    420
aggacacgtt tttagtata tgtgggaact aaattatacg ttttgcagta gaaactatag    480
gtggcttaaa ctttgggata tgcttatatt atatggataa acagtcagat attcttttac    540
atttgttaat tcttctaaaa aaattaaaaa ataagcctgt ttctacattc ttcacaaaat    600
aatttacgaa gagtgcaaaa caagcttatt ttttcgtgtg tgttaagcgg ttttattctt    660 aatttttat tactttaca attattcgat tggattatct actttattac tatatttcgg    720
ataaagcgtg gtgccccaga tggagatatt tctatttttc acaagtggta agttccggtc    780
atcaattacc gttctccacc attcccaagc taaaccagtg cattctttag cgtaaacatt    840
aatatttctc gcgttacctg gcaaatagat ggacgatgtg aaatgagcta gcttgctttt    900
attgttttcg ctccagtttt tatgttgaac aatttcgtta ccttcaggat cataatttac    960
ttcatcccaa gaaatgttga attgagcaac gtatcctcca gagtgatcga tgttaatttt    1020
tccatctgta taagcttttg aagttgtttc aatatattct gagttgtttt taataacagc    1080
taattcattg tcttttagga agtttgttgt ataagcaatg ggaactcctg gtgtttctcg    1140
attaaaagta gcgcctttt tcaaaatatc gcgtaagtct ccgaggttgc cgtcgatgat    1200
ttgaacttca tcttttgcgg aacctccgta aattacggct tgaaggaag aattttttgat    1260 gatatttgtt agttctacat cacctgagac agatttccg cttacggcag catcaaaagc    1320
agcttttact ttagtactat gggaattagt tgataatttc aaataaactt gacggccata    1380
```

```
cgccacactt gagatatatg caggaggatt ttctgcattc actccaagcg cttgcaactg    1440
ctctttagta acagctttgc cgaaaaatct ggaaggtctt gtaggttcat taacattcac    1500
gttatagtaa atttgtttaa aactaatgac ttcttcttgc attttcoctt cactgattgc    1560 gccgaagttt acattcaagc tattatttac agctttaaat gctgtaccaa atttcgcaat    1620
taattgtgat tcactgtaag ccatttcgtc atcataatca attttgcac ttacatttgg     1680 ataagcttga gcatattttt cattccatct ttccactaat gtatttactg cgttgttaac    1740
gtttgattta gtggcatttt ttacaacgat tttattgtct tgattagtca tacctggcaa    1800
atcaatgctg agtgttaatg aatcacgttt tacagggaga acatctggtt gattttctac    1860
taattccgaa ttcgctttta cgagagcacc tggataggtt aggctcgaaa ttgcattcac    1920
aacttgaatg tctgcattat tttgattgat ggatttcttc tttttctcca caacaatata    1980
ttcatttcca tctttgtaac cttttcttgg cggcacattt gtcactgcat ctccgtggta    2040
tactaataca ttgtttttat tgtaatccaa tccttgtata tacttatcga tttcatccgc    2100
gtgtttcttt tcgattggcg tcttaggact tgcaggcgga gatgctggtg gtgccatgga    2160
tgaaattgaa ttttctttat tgaatgcaga tgcatccttt gcttcagttt gttgcgcaat    2220
tggtagacta actaatataa gtgtaataaa aactagcatt attttttttca tgggtttcac    2280 tctccttcta cattttttaa cctaataatg ccaaataccg tttgccaccc ctctcttttg    2340
ataattataa tattggcgaa attcgcttct aaagatgaaa cgcaatatta tatgcttgct    2400
ttatagcttt attctagtcc tgctgtccct ttatcgtcgt taacaaatgt taatgcctca    2460
acataaaagt cactttaaga taggaatata ctaatcaaag gagggatcga attcctgcag    2520
tcatcaaggc aaccatcagg attaatgcgg atattgcgga gtaacacttc agactgaaag    2580
tagaaataaa aaccgcagca gacaactgac aacatcaaat gaagggggct tattctaatt    2640
gatattattt atatgataat agttcatttt gtattttgt ttttttttgat attctcacct    2700 gcttagttac aataaatcaa ttctatcgct gtatggtata gactgtttta ttatatattt    2760
tgaatatttt taatctgccc agtctggttt tttaaaaaag tgctatcctc ttaatgtctt    2820
tactaaatta gaaaacaagt ttcactttca actattgcat ctttaattaa tggtcaaggt    2880
gatttcaaat gctcgtttgt ggccagttat acctcaaata actcaagttg ttgagcacag    2940
ccaacgcaca tgcagtttga cgtatgacag gtatgcttta tttcatttaa attatgatgg    3000
ttttccagcc aatcagtgag tttctcttga taaggaatgc gggaatgtct atgtatttta    3060
ataaaataat ttcatttaat attatttcac gaatagttat ttgtatcttt ttgatatgtg    3120
gaatgttcat ggctggggct tcagaaaaat atgatgctaa cgcaccgcaa caggtccagc    3180
cttattctgt ctcttcatct gcatttgaaa atctccatcc taataatgaa atggagagtt    3240
caatcaatcc cttttccgca tcggatacag aaagaaatgc tgcaataata gatcgcgcca    3300
ataaggagca ggagactgaa gcggtgaata agatgataag caccggggcc aggttagctg    3360
catcaggcag ggcatctgat gttgctcact caatggtggg cgatgcggtt aatcaagaaa    3420
tcaaacagtg gttaaatcga ttcggtacgg ctcaagttaa tctgaatttt gacaaaaatt    3480
tttcgctaaa agaagctctc ttgattggc tggctccttg gtatgactct gcttcattcc    3540 tctttttttag tcagttaggt attcgcaata aagacagccg caacacactt aaccttggcg    3600
tcgggatacg tacattggag aacggttggc tgtacggact taatacttt tatgataatg    3660 atttgaccgg ccacaaccac cgtatcggtc ttggtgccga ggcctggacc gattatttac    3720
agttggctgc caatgggtat tttcgcctca atggatggca ctcgtcgcgt gatttctccg    3780
```

```
actataaaga gcgcccagcc actgggggggg atttgcgcgc gaatgcttat ttacctgcac   3840
tcccacaact ggggggggaag ttgatgtatg agcaatacac cggtgagcgt gttgctttat   3900
ttggtaaaga taatctgcaa cgcaaccctt atgccgtgac tgccgggatc aattacaccc   3960
ccgtgcctct actcactgtc ggggtagatc agcgtatggg gaaaagcagt aagcatgaaa   4020
cacagtggaa cctccaaatg aactatcgcc tgggcgagag ttttcagtcg caacttagcc   4080
cttcagcggt ggcaggaaca cgtctactgg cggagagccg ctataacctt gtcgatcgta   4140
acaataatat cgtgttggag tatcagaaac agcaggtggt taaactgaca ttatcgccag   4200
caactatctc cggcctgccg ggtcaggttt atcaggtgaa cgcacaagta caaggggcat   4260
ctgctgtaag ggaaattgtc tggagtgatg ccgaactgat tgccgctggc ggcacattaa   4320
caccactgag taccacacaa ttcaacttgg ttttaccgcc ttataaacgc acagcacaag   4380
tgagtcgggt aacggacgac ctgacagcca acttttattc gcttagtgcg ctcgcggttg   4440
atcaccaagg aaaccgatct aactcattca cattgagcgt caccgttcag cagcctcagt   4500
tgacattaac ggcggccgtc attggtgatg gcgcaccggc taatgggaaa actgcaatca   4560
ccgttgagtt caccgttgct gattttgagg ggaaaccctt agccgggcag gaggtggtga   4620
taaccaccaa taatggtgcg ctaccgaata aaatcacgga aaagacagat gcaaatggcg   4680
tcgcgcgcat tgcattaacc aatacgacag atggcgtgac ggtagtcaca gcagaagtgg   4740
aggggcaacg gcaaagtgtt gatacccact ttgttaaggg tactatcgcg gcggataaat   4800
ccactctggc tgcggtaccg acatctatca tcgctgatgg tctaatggct tcaaccatca   4860
cgttggagtt gaaggatacc tatggggacc cgcaggctgg cgcgaatgtg gcttttgaca   4920
caaccttagg caatatgggc gttatcacgg atcacaatga cggcacttat agcgcaccat   4980
tgaccagtac cacgttgggg gtagcaacag taacggtgaa agtggatggg gctgcgttca   5040
gtgtgccgag tgtgacggtt aatttcacgg cagatcctat tccagatgct ggccgctcca   5100
gtttcaccgt ctccacaccg gatatcttgg ctgatggcac gatgagttcc acattatcct   5160
ttgtccctgt cgataagaat ggccatttta tcagtgggat gcagggcttg agttttactc   5220
aaaacggtgt gccggtgagt attagcccca ttaccgagca gccagatagc tataccgcga   5280
cggtggttgg gaatagtgtc ggtgatgtca caatcacgcc gcaggttgat accctgatac   5340
tgagtacatt gcagaaaaaa atatccctat tcccggtacc tacgctgacc ggtattctgg   5400
ttaacgggca aaatttcgct acggataaag ggttcccgaa aacgatcttt aaaaacgcca   5460
cattccagtt acagatggat aacgatgttg ctaataatac tcagtatgag tggtcgtcgt   5520
cattcacacc caatgtatcg gttaacgatc agggtcaggt gacgattacc taccaaacct   5580
atagcgaagt ggctgtgacg gcgaaaagta aaaaattccc aagttattcg gtgagttatc   5640
ggttctaccc aaatcggtgg atatacgatg gcggcagatc gctggtatcc agtctcgagg   5700
ccagcagaca atgccaaggt tcagatatgt ctgcggttct tgaatcctca cgtgcaacca   5760
acggaacgcg tgcgcctgac gggacattgt ggggcgagtg ggggagcttg accgcgtata   5820
gttctgattg gcaatctggt gaatattggg tcaaaaagac cagcacggat tttgaaacca   5880
tgaatatgga cacaggcgca ctgcaaccag ggcctgcata cttggcgttc ccgctctgtg   5940
cgctgtcaat ataaccagat aacagatagc aataagaaca gtttaatgag ctgattattt   6000
ggggcgcgaa tggagtccg gcaatcctag actcgcccca taagtagcaa acgtccagaa   6060
gaacaacgcc gctcaggtta attgagcggc gctgtttttt taaaaggatt gtcgcgatta   6120
```

```
aatgccgatc ttacggccca gctgcagccc gggggatcta tgcggtgtga ataccgcac     6180 agatgcgtaa ggagaaaata ccgcatcagg cgccattcgc cattcaggct gcgcaactgt    6240
tgggaagggc gatcggtgcg ggcctcttcg ctattacgcc aggacttcat atacccaagc    6300
ttggaaaatt ttttttaaaa aagtcttgac actttatgct tccggctcgt ataatggatc    6360
caggagtaac aatacaaatg gattcaagag atccatttgt attgttactc cttttttttt    6420
ttgtcgacga tccttagcga aagctaagga ttttttttt actcgagcgg attactacat    6480
acctgcatta atgaatcggc caacgcgcgg ggagaggcgg tttgcgtatt gggcgctctt    6540
ccgcttcctc gctcactgac tcgctgcgct cggtcgttcg gctgcggcga gcggtatcag    6600
ctcactcaaa ggcggtaata cggttatcca cagaatcagg ggataacgca ggaaagaaca    6660
tgtgagcaaa aggccagcaa aaggccagga accgtaaaaa ggccgcgttg ctggcgtttt    6720
tccataggct ccgcccccct gacgagcatc acaaaaatcg acgctcaagt cagaggtggc    6780
gaaacccgac aggactataa agataccagg cgtttccccc tggaagctcc ctcgtgcgct    6840
ctcctgttcc gaccctgccg cttaccggat acctgtccgc ctttctccct tcgggaagcg    6900
tggcgctttc tcatagctca cgctgtaggt atctcagttc ggtgtaggtc gttcgctcca    6960
agctgggctg tgtgcacgaa ccccccgttc agcccgaccg ctgcgcctta tccggtaact    7020
atcgtcttga gtccaacccg gtaagacacg acttatcgcc actggcagca gccactggta    7080
acaggattag cagagcgagg tatgtaggcg gtgctacaga gttcttgaag tggtggccta    7140
actacggcta cactagaagg acagtatttg gtatctgcgc tctgctgaag ccagttacct    7200
tcggaaaaag agttggtagc tcttgatccg gcaaacaaac caccgctggt agcggtggtt    7260
tttttgtttg caagcagcag attacgcgca gaaaaaaagg atctcaagaa gatcctttga    7320
tcttttctac ggggtctgac gctcagtgga acgaaaactc acgttaaggg attttggtca    7380
tgagattatc aaaaaggatc ttcacctaga tccttttaaa ttaaaaatga agttttaaat    7440
caatctaaag tatatatgag taaacttggt ctgacagtta ccaatgctta atcagtgagg    7500
cacctatctc agcgatctgt ctatttcgtt catccatagt tgcctgactc cccgtcgtgt    7560
agataactac gatacgggag ggcttaccat ctggccccag tgctgcaatg ataccgcgag    7620
acccacgctc accggctcca gatttatcag caataaacca gccagccgga agggccgagc    7680
gcagaagtgg tcctgcaact ttatccgcct ccatccagtc tattaattgt tgccgggaag    7740
ctagagtaag tagttcgcca gttaatagtt tgcgcaacgt tgttgccatt gctacaggca    7800
tcgtggtgtc acgctcgtcg tttggtatgg cttcattcag ctccggttcc caacgatcaa    7860
ggcgagttac atgatccccc atgttgtgca aaaaagcggt tagctccttc ggtcctccga    7920
tcgttgtcag aagtaagttg gccgcagtgt tatcactcat ggttatggca gcactgcata    7980
attctcttac tgtcatgcca tccgtaagat gcttttctgt gactggtgag tactcaacca    8040
agtcattctg agaatagtgt atgcggcgac cgagttgctc ttgcccggcg tcaatacggg    8100
ataataccgc gccacatagc agaactttaa aagtgctcat cattggaaaa cgttcttcgg    8160
ggcgaaaact ctcaaggatc ttaccgctgt tgagatccag ttcgatgtaa cccactcgtg    8220
cacccaactg atcttcagca tcttttactt tcaccagcgt ttctgggtga gcaaaaacag    8280
gaaggcaaaa tgccgcaaaa aagggaataa gggcgacacg gaaatgttga atactcatac    8340
tcttcctttt tcaatattat tgaagcattt atcagggtta ttgtctcatg agcggataca    8400
tatttgaatg tatttagaaa aataaacaaa taggggttcc gcgcacattt ccccgaaaag    8460
tgccacctga cgtctaagaa accattatta tcatgacatt aacctataaa aataggcgta    8520
```

<210> SEQ ID NO 560
<211> LENGTH: 8427
<212> TYPE: DNA
<213> ORGANISM: Artificial Sequence
<220> FEATURE:
<223> OTHER INFORMATION: pMBV43

<400> SEQUENCE: 560

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatcga cggtatcgat aagcttgata agcttttaaa tcagcagggg tcttttttggc    240
ttgtgtatta ttttgaagtt tttcttcccc gacagaatct gcttttaccg tcatagtgaa     300
atgagcctga aaagctatta ccatgatgat acaaataagt ttacttttca tttcaccgct     360
ccttttttaat tcgtaaaact aagtttaagc cacctacaac taatctgaca gagagagtta    420
aggacacgtt tttagtata tgtgggaact aaattatacg ttttgcagta gaaactatag      480
gtggcttaaa ctttgggata tgcttatatt atatggataa acagtcagat attcttttac    540
atttgttaat tcttctaaaa aaattaaaaa ataagcctgt ttctacattc ttcacaaaat    600
aatttacgaa gagtgcaaaa caagcttatt ttttcgtgtg tgttaagcgg ttttattctt     660
aattttttat tacttttaca attattcgat tggattatct actttattac tatatttcgg    720
ataaagcgtg gtgccccaga tggagatatt tctattttc acaagtggta agttccggtc     780
atcaattacc gttctccacc attcccaagc taaaccagtg cattcttag cgtaaacatt      840
aatatttctc gcgttacctg gcaaatagat ggacgatgtg aaatgagcta gcttgctttt     900
attgttttcg ctccagtttt tatgttgaac aatttcgtta ccttcaggat cataatttac    960
ttcatcccaa gaaatgttga attgagcaac gtatcctcca gagtgatcga tgttaatttt  1020
tccatctgta taagcttttg aagttgtttc aatatattct gagttgtttt taataacagc   1080
taattcattg tcttttagga agtttgttgt ataagcaatg ggaactcctg gtgtttctcg   1140
attaaaagta gcgccttttt tcaaaatatc gcgtaagtct ccgaggttgc cgtcgatgat   1200
ttgaacttca tcttttgcgg aacctccgta aattacggct ttgaaggaag aatttttgat   1260
gatatttgtt agttctacat cacctgagac agattttccg cttacggcag catcaaaagc   1320
agcttttact ttagtactat gggaattagt tgataaattc aaataaactt gacggccata   1380
cgccacactt gagatatatg caggaggatt ttctgcattc actccaagcg cttgcaactg   1440
ctctttagta acagctttgc cgaaaaatct ggaaggtctt gtaggttcat taacattcac   1500
gttatagtaa atttgtttaa aactaatgac ttcttcttgc attttccctt cactgattgc   1560
gccgaagttt acattcaagc tattatttac agctttaaat gctgtaccaa atttcgcaat   1620
taattgtgat tcactgtaag ccatttcgtc atcataatca attttgcac ttacatttgg    1680
ataagcttga gcatattttt cattccatct ttccactaat gtatttactg cgttgttaac   1740
gtttgattta gtggcatttt ttacaacgat tttattgtct tgattagtca tacctggcaa   1800
atcaatgctg agtgttaatg aatcacgttt tacagggaga acatctggtt gattttctac   1860
taattccgaa ttcgcttta cgagagcacc tggataggtt aggctcgaaa ttgcattcac    1920
aacttgaatg tctgcattat tttgattgat ggatttcttc ttttttctcca caacaatata  1980
```

```
ttcatttcca tctttgtaac cttttcttgg cggcacattt gtcactgcat ctccgtggta    2040
tactaataca ttgtttttat tgtaatccaa tccttgtata tacttatcga tttcatccgc    2100
gtgtttcttt tcgattggcg tcttaggact tgcaggcgga gatgctggtg gtgccatgga    2160
tgaaattgaa ttttctttat tgaatgcaga tgcatccttt gcttcagttt gttgcgcaat    2220
tggtagacta actaatataa gtgtaataaa aactagcatt attttttca tgggtttcac     2280 tctccttcta cattttttaa cctaataatg ccaaataccg tttgccaccc ctctcttttg    2340
ataattataa tattggcgaa attcgcttct aaagatgaaa cgcaatatta tatgcttgct    2400
ttatagcttt attctagtcc tgctgtccct ttatcgtcgt taacaaatgt taatgcctca    2460
acataaaagt cactttaaga taggaatata ctaatcaaag gagggatcga attcctgcag    2520
tcatcaaggc aaccatcagg attaatgcgg atattgcgga gtaacacttc agactgaaag    2580
tagaaataaa accgcagca gacaactgac aacatcaaat gaaggggggct tattctaatt    2640 gatattattt atatgataat agttcatttt gtattttgt tttttttgat attctcacct     2700
gcttagttac aataaatcaa ttctatcgct gtatggtata gactgttta ttatatattt     2760 tgaatatttt taatctgccc agtctggttt tttaaaaag tgctatcctc ttaatgtctt     2820
tactaaatta gaaaacaagt ttcactttca actattgcat cttaattaa tggtcaaggt     2880 gatttcaaat gctcgtttgt ggccagttat acctcaaata actcaagttg ttgagcacag    2940
ccaacgcaca tgcagtttga cgtatgacag gtatgcttta tttcatttaa attatgatgg    3000
ttttccagcc aatcagtgag tttctcttga taaggaatgc gggaatgtct atgtattta    3060 ataaaataat ttcatttaat attatttcac gaatagttat ttgtatcttt ttgatatgtg    3120
gaatgttcat ggctggggct tcagaaaaat atgatgctaa cgcaccgcaa caggtccagc    3180
cttattctgt ctcttcatct gcatttgaaa atctccatcc taataatgaa atggagagtt    3240
caatcaatcc cttttccgca tcggatacag aaagaaatgc tgcaataata gatcgcgcca    3300
ataaggagca ggagactgaa gcggtgaata agatgataag caccggggcc aggttagctg    3360
catcaggcag ggcatctgat gttgctcact caatggtggg cgatgcggtt aatcaagaaa    3420
tcaaacagtg gttaaatcga ttcggtacgg ctcaagttaa tctgaatttt gacaaaaatt    3480
tttcgctaaa agaaagctct cttgattggc tggctccttg gtatgactct gcttcattcc    3540 tctttttag tcagttaggt attcgcaata aagacagccg caacacactt aaccttggcg    3600
tcgggatacg tacattggag aacggttggc tgtacggact taatactttt tatgataatg    3660
atttgaccgg ccacaaccac cgtatcggtc ttggtgccga ggcctggacc gattatttac    3720
agttggctgc caatgggtat tttcgcctca atggatggca ctcgtcgcgt gatttctccg    3780
actataaaga gcgcccagcc actgggggg atttgcgcgc gaatgcttat ttacctgcac    3840
tcccacaact gggggggaag ttgatgtatg agcaatacac cggtgagcgt gttgctttat    3900
ttggtaaaga taatctgcaa cgcaaccctt atgccgtgac tgccgggatc aattacaccc    3960
ccgtgcctct actcactgtc ggggtagatc agcgtatggg gaaaagcagt aagcatgaaa    4020
cacagtggaa cctccaaatg aactatcgcc tgggcgagag ttttcagtcg caacttagcc    4080
cttcagcggg ggcaggaaca cgtctactgg cggagagccg ctataacctt gtcgatcgta    4140
acaataatat cgtgttggag tatcagaaac agcaggtggt taaactgaca ttatcgccag    4200
caactatctc cggcctgccg ggtcaggttt atcaggtgaa cgcacaagta caaggggcat    4260
ctgctgtaag ggaaattgtc tggagtgatg ccgaactgat tgccgctggc ggcacattaa    4320
caccactgag taccacacaa ttcaacttgg ttttaccgcc ttataaacgc acagcacaag    4380
```

```
tgagtcgggt aacggacgac ctgacagcca actttattc gcttagtgcg ctcgcggttg    4440
atcaccaagg aaaccgatct aactcattca cattgagcgt caccgttcag cagcctcagt    4500
tgacattaac ggcggccgtc attggtgatg gcgcaccggc taatgggaaa actgcaatca    4560
ccgttgagtt caccgttgct gattttgagg ggaaacccctt agccgggcag gaggtggtga    4620
taaccaccaa taatggtgcg ctaccgaata aaatcacgga aaagacagat gcaaatggcg    4680
tcgcgcgcat tgcattaacc aatacgacag atggcgtgac ggtagtcaca gcagaagtgg    4740
aggggcaacg gcaaagtgtt gatacccact ttgttaaggg tactatcgcg gcggataaat    4800
ccactctggc tgcggtaccg acatctatca tcgctgatgg tctaatggct tcaaccatca    4860
cgttggagtt gaaggatacc tatggggacc cgcaggctgg cgcgaatgtg gcttttgaca    4920
caaccttagg caatatgggc gttatcacgg atcacaatga cggcacttat agcgcaccat    4980
tgaccagtac cacgttgggg gtagcaacag taacggtgaa agtggatggg gctgcgttca    5040
gtgtgccgag tgtgacggtt aatttcacgg cagatcctat tccagatgct ggccgctcca    5100
gtttcaccgt ctccacaccg gatatcttgg ctgatggcac gatgagttcc acattatcct    5160
ttgtccctgt cgataagaat ggccatttta tcagtgggat gcagggcttg agttttactc    5220
aaaacggtgt gccggtgagt attagcccca ttaccgagca gccagatagc tataccgcga    5280
cggtggttgg gaatagtgtc ggtgatgtca caatcacgcc gcaggttgat accctgatac    5340
tgagtacatt gcagaaaaaa atatccctat tcccggtacc tacgctgacc ggtattctgg    5400
ttaacgggca aaatttcgct acggataaag ggttcccgaa aacgatcttt aaaaacgcca    5460
cattccagtt acagatggat aacgatgttg ctaataatac tcagtatgag tggtcgtcgt    5520
cattcacacc caatgtatcg gttaacgatc agggtcaggt gacgattacc taccaaacct    5580
atagcgaagt ggctgtgacg gcgaaaagta aaaaattccc aagttattcg gtgagttatc    5640
ggttctaccc aaatcggtgg atatacgatg gcggcagatc gctggtatcc agtctcgagg    5700
ccagcagaca atgccaaggt tcagatatgt ctgcggttct tgaatcctca cgtgcaacca    5760
acggaacgcg tgcgcctgac gggacattgt ggggcgagtg ggggagcttg accgcgtata    5820
gttctgattg gcaatctggt gaatattggg tcaaaaagac cagcacggat tttgaaacca    5880
tgaatatgga cacaggcgca ctgcaaccag ggcctgcata cttggcgttc ccgctctgtg    5940
cgctgtcaat ataaccagat aacagatagc aataagaaca gtttaatgag ctgattattt    6000
ggggcgcgaa tgggagtccg gcaatcctag actcgcccca taagtagcaa acgtccagaa    6060
gaacaacgcc gctcaggtta attgagcggc gctgtttttt taaaaggatt gtcgcgatta    6120
aatgccgatc ttacggccca gctgcagccc gggggatcta tgcggtgtga ataccgcac    6180 agatgcgtaa ggagaaaata ccgcatcagg cgccattcgc cattcaggct gcgcaactgt    6240
tgggaagggc gatcggtgcg ggcctcttcg ctattacgcc aggacttcat atacccaagc    6300
ttggaaaatt tttttaaaa aagtcttgac actttatgct tccggctcgt ataatggatc    6360
caggagtaac aatacaaatg gattcaagag atccatttgt attgttactc ctttttttt    6420 ttgtcgacga tccttagcga aagctaagga tttttttttt actcgagcgg attactacat    6480
acctgcatta atgaatcggc caacgcgcgg ggagaggcgg tttgcgtatt gggcgctctt    6540
ccgcttcctc gctcactgac tcgctgcgct cggtcgttcg gctgcggcga gcggtatcag    6600
ctcactcaaa ggcggtaata cggttatcca cagaatcagg ggataacgca ggaaagaaca    6660
tgtgagcaaa aggccagcaa aaggccagga accgtaaaaa ggccgcgttg ctggcgtttt    6720
```

```
tccataggct ccgcccccct gacgagcatc acaaaaatcg acgctcaagt cagaggtggc    6780
gaaacccgac aggactataa agataccagg cgtttccccc tggaagctcc ctcgtgcgct    6840
ctcctgttcc gaccctgccg cttaccggat acctgtccgc ctttctccct tcgggaagcg    6900
tggcgctttc tcatagctca cgctgtaggt atctcagttc ggtgtaggtc gttcgctcca    6960
agctgggctg tgtgcacgaa ccccccgttc agcccgaccg ctgcgcctta tccggtaact    7020
atcgtcttga gtccaacccg gtaagacacg acttatcgcc actggcagca gccactggta    7080
acaggattag cagagcgagg tatgtaggcg gtgctacaga gttcttgaag tggtggccta    7140
actacggcta cactagaagg acagtatttg gtatctgcgc tctgctgaag ccagttacct    7200
tcggaaaaag agttggtagc tcttgatccg gcaaacaaac caccgctggt agcggtggtt    7260
tttttgtttg caagcagcag attacgcgca gaaaaaagg atctcaagaa gatcctttga    7320
tcttttctac ggggtctgac gctcagtgga acgaaaactc acgttaaggg attttggtca    7380
tgatctggta aggttgggaa gccctgcaaa gtaaactgga tggctttctt gccgccaagg    7440
atctgatggc gcagggatc aagatctgat caagagacag gatgaggatc gtttcgcatg    7500
attgaacaag atggattgca cgcaggttct ccggccgctt gggtggagag gctattcggc    7560
tatgactggg cacaacagac aatcggctgc tctgatgccg ccgtgttccg gctgtcagcg    7620
caggggcgcc cggttctttt tgtcaagacc gacctgtccg gtgccctgaa tgaactgcag    7680
gacgaggcag cgcggctatc gtggctggcc acgacgggcg ttccttgcgc agctgtgctc    7740
gacgttgtca ctgaagcggg aagggactgg ctgctattgg gcgaagtgcc ggggcaggat    7800
ctcctgtcat ctcaccttgc tcctgccgag aaagtatcca tcatggctga tgcaatgcgg    7860
cggctgcata cgcttgatcc ggctacctgc ccattcgacc accaagcgaa acatcgcatc    7920
gagcgagcac gtactcggat ggaagccggt cttgtcgatc aggatgatct ggacgaagag    7980
catcagggc tcgcgccagc cgaactgttc gccaggctca aggcgcgcat gcccgacggc    8040
gaggatctcg tcgtgaccca tggcgatgcc tgcttgccga atatcatggt ggaaaatggc    8100
cgcttttctg gattcatcga ctgtggccgg ctgggtgtgg cggaccgcta tcaggacata    8160
gcgttggcta cccgtgatat tgctgaagag cttggcggcg aatgggctga ccgcttcctc    8220
gtgctttacg gtatcgccgc tcccgattcg cagcgcatcg ccttctatcg ccttcttgac    8280
gagttcttct gagcgggact ctggggttcg aaatgaccga ccaagcgacg cccaacctgc    8340
catcacgaga tttcgattcc accgccgcct tctatgaaat catgacatta acctataaaa    8400
ataggcgtat cacgaggccc tttcgtc                                        8427
```

<210> SEQ ID NO 561
<211> LENGTH: 8427
<212> TYPE: DNA
<213> ORGANISM: Artificial Sequence
<220> FEATURE:
<223> OTHER INFORMATION: pMBV44

<400> SEQUENCE: 561

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatcga cggtatcgat aagcttgata agcttttaaa tcagcagggg tcttttggc    240
ttgtgtatta ttttgaagtt tttcttcccc gacagaatct gcttttaccg tcatagtgaa    300
atgagcctga aaagctatta ccatgatgat acaaataagt ttacttttca tttcaccgct    360
```

```
ccttttaat tcgtaaaact aagtttaagc cacctacaac taatctgaca gagagagtta    420
aggacacgtt ttttagtata tgtgggaact aaattatacg ttttgcagta gaaactatag    480
gtggcttaaa ctttgggata tgcttatatt atatggataa acagtcagat attcttttac    540
atttgttaat tcttctaaaa aaattaaaaa ataagcctgt ttctacattc ttcacaaaat    600
aatttacgaa gagtgcaaaa caagcttatt ttttcgtgtg tgttaagcgg ttttattctt    660 aatttttat tacttttaca attattcgat tggattatct actttattac tatatttcgg    720
ataaagcgtg gtgccccaga tggagatatt tctattttc acaagtggta agttccggtc    780
atcaattacc gttctccacc attcccaagc taaaccagtg cattctttag cgtaaacatt    840
aatatttctc gcgttacctg gcaaatagat ggacgatgtg aaatgagcta gcttgctttt    900
attgttttcg ctccagtttt tatgttgaac aatttcgtta ccttcaggat cataatttac    960
ttcatcccaa gaaatgttga attgagcaac gtatcctcca gagtgatcga tgttaatttt   1020
tccatctgta taagcttttg aagttgtttc aatatattct gagttgtttt taataacagc   1080
taattcattg tcttttagga agtttgttgt ataagcaatg ggaactcctg tgtttctcg    1140 attaaaagta gcgccttttt tcaaaatatc gcgtaagtct ccgaggttgc cgtcgatgat   1200
ttgaacttca tcttttgcgg aacctccgta aattacggct ttgaaggaag aattttgat    1260 gatatttgtt agttctacat cacctgagac agattttccg cttacggcag catcaaaagc   1320
agcttttact ttagtactat gggaattagt tgataatttc aaataaactt gacggccata   1380
cgccacactt gagatatatg caggaggatt ttctgcattc actccaagcg cttgcaactg   1440
ctctttagta acagctttgc cgaaaaatct ggaaggtctt gtaggttcat taacattcac   1500
gttatagtaa atttgtttaa aactaatgac ttcttcttgc attttcccctt cactgattgc   1560 gccgaagttt acattcaagc tattatttac agctttaaat gctgtaccaa atttcgcaat   1620
taattgtgat tcactgtaag ccatttcgtc atcataatca attttttgcac ttacatttgg   1680 ataagcttga gcatattttt cattccatct ttccactaat gtatttactg cgttgttaac   1740
gtttgattta gtggcatttt ttacaacgat tttattgtct tgattagtca tacctggcaa   1800
atcaatgctg agtgttaatg aatcacgttt tacagggaga acatctggtt gattttctac   1860
taattccgaa ttcgctttta cgagagcacc tggataggtt aggctcgaaa ttgcattcac   1920
aacttgaatg tctgcattat tttgattgat ggatttcttc tttttctcca caacaatata   1980
ttcatttcca tctttgtaac cttttcttgg cggcacattt gtcactgcat ctccgtggta   2040
tactaataca ttgtttttat tgtaatccaa tccttgtata tacttatcga tttcatccgc   2100
gtgtttcttt tcgattggcg tcttaggact tgcaggcgga gatgctggtg gtgccatgga   2160
tgaaattgaa ttttctttat tgaatgcaga tgcatccttt gcttcagttt gttgcgcaat   2220
tggtagacta actaatataa gtgtaataaa aactagcatt attttttca tgggtttcac    2280 tctccttcta catttttaa cctaataatg ccaaataccg tttgccaccc ctctctttg    2340 ataattataa tattggcgaa attcgcttct aaagatgaaa cgcaatatta tatgcttgct   2400
ttatagcttt attctagtcc tgctgtccct ttatcgtcgt taacaaatgt taatgcctca   2460
acataaaagt cactttaaga taggaatata ctaatcaaag gagggatcga attcctgcag   2520
tcatcaaggc aaccatcagg attaatgcgg atattgcgga gtaacacttc agactgaaag   2580
tagaaataaa aaccgcagca gacaactgac aacatcaaat gaaggggggct tattctaatt   2640 gatattattt atatgataat agttcatttt gtattttttgt ttttttgat attctcacct   2700
```

```
gcttagttac aataaatcaa ttctatcgct gtatggtata gactgtttta ttatatattt    2760
tgaatatttt taatctgccc agtctggttt tttaaaaaag tgctatcctc ttaatgtctt    2820
tactaaatta gaaaacaagt ttcactttca actattgcat ctttaattaa tggtcaaggt    2880
gatttcaaat gctcgtttgt ggccagttat acctcaaata actcaagttg ttgagcacag    2940
ccaacgcaca tgcagtttga cgtatgacag gtatgcttta tttcatttaa attatgatgg    3000
ttttccagcc aatcagtgag tttctcttga taaggaatgc gggaatgtct atgtatttta    3060
ataaataat ttcatttaat attatttcac gaatagttat ttgtatcttt ttgatatgtg     3120
gaatgttcat ggctggggct tcagaaaaat atgatgctaa cgcaccgcaa caggtccagc    3180
cttattctgt ctcttcatct gcatttgaaa atctccatcc taataatgaa atggagagtt    3240
caatcaatcc ctttccgca tcggatacag aaagaaatgc tgcaataata gatcgcgcca     3300
ataaggagca ggagactgaa gcggtgaata agatgataag caccggggcc aggttagctg    3360
catcaggcag ggcatctgat gttgctcact caatggtggg cgatgcggtt aatcaagaaa    3420
tcaaacagtg gttaaatcga ttcggtacgg ctcaagttaa tctgaatttt gacaaaaatt    3480
tttcgctaaa agaagctct cttgattggc tggctccttg gtatgactct gcttcattcc     3540
tctttttag tcagttaggt attcgcaata agacagccg caacacactt aaccttggcg      3600
tcgggatacg tacattggag aacggttggc tgtacggact taatactttt tatgataatg    3660
atttgaccgg ccacaaccac cgtatcggtc ttggtgccga ggcctggacc gattatttac    3720
agttggctgc caatgggtat tttcgcctca atggatggca ctcgtcgcgt gatttctccg    3780
actataaaga gcgcccagcc actgggggg atttgcgcgc gaatgcttat ttacctgcac     3840
tcccacaact gggggggaag ttgatgtatg agcaatacac cggtgagcgt gttgctttat    3900
ttggtaaaga taatctgcaa cgcaacccctt atgccgtgac tgccgggatc aattacaccc   3960
ccgtgcctct actcactgtc ggggtagatc agcgtatggg gaaaagcagt aagcatgaaa    4020
cacagtggaa cctccaaatg aactatcgcc tgggcgagag ttttcagtcg caacttagcc    4080
cttcagcggt ggcaggaaca cgtctactgg cggagagccg ctataacctt gtcgatcgta    4140
acaataatat cgtgttggag tatcagaaac agcaggtggt taaactgaca ttatcgccag    4200
caactatctc cggcctgccg ggtcaggttt atcaggtgaa cgcacaagta caaggggcat    4260
ctgctgtaag ggaaattgtc tggagtgatg ccgaactgat tgccgctggc ggcacattaa    4320
caccactgag taccacacaa ttcaacttgg ttttaccgcc ttataaacgc acagcacaag    4380
tgagtcgggt aacggacgac ctgacagcca acttttattc gcttagtgcg ctcgcggttg    4440
atcaccaagg aaaccgatct aactcattca cattgagcgt caccgttcag cagcctcagt    4500
tgacattaac ggcggccgtc attggtgatg gcgcaccggc taatgggaaa actgcaatca    4560
ccgttgagtt caccgttgct gattttgagg ggaaaccctt agccgggcag gaggtggtga    4620
taaccaccaa taatggtgcg ctaccgaata aaatcacgga aaagacagat gcaaatggcg    4680
tcgcgcgcat tgcattaacc aatacgacag atggcgtgac ggtagtcaca gcagaagtgg    4740
agggcaacg gcaaagtgtt gatcccact ttgttaaggg tactatcgcg gcggataaat       4800
ccactctggc tgcggtaccg acatctatca tcgctgatgg tctaatggct tcaaccatca    4860
cgttggagtt gaaggatacc tatggggacc cgcaggctgg cgcgaatgtg gcttttgaca    4920
caaccttagg caatatggcg gttatcacgg atcacaatga cggcacttat agcgcaccat    4980
tgaccagtac cacgttgggg gtagcaacag taacggtgaa agtggatggg gctgcgttca    5040
gtgtgccgag tgtgacggtt aatttcacgg cagatcctat tccagatgct ggccgctcca    5100
```

```
gtttcaccgt ctccacaccg gatatcttgg ctgatggcac gatgagttcc acattatcct    5160
ttgtccctgt cgataagaat ggccatttta tcagtgggat gcagggcttg agttttactc    5220
aaaacggtgt gccggtgagt attagcccca ttaccgagca gccagatagc tataccgcga    5280
cggtggttgg gaatagtgtc ggtgatgtca caatcacgcc gcaggttgat accctgatac    5340
tgagtacatt gcagaaaaaa atatccctat tcccggtacc tacgctgacc ggtattctgg    5400
ttaacgggca aaatttcgct acggataaag gttcccgaa aacgatcttt aaaaacgcca     5460
cattccagtt acagatggat aacgatgttg ctaataatac tcagtatgag tggtcgtcgt    5520
cattcacacc caatgtatcg gttaacgatc agggtcaggt gacgattacc taccaaacct    5580
atagcgaagt ggctgtgacg gcgaaaagta aaaaattccc aagttattcg gtgagttatc    5640
ggttctaccc aaatcggtgg atatacgatg gcggcagatc gctggtatcc agtctcgagg    5700
ccagcagaca atgccaaggt tcagatatgt ctgcggttct tgaatcctca cgtgcaacca    5760
acggaacgcg tgcgcctgac gggacattgt ggggcgagtg ggggagcttg accgcgtata    5820
gttctgattg gcaatctggt gaatattggg tcaaaaagac cagcacggat tttgaaacca    5880
tgaatatgga cacaggcgca ctgcaaccag ggcctgcata cttggcgttc ccgctctgtg    5940
cgctgtcaat ataaccagat aacagatagc aataagaaca gtttaatgag ctgattattt    6000
ggggcgcgaa tgggagtccg gcaatcctag actcgcccca taagtagcaa acgtccagaa    6060
gaacaacgcc gctcaggtta attgagcggc gctgtttttt taaaaggatt gtcgcgatta    6120
aatgccgatc ttacgcccca gctgcagccc gggggatcta tgcggtgtga ataccgcac    6180 agatgcgtaa ggagaaaata ccgcatcagg cgccattcgc cattcaggct gcgcaactgt    6240
tgggaagggc gatcggtgcg ggcctcttcg ctattacgcc aggacttcat atacccaagc    6300
ttggaaaatt ttttttaaaa aagtcttgac actttatgct tccggctcgt ataatggatc    6360
caggagtaac aatacaaatg gattcaagag atccatttgt attgttactc cttttttttt    6420
ttgtcgacga tccttagcga aagctaagga ttttttttt actcgagcgg attactacat    6480
acctgcatta atgaatcggc caacgcgcgg ggagaggcgg tttgcgtatt gggcgctctt    6540
ccgcttcctc gctcactgac tcgctgcgct cggtcgttcg gctgcggcga gcggtatcag    6600
ctcactcaaa ggcggtaata cggttatcca cagaatcagg ggataacgca ggaaagaaca    6660
tgtgagcaaa aggccagcaa aaggccagga accgtaaaaa ggccgcgttg ctggcgtttt    6720
tccataggct ccgcccccct gacgagcatc acaaaaatcg acgctcaagt cagaggtggc    6780
gaaacccgac aggactataa agataccagg cgtttccccc tggaagctcc ctcgtgcgct    6840
ctcctgttcc gaccctgccg cttaccggat acctgtccgc ctttctccct tcgggaagcg    6900
tggcgctttc tcatagctca cgctgtaggt atctcagttc ggtgtaggtc gttcgctcca    6960
agctgggctg tgtgcacgaa ccccccgttc agcccgaccg ctgcgcctta tccggtaact    7020
atcgtcttga gtccaacccg gtaagacacg acttatcgcc actggcagca gccactggta    7080
acaggattag cagagcgagg tatgtaggcg gtgctacaga gttcttgaag tggtggccta    7140
actacggcta cactagaagg acagtatttg gtatctgcgc tctgctgaag ccagttacct    7200
tcggaaaaag agttggtagc tcttgatccg gcaaacaaac caccgctggt agcggtggtt    7260 ttttgtttg caagcagcag attacgcgca gaaaaaaagg atctcaagaa gatcctttga    7320
tcttttctac ggggtctgac gctcagtgga acgaaaactc acgttaaggg attttggtca    7380
tgatttcata gaaggcggcg gtggaatcga aatctcgtga tggcaggttg ggcgtcgctt    7440
```

-continued

| | |
|---|---|
| ggtcggtcat ttcgaacccc agagtcccgc tcagaagaac tcgtcaagaa ggcgatagaa | 7500 |
| ggcgatgcgc tgcgaatcgg gagcggcgat accgtaaagc acgaggaagc ggtcagccca | 7560 |
| ttcgccgcca agctcttcag caatatcacg ggtagccaac gctatgtcct gatagcggtc | 7620 |
| cgccacaccc agccgccac agtcgatgaa tccagaaaag cggccatttt ccaccatgat | 7680 |
| attcggcaag caggcatcgc catgggtcac gacgagatcc tcgccgtcgg gcatgcgcgc | 7740 |
| cttgagcctg gcgaacagtt cggctggcgc gagcccctga tgctcttcgt ccagatcatc | 7800 |
| ctgatcgaca agaccggctt ccatccgagt acgtgctcgc tcgatgcgat gtttcgcttg | 7860 |
| gtggtcgaat gggcaggtag ccggatcaag cgtatgcagc cgccgcattg catcagccat | 7920 |
| gatggatact ttctcggcag gagcaaggtg agatgacagg agatcctgcc ccggcacttc | 7980 |
| gcccaatagc agccagtccc ttcccgcttc agtgacaacg tcgagcacag ctgcgcaagg | 8040 |
| aacgcccgtc gtggccagcc acgatagccg cgctgcctcg tcctgcagtt cattcagggc | 8100 |
| accggacagg tcggtcttga caaaaagaac cgggcgcccc tgcgctgaca gccggaacac | 8160 |
| ggcggcatca gagcagccga ttgtctgttg tgcccagtca tagccgaata gcctctccac | 8220 |
| ccaagcggcc ggagaacctg cgtgcaatcc atcttgttca atcatgcgaa acgatcctca | 8280 |
| tcctgtctct tgatcagatc ttgatcccct gcgccatcag atccttggcg caagaaagc | 8340 |
| catccagttt actttgcagg gcttcccaac cttaccagat catgacatta acctataaaa | 8400 |
| ataggcgtat cacgaggccc tttcgtc | 8427 |

<210> SEQ ID NO 562
<211> LENGTH: 18936
<212> TYPE: DNA
<213> ORGANISM: Artificial Sequence
<220> FEATURE:
<223> OTHER INFORMATION: pNJSZc

<400> SEQUENCE: 562

| | |
|---|---|
| ggccgctcga gcatgcatct agagggccca attcgcccta gtgagtcg tattacaatt | 60 |
| cactggccgt cgttttacaa cgtcgtgact gggaaaaccc tggcgttacc caacttaatc | 120 |
| gccttgcagc acatccccct ttcgccagct ggcgtaatag cgaagaggcc cgcaccgatc | 180 |
| gcccttccca acagttgcgc agcctgaaaa accgcgccat ggtgtgtagg ctggagctgc | 240 |
| ttcgaagttc ctatactttc tagagaatag gaacttcgga ataggaactt caagatcccc | 300 |
| cacgctgccg caagcactca gggcgcaagg gctgctaaag gaaacggaac acgtagaaag | 360 |
| ccagtccgca gaaacggtgc tgaccccgga tgaatgtcag ctactgggct atctggacaa | 420 |
| gggaaaacgc aagcgcaaag agaaagcagg tagcttgcag tgggcttaca tggcgatagc | 480 |
| tagactgggc ggttttatgg acagcaagcg aaccggaatt gccagctggg gcgccctctg | 540 |
| gtaaggttgg gaagccctgc aaagtaaact ggatggcttt cttgccgcca aggatctgat | 600 |
| ggcgcagggg atcaagatct gatcaagaga caggatgagg atcgtttcgc atgattgaac | 660 |
| aagatggatt gcacgcaggt tctccggccg cttgggtgga gaggctattc ggctatgact | 720 |
| gggcacaaca gacaatcggc tgctctgatg ccgccgtgtt ccggctgtca gcgcaggggc | 780 |
| gcccggttct ttttgtcaag accgacctgt ccggtgccct gaatgaactg caggacgagg | 840 |
| cagcgcggct atcgtggctg gccacgacgg gcgttccttg cgcagctgtg ctcgacgttg | 900 |
| tcactgaagc gggaagggac tggctgctat tgggcgaagt gccggggcag gatctcctgt | 960 |
| catctcacct tgctcctgcc gagaaagtat ccatcatggc tgatgcaatg cggcggctgc | 1020 |
| atacgcttga tccggctacc tgcccattcg accaccaagc gaaacatcgc atcgagcgag | 1080 |

```
cacgtactcg gatggaagcc ggtcttgtcg atcaggatga tctggacgaa gagcatcagg    1140
ggctcgcgcc agccgaactg ttcgccaggc tcaaggcgcg catgcccgac ggcgaggatc    1200
tcgtcgtgac ccatggcgat gcctgcttgc cgaatatcat ggtggaaaat ggccgctttt    1260
ctggattcat cgactgtggc cggctgggtg tggcggaccg ctatcaggac atagcgttgg    1320
ctacccgtga tattgctgaa gagcttggcg gcgagtgggc tgaccgcttc ctcgtgcttt    1380
acggtatcgc cgctcccgat tcgcagcgca tcgccttcta tcgccttctt gacgagttct    1440
tctgagcggg actctggggt tcgaaatgac cgaccaagcg acgcccaacc tgccatcacg    1500
agatttcgat tccaccgccg ccttctatga aggttgggc ttcggaatcg ttttccggga    1560
cgccggctgg atgatcctcc agcgcgggga tctcatgctg gagttcttcg cccaccccag    1620
cttcaaaagc gctctgaagt tcctatactt tctagagaat aggaacttcg aataggaac    1680 taaggaggat attcatatgg accatggcgc ggcatgcaag ctcggtatca ttgcagcact    1740
ggggccagat ggtaagccct cccgtatcgt agttatctac acgacgggga gtcaggcaac    1800
tatggatgaa cgaaatagac agatcgctga gataggtgcc tcactgatta agcattggta    1860
actgtcagac caagtttact catatatact ttagattgat ttaaaacttc attttaatt    1920 taaaaggatc taggtgaaga tcctttttga taatctcatg accaaaatcc cttaacgtga    1980
gttttcgttc cactgagcgt cagacccccgt agaaaagatc aaaggatctt cttgagatcc    2040 ttttttttctg cgcgtaatct gctgcttgca acaaaaaaa ccaccgctac cagcggtggt    2100
ttgtttgccg gatcaagagc taccaactct ttttccgaag gtaactggct tcagcagagc    2160
gcagatacca atactgttc ttctagtgta gccgtagtta ggccaccact tcaagaactc    2220
tgtagcaccg cctacatacc tcgctctgct aatcctgtta ccagtggctg ctgccagtgg    2280
cgataagtcg tgtcttaccg ggttggactc aagacgatag ttaccggata aggcgcagcg    2340
gtcgggctga acggggggtt cgtgcacaca gcccagcttg gagcgaacga cctacaccga    2400
actgagatac ctacagcgtg agctatgaga aagcgccacg cttcccgaag ggagaaaggc    2460
ggacaggtat ccggtaagcg gcagggtcgg aacaggagag cgcacgaggg agcttccagg    2520
gggaaacgcc tggtatcttt atagtcctgt cgggtttcgc cacctctgac ttgagcgtcg    2580
atttttgtga tgctcgtcag ggggggcgag cctatggaaa aacgccagca acgcggcctt    2640
tttacggttc ctggcctttt gctggccttt tgctcacatg ttctttcctg cgttatcccc    2700
tgattctgtg ataaccgta ttaccgcctt tgagtgagct gataccgctc gccgcagccg    2760
aacgaccgag cgcagcgagt cagtgagcga ggaagcggaa gagcgcccaa tacgcaaacc    2820
gcctctcccc gcgcgttggc cgattcatta atgcagctgg cacgacagta tcgataagct    2880
tgataagctt ttaaatcagc aggggtcttt ttggcttgtg tattattttg aagtttttct    2940
tccccgacag aatctgcttt taccgtcata gtgaaatgag cctgaaaagc tattaccatg    3000
atgatacaaa taagtttact tttcatttca ccgctccttt ttaattcgta aaactaagtt    3060
taagccacct acaactaatc tgacagagag agttaaggac acgttttta gtatatgtgg    3120 gaactaaatt atacgttttg cagtagaaac tataggtggc ttaaactttg ggatatgctt    3180
atattatatg gataaacagt cagatattct tttacatttg ttaattcttc taaaaaaatt    3240
aaaaaataag cctgtttcta cattcttcac aaaataattt acgaagagtg caaacaagc    3300 ttattttttc gtgtgtgtta agcggtttta ttcttaattt tttattactt ttacaattat    3360
tcgattggat tatctacttt attactatat ttcggataaa gcgtgtgcc ccagatggag    3420
```

```
atatttctat ttttcacaag tggtaagttc cggtcatcaa ttaccgttct ccaccattcc    3480
caagctaaac cagtgcattc tttagcgtaa acattaatat ttctcgcgtt acctggcaaa    3540
tagatggacg atgtgaaatg agctagcttg cttttattgt tttcgctcca gttttatgt    3600
tgaacaattt cgttaccttc aggatcataa tttacttcat cccaagaaat gttgaattga    3660
gcaacgtatc ctccagagtg atcgatgtta attttttccat ctgtataagc ttttgaagtt   3720
gtttcaatat attctgagtt gttttttaata acagctaatt cattgtcttt taggaagttt    3780
gttgtataag caatgggaac tcctggtgtt tctcgattaa aagtagcgcc ttttttcaaa    3840
atatcgcgta agtctccgag gttgccgtcg atgatttgaa cttcatcttt tgcggaacct    3900
ccgtaaatta cggctttgaa ggaagaattt ttgatgatat ttgttagttc tacatcacct    3960
gagacagatt ttccgcttac ggcagcatca aaagcagctt ttactttagt actatgggaa    4020
ttagttgata atttcaaata aacttgacgg ccatacgcca cacttgagat atatgcagga    4080
ggattttctg cattcactcc aagcgcttgc aactgctctt tagtaacagc tttgccgaaa    4140
aatctggaag gtcttgtagg ttcattaaca ttcacgttat agtaaatttg tttaaaacta    4200
atgacttctt cttgcatttt cccttcactg attgcgccga gtttacatt caagctatta    4260
tttacagctt taaatgctgt accaaatttc gcaattaatt gtgattcact gtaagccatt    4320
tcgtcatcat aatcaatttt tgcacttaca tttggataag cttgagcata ttttcattc    4380
catctttcca ctaatgtatt tactgcgttg ttaacgtttg atttagtggc atttttaca    4440
acgattttat tgtcttgatt agtcataccc ggcaaatcaa tgctgagtgt taatgaatca    4500
cgttttacag ggagaacatc tggttgattt tctactaatt ccgaattcgc ttttacgaga    4560
gcacctggat aggttaggct cgaaattgca ttcacaactt gaatgtctgc attattttga    4620
ttgatggatt tcttctttt ctccacaaca atatattcat ttccatcttt gtaacctttt    4680
cttggcggca catttgtcac tgcatctccg tggtatacta atacattgtt tttattgtaa    4740
tccaatcctt gtatatactt atcgatttca tcctttcgat tcttttcgat tggcgtctta    4800
ggacttgcag gcggagatgc tggtggtgcc atggatgaaa ttgaattttc tttattgaat    4860
gcagatgcat cctttgcttc agtttgttgc gcaattggta gactaactaa tataagtgta    4920
ataaaaacta gcattatttt tttcatgggt ttcactctcc ttctacattt tttaacctaa    4980
taatgccaaa taccgtttgc cacccctctc ttttgataat tataatattg gcgaaattcg    5040
cttctaaaga tgaaacgcaa tattatatgc ttgctttata gctttattct agtcctgctg    5100
tcccttatc gtcgttaaca aatgttaatg cctcaacata aaagtcactt taagatagga    5160
atatactaat caaaggaggg atcgaattcc tgcagtcatc aaggcaacca tcaggattaa    5220
tgcggatatt gcggagtaac acttcagact gaaagtagaa ataaaaaccg cagcagacaa    5280
ctgacaacat caaatgaagg gggcttattc taattgatat tatttatatg ataatagttc    5340
attttgtatt ttgttttttt gatattctca cctgcttagt tacaataaat caattctatc    5400
gctgtatggt atagactgtt ttattatata ttttgaatat tttaatctg cccagtctgg    5460
ttttttaaaa aagtgctatc ctcttaatgt ctttactaaa ttagaaaaca gtttcactt    5520
tcaactattg catctttaat taatggtcaa ggtgatttca aatgctcgtt tgtggccagt    5580
tatacctcaa ataactcaag ttgttgagca cagccaacgc acatgcagtt tgacgtatga    5640
caggtatgct ttatttcatt taaattatga tggtttttcca gccaatcagt gagtttctct    5700
tgataaggaa tgcggaatg tctatgtatt ttaataaaat aatttcattt aatattttt    5760
cacgaatagt tatttgtatc ttttttgatat gtggaatgtt catggctggg gcttcagaaa    5820
```

```
aatatgatgc taacgcaccg caacaggtcc agccttattc tgtctcttca tctgcatttg   5880
aaaatctcca tcctaataat gaaatggaga gttcaatcaa tcccttttcc gcatcggata   5940
cagaaagaaa tgctgcaata atagatcgcg ccaataagga gcaggagact gaagcggtga   6000
ataagatgat aagcaccggg gccaggttag ctgcatcagg cagggcatct gatgttgctc   6060
actcaatggt gggcgatgcg gttaatcaag aaatcaaaca gtggttaaat cgattcggta   6120
cggctcaagt taatctgaat tttgacaaaa atttttcgct aaagaaagc tctcttgatt    6180 ggctggctcc ttggtatgac tctgcttcat tcctcttttt tagtcagtta ggtattcgca   6240
ataaagacag ccgcaacaca cttaaccttg gcgtcgggat acgtacattg gagaacggtt   6300
ggctgtacgg acttaatact ttttatgata atgatttgac cggccacaac caccgtatcg   6360
gtcttggtgc cgaggcctgg accgattatt acagttggc tgccaatggg tattttcgcc    6420
tcaatggatg gcactcgtcg cgtgatttct ccgactataa agagcgccca gccactgggg   6480
gggatttgcg cgcgaatgct tatttacctg cactcccaca actgggggg aagttgatgt    6540 atgagcaata caccggtgag cgtgttgctt tatttggtaa agataatctg caacgcaacc   6600
cttatgccgt gactgccggg atcaattaca ccccgtgcc tctactcact gtcgggtag     6660 atcagcgtat ggggaaaagc agtaagcatg aaacacagtg gaacctccaa atgaactatc   6720
gcctgggcga gagttttcag tcgcaactta gcccttcagc ggtggcagga acacgtctac   6780
tggcggagag ccgctataac cttgtcgatc gtaacaataa tatcgtgttg gagtatcaga   6840
aacagcaggt ggttaaactg acattatcgc cagcaactat ctccggcctg ccgggtcagg   6900
tttatcaggt gaacgcacaa gtacaagggg catctgctgt aagggaaatt gtctggagtg   6960
atgccgaact gattgccgct ggcggcacat taacaccact gagtaccaca caattcaact   7020
tggttttacc gccttataaa cgcacagcac aagtgagtcg ggtaacggac gacctgacag   7080
ccaactttta ttcgcttagt gcgctcgcgg ttgatcacca aggaaaccga tctaactcat   7140
tcacattgag cgtcaccgtt cagcagcctc agttgacatt aacggcggcc gtcattggtg   7200
atggcgcacc ggctaatggg aaaactgcaa tcaccgttga gttcaccgtt gctgattttg   7260
aggggaaacc cttagccggg caggaggtgg tgataaccac caataatggt gcgctaccga   7320
ataaaatcac ggaaaagaca gatgcaaatg gcgtcgcgcg cattgcatta accaatacga   7380
cagatggcgt gacggtagtc acagcagaag tggaggggca acggcaaagt gttgataccc   7440
actttgttaa gggtactatc gcggcggata aatccactct ggctgcggta ccgacatcta   7500
tcatcgctga tggtctaatg gcttcaacca tcacgttgga gttgaaggat acctatgggg   7560
acccgcaggc tggcgcgaat gtggcttttg acacaacctt aggcaatatg ggcgttatca   7620
cggatcacaa tgacgcact tatagcgcac cattgaccag taccacgttg ggggtagcaa    7680
cagtaacggt gaaagtggat ggggctgcgt tcagtgtgcc gagtgtgacg gttaatttca   7740
cggcagatcc tattccagat gctggccgct ccagtttcac cgtctccaca ccggatatct   7800
tggctgatgg cacgatgagt tccacattat cctttgtccc tgtcgataag aatggccatt   7860
ttatcagtgg gatgcagggc ttgagtttta ctcaaaacgg tgtgccggtg agtattagcc   7920
ccattaccga gcagccagat agctataccg cgacggtggt tgggaatagt gtcggtgatg   7980
tcacaatcac gccgcaggtt gatacctga tactgagtac attgcagaaa aaaatatccc    8040
tattcccggt acctacgctg accggtattc tggttaacgg gcaaaatttc gctacggata   8100
aagggttccc gaaaacgatc tttaaaaacg ccacattcca gttacagatg gataacgatg   8160
```

```
ttgctaataa tactcagtat gagtggtcgt cgtcattcac acccaatgta tcggttaacg   8220
atcagggtca ggtgacgatt acctaccaaa cctatagcga agtggctgtg acggcgaaaa   8280
gtaaaaaatt cccaagttat tcggtgagtt atcggttcta cccaaatcgg tggatatacg   8340
atggcggcag atcgctggta tccagtctcg aggccagcag acaatgccaa ggttcagata   8400
tgtctgcggt tcttgaatcc tcacgtgcaa ccaacggaac gcgtgcgcct gacgggacat   8460
tgtggggcga gtgggggagc ttgaccgcgt atagttctga ttggcaatct ggtgaatatt   8520
gggtcaaaaa gaccagcacg gattttgaaa ccatgaatat ggacacaggc gcactgcaac   8580
cagggcctgc atacttggcg ttcccgctct gtgcgctgtc aatataacca gataacagat   8640
agcaataaga acagtttaat gagctgatta tttggggcgc gaatgggagt ccggcaatcc   8700
tagactcgcc ccataagtag caaacgtcca gagaacaacg ccgctcaggt taattgagcg   8760
gcgttgtttt tttaaaagga tttgtcgcga taagcgtgag ctggcgttaa atgccgatct   8820
tacgcccag ctgcagcccg gctagtaacg gccgccagtg tgctggaatt cgcccttaat   8880
cggcatcatt caccaagctt gccaggcgac tgtcttcaat attacagccg caactactga   8940
catggcgggt gatggtgttc actattccag ggcgatcggc acccaacgca gtgatcacca   9000
gataatgttg cgatgacagt gtcaaactgg ttattccttc aaggggtgag ttgttcttaa   9060
gcatgccggt ttgctgtaaa gtttagggag atttgatggc ttactctgtt caaaagtcgc   9120
gcctggcaaa ggttgcgggt gtttcgcttg ttttattact cgctgcctgt agttctgact   9180
cacgctataa gcgtcaggtc agtggtgatg aagcctacct ggaagcgcca tggcatgcaa   9240
gggcgaattc tgcagatatc catcacactg gcggccctag accaggcttt acactttatg   9300
cttccggctc gtataatgtg tggaaggatc caggagtaac aatacaaatg gattcaagag   9360
atccatttgt attgttactc ctttgtcgac tggacagttc aagagactgt ccatcaatat   9420
cagctttgtc acaaaccccg ccaccggcgg ggtttttttc tgctctaggg ccgctcgagc   9480
atgcatctag agggcccaat tcgccctata gtgagtcgta ttacaattca ctggccgtcg   9540
ttttacaacg tcgtgactgg gaaaaccctg gcgttaccca acttaatcgc cttgcagcac   9600
atccccctt cgccagctgg cgtaatagcg aagaggcccg caccgatcgc ccttcccaac   9660
agttgcgcag cctgaaaaac gcgccatgg tgtgtaggct ggagctgctt cgaagttcct   9720
atactttcta gagaatagga acttcggaat aggaacttca agatccccca cgctgccgca   9780
agcactcagg gcgcaagggc tgctaaagga acggaacac gtagaaagcc agtccgcaga   9840
aacggtgctg accccggatg aatgtcagct actgggctat ctggacaagg gaaaacgcaa   9900
gcgcaaagag aaagcaggta gcttgcagtg gcttacatg gcgatagcta gactgggcgg   9960
ttttatggac agcaagcgaa ccggaattgc cagctgggc gccctctggt aaggttggga  10020
agccctgcaa agtaaactgg atggctttct tgccgccaag gatctgatgg cgcaggggat  10080
caagatctga tcaagagaca ggatgaggat cgtttcgcat gattgaacaa gatggattgc  10140
acgcaggttc tccggccgct tgggtggaga ggctattcgg ctatgactgg gcacaacaga  10200
caatcggctg ctctgatgcc gccgtgttcc ggctgtcagc gcaggggcgc ccggttcttt  10260
ttgtcaagac cgacctgtcc ggtgccctga atgaactgca ggacgaggca gcgcggctat  10320
cgtggctggc cacgacgggc gttccttgcg cagctgtgct cgacgttgtc actgaagcgg  10380
gaagggactg gctgctattg ggcgaagtgc cggggcagga tctcctgtca tctcaccttg  10440
ctcctgccga gaaagtatcc atcatggctg atgcaatgcg gcggctgcat acgcttgatc  10500
cggctacctg cccattcgac caccaagcga aacatcgcat cgagcgagca cgtactcgga  10560
```

```
tggaagccgg tcttgtcgat caggatgatc tggacgaaga gcatcagggg ctcgcgccag    10620
ccgaactgtt cgccaggctc aaggcgcgca tgcccgacgg cgaggatctc gtcgtgaccc    10680
atggcgatgc ctgcttgccg aatatcatgg tggaaaatgg ccgcttttct ggattcatcg    10740 actgtgccg gctgggtgtg gcggaccgct atcaggacat agcgttggct acccgtgata    10800
ttgctgaaga gcttggcggc gagtgggctg accgcttcct cgtgctttac ggtatcgccg    10860
ctcccgattc gcagcgcatc gccttctatc gccttcttga cgagttcttc tgagcgggac    10920
tctggggttc gaaatgaccg accaagcgac gcccaacctg ccatcacgag atttcgattc    10980
caccgccgcc ttctatgaaa ggttgggctt cggaatcgtt ttccgggacg ccggctggat    11040
gatcctccag cgcggggatc tcatgctgga gttcttcgcc caccccagct caaaagcgc    11100 tctgaagttc ctatactttc tagagaatag gaacttcgga ataggaacta aggaggatat    11160
tcatatggac catggcgcgg catgcaagct cggtatcatt gcagcactgg ggccagatgg    11220
taagccctcc cgtatcgtag ttatctacac gacggggagt caggcaacta tggatgaacg    11280
aaatagacag atcgctgaga taggtgcctc actgattaag cattggtaac tgtcagacca    11340
agtttactca tatatacttt agattgattt aaaacttcat ttttaattta aaaggatcta    11400
ggtgaagatc cttttgata atctcatgac caaaatccct taacgtgagt tttcgttcca    11460
ctgagcgtca gacccgtag aaaagatcaa aggatcttct tgagatcctt ttttctgcg    11520 cgtaatctgc tgcttgcaaa caaaaaaacc accgctacca gcggtggttt gtttgccgga    11580
tcaagagcta ccaactcttt ttccgaaggt aactggcttc agcagagcgc agataccaaa    11640
tactgttctt ctagtgtagc cgtagttagg ccaccacttc aagaactctg tagcaccgcc    11700 tacataccte gctctgctaa tcctgttacc agtggctgct gccagtggcg ataagtcgtg    11760
tcttaccggg ttggactcaa gacgatagtt accggataag gcgcagcggt cgggctgaac    11820
ggggggttcg tgcacacagc ccagcttgga gcgaacgacc tacaccgaac tgagatacct    11880
acagcgtgag ctatgagaaa gcgccacgct tcccgaaggg agaaaggcgg acaggtatcc    11940
ggtaagcggc agggtcggaa caggagagcg cacgagggag cttccagggg gaaacgcctg    12000
gtatctttat agtcctgtcg ggtttcgcca cctctgactt gagcgtcgat ttttgtgatg    12060
ctcgtcaggg gggcggagcc tatggaaaaa cgccagcaac gcggccttt tacggttcct    12120 ggccttttgc tggccttttg ctcacatgtt ctttcctgcg ttatcccctg attctgtgga    12180
taaccgtatt accgcctttg agtgagctga taccgctcgc cgcagccgaa cgaccgagcg    12240
cagcgagtca gtgagcgagg aagcggaaga gcgcccaata cgcaaaccgc ctctccccgc    12300
gcgttggccg attcattaat gcagctggca cgacagtatc gataagcttg ataagctttt    12360
aaatcagcag gggtctttt ggcttgtgta ttatttgaa gtttttcttc cccgacagaa    12420 tctgcttta ccgtcatagt gaaatgagcc tgaaagcta ttaccatgat gatacaaata    12480
agtttacttt tcatttcacc gctccttttt aattcgtaaa actaagttta gccaccctac    12540
aactaatctg acagagagag ttaaggacac gttttttagt atatgtggga actaaattat    12600
acgttttgca gtagaaacta taggtggctt aaacttggg atatgcttat attatatgga    12660
taaacagtca gatattcttt tacatttgtt aattcttcta aaaaaattaa aaaataagcc    12720
tgtttctaca ttcttcacaa aataatttac gaagagtgca aaacaagctt attttttcgt    12780
gtgtgttaag cggttttatt cttaattttt tattactttt acaattattc gattggatta    12840
tctactttat tactatattt cggataaagc gtggtgcccc agatggagat atttctattt    12900
```

-continued

```
ttcacaagtg gtaagttccg gtcatcaatt accgttctcc accattccca agctaaacca    12960
gtgcattctt tagcgtaaac attaatattt ctcgcgttac ctggcaaata gatggacgat    13020
gtgaaatgag ctagcttgct tttattgttt tcgctccagt ttttatgttg aacaatttcg    13080
ttaccttcag gatcataatt tacttcatcc caagaaatgt tgaattgagc aacgtatcct    13140
ccagagtgat cgatgttaat ttttccatct gtataagctt ttgaagttgt ttcaatatat    13200
tctgagttgt ttttaataac agctaattca ttgtctttta ggaagtttgt tgtataagca    13260
atgggaactc ctggtgtttc tcgattaaaa gtagcgcctt ttttcaaaat atcgcgtaag    13320
tctccgaggt tgccgtcgat gatttgaact tcatcttttg cggaacctcc gtaaattacg    13380
gctttgaagg aagaattttt gatgatattt gttagttcta catcacctga gacagatttt    13440
ccgcttacgg cagcatcaaa agcagctttt actttagtac tatgggaatt agttgataat    13500
ttcaaataaa cttgacggcc atacgccaca cttgagatat atgcaggagg attttctgca    13560
ttcactccaa gcgcttgcaa ctgctcttta gtaacagctt tgccgaaaaa tctggaaggt    13620
cttgtaggtt cattaacatt cacgttatag taaatttgtt taaaactaat gacttcttct    13680
tgcattttcc cttcactgat tgcgccgaag tttacattca agctattatt tacagcttta    13740
aatgctgtac caaatttcgc aattaattgt gattcactgt aagccatttc gtcatcataa    13800
tcaattttg cacttacatt tggataagct tgagcatatt tttcattcca tctttccact    13860
aatgtattta ctgcgttgtt aacgtttgat ttagtggcat ttttttacaac gattttattg    13920
tcttgattag tcatacctgg caaatcaatg ctgagtgtta atgaatcacg ttttacaggg    13980
agaacatctg gttgattttc tactaattcc gaattcgctt ttacgagagc acctggatag    14040
gttaggctcg aaattgcatt cacaacttga atgtctgcat tattttgatt gatggatttc    14100
ttcttttct ccacaacaat atattcattt ccatctttgt aaccttttct tggcggcaca    14160
tttgtcactg catctccgtg gtatactaat acattgtttt tattgtaatc caatccttgt    14220
atatacttat cgatttcatc cgcgtgtttc ttttcgattg gcgtcttagg acttgcaggc    14280
ggagatgctg gtggtgccat ggatgaaatt gaattttctt tattgaatgc agatgcatcc    14340
tttgcttcag tttgttgcgc aattggtaga ctaactaata taagtgtaat aaaaactagc    14400
attatttttt tcatgggttt cactctcctt ctacattttt taacctaata atgccaaata    14460
ccgtttgcca cccctctctt ttgataatta taatattggc gaaattcgct tctaaagatg    14520
aaacgcaata ttatatgctt gctttatagc tttattctag tcctgctgtc cctttatcgt    14580
cgttaacaaa tgttaatgcc tcaacataaa agtcacttta agataggaat atactaatca    14640
aaggagggat cgaattcctg cagtcatcaa ggcaaccatc aggattaatg cggatattgc    14700
ggagtaacac ttcagactga aagtagaaat aaaaaccgca gcagacaact gacaacatca    14760
aatgaagggg gcttattcta attgatatta tttatatgat aatagttcat tttgtatttt    14820
gtttttttga tattctcacc tgcttagtta caataaatca attctatcgc tgtatggtat    14880
agactgtttt attatatatt ttgaatattt ttaatctgcc cagtctggtt ttttaaaaaa    14940
gtgctatcct cttaatgtct ttactaaatt agaaaacaag tttcactttc aactattgca    15000
tctttaatta atggtcaagg tgatttcaaa tgctcgtttg tggccagtta tacctcaaat    15060
aactcaagtt gttgagcaca gccaacgcac atgcagtttg acgtatgaca ggtatgcttt    15120
atttcattta aattatgatg gttttccagc caatcagtga gtttctcttg ataaggaatg    15180
cgggaatgtc tatgtatttt aataaaataa tttcatttaa tattatttca cgaatagtta    15240
tttgtatctt tttgatatgt ggaatgttca tggctggggc ttcagaaaaa tatgatgcta    15300
```

```
acgcaccgca acaggtccag ccttattctg tctcttcatc tgcatttgaa aatctccatc   15360
ctaataatga aatggagagt tcaatcaatc ccttttccgc atcggataca gaaagaaatg   15420
ctgcaataat agatcgcgcc aataaggagc aggagactga agcggtgaat aagatgataa   15480
gcaccggggc caggttagct gcatcaggca gggcatctga tgttgctcac tcaatggtgg   15540
gcgatgcggt taatcaagaa atcaaacagt ggttaaatcg attcggtacg gctcaagtta   15600
atctgaattt tgacaaaaat ttttcgctaa agaaagctc tcttgattgg ctggctcctt    15660
ggtatgactc tgcttcattc ctcttttta gtcagttagg tattcgcaat aaagacagcc    15720
gcaacacact taaccttggc gtcgggatac gtacattgga gaacggttgg ctgtacggac   15780
ttaatacttt ttatgataat gatttgaccg gccacaacca ccgtatcggt cttggtgccg   15840
aggcctggac cgattattta cagttggctg ccaatgggta ttttcgcctc aatggatggc   15900
actcgtcgcg tgatttctcc gactataaag agcgcccagc cactgggggg gatttgcgcg   15960
cgaatgctta tttacctgca ctcccacaac tggggggaa gttgatgtat gagcaataca    16020
ccggtgagcg tgttgcttta tttggtaaag ataatctgca acgcaaccct tatgccgtga   16080
ctgccgggat caattacacc cccgtgcctc tactcactgt cggggtagat cagcgtatgg   16140
ggaaaagcag taagcatgaa acacagtgga acctccaaat gaactatcgc ctgggcgaga   16200
gttttcagtc gcaacttagc ccttcagcgg tggcaggaac acgtctactg gcggagagcc   16260
gctataacct tgtcgatcgt aacaataata tcgtgttgga gtatcagaaa cagcaggtgg   16320
ttaaactgac attatcgcca gcaactatct ccggcctgcc gggtcaggtt tatcaggtga   16380
acgcacaagt acaaggggca tctgctgtaa gggaaattgt ctggagtgat gccgaactga   16440
ttgccgctgg cggcacatta acaccactga gtaccacaca attcaacttg gttttaccgc   16500
cttataaacg cacagcacaa gtgagtcggg taacggacga cctgacagcc aactttttatt  16560 cgcttagtgc gctcgcggtt gatcaccaag gaaaccgatc taactcattc acattgagcg   16620
tcaccgttca gcagcctcag ttgacattaa cggcggccgt cattggtgat ggcgcaccgg   16680
ctaatgggaa aactgcaatc accgttgagt tcaccgttgc tgattttgag gggaaaccct    16740
tagccgggca ggaggtggtg ataaccacca ataatggtgc gctaccgaat aaaatcacgg   16800
aaaagacaga tgcaaatggc gtcgcgcgca ttgcattaac caatacgaca gatggcgtga   16860
cggtagtcac agcagaagtg gaggggcaac ggcaaagtgt tgatacccac tttgttaagg   16920
gtactatcgc ggcggataaa tccactctgg ctgcggtacc gacatctatc atcgctgatg   16980
gtctaatggc ttcaaccatc acgttggagt tgaaggatac ctatggggac ccgcaggctg   17040
gcgcgaatgt ggcttttgac acaaccttag gcaatatggg cgttatcacg gatcacaatg   17100
acggcactta tagcgcacca ttgaccagta ccacgttggg ggtagcaaca gtaacggtga   17160
aagtggatgg ggctgcgttc agtgtgccga gtgtgacggt taatttcacg gcagatccta    17220
ttccagatgc tggccgctcc agtttcaccg tctccacacc ggatatcttg gctgatggca   17280
cgatgagttc cacattatcc tttgtccctg tcgataagaa tggccatttt atcagtggga    17340
tgcagggctt gagttttact caaaacggtg tgccggtgag tattagcccc attaccgagc   17400
agccagatag ctataccgcg acggtggttg ggaatagtgt cggtgatgtc acaatcacgc   17460
cgcaggttga taccctgata ctgagtacat tgcagaaaaa aatatcccta ttcccggtac   17520
ctacgctgac cggtattctg gttaacgggc aaaatttcgc tacggataaa gggttcccga   17580
aaacgatctt taaaaacgcc acattccagt tacagatgga taacgatgtt gctaataata   17640
```

```
ctcagtatga gtggtcgtcg tcattcacac ccaatgtatc ggttaacgat cagggtcagg  17700
tgacgattac ctaccaaacc tatagcgaag tggctgtgac ggcgaaaagt aaaaaattcc  17760
caagttattc ggtgagttat cggttctacc caaatcggtg gatatacgat ggcggcagat  17820
cgctggtatc cagtctcgag gccagcagac aatgccaagg ttcagatatg tctgcggttc  17880
ttgaatcctc acgtgcaacc aacggaacgc gtgcgcctga cgggacattg tggggcgagt  17940
gggggagctt gaccgcgtat agttctgatt ggcaatctgg tgaatattgg gtcaaaaaga  18000
ccagcacgga ttttgaaacc atgaatatgg acacaggcgc actgcaacca gggcctgcat  18060
acttggcgtt cccgctctgt gcgctgtcaa tataaccaga taacagatag caataagaac  18120
agtttaatga gctgattatt tggggcgcga atgggagtcc ggcaatccta gactcgcccc  18180
ataagtagca aacgtccaga gaacaacgcc gctcaggtta attgagcggc gttgttttt   18240 taaaaggatt tgtcgcgata agcgtgagct ggcgttaaat gccgatctta cggcccagct  18300
gcagcccggc tagtaacggc cgccagtgtg ctggaattcg cccttaatcg gcatcattca  18360
ccaagcttgc caggcgactg tcttcaatat tacagccgca actactgaca tggcgggtga  18420
tggtgttcac tattccaggg cgatcggcac ccaacgcagt gatcaccaga taatgttgcg  18480
atgacagtgt caaactggtt attccttcaa ggggtgagtt gttcttaagc atgccggttt  18540
gctgtaaagt ttagggagat ttgatggctt actctgttca aaagtcgcgc ctggcaaagg  18600
ttgcgggtgt ttcgcttgtt ttattactcg ctgcctgtag ttctgactca cgctataagc  18660
gtcaggtcag tggtgatgaa gcctacctgg aagcgccatg gcatgcaagg gcgaattctg  18720
cagatatcca tcacactggc ggccctagac caggctttac actttatgct tccggctcgt  18780
ataatgtgtg gaaggatcca ggagtaacaa tacaaatgga ttcaagagat ccatttgtat  18840
tgttactcct ttgtcgactg gacagttcaa gagactgtcc atcaatatca gctttgtcac  18900 aaacccccgcc accggcgggg ttttttttctg ctctag                         18936
```

<210> SEQ ID NO 563
<211> LENGTH: 8
<212> TYPE: DNA
<213> ORGANISM: Artificial Sequence
<220> FEATURE:
<223> OTHER INFORMATION: Loop Sequence

<400> SEQUENCE: 563 gagacagg                                                                8

BACTERIA MEDIATED GENE SILENCING

RELATED APPLICATIONS

This application is a continuation of U.S. application Ser. No. 12/157,969, which claims priority to, and the benefit of, U.S. Provisional Patent Application No. 60/934,751, filed Jun. 15, 2007 and U.S. Provisional Patent Application No. 61/010,028, filed Jan. 4, 2008. The contents of each of these applications are herein incorporated by reference in their entireties.

SEQUENCE LISTING

This application includes a sequence listing submitted electronically as an ASCII file created on Oct. 30, 2016, named MAR363US_SL.txt, which is 183,172 bytes in size, and is hereby incorporated by reference in its entirety.

BACKGROUND

Gene silencing through RNAi (RNA-interference) by use of short interfering RNA (siRNA) has emerged as a powerful tool for molecular biology and holds the potential to be used for therapeutic gene silencing. Short hairpin RNA (shRNA) transcribed from small DNA plasmids within the target cell has also been shown to mediate stable gene silencing and achieve gene knockdown at levels comparable to those obtained by transfection with chemically synthesized siRNA (T. R. Brummelkamp, R. Bernards, R. Agami, *Science* 296, 550 (2002), P. J. Paddison, A. A. Caudiy, G. J. Hannon, *PNAS* 99, 1443 (2002)).

Possible applications of RNAi for therapeutic purposes are extensive and include silencing and knockdown of disease genes such as oncogenes or viral genes. One major obstacle for the therapeutic use of RNAi is the delivery of siRNA to the target cell (Zamore P D, Aronin N. *Nature Medicine* 9,(3):266-8 (2003)). In fact, delivery has been described as the major hurdle now for RNAi (Phillip Sharp, cited by Nature news feature, Vol 425, 2003, 10-12).

Therefore, new methods are needed for the safe and predictable administration of interfering RNAs to mammals.

SUMMARY OF THE INVENTION

The present invention provides at least one invasive bacterium, or at least one bacterial therapeutic particle (BTP), including one or more siRNAs or one or more DNA molecules encoding one or more siRNAs. The present invention also provides at least one prokaryotic vector including at least one DNA molecule encoding one or more siRNAs and at least one RNA-polymerase III compatible promoter or at least one prokaryotic promoter, wherein the expressed siRNAs interfere with at least one mRNA of a gene of interest.

The present invention also provides methods of using the various bacterium, BTP and vectors provided in the invention. For example, the present invention provides methods of delivering one or more siRNAs to mammalian cells. The methods include introducing at least one invasive bacterium, or at least one bacterial therapeutic particle (BTP), containing one or more siRNAs or one or more DNA molecules encoding one or more siRNAs to the mammalian cells.

The present invention also provides methods of regulating gene expression in mammalian cells. The method includes introducing at least one invasive bacterium, or at least one bacterial therapeutic particle (BTP), containing one or more siRNAs or one or more DNA molecules encoding one or more siRNAs to the mammalian cells, where the expressed siRNAs interfere with at least one mRNA of a gene of interest thereby regulating gene expression.

The present invention also provides methods of treating or preventing a viral disease or disorder in a mammal. The methods include regulating the expression of at least one gene in a cell known to cause a viral disease or disorder (e.g., known to increase proliferation, growth or dysplasia) by introducing to the cells of the mammal at least one invasive bacterium, or at least one bacterial therapeutic particle (BTP), containing one or more siRNAs or one or more DNA molecules encoding one or more siRNAs, where the expressed siRNAs interfere with the mRNA of the gene known to cause a viral disease or disorder.

Preferably, the viral disease or disorder can be, but is not limited to, infection, epithelial dysplasia and cancer caused by HPV infection The present invention also provides a composition containing at least one invasive bacterium or BTP and a pharmaceutically acceptable carrier. The present invention also provides a eukaryotic host cell containing at least one invasive bacterium or BTP and a pharmaceutically acceptable carrier.

The invasive bacterium or BTPs of the present invention can be non-pathogenic, non-virulent bacterium or therapeutic bacterium The mammalian cells can be ex vivo, in vivo or in vitro. The mammalian cells can be, but are not limited to, human, bovine, ovine, porcine, feline, buffalo, canine, goat, equine, donkey, deer, avian, bird, chicken, and primate cells. Preferably, the mammalian cells are human cells. In some preferred embodiments, the mammalian cells can be, but are not limited to, gastrointestinal epithelial cells, macrophages, cervical epithelial cells, rectal epithelial cells and a pharyngeal epithelial cells.

The mammalian cells can be infected with about $10^3$ to $10^{11}$ viable invasive bacterium or BTPs (or any integer within said ranges). Preferably, the mammalian cells can be infected with about $10^5$ to $10^9$ viable invasive bacterium or BTPs (or any integer within said ranges). The mammalian cells can be infected at a multiplicity of infection ranging from about 0.1 to $10^6$ (or any integer within said ranges). Preferably, the mammalian cells can be infected at a multiplicity of infection ranging from about $10^2$ to $10^4$ (or any integer within said ranges).

The mammal can be, but is not limited to, human, bovine, ovine, porcine, feline, buffalo, canine, goat, equine, donkey, deer, avian, bird, chicken, and primate. Preferably, the mammal is a human.

The one or more DNA molecules encoding the one or more siRNAs can be transcribed within the animal cell or transcribed within the bacterium. Preferably, the one or more siRNAs are transcribed within the animal cell as shRNAs.

The one or more DNA molecules encoding the one or more siRNAs can include one or more promoter sequences, enhancer sequences, terminator sequences, invasion factor sequences or lysis regulation sequences. The promoter can be a prokaryotic promoter. Preferably, the prokaryotic promoter is a T7 promoter, a $P_{gapA}$ promoter, a $P_{araBAD}$ promoter, a $P_{tac}$ promoter, a $P_{lacUV5}$ promoter, or a recA promoter.

The expressed siRNAs can direct the multienzyme complex RNA-induced silencing complex of the cell to interact with the mRNA of one or more genes of interest. Preferably, the siRNAs interact with the mRNA of one or more HPV oncogenes. Preferably, the complex can degrade the mRNA.

Preferably, the expression of one or more genes of interest is decreased or inhibited. The expression is decreased or inhibited as compared to the expression of the gene prior to administration or treatment with an invasive bacterium or BTP containing one or more siRNA or a DNA encoding for one or more siRNAs. Preferably, the expression of one or more HPV oncogenes is decreased or inhibited.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents, and other references mentioned herein are incorporated by reference. In the case of conflict, the present specification, including definitions, will control. In addition, the materials, methods, and examples are illustrative only and are not intended to be limiting.

Other features and advantages of the invention will be apparent from the following detailed description and claims.

DETAILED DESCRIPTION OF THE INVENTION

Figure 1:
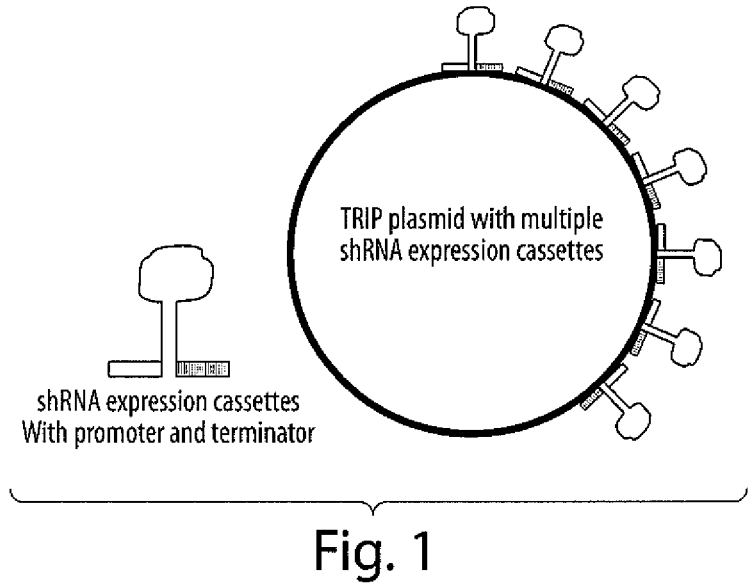
FIG. 1 is a schematic showing the Transkingdom RNA Interference Plasmid (TRIP) with multiple hairpin express cassettes.

The invention pertains to compositions and methods of delivering small interfering RNAs (siRNAs) to eukaryotic cells using non-pathogenic or therapeutic strains of bacteria or bacterial therapeutic particles (BTPs). The bacteria or BTPs deliver DNA encoding siRNA, or siRNA itself, to effect RNA interference (RNAi)) by invading into the eukaryotic host cells. Generally, to trigger RNA interference in a target cell, it is required to introduce siRNA into the cell. The siRNA is either introduced into the target cell directly or by transfection or can be transcribed within the target cell as hairpin-structured dsRNA (shRNA) from specific plasmids with RNA-polymerase III compatible promoters (e.g., U6, H1) (P. J. Paddison, A. A. Caudiy, G. J. Hannon, *PNAS* 99, 1443 (2002), T. R. Brummelkamp, R. Bernards, R. Agami, *Science* 296, 550 (2002)).

The interfering RNA of the invention regulates gene expression in eukaryotic cells. It silences or knocks down genes of interest inside target cells (e.g., decreases gene activity). The interfering RNA directs the cell-owned multienzyme-complex RISC (RNA-induced silencing complex) to the mRNA of the gene to be silenced. Interaction of RISC and mRNA results in degradation or sequestration of the mRNA. This leads to effective post-transcriptional silencing of the gene of interest. This method is referred to as Bacteria Mediated Gene Silencing (BMGS).

In the case of BMGS through delivery of siRNA expressing DNA plasmids, shRNA or siRNA are produced within the target cell after liberation of the eukaryotic transcription plasmid and trigger the highly specific process of mRNA degradation, which results in silencing of the targeted gene. Additionally, one or more cell-specific eukaryotic promoters may be used that limit the expression of siRNA or shRNA to specific target cells or tissues that are in particular metabolic states. In one embodiment of this method, the cell-specific promoter is albumin and the target cell or tissue is the liver. In another embodiment of this method, the cell-specific promoter is keratin and the specific target cell or tissue is the skin.

The non-virulent bacteria and BTPs of the invention have invasive properties (or are modified to have invasive properties) and may enter a mammalian host cell through various mechanisms. In contrast to uptake of bacteria or BTPs by professional phagocytes, which normally results in the destruction of the bacterium or BTP within a specialized lysosome, invasive bacteria or BTP strains have the ability to invade non-phagocytic host cells. Naturally occurring examples of such bacteria or BTPs are intracellular pathogens such as *Yersinia, Rickettsia, Legionella, Brucella, Mycobacterium, Helicobacter, Coxiella, Chlamydia, Neisseria, Burkolderia, Bordetella, Borrelia, Listeria, Shigella, Salmonella, Staphylococcus, Streptococcus, Porphyromonas, Treponema,* and *Vibrio,* but this property can also be transferred to other bacteria or BTPs such as *E. coli, Lactobacillus* or *Bifidobacteriae,* including probiotics through transfer of invasion-related genes (P. Courvalin, S. Goussard, C. Grillot-Courvalin, *C.R. Acad. Sci. Paris* 318, 1207 (1995)). In other embodiments of the invention, bacteria or BTPs used to deliver interfering RNAs to host cells include *Shigella flexneri* (D. R. Sizemore, A. A. Branstrom, J. C. Sadoff, *Science* 270, 299 (1995)), invasive *E. coli* (P. Courvalin, S. Goussard, C. Grillot-Courvalin, *C.R. Acad. Sci. Paris* 318,1207 (1995), C. Grillot-Courvalin, S. Goussard, F. Huetz, D. M. Ojcius, P. Courvalin, *Nat Biotechnol* 16, 862 (1998)), *Yersinia enterocolitica* (A. Al-Mariri A, A. Tibor, P. Lestrate, P. Mertens, X. De Bolle, J. J. Letesson *Infect Immun* 70, 1915 (2002)) and *Listeria monocytogenes* (M. Hense, E. Domann, S. Krusch, P. Wachholz, K. E. Dittmar, M. Rohde, J. Wehland, T. Chakraborty, S. Weiss, *Cell Microbiol* 3, 599 (2001), S. Pilgrim, J. Stritzker, C. Schoen, A. Kolb-Mäurer, G. Geginat, M. J. Loessner, I. Gentschev, W. Goebel, *Gene Therapy* 10, 2036 (2003)). Any invasive bacterium or BTP is useful for DNA transfer into eukaryotic cells (S. Weiss, T. Chakraborty, *Curr Opinion Biotechnol* 12, 467 (2001)).

BMGS is performed using the naturally invasive pathogen *Salmonella typhimurium.* In one aspect of this embodiment, the strains of *Salmonella typhimurium* include SL 7207 and VNP20009 (S. K. Hoiseth, B. A. D. Stocker, *Nature* 291, 238 (1981); Pawelek J M, Low K B, Bermudes D. *Cancer Res.* 57(20): 4537-44 (Oct. 15, 1997)). In another embodiment of the invention, BMGS is performed using attenuated *E. coli.* In another aspect of this embodiment, the CEQ201strain is engineered to possess cell-invading properties through an invasion plasmid. In one aspect of the invention, this plasmid is a TRIP (Transkingdom RNA interference plasmid) plasmid or pNJSZ.

A double "trojan horse" technique is also used with an invasive and auxotrophic bacterium or BTP carrying a eukaryotic transcription plasmid. This plasmid is, in turn, transcribed by the target cell to form one or more hairpin RNA structures that triggers the intracellular process of RNAi. This method of the invention induces significant gene silencing of a variety of genes. In certain aspects of this embodiment, the genes include a transgene (GFP), a mutated oncogene (k-Ras) and a cancer related gene (β-catenin) in vitro.

Another aspect of BMGS according to this invention is termed Transkingdom RNAi (tkRNAi). In this aspect of the invention, siRNA is directly produced by the invasive bacteria, or accumulated in the BTPs after production in the bacteria, as opposed to the target cell. A transcription plasmid controlled by a prokaryotic promoter (e.g., T7) is inserted into the carrier bacteria through standard transformation protocols. siRNA is produced within the bacteria and is liberated within the mammalian target cell after bacterial lysis triggered either by auxotrophy or by timed addition of antibiotics.

The RNAi methods of the invention, including BMGS and tkRNAi are used to create transient "knockdown" genetic animal models as opposed to genetically engineered knockout models to discover gene functions. The methods are also used as in vitro transfection tool for research and drug development These methods use bacteria with desirable properties (invasiveness, attenuation, steerability) to perform BMGS and tkRNAi. Invasiveness as well as eukaryotic or prokaryotic transcription of one or several shRNA is conferred to a bacterium or BTP using plasmids (e.g., TRIP) and vectors as described in greater detail herein.

1. Bacterium and/or Bacterial Therapeutic Particles (BTPs)

The present invention provides at least one invasive bacterium, or at least one bacterial therapeutic particle (BTP), including one or more siRNAs or one or more DNA molecules encoding one or more siRNAs.

According to the invention, any microorganism that is capable of delivering a molecule, e.g., an RNA molecule or an RNA-encoding DNA molecule, into the cytoplasm of a target cell, such as by traversing the membrane and entering the cytoplasm of a cell, can be used to deliver RNA to such cells. In a preferred embodiment, the microorganism is a prokaryote. In an even more preferred embodiment, the prokaryote is a bacterium or BTP. Also within the scope of the invention are microorganisms other than bacteria that can be used for delivering RNA to a cell. For example, the microorganism can be a fungus, e.g., *Cryptococcus neoformans,* protozoan, e.g., *Trypanosoma cruzi, Toxoplasma gondii, Leishmania donovani,* and *plasmodia.*

In a preferred embodiment, the microorganism is a bacterium or BTP. A preferred invasive bacterium or BTP is capable of delivering at least one molecule, e.g., an RNA or RNA-encoding DNA molecule, to a target cells, such as by entering the cytoplasm of a eukaryotic cell. Preferably, the RNA is siRNA or shRNA and the RNA-encoding DNA molecule encodes for siRNA or shRNA.

BTPs are fragments of bacteria used for therapeutic or preventive purposes. BTPs may include particles known in the art as minicells. Minicells are small cells produced by cell division that is faulty near the pole. They are devoid of nucleoid and, therefore, unable to grow and form colonies (Alder et al., (1967) Proc. Nat. Acad. Sci. U.S.A. 57, 321-326; for reviews see Sullivan and Maddock, (2000) Curr. Biol. 10:R249-R252; Margolin, (2001) Curr. Biol. 11, R395-R398; Howard and Kruse, (2005) J. Cell Biol. 168, 533-536). Minicell formation results due to mutations causing a defect in selection of the site for the septum formation for cell division. Such mutations include null alleles of minC, minD (Davie et al, (1984) J. Bacteriol. 158, 1202-1203; de Boer et al., 1988) J. Bacteriol. 170, 2106-2112) and certain alleles of ftsZ (Bi and Lutkenhaus, (1992) J. Bacteriol. 174, 5414-5423). Overexpression of FtsZ or MinC-MinD proteins has also been reported to cause the formation of minicells (Ward and Lutkenhaus, 1985; de Boer et al., 1988). Although minicells are devoid of nucleoid, they are capable of transcription and translation (Roozen et al., (1971) J. Bacteriol. 107, 21-33; Shepherd et al., (2001) J. Bacteriol. 183, 2527-34).

BTPs are distinct from bacteria in that they lack the bacterial genome and, therefore, provide a decreased risk of bacterial proliferation in patients. This is of particular value for immune-compromised patients. Furthermore, the inability of BTPs to proliferate allows for their use in sensitive tissues, e.g., the brain, and other areas of the body traditionally considered inaccessible to traditional siRNA. For example, the intraperitoneal delivery of bacteria can include the risk of adhesions and peritonitis, which is eliminated by utilizing BTPs. However, like the bacteria of this invention, BTPs contain the bacterial cell wall, some bacterial plasma contents and subcellular particles, one or more therapeutic components, e.g., one or more siRNAs, one or more invasion factors, one or more phagosome degradation factors, and one or more factors for targeting specific tissues. The BTPs are produced from bacteria that have produced and accumulated siRNAs inside the bacteria, and then segregate the bacterial fragment (BTP) during cell division. In one embodiment of this invention, BTPs are obtained by fermenting the bacteria, during which the BTPs form abundantly, followed by isolation of the BTPs from live bacteria using differential size filtration, which will retain the bacteria but allow passage and collection of BTPs. In another embodiment of this invention, BTPs are separated from bacteria by centrifugation. In another embodiment of this invention, live bacterial cells are lysed through activation of a death signal. Once isolated, the BTPs can be lyophilized and formulated for use.

As used herein, the term "invasive" when referring to a microorganism, e.g., a bacterium or BTP, refers to a microorganism that is capable of delivering at least one molecule, e.g., an RNA or RNA-encoding DNA molecule, to a target cell. An invasive microorganism can be a microorganism that is capable of traversing a cell membrane, thereby entering the cytoplasm of said cell, and delivering at least some of its content, e.g., RNA or RNA-encoding DNA, into the target cell. The process of delivery of the at least one molecule into the target cell preferably does not significantly modify the invasion apparatus.

Invasive microorganisms include microorganisms that are naturally capable of delivering at least one molecule to a target cell, such as by traversing the cell membrane, e.g., a eukaryotic cell membrane, and entering the cytoplasm, as well as microorganisms which are not naturally invasive and which have been modified, e.g., genetically modified, to be invasive. In another preferred embodiment, a microorganism that is not naturally invasive can be modified to become invasive by linking the bacterium or BTP to an "invasion factor", also termed "entry factor" or "cytoplasm-targeting factor". As used herein, an "invasion factor" is a factor, e.g., a protein or a group of proteins which, when expressed by a non-invasive bacterium or BTP, render the bacterium or BTP invasive. As used herein, an "invasion factor" is encoded by a "cytoplasm-targeting gene".

In one embodiment of this invention, the microorganism is a naturally invasive bacterium or BTP selected from the group that includes, but is not limited to, *Yersinia*, *Rickettsia*, *Legionella*, *Brucella*, *Mycobacterium*, *Helicobacter*, *Coxiella*, *Chlamydia*, *Neisseria*, *Burkolderia*, *Bordetella*, *Borrelia*, *Listeria*, *Shigella*, *Salmonella*, *Staphylococcus*, *Streptococcus*, *Porphyromonas*, *Treponema*, *Vibrio*, *E. coli*, and *Bifidobacteriae*. Optionally, the naturally invasive bacterium or BTP is *Yersinia* expressing an invasion factor selected from the group including, but not limited to, invasin and YadA (*Yersinia enterocolitica* plasmid adhesion factor). Optionally, the naturally invasive bacterium or BTP is *Rickettsia* expressing the invasion factor RickA (actin polymerization protein). Optionally, the naturally invasive bacterium or BTP is *Legionella* expressing the invasion factor RaIF (guanine exchange factor). Optionally, the naturally invasive bacterium or BTP is *Neisseria* expressing an invasion factor selected from the group including, but not limited to, NadA (*Neisseria* adhesion/invasion factor), OpA and OpC (opacity-associated adhesions). Optionally, the naturally invasive bacterium or BTP is *Listeria* expressing an invasion factor selected from the group including, but not limited to, In1A (internalin factor), In1B (internalin factor), Hpt (hexose phosphate transporter), and ActA (actin polymerization protein). Optionally, the naturally invasive bacterium or BTP is *Shigella* expressing an invasion factor selected from the group including, but not limited to, the *Shigella* secreting factors IpaA (invasion plasmid antigen), IpaB, IpaC, IpgD, IpaB-IpaC complex, VirA, and IcsA. Optionally, the naturally invasive bacterium or BTP is *Salmonella* expressing an invasion factor selected from the group including, but not limited to, *Salmonella* secreting/exchange factors SipA, SipC, SpiC, SigD, SopB, SopE, SopE2, and SptP. Optionally, the naturally invasive bacterium or BTP is *Staphylococcus* expressing an invasion factor selected from the group including, but not limited to, the fibronectin binding proteins FnBPA and FnBPB. Optionally, the naturally invasive bacterium or BTP is *Streptococcus* expressing an invasion factor selected from the group including, but not limited to, the fibronectin binding proteins ACP, Fba, F2, Sfb1, Sfb2, SOF, and PFBP. Optionally, the naturally invasive bacterium or BTP is *Porphyromonas gingivalis* expressing the invasion factor FimB (integrin binding protein fibriae).

In another embodiment of this invention, the microorganism is a bacterium or BTP that is not naturally invasive but has been modified, e.g., genetically modified, to be invasive. Optionally, the bacterium or BTP that is not naturally invasive has been genetically modified to be invasive by expressing an invasion factor selected from the group including, but not limited to, invasin, YadA, RickA, RaIF, NadA, OpA, OpC, In1A, In1B, Hpt, ActA, IpaA, IpaB, IpaC, IpgD, IpaB-IpaC complex, VirA, IcsA, SipA, SipC, SpiC, SigD, SopB, SopE, SopE2, SptP, FnBPA, FnBPB, ACP, Fba, F2, Sfb1, Sfb2, SOF, PFBP, and FimB.

In another embodiment of this invention, the microorganism is a bacterium or BTP that may be naturally invasive but has been modified, e.g., genetically modified, to express one or more additional invasion factors. Optionally, the invasion factor is selected from the group that includes, but is not limited to, invasin, YadA, RickA, RaIF, NadA, OpA, OpC, In1A, In1B, Hpt, ActA, IpaA, IpaB, IpaC, IpgD, IpaB-IpaC complex, VirA, IcsA, SipA, SipC, SpiC, SigD, SopB, SopE, SopE2, SptP, FnBPA, FnBPB, ACP, Fba, F2, Sfb1, Sfb2, SOF, PFBP, and FimB Naturally invasive microorganisms, e.g., bacteria or BTPs, may have a certain tropism, i.e., preferred target cells. Alternatively, microorganisms, e.g., bacteria or BTPs can be modified, e.g., genetically, to mimic the tropism of a second microorganism. Optionally, the bacterium or BTP is *Strep-* tococcus and the preferred target cells are selected from the group including, but not limited to, pharyngeal epithelial cells, buccal epithelial cells of the tongue, and mucosal epithelial cells. Optionally, the bacterium or BTP is *Porphyromonas* and the preferred target cells are selected from the group including, but not limited to, oral epithelial cells. Optionally, the bacterium or BTP is *Staphylococcus* and the preferred target cells are mucosal epithelial cells. Optionally, the bacterium or BTP is *Neisseria* and the preferred target cells are selected from the group including, but not limited to, urethral epithelial cells and cervical epithelial cells. Optionally, the bacterium or BTP is *E. coli* and the preferred target cells are selected from the group, including but not limited to, intestinal epithelial cells, urethral epithelial cells, and the cells of the upper urinary tract. Optionally, the bacterium or BTP is *Bordetella* and the preferred target cells are respiratory epithelial cells. Optionally, the bacterium or BTP is *Vibrio* and the preferred target cells are intestinal epithelial cells. Optionally, the bacterium or BTP is *Treponema* and the preferred target cells are mucosal epithelial cells. Optionally, the bacterium or BTP is *Mycoplasma* and the preferred target cells are respiratory epithelial cells. Optionally, the bacterium or BTP is *Helicobacter* and the preferred target cells are the endothelial cells of the stomach. Optionally, the bacterium or BTP is *Chlamydia* and the preferred target cells are selected from the group including, but not limited to, conjunctival cells and urethral epithelial cells.

In another embodiment of this invention, the microorganism is a bacterium or BTP that has been modified, e.g., genetically modified, to have a certain tropism. Optionally, the preferred target cells are selected from the group including, but not limited to, pharyngeal epithelial cells, buccal epithelial cells of the tongue, mucosal epithelial cells, oral epithelial cells, epithelial cells of the urethra, cervical epithelial cells, intestinal epithelial cells, respiratory epithelial cells, cells of the upper urinary tract, epithelial cells of the stomach, and conjunctival cells. Optionally, the preferred target cells are dysplastic or cancerous epithelial cells. Optionally, the preferred target cells are activated or resting immune cells.

Delivery of at least one molecule into a target cell can be determined according to methods known in the art. For example, the presence of the molecule, by the decrease in expression of an RNA or protein silenced thereby, can be detected by hybridization or PCR methods, or by immunological methods that may include the use of an antibody.

Determining whether a microorganism is sufficiently invasive for use in the invention may include determining whether sufficient siRNA was delivered to host cells, relative to the number of microorganisms contacted with the host cells. If the amount of siRNA is low relative to the number of microorganisms used, it may be desirable to further modify the microorganism to increase its invasive potential.

Bacterial or BTP entry into cells can be measured by various methods. Intracellular bacteria or BTPs survive treatment by aminoglycoside antibiotics, whereas extracellular bacteria are rapidly killed. A quantitative estimate of bacterial or BTP uptake can be achieved by treating cell monolayers with the antibiotic gentamicin to inactivate extracellular bacteria or BTPs, then by removing said antibiotic before liberating the surviving intracellular organisms with gentle detergent and determining viable counts on standard bacteriological medium. Furthermore, bacterial or BTP entry into cells can be directly observed, e.g., by thin-section-transmission electron microscopy of cell layers or by immunofluorescent techniques (Falkow et al. (1992) Annual Rev. Cell Biol. 8:333). Thus, various techniques can be used to determine whether a specific bacterium or BTP is capable of invading a specific type of cell or to confirm bacterial invasion following modification of the bacteria or BTP, such modification of the tropism of the bacteria to mimic that of a second bacterium.

Bacteria or BTPs that can be used for delivering RNA according to the method of the invention are preferably non-pathogenic. However, pathogenic bacteria or BTP s can also be used, so long as their pathogenicity has been attenuated, to thereby render the bacteria non-harmful to a subject to which it is administered. As used herein, the term "attenuated bacterium or BTP" refers to a bacterium or BTP that has been modified to significantly reduce or eliminate its harmfulness to a subject. A pathogenic bacterium or BTP can be attenuated by various methods, set forth below.

Without wanting to be limited to a specific mechanism of action, the bacterium or BTP delivering the RNA into the eukaryotic cell can enter various compartments of the cell, depending on the type of bacterium or BTP. For example, the bacterium or BTP can be in a vesicle, e.g., a phagocytic vesicle. Once inside the cell, the bacterium or BTP can be destroyed or lysed and its contents delivered to the eukaryotic cell. A bacterium or BTP can also be engineered to express a phagosome degrading protein to allow leakage of RNA from the phagosome. In one embodiment of this invention, the bacterium or BTP expresses, either naturally or through modification, e.g., genetic modification, a protein that contributes to pore-formation, breakage or degradation of the phagosome. Optionally, the protein is a cholesterol-dependent cytolysin. Optionally, the protein is selected from the group consisting of listeriolysin, ivanolysin, streptolysin, sphingomyelinase, perfringolysin, botulinolysin, leukocidin, anthrax toxin, phospholipase, IpaB (invasion plasmid antigen), IpaH, IcsB (intercellular spread), DOT/Icm (defect in organelle trafficking/intracellular multiplication defective), DOTU (stabilization factor for the DOT/Icm complex), IcmF, and PmrA (multidrug resistance efflux pump).

In some embodiments, the bacterium can stay alive for various times in the eukaryotic cell and may continue to produce RNA. The RNA or RNA-encoding DNA can then be released from the bacterium into the cell by, e.g., leakage. In certain embodiments of the invention, the bacterium can also replicate in the eukaryotic cell. In a preferred embodiment, bacterial replication does not kill the host cell. The invention is not limited to delivery of RNA or RNA-encoding DNA by a specific mechanism and is intended to encompass methods and compositions permitting delivery of RNA or RNA-encoding DNA by a bacterium independently of the mechanism of delivery. In one embodiment, the bacterium or BTP for use in the present invention is non-pathogenic or non-virulent. In another aspect of this embodiment, the bacterium or BTP is therapeutic. In another aspect of this embodiment, the bacterium or BTP is an attenuated strain or derivative thereof selected from, but not limited to, *Yersinia, Rickettsia, Legionella, Brucella, Mycobacterium, Helicobacter, Haemophilus, Coxiella, Chlamydia, Neisseria, Burkolderia, Bordetella, Borrelia, Listeria, Shigella, Salmonella, Staphylococcus, Streptococcus, Porphyromonas, Treponema, Vibrio, E. coli,* and *Bifidobacteriae*. Optionally, the *Yersinia* strain is an attenuated strain of the *Yersinia pseudotuberculosis* species. Optionally, the *Yersinia* strain is an attenuated strain of the *Yersinia enterocolitica* species. Optionally, the *Rickettsia* strain is an attenuated strain of the *Rickettsia coronii* species. Optionally, the *Legionella* strain is an attenuated strain of the *Legionella pneumophilia* species. Optionally, the *Mycobacterium* strain is an attenuated strain of the *Mycobacterium tuberculosis* species. Optionally, the *Mycobacterium* strain is an attenuated strain of the *Mycobacterium bovis* BCG species. Optionally, the *Helicobacter* strain is an attenuated strain of the *Helicobacter pylori* species. Optionally, the *Coxiella* strain is an attenuated strain of *Coxiella burnetti*. Optionally, the *Haemophilus* strain is an attenuated strain of the *Haemophilus influenza* species. Optionally, the *Chlamydia* strain is an attenuated strain of the *Chlamydia trachomatis* species. Optionally, the *Chlamydia* strain is an attenuated strain of the *Chlamydia pneumoniae* species. Optionally, the *Neisseria* strain is an attenuated strain of the *Neisseria gonorrheae* species. Optionally, the *Neisseria* strain is an attenuated strain of the *Neisseria meningitidis* species. Optionally, the *Burkolderia* strain is an attenuated strain of the *Burkolderia cepacia* species. Optionally, the *Bordetella* strain is an attenuated strain of the *Bordetella pertussis* species. Optionally, the *Borrelia* strain is an attenuated strain of the *Borrelia hermisii* species. Optionally, the *Listeria* strain is an attenuated strain of the *Listeria monocytogenes* species. Optionally, the *Listeria* strain is an attenuated strain of the *Listeria ivanovii* species. Optionally, the *Salmonella* strain is an attenuated strain of the *Salmonella enterica* species. Optionally, the *Salmonella* strain is an attenuated strain of the *Salmonella typhimurium* species. Optionally, the *Salmonella typhimurium* strain is SL 7207 or VNP20009. Optionally, the *Staphylococcus* strain is an attenuated strain of the *Staphylococcus aureus* species. Optionally, the *Streptococcus* strain is an attenuated strain of the *Streptococcus pyogenes* species. Optionally, the *Streptococcus* strain is an attenuated strain of the *Streptococcus mutans* species. Optionally, the *Streptococcus* strain is an attenuated strain of the *Streptococcus salivarius* species. Optionally, the *Streptococcus* strain is an attenuated strain of the *Streptococcus pneumonia* species. Optionally, the *Porphyromonas* strain is an attenuated strain of the *Porphyromonas gingivalis* species. Optionally, the *Pseudomonas* strain is an attenuated strain of the *Pseudomonas aeruginosa* species. Optionally, the *Treponema* strain is an attenuated strain of the *Treponema pallidum* species. Optionally, the *Vibrio* strain is an attenuated strain of the *Vibrio cholerae* species. Optionally, the *E. coli* strain is MM294.

Set forth below are examples of bacteria that have been described in the literature as being naturally invasive (section 1.1), as well as bacteria which have been described in the literature as being naturally non-invasive bacteria (section 1.2), as well as bacteria which are naturally non-pathogenic or which are attenuated. Although some bacteria have been described as being non-invasive (section 1.2), these may still be sufficiently invasive for use according to the invention. Whether traditionally described as naturally invasive or non-invasive, any bacterial strain can be modified to modulate, in particular to increase, its invasive characteristics (e.g., as described in section 1.3).

1.1 Naturally Invasive Bacteria

The particular naturally invasive bacteria employed in the present invention are not critical thereto. Examples of such naturally occurring invasive bacteria include, but are not limited to, *Shigella* spp., *Salmonella* spp., *Listeria* spp., *Rickettsia* spp., and enteroinvasive *Escherichia coli*.

The particular *Shigella* strain employed is not critical to the present invention. Examples of *Shigella* strains that can be employed in the present invention include *Shigella flexneri* 2a (ATCC No. 29903), *Shigella sonnei* (ATCC No. 29930), and *Shigella disenteriae* (ATCC No. 13313). An attenuated *Shigella* strain, such as *Shigella flexneri* 2a 2457T aroA virG mutant CVD 1203 (Noriega et al. supra), *Shigella flexneri* M90T icsA mutant (Goldberg et al. Infect. Immun., 62:5664-5668 (1994)), *Shigella flexneri* Y SFL114 aroD mutant (Karnell et al. Vacc., 10:167-174 (1992)), and *Shigella flexneri* aroA aroD mutant (Verma et al. Vacc., 9:6-9 (1991)) are preferably employed in the present invention. Alternatively, new attenuated *Shigella* spp. strains can be constructed by introducing an attenuating mutation either singularly or in conjunction with one or more additional attenuating mutations.

At least one advantage to *Shigella* bacteria as delivery vectors is their tropism for lymphoid tissue in the colonic mucosal surface. In addition, the primary site of *Shigella* replication is believed to be within dendritic cells and macrophages, which are commonly found at the basal lateral surface of M cells in mucosal lymphoid tissues (reviewed by McGhee, J. R. et al. (1994) Reproduction, Fertility, & Development 6:369; Pascual, D. W. et al. (1994) Immunomethods 5:56). As such, *Shigella* vectors may provide a means to target RNA interference or deliver therapeutic molecules to these professional antigen-presenting cells. Another advantage of *Shigella* vectors is that attenuated *Shigella* strains deliver nucleic acid reporter genes in vitro and in vivo (Sizemore, D. R. et al. (1995) Science 270:299; Courvalin, P. et al. (1995) Comptes Rendus de l Academie des Sciences Serie III-Sciences de la Vie-Life Sciences 318:1207; Powell, R. J. et al. (1996) In: Molecular approaches to the control of infectious diseases. F. Brown, E. Norrby, D. Burton and J. Mekalanos, eds. Cold Spring Harbor Laboratory Press, New York. 183; Anderson, R. J. et al. (1997) Abstracts for the 97th General Meeting of the American Society for Microbiology: E.). On the practical side, the tightly restricted host specificity of *Shigella* stands to prevent the spread of *Shigella* vectors into the food chain via intermediate hosts. Furthermore, attenuated strains that are highly attenuated in rodents, primates and volunteers have been developed (Anderson et al. (1997) supra; Li, A. et al. (1992) Vaccine 10:395; Li, A. et al. (1993) Vaccine 11:180; Karnell, A. et al. (1995) Vaccine 13:88; Sansonetti, P. J. and J. Arondel (1989) Vaccine 7:443; Fontaine, A. et al. (1990) Research in Microbiology 141:907; Sansonetti, P. J. et al. (1991) Vaccine 9:416; Noriega, F. R. et al. (1994) Infection & Immunity 62:5168; Noriega, F. R. et al. (1996) Infection & Immunity 64:3055; Noriega, F. R. et al. (1996) Infection & Immunity 64:23; Noriega, F. R. et al. (1996) Infection & Immunity 64:3055; Kotloff, K. L. et al. (1996) Infection & Immunity 64:4542). This latter knowledge will allow the development of well-tolerated *Shigella* vectors for use in humans.

Attenuating mutations can be introduced into bacterial pathogens using non-specific mutagenesis either chemically, using agents such as N-methyl-N'-nitro-N-nitrosoguanidine, or using recombinant DNA techniques; classic genetic techniques, such as Tn10 mutagenesis, P22-mediated transduction, λ, phage mediated crossover, and conjugational transfer; or site-directed mutagenesis using recombinant DNA techniques. Recombinant DNA techniques are preferable since strains constructed by recombinant DNA techniques are far more defined. Examples of such attenuating mutations include, but are not limited to:

(i) auxotrophic mutations, such as aro (Hoiseth et al. Nature, 291:238-239 (1981)), gua (McFarland et al. Microbiol. Path., 3:129-141 (1987)), nad (Park et al. J. Bact., 170:3725-3730 (1988), thy (Nnalue et al. Infect. Immun., 55:955-962 (1987)), and asd (Curtiss, supra) mutations;

(ii) mutations that inactivate global regulatory functions, such as cya (Curtiss et al. Infect. Immun., 55:3035-3043 (1987)), crp (Curtiss et al (1987), supra), phoP/phoQ (Groisman et al. Proc. Natl. Acad. Sci., USA, 86:7077-7081 (1989); and Miller et al. Proc. Natl. Acad. Sci., USA, 86:5054-5058 (1989)), phop$^c$ (Miller et al. J. Bact., 172:2485-2490 (1990)) or ompR (Dorman et al. Infect. Immun., 57:2136-2140 (1989)) mutations;

(iii) mutations that modify the stress response, such as recA (Buchmeier et al. Mol. Micro., 7:933-936 (1993)), htrA (Johnson et al. Mol. Micro., 5:401-407 (1991)), htpR (Neidhardt et al. Biochem. Biophys. Res. Com., 100:894-900 (1981)), hsp (Neidhardt et al. Ann. Rev. Genet., 18:295-329 (1984)) and groEL (Buchmeier et al. Sci., 248:730-732 (1990)) mutations;

(iv) mutations in specific virulence factors, such as IsyA (Libby et al. Proc. Natl. Acad. Sci., USA, 91:489-493 (1994)), pag or prg (Miller et al (1990), supra; and Miller et al (1989), supra), iscA or virG (d'Hauteville et al. Mol. Micro., 6:833-841 (1992)), plcA (Mengaud et al. Mol. Microbiol., 5:367-72 (1991); Camilli et al. J. Exp. Med, 173:751-754 (1991)), and act (Brundage et al. Proc. Natl. Acad. Sci., USA, 90:11890-11894 (1993)) mutations;

(v) mutations that affect DNA topology, such as topA (Galan et al. Infect. Immun., 58:1879-1885 (1990));

(vi) mutations that disrupt or modify the cell cycle, such as min (de Boer et al. Cell, 56:641-649 (1989)).

(vii) introduction of a gene encoding a suicide system, such as sacB (Recorbet et al. App. Environ. Micro., 59:1361-1366 (1993); Quandt et al. Gene, 127:15-21 (1993)), nuc (Ahrenholtz et al. App. Environ. Micro., 60:3746-3751 (1994)), hok, gef, kil, or phlA (Molin et al. Ann. Rev. Microbiol., 47:139-166 (1993));

(viii) mutations that alter the biogenesis of lipopolysaccharide and/or lipid A, such as rFb (Raetz in *Escherichia coli* and *Salmonella typhimurium*, Neidhardt et al., Ed., ASM Press, Washington, D.C. pp 1035-1063 (1996)), galE (Hone et al. J. Infect. Dis., 156:164-167 (1987)) and htrB (Raetz, supra), msbB (Reatz, supra)

(ix) introduction of a bacteriophage lysis system, such as lysogens encoded by P22 (Rennell et al. Virol, 143:280-289 (1985)), λ murein transglycosylase (Bienkowska-Szewczyk et al. Mol. Gen. Genet., 184:111-114 (1981)) or S-gene (Reader et al. Virol, 43:623-628 (1971)); and The attenuating mutations can be either constitutively expressed or under the control of inducible promoters, such as the temperature sensitive heat shock family of promoters (Neidhardt et al. supra), or the anaerobically induced nirB promoter (Harborne et al. Mol. Micro., 6:2805-2813 (1992)) or repressible promoters, such as uapA (Gorfinkiel et al. J. Biol. Chem., 268:23376-23381 (1993)) or gcv (Stauffer et al. J. Bact., 176:6159-6164 (1994)).

The particular *Listeria* strain employed is not critical to the present invention. Examples of *Listeria* strains that can be employed in the present invention include *Listeria monocytogenes* (ATCC No. 15313). Attenuated *Listeria* strains, such as *L. monocytogenes* actA mutant (Brundage et al. supra) or *L. monocytogenes* plcA (Camilli et al. J. Exp. Med., 173:751-754 (1991)) are preferably used in the present invention. Alternatively, new attenuated *Listeria* strains can be constructed by introducing one or more attenuating mutations in groups (i) to (vii) as described for *Shigella* spp. above.

The particular *Salmonella* strain employed is not critical to the present invention. Examples of *Salmonella* strains that can be employed in the present invention include *Salmonella typhi* (ATCC No. 7251) and *S. typhimurium* (ATCC No. 13311). Attenuated *Salmonella* strains are preferably used in the present invention and include *S. typhi*-aroC-aroD (Hone et al. Vacc. 9:810 (1991) and *S. typhimurium*-aroA mutant (Mastroeni et al. Micro. Pathol. 13:477 (1992)). Alternatively, new attenuated *Salmonella* strains can be constructed by introducing one or more attenuating mutations as described for *Shigella* spp. above.

The particular *Rickettsia* strain employed is not critical to the present invention. Examples of *Rickettsia* strains which can be employed in the present invention include *Rickettsia Rickettsiae* (ATCC Nos. VR149 and VR891), *Rickettsia prowaseckii* (ATCC No. VR233), *Rickettsia tsutsugamuchi* (ATCC Nos. VR312, VR150 and VR609), *Rickettsia mooseri* (ATCC No. VR144), *Rickettsia sibirica* (ATCC No. VR151), and *Rochalimaea quitana* (ATCC No. VR358). Attenuated *Rickettsia* strains are preferably used in the present invention and can be constructed by introducing one or more attenuating mutations in groups (i) to (vii) as described for *Shigella* spp. above. The particular enteroinvasive *Escherichia* strain employed is not critical to the present invention. Examples of enteroinvasive *Escherichia* strains which can be employed in the present invention include *Escherichia coli* strains 4608-58, 1184-68, 53638-C-17, 13-80, and 6-81 (Sansonetti et al. Ann. Microbiol. (Inst. Pasteur), 132A:351-355 (1982)). Attenuated enteroinvasive *Escherichia* strains are preferably used in the present invention and can be constructed by introducing one or more attenuating mutations in groups (i) to (vii) as described for *Shigella* spp. above.

Furthermore, since certain microorganisms other than bacteria can also interact with integrin molecules (which are receptors for certain invasion factors) for cellular uptake, such microorganisms can also be used for introducing RNA into target cells. For example, viruses, e.g., foot-and-mouth disease virus, echovirus, and adenovirus, and eukaryotic pathogens, e.g., *Histoplasma capsulatum* and *Leishmania major* interact with integrin molecules.

1.2 Less Invasive Bacteria

Examples of bacteria which can be used in the invention and which have been described in the literature as being non-invasive or at least less invasive than the bacteria listed in the previous section (1.1) include, but are not limited to, *Yersinia* spp., *Escherichia* spp., *Klebsiella* spp., *Bordetella* spp., *Neisseria* spp., *Aeromonas* spp., *Francisella* spp., *Corynebacterium* spp., *Citrobacter* spp., *Chlamydia* spp., *Haemophilus* spp., *Brucella* spp., *Mycobacterium* spp., *Legionella* spp., *Rhodococcus* spp., *Pseudomonas* spp., *Helicobacter* spp., *Vibrio* spp., *Bacillus* spp., and *Erysipelothrix* spp. It may be necessary to modify these bacteria to increase their invasive potential.

The particular *Yersinia* strain employed is not critical to the present invention. Examples of *Yersinia* strains that can be employed in the present invention include *Y. enterocolitica* (ATCC No. 9610) or *Y. pestis* (ATCC No. 19428). Attenuated *Yersinia* strains, such as *Y. enterocolitica* Ye03-R2 (al-Hendy et al. Infect. Immun., 60:870-875 (1992)) or *Y. enterocolitica* aroA (O'Gaora et al. Micro. Path., 9:105-116 (1990)) are preferably used in the present invention. Alternatively, new attenuated *Yersinia* strains can be constructed by introducing one or more attenuating mutations in groups (i) to (vii) as described for *Shigella* spp. above.

The particular *Escherichia* strain employed is not critical to the present invention. Examples of *Escherichia* strains that can be employed in the present invention include *E. coli* Nissle 1917, MM294, H10407 (Elinghorst et al. Infect. Immun., 60:2409-2417 (1992)), and *E. coli* EFC4, CFT325 and CPZ005 (Donnenberg et al. J. Infect. Dis., 169:831-838 (1994)). Attenuated *Escherichia* strains, such as the attenuated turkey pathogen *E. coli* 02 carAB mutant (Kwaga et al. Infect. Immun., 62:3766-3772 (1994)) or CEQ201 are preferably used in the present invention. Alternatively, new attenuated *Escherichia* strains can be constructed by introducing one or more attenuating mutations in groups (i) to (vii) as described for *Shigella* spp. above.

The particular *Klebsiella* strain employed is not critical to the present invention. Examples of *Klebsiella* strains that can be employed in the present invention include *K. pneumoniae* (ATCC No. 13884). Attenuated *Klebsiella* strains are preferably used in the present invention, and can be constructed by introducing one or more attenuating mutations in groups (i) to (vii) as described for *Shigella* spp. above.

The particular *Bordetella* strain employed is not critical to the present invention. Examples of *Bordetella* strains that can be employed in the present invention include *B. bronchiseptica* (ATCC No. 19395). Attenuated *Bordetella* strains are preferably used in the present invention, and can be constructed by introducing one or more attenuating mutations in groups (i) to (vii) as described for *Shigella* spp. above.

The particular *Neisseria* strain employed is not critical to the present invention. Examples of *Neisseria* strains that can be employed in the present invention include *N. meningitidis* (ATCC No. 13077) and *N. gonorrhoeae* (ATCC No. 19424). Attenuated *Neisseria* strains, such as *N. gonorrhoeae* MS11 aro mutant (Chamberlain et al. Micro. Path., 15:51-63 (1993)) are preferably used in the present invention. Alternatively, new attenuated *Neisseria* strains can be constructed by introducing one or more attenuating mutations in groups (i) to (vii) as described for *Shigella* spp. above. The particular *Aeromonas* strain employed is not critical to the present invention. Examples of *Aeromonas* strains that can be employed in the present invention include *A. eucrenophila* (ATCC No. 23309). Alternatively, new attenuated *Aeromonas* strains can be constructed by introducing one or more attenuating mutations in groups (i) to (vii) as described for *Shigella* spp. above.

The particular *Francisella* strain employed is not critical to the present invention. Examples of *Francisella* strains that can be employed in the present invention include *F. tularensis* (ATCC No. 15482). Attenuated *Francisella* strains are preferably used in the present invention, and can be constructed by introducing one or more attenuating mutations in groups (i) to (vii) as described for *Shigella* spp. above.

The particular *Corynebacterium* strain employed is not critical to the present invention. Examples of *Corynebacterium* strains that can be employed in the present invention include *C. pseudotuberculosis* (ATCC No. 19410). Attenuated *Corynebacterium* strains are preferably used in the present invention, and can be constructed by introducing one or more attenuating mutations in groups (i) to (vii) as described for *Shigella* spp. above.

The particular *Citrobacter* strain employed is not critical to the present invention. Examples of *Citrobacter* strains that can be employed in the present invention include *C. freundii* (ATCC No. 8090). Attenuated *Citrobacter* strains are preferably used in the present invention, and can be constructed by introducing one or more attenuating mutations in groups (i) to (vii) as described for *Shigella* spp. above.

The particular *Chlamydia* strain employed is not critical to the present invention. Examples of *Chlamydia* strains that can be employed in the present invention include *C. pneumoniae* (ATCC No. VR1310). Attenuated *Chlamydia* strains are preferably used in the present invention, and can be constructed by introducing one or more attenuating mutations in groups (i) to (vii) as described for *Shigella* spp. above.

The particular *Haemophilus* strain employed is not critical to the present invention. Examples of *Haemophilus* strains that can be employed in the present invention include *H. sornnus* (ATCC No. 43625). Attenuated *Haemophilus* strains are preferably used in the present invention, and can be constructed by introducing one or more attenuating mutations in groups (i) to (vii) as described for *Shigella* spp. above.

The particular *Brucella* strain employed is not critical to the present invention. Examples of *Brucella* strains that can be employed in the present invention include *B. abortus* (ATCC No. 23448). Attenuated *Brucella* strains are preferably used in the present invention, and can be constructed by introducing one or more attenuating mutations in groups (i) to (vii) as described for *Shigella* spp. above.

The particular *Mycobacterium* strain employed is not critical to the present invention. Examples of *Mycobacterium* strains that can be employed in the present invention include *M. intracellulare* (ATCC No. 13950) and *M. tuberculosis* (ATCC No. 27294). Attenuated *Mycobacterium* strains are preferably used in the present invention, and can be constructed by introducing one or more attenuating mutations in groups (i) to (vii) as described for *Shigella* spp. above.

The particular *Legionella* strain employed is not critical to the present invention. Examples of *Legionella* strains that can be employed in the present invention include *L. pneumophila* (ATCC No. 33156). Attenuated *Legionella* strains, such as a *L. pneumophila* mip mutant (Ott, FEMS Micro. Rev., 14:161-176 (1994)) are preferably used in the present invention. Alternatively, new attenuated *Legionella* strains can be constructed by introducing one or more attenuating mutations in groups (i) to (vii) as described for *Shigella* spp. above.

The particular *Rhodococcus* strain employed is not critical to the present invention. Examples of *Rhodococcus* strains that can be employed in the present invention include *R. equi* (ATCC No. 6939). Attenuated *Rhodococcus* strains are preferably used in the present invention, and can be constructed by introducing one or more attenuating mutations in groups (i) to (vii) as described for *Shigella* spp. above.

The particular *Pseudomonas* strain employed is not critical to the present invention. Examples of *Pseudomonas* strains that can be employed in the present invention include *P. aeruginosa* (ATCC No. 23267). Attenuated *Pseudomonas* strains are preferably used in the present invention, and can be constructed by introducing one or more attenuating mutations in groups (i) to (vii) as described for *Shigella* spp. above.

The particular *Helicobacter* strain employed is not critical to the present invention. Examples of *Helicobacter* strains that can be employed in the present invention include *H. mustelae* (ATCC No. 43772). Attenuated *Helicobacter* strains are preferably used in the present invention, and can be constructed by introducing one or more attenuating mutations in groups (i) to (vii) as described for *Shigella* spp. above.

The particular *Salmonella* strain employed is not critical to the present invention. Examples of *Salmonella* strains that can be employed in the present invention include *Salmonella typhi* (ATCC No. 7251) and *S. typhimurium* (ATCC No. 13311). Attenuated *Salmonella* strains are preferably used in the present invention and include *S. typhi* aroC aroD (Hone et al. Vacc., 9:810-816 (1991)) and *S. typhimurium* aroA mutant (Mastroeni et al. Micro. Pathol, 13:477-491 (1992))). Alternatively, new attenuated *Salmonella* strains can be constructed by introducing one or more attenuating mutations in groups (i) to (vii) as described for *Shigella* spp. above.

The particular *Vibrio* strain employed is not critical to the present invention. Examples of *Vibrio* strains that can be employed in the present invention include *Vibrio cholerae* (ATCC No. 14035) and *Vibrio cincinnatiensis* (ATCC No. 35912). Attenuated *Vibrio* strains are preferably used in the present invention and include *V. cholerae* RSI virulence mutant (Taylor et al. J. Infect. Dis., 170:1518-1523 (1994)) and *V. cholerae* ctxA, ace, zot, cep mutant (Waldor et al. J. Infect. Dis., 170:278-283 (1994)). Alternatively, new attenuated *Vibrio* strains can be constructed by introducing one or more attenuating mutations in groups (i) to (vii) as described for *Shigella* spp. above.

The particular *Bacillus* strain employed is not critical to the present invention. Examples of *Bacillus* strains that can be employed in the present invention include *Bacillus subtilis* (ATCC No. 6051). Attenuated *Bacillus* strains are preferably used in the present invention and include *B. anthracis* mutant pX01 (Welkos et al. Micro. Pathol, 14:381-388 (1993)) and attenuated BCG strains (Stover et al. Nat., 351:456-460 (1991)). Alternatively, new attenuated *Bacillus* strains can be constructed by introducing one or more attenuating mutations in groups (i) to (vii) as described for *Shigella* spp. above.

The particular *Erysipelothrix* strain employed is not critical to the present invention. Examples of *Erysipelothrix* strains that can be employed in the present invention include *Erysipelothrix rhusiopathiae* (ATCC No. 19414) and *Erysipelothrix tonsillarum* (ATCC No. 43339). Attenuated *Erysipelothrix* strains are preferably used in the present invention and include *E. rhusiopathiae* Kg-1a and Kg-2 (Watarai et al. J. Vet. Med. Sci., 55:595-600 (1993)) and *E. rhusiopathiae* ORVAC mutant (Markowska-Daniel et al. Int. J. Med. Microb. Virol. Parisit. Infect. Dis., 277:547-553 (1992)). Alternatively, new attenuated *Erysipelothrix* strains can be constructed by introducing one or more attenuating mutations in groups (i) to (vii) as described for *Shigella* spp. above.

1.3. Methods for Increasing the Invasive Properties of a Bacterial Strain

Whether organisms have been traditionally described as invasive or non-invasive, these organisms can be engineered to increase their invasive properties, e.g., by mimicking the invasive properties of *Shigella* spp., *Listeria* spp., *Rickettsia* spp., or enteroinvasive *E. coli* spp. For example, one or more genes that enable the microorganism to access the cytoplasm of a cell, e.g., a cell in the natural host of said non-invasive bacteria, can be introduced into the microorganism.

Examples of such genes referred to herein as "cytoplasm-targeting genes" include genes encoding the proteins that enable invasion by *Shigella* or the analogous invasion genes of entero-invasive *Escherichia*, or listeriolysin O of *Listeria*, as such techniques are known to result in rendering a wide array of invasive bacteria capable of invading and entering the cytoplasm of animal cells (Formal et al. Infect. Immun., 46:465 (1984); Bielecke et al. Nature, 345:175-176 (1990); Small et al. In: Microbiology-1986, pages 121-124, Levine et al. Eds., American Society for Microbiology, Washington, D.C. (1986); Zychlinsky et al. Molec. Micro., 11:619-627 (1994); Gentschev et al. (1995) Infection & Immunity 63:4202; Isberg, R. R. and S. Falkow (1985) Nature 317: 262; and Isberg, R. R. et al. (1987) Cell 50:769). Methods for transferring the above cytoplasm-targeting genes into a bacterial strain are well known in the art. Another preferred gene that can be introduced into bacteria to increase their invasive character encodes the invasin protein from *Yersinia pseudotuberculosis*, (Leong et al. EMBO J., 9:1979 (1990)). Invasin can also be introduced in combination with listeriolysin, thereby further increasing the invasive character of the bacteria relative to the introduction of either of these genes. The above genes have been described for illustrative purposes; however, it will be obvious to those skilled in the art that any gene or combination of genes, from one or more sources, that participates in the delivery of a molecule, in particular an RNA or RNA-encoding DNA molecule, from a microorganism into the cytoplasm of a cell, e.g., an animal cell, will suffice. Thus, such genes are not limited to bacterial genes, and include viral genes, such as influenza virus hemagglutinin HA-2 that promotes endosmolysis (Plank et al. J. Biol. Chem., 269:12918-12924 (1994)).

The above cytoplasm-targeting genes can be obtained by, e.g., PCR amplification from DNA isolated from an invasive bacterium carrying the desired cytoplasm-targeting gene. Primers for PCR can be designed from the nucleotide sequences available in the art, e.g., in the above-listed references and/or in GenBank, which is publicly available on the internet (www.ncbi.nlm.nih.gov/). The PCR primers can be designed to amplify a cytoplasm-targeting gene, a cytoplasm-targeting operon, a cluster of cytoplasm-targeting genes, or a regulon of cytoplasm-targeting genes. The PCR strategy employed will depend on the genetic organization of the cytoplasm-targeting gene or genes in the target invasive bacteria. The PCR primers are designed to contain a sequence that is homologous to DNA sequences at the beginning and end of the target DNA sequence. The cytoplasm-targeting genes can then be introduced into the target bacterial strain, e.g., by using Hfr transfer or plasmid mobilization (Miller, A Short Course in Bacterial Genetics, Cold Spring Harbor Laboratory Press, Cold Spring Harbor, N.Y. (1992); Bothwell et al. supra; and Ausubel et al. supra), bacteriophage-mediated transduction (de Boer, supra; Miller, supra; and Ausubel et al. supra), chemical transformation (Bothwell et al. supra; Ausubel et al. supra), electroporation (Bothwel et al. supra; Ausubel et al. supra; and Sambrook, Molecular Cloning: A Laboratory Manual, Cold Spring Harbor Laboratory Press, Cold Spring Harbor, N.Y.) and physical transformation techniques (Johnston et al. supra; and Bothwell, supra). The cytoplasm-targeting genes can be incorporated into lysogenic bacteriophage (de Boer et al. Cell, 56:641-649 (1989)), plasmids vectors (Curtiss et al. supra) or spliced into the chromosome (Hone et al. supra) of the target strain.

In addition to genetically engineering bacteria and BTPs to increase their invasive properties, as set forth above, bacteria and can also be modified by linking an invasion factor to the bacteria. Accordingly, in one embodiment, a bacterium is rendered more invasive by coating the bacterium, either covalently or non-covalently, with an invasion factor, e.g., the protein invasin, invasin derivatives, or a fragment thereof sufficient for invasiveness. In fact, it has been shown that non-invasive bacterial cells coated with purified invasin from *Yersinia pseudotuberculosis* or the carboxyl-terminal 192 amino acids of invasin are able to enter mammalian cells (Leong et al. (1990) EMBO J. 9:1979). Furthermore, latex beads coated with the carboxyl terminal region of invasin are efficiently internalized by mammalian cells, as are strains of *Staphylococcus aureus* coated with antibody-immobilized invasin (reviewed in Isberg and Tran van Nhieu (1994) Ann. Rev. Genet. 27:395). Alternatively, a bacterium can also be coated with an antibody, variant thereof, or fragment thereof, which binds specifically to a surface molecule recognized by a bacterial entry factor. For example, it has been shown that bacteria are internalized if they are coated with a monoclonal antibody directed against an integrin molecule, e.g., α5β1, known to be the surface molecule with which the bacterial invasin protein interacts (Isberg and Tran van Nhieu, supra). Such antibodies can be prepared according to methods known in the art. The antibodies can be tested for efficacy in mediating bacterial invasiveness by, e.g., coating bacteria with the antibody, contacting the bacteria with eukaryotic cells having a surface receptor recognized by the antibody, and monitoring the presence of intracellular bacteria, according to the methods described above. Methods for linking an invasion factor to the surface of a bacterium are known in the art and include cross-linking.

3. Plasmids and Vectors

The present invention also provides at least one vector or plasmid including at least one DNA molecule encoding one or more siRNAs and at least one promoter, wherein the expressed siRNAs interfere with at least one mRNA of a gene of interest. In one preferred embodiment, the present invention provides at least one prokaryotic vector including at least one DNA molecule encoding one or more siRNAs and at least one RNA-polymerase III compatible promoter or at least one prokaryotic promoter, wherein the expressed siRNAs interfere with at least one mRNA of a gene of interest.

The TRIP (transkingdom RNA interference plasmid) vectors and plasmids of the present invention include a multiple cloning site, a promoter sequence and a terminator sequence. The TRIP vectors and plasmids also include one or more sequences encoding for an invasion factor to permit the non-invasive bacterium or BTP to enter mammalian cells (e.g., the Inv locus that encodes invasion that permits the bacterium or BTP to enter β1-integrin-positive mammalian cells) (Young et al., J. Cell Biol. 116, 197-207 (1992)) and one or more sequences to permit the genetic material to escape from the entry vesicles (e.g., Hly A gene that encodes listeriolysin O) (Mathew et al., Gene Ther. 10, 1105-1115 (2003) and Grillot-Courvalin et al., Nat. Biotechnol. 16, 862-866 (1998)). TRIP is further described (including a vector/plasmid schematic) in PCT Publication No. WO 06/066048. In preferred embodiments, the TRIP vectors and plasmids will incorporate a hairpin RNA expression cassette encoding short hairpin RNA under the control of an appropriate promoter sequence and terminator sequence.

In the design of these constructs, an algorithm was utilized to take into account some known difficulties with the development of siRNA, namely: (1) Exclusion of disqualifying properties (SNPs, interferon motifs); (2) Exclusion of the sequence if there was homology in ref seq (19/21, >17 contiguous to any other genes) and (3) Exclusion of the sequence if there were significant miRNA seed type matches.

As described herein, the one or more DNA molecules encoding the one or more siRNAs are transcribed within the eukaryotic target cell or transcribed within the bacterium or BTP.

In embodiments where the DNA is transcribed within the eukaryotic cell, the one or more siRNAs are transcribed within the eukaryotic cells as shRNAs. The eukaryotic cell can be in vivo, in vitro or ex vivo. In one aspect of this embodiment, the one or more DNA molecules encoding the one or more siRNAs contain a eukaryotic promoter. Optionally, the eukaryotic promoter is a RNA polymerase III promoter. Optionally, the RNA polymerase III promoter is a U6 promoter or an H1 promoter.

In embodiments where the DNA is transcribed within the bacterium or BTP, the one or more DNA molecules contain a prokaryotic promoter. Optionally, the prokaryotic promoter is an E. coli promoter. Preferably, the E. coli promoter can be a T7 promoter, lacUV5 promoter, RNA polymerase promoter, gapA promoter, pA1 promoter, lac regulated promoter, araC+P$_{araBAD}$ promoter, T5 promoter, P$_{tac}$ promoter (Estrem et al, 1998, Proc. Natl. Acad. Sci. USA 95, 9761-9766; Meng et al., 2001, Nucleic Acids Res. 29, 4166-417; De Boer et al., 1983, Proc. NatL Acad. Sci. USA 80, 21-25) or recA promoter.

Preferable, promoter sequences are recited in Table 1.

TABLE 1

| Promoter | Sequence | SEQ ID NO: |
|---|---|---|
| T7 promoter | TAATACGACTCACTATAG | 1 |
| lacUV5 promoter | TAACCAGGCTTTACACTTTATG CTTCCGGCTCGTATAATGTGTG GAAGGATCC | 2 |
| RNA polymerase promoter | TAACCAGGCTTTACACTTTATG CTTCCGGCTCGTATAATGTGTG GAA | 3 |
| RNA polymerase promoter | TAAAATTCAAAAATTTATTTGC TTTCAGGAAAATTTTTCTGTAT AATAGATTC | 4 |
| RNA polymerase promoter | TAATTGATACTTTATGCTTTTT TCTGTATAAT | 5 |
| gapA promoter | AAGCTTTCAGTCGCGTAATGCT TAGGCACAGGATTGATTTGTCG CAATGATTGACACGATTCCGCT TGACACTGCGTAAGTTTTGTGT TATAATGGATCC | 6 |
| pA1 promoter | AAGCTTAAGGAGAGACAACTTA AAGAGACTTAAAAGATTAATTT AAAATTTATCAAAAAGAGTATT GACTTAAAGTCTAACCTATAGG ATACTTGGATCC | 7 |
| lac regulated promoter | AAGCTTTGTGTGGAATTGTGAG CGGATAACAATTCCACACATTG ACACTTTATGCTTCCGGCTCGT ATAATGGATCC | 8 |
| lac regulated promoter | AAGCTTGGAAAATTTTTTTTAA AAAAGTCATGTGTGGAATTGTG AGCGGATAACAATTCCACATAT AATGGATCC | 9 |
| araC+ P$_{araBAD}$ promoter | GACTTCATATACCCAAGCTTTA AAAAAAAATCCTTAGCTTTCG CTAAGGATCTCCGTCAAGCCGT CAATTGTCTGATTCGTTACCAA TTATGACAACTTGACGGCTACA TCATTCACTTTTTCTTCACAAC CGGCACGAAACTCGCTCGGGCT GGCCCCGGTGCATTTTTTAAAT ACTCGCGAGAAATAGAGTTGAT CGTCAAAACCAACATTGCGACC GACGGTGGCGATAGGCATCCGG GTAGTGCTCAAAAGCAGCTTCG CCTGACTAATGCGTTGGTCCTC GCGCCAGCTTAAGACGCTAATC CCTAACTGCTGGCGGAAAAGAT GTGACAGACGCGACGGCGACAA GCAAACATGCTGTGCGACGCTG GCGATATCAAAATTGCTGTCTG CCAGGTGATCGCTGATGTACTG ACAAGCCTCGCGTACCCGATTA | 10 |

TABLE 1-continued

| Promoter | Sequence | SEQ ID NO: |
|---|---|---|
|  | TCCATCGGTGGATGGAGCGACT CGTTAATCGCTTCCATGCGCCG CAGTAACAATTGCTCAAGCAGA TTTATCGCCAGCAGCTCCGAAT AGCGCCCTTCCCCTTGCCCGGC GTTAATGATTTGCCCAAACAGG TCGCTGAAATGCGGCTGGTGCG CTTCATCCGGGCGAAAGAAACC CGTATTGGCAAATATTGACGGC CAGTTAAGCCATTCATGCCAGT AGGCGCGCGGACGAAAGTAAAC CCACTGGTGATACCATTCGCGA GCCTCCGGATGACGACCGTAGT GATGAATCTCTCCTGGCGGGAA CAGCAAAATATCACCCGGTCGG CAGACAAATTCTCGTCCCTGAT TTTTCACCACCCCTGACCGCG AATGGTGAGATTGAGAATATAA CCTTTCATTCCCAGCGGTCGGT CGATAAAAAATCGAGATAACC GTTGGCCTCAATCGGCGTTAAA CCCGCCACCAGATGGGCGTTAA ACGAGTATCCCGGCAGCAGGGG ATCATTTTGCGCTTCAGCCATA CTTTTCATACTCCCACCATTCA GAGAAGAAACCAATTGTCCATA TTGCATCAGACATTGCCGTCAC TGCGTCTTTTACTGGCTCTTCT CGCTAACCCAACCGGTAACCCC GCTTATTAAAAGCATTCTGTAA CAAAGCGGGACCAAAGCCATGA CAAAAACGCGTAACAAAAGTGT CTATAATCACGGCAGAAAAGTC CACATTGATTATTTGCACGGCG TCACACTTTGCTATGCCATAGC ATTTTTATCCATAAGATTAGCG GATCCTACCTGACGCTTTTTAT CGCAACTCTCTACTGTAGATCT ATCTGCGAT |  |
| T5 promoter | TAAAAATTCAAAAATTTATTTGC TTTCAGGAAAATTTTTCTGTAT AATAGATTCGGATCC | 11 |
| recA promoter | TAATTGATACTTTATGCTTTTT TCTGTATAATGGATCC | 12 |
| P$_{tac}$ promoter | GACTTCATATACCCAAGCTTGG AAAATTTTTTTAAAAAAGTCT TGACACTTTATGCTTCCGGCTC GTATAATGGATCC | 378 |
| P$_{atac}$ promoter | GGAAAATTTTTTTAAAAAAGT C | 379 |

In embodiments where the DNA is transcribed within the bacterium or BTP, the *E. coli* promoter is associated with a terminator. Preferably, the *E. coli* terminator can be a T7 terminator, lacUV5 terminator, Rho-independent terminator, Rho-dependent terminator, or RNA polymerase terminator.

Preferable, terminator sequences are recited in Table 2.

TABLE 2

| Terminator | Sequence | SEQ ID NO: |
|---|---|---|
| T7 terminator | TAGCATAACCCCTTGGGGCCTC TAAACGGGTCTTGAGGGGTTTT TTG | 13 |
| lacUV5 terminator | TTGTCACGTGAGCGGATAACAA TTTCACACAGGAAACAGAATTC TTAAT | 14 |

TABLE 2-continued

| Terminator | Sequence | SEQ ID NO: |
|---|---|---|
| Rho-independent terminator | TTGTCACAAACCCCGCCACCGG CGGGGTTTTTTTCTGCTTAAT | 15 |
| Rho-dependent terminator | TTGTCACAATTCTATGGTGTAT GCATTTATTTGCATACATTCAA TCAATTGGATCCTGCATTAAT | 16 |
| RNA polymerase terminator | GTGAGCGGATAACAATTTCACA CAGGAAACAGAATTCTTAAT | 17 |
| RNA polymerase terminator | AAACCCCGCCACCGGCGGGGTT TTTTTCTGCTTAAT | 18 |
| RNA polymerase terminator | AATTCTATGGTGTATGCATTTA TTTGCATACATTCAATCAATTG GATCCTGCATTAAT | 19 |

In additional embodiments, the vectors and plasmids of the present invention further include one or more enhancer sequences, selection markers, or lysis regulation system sequences.

In one aspect of the invention, the one or more DNA molecules contain a prokaryotic enhancer. Optionally, the prokaryotic enhancer is a T7 enhancer. Optionally, the T7 enhancer has the sequence GAGACAGG (SEQ ID NO: 563). In another aspect of this embodiment, the one or more DNA molecules contain a prokaryotic terminator.

In another aspect of the, the one or more DNA molecules are associated with one or more selection markers. In one aspect of this embodiment, the selection marker is an amber suppressor containing one or more mutations or an diamino pimelic acid (DAP) containing one or more mutations. Optionally, the dap gene is selected from, but not limited to, dapA and dapE.

Preferable, selection marker sequences are recited in Table 3.

TABLE 3

| Selection Marker | Sequence | SEQ ID NO: |
|---|---|---|
| amber suppressor gene sequence | AATTCGGGGCTATAGCTCAGCT GGGAGAGCGCTTGCATCTAATG CAAGAGGTCAGCGGTTCGATCC CGCTTAGCTCCACCACTGCA | 20 |
| amber suppressor sequence | AATTCGCCCGGATAGCTCAGTC GGTAGAGCAGGGGATTCTAAAT CCCCGTGTCCTTGGTTCGATTC CGAGTCCGGGCACTGCA | 21 |
| Rho- lgt with double amber mutation (lgt am-am allele of lgt gene) sequence | ATGACCAGTAGCTATCTGCATT AGCCGGAGTAGGATCCGGTCAT TTTCTCAATAGGACCCGTGGCG CTTCACTGGTACGGCCTGATGT ATCTGGTGGGTTTCATTTTTGC AATGTGGCTGGCAACACGACGG GCGAATCGTCCGGCAGCGGCT GGACCAAAAATGAAGTTGAAAA CTTACTCTATGCGGGCTTCCTC GGCGTCTTCCTCGGGGGACGTA TTGGTTATGTTCTGTTCTACAA TTTCCCGCAGTTTATGGCCGAT CCGCTGTATCTGTTCCGTGTCT GGGACGGCGGCATGTCTTTCCA CGGCGGCCTGATTGGCGTTATC GTGGTGATGATTATCTTCGCCC GCCGTACTAAACGTTCCTTCTT CCAGGTCTCTGATTTTATCGCA CCACTCATTCCGTTTGGTCTTG GTGCCGGGCGTCTGGGCAACTT | 22 |

TABLE 3-continued

| Selection Marker | Sequence | SEQ ID NO: |
|---|---|---|
| | TATTAACGGTGAATTGTGGGGC CGCGTTGACCCGAACTTCCGT TTGCCATGCTGTTCCCTGGCTC CCGTACAGAAGATATTTTGCTG CTGCAAACCAACCCGCAGTGGC AATCCATTTTCGACACTTACGG TGTGCTGCCGCGCCACCCATCA CAGCTTTACGAGCTGCTGCTGG AAGGTGTGGTGCTGTTTATTAT CCTCAACCTGTATATTCGTAAA CCACGCCCAATGGGAGCTGTCT CAGGTTTGTTCCTGATTGGTTA CGGCGCGTTTCGCATCATTGTT GAGTTTTTCCGCCAGCCCGACG CGCAGTTTACCGGTGCCTGGGT GCAGTACATCAGCATGGGGCAA ATTCTTTCCATCCCGATGATTG TCGCGGGTGTGATCATGATGGT CTGGGCATATCGTCGCAGCCCA CAGCAACACGTTTCCTGA | 5 |
| murA with double amber mutation (murA am-am allele of murA gene) sequence | ATGGATAAATTTCGTGTTCAGG GGCCAACGAAGCTCCAGGGCGA AGTCACAATTTCCGGCGCTAAA AATTAGTAGCTGCCTATCCTTT TTGCCGCACTACTGGCGGAAGA ACCGGTAGAGATCCAGAACGTC CCGAAACTGAAAGACGTCGATA CATCAATGAAGCTGCTAAGCCA GCTGGGTGCGAAAGTAGAACGT AATGGTTCTGTGCATATTGATG CCCGCGACGTTAATGTATTCTG CGCACCTTACGATCTGGTTAAA ACCATGCGTGCTTCTATCTGGG CGCTGGGGCCGCTGGTAGCGCG CTTTGGTCAGGGGCAAGTTTCA CTACCTGGCGGTTGTACGATCG GTGCGCGTCCGGTTGATCTACA CATTTCTGGCCTCGAACAATTA GGCGCGACCATCAAACTGGAAG AAGGTTACGTTAAAGCTTCCGT CGATGGTCGTTTGAAAGGTGCA CATATCGTGATGGATAAAGTCA GCGTTGGCGCAACGGTGACCAT CATGTGTGCTGCAACCCTGGCG GAAGGCACCACGATTATTGAAA ACGCAGCGCGTGAACCGGAAAT CGTCGATACCGCGAACTTCCTG ATTACGCTGGGTGCGAAAATTA GCGGTCAGGGCACCGATCGTAT CGTCATCGAAGGTGTGGAACGT TTAGGCGGCGGTGTCTATCGCG TTCTGCCGGATCGTATCGAAAC CGGTACTTTCCTGGTGGCGGCG GCGATTTCTCGCGGCAAAATTA TCTGCCGTAACGCGCAGCCAGA TACTCTCGACGCCGTGCTGGCG AAACTGCGTGACGCTGGAGCGG ACATCGAAGTCGGCGAAGACTG GATTAGCCTGGATATGCATGGC AAACGTCCGAAGGCTGTTAACG TACGTACCGCGCCGCATCCGGC ATTCCCGACCGATATGCAGGCC CAGTTCACGCTGTTGAACCTGG TGGCAGAAGGGACCGGGTTTAT CACCGAAACGGTCTTTGAAAAC CGCTTTATGCATGTGCCAGAGC TGAGCCGTATGGGCGCGCACGC CGAAATCGAAAGCAATACCGTT ATTTGTCACGGTGTTGAAAAAC TTTCTGGCGCACAGGTTATGGC AACCGATCTGCGTGCATCAGCA AGCCTGGTGCTGGCTGGCTGTA TTGCGGAAGGGACGACGGTGGT | 23 |
| | TGATCGTATTTATCACATCGAT CGTGGCTACGAACGCATTGAAG ACAAACTGCGCGCTTTAGGTGC AAATATTGAGCGTGTGAAAGGC GAATAA | |
| dapA sequence | GCCAGGCGACTGTCTTCAATAT TACAGCCGCAACTACTGACATG ACGGGTGATGGTGTTCACAATT CCAGGGCGATCGGCACCCAACG CAGTGATCACCAGATAATGTTG CGATGACAGTGTCAAACTGGTT ATTCCTTTAAGGGGTGAGTTGT TCTTAAGGAAAGCATAAAAAAA ACATGCATACAACAATCAGAAC GGTTCTGTCTGCTTGCTTTTAA TGCCATACCAAACGTACCATTG AGACACTTGTTTGCACAGAGGA TGGCCCATGTTCACGGGAAGTA TTGTCGCGATTGTTACTCCGAT GGATGAAAAAGGTAATGTCTGT CGGGGTAGCTTGAAAAAACTGA TTGATTATCATGTCGCCAGCGG TACTTCGGCGATCGTTTCTGTT GGCACCACTGGCGAGTCCGCTA CCTTAAATCATGACGAACATGC TGATGTGGTGATGATGACGCTG GATGTGGCTGATGGGCGCATTC CGGTAATTGCCGGGACCGGCGC TAACGCTACTGCGGAAGCCATT AGCCTGACGCAGCGCTTCAATG ACAGTGGTATCGTCGGCTGCCT GACGGTAACCCCTTACTACAAT CGTCCGTCGCAAGAAGGTTTGT ATCAGCATTTCAAAGCCATCGC TGAGCATACTGACCTGCCGCAA ATTCTGTATAATGTGCCGTCCC GTACTGGCTGCGATCTGCTCCC GGAAACGGTGGGCCGTCTGGCG AAAGTAAAAAATATTATCGGAA TCAAAGAGGCAACAGGGAACTT AACGCGTGTAAACCAGATCAAA GAGCTGGTTTCAGATGATTTTG TTCTGCTGAGCGGCGATGATGC GAGCGCGCTGGACTTCATGCAA TTGGGCGGTCATGGGGTTATTT CCGTTACGGCTAACGTCGCAGC GCGTGATATGGGCCAGATGTGC AAACTGGCAGCAGAAGGGCATT TTGCCGAGGCACGCGTTATTAA TCAGCGTCTGATGCCATTACAC AACAAACTATTTGTCGAACCCA ATCCAATCCCGGTGAAATGGGC ATGTAAGGAACTGGGTCTTGTG GCGACCGATACGCTGCGCCTGC CAATGACACCAATCACCGACAG TGGTCGTGAGACGGTCAGAGCG GCGCTTAAGCATGCCGGTTTGC TGTAAAGTTTAGGGAGATTTGA TGGCTTACTCTGTTCAAAAGTC GCGCCTGGCAAAGGTTGCGGGT GTTTCGCTTGTTTTATTACTCG CTGCCTGTAGTTCTGACTCACG CTATAAGCGTCAGGTCAGTGGT GATGAAGCCTACCTGGAAGCG | 24 |

Optionally, the amber suppressor is associated with a promoter or a terminator. Optionally, the promoter is a lipoprotein promoter. Preferable, promoter sequences are recited in Table 4.

TABLE 4

| Amber Suppressor Promoter Sequence | Sequence | SEQ ID NO: |
|---|---|---|
| lipoprotein promoter | CATGGCGCCGCTTCTTTGAGCG AACGATCAAAAATAAGTGGCGC CCCATCAAAAAAATATTCTCAA CATAAAAAACTTTGTGTAATAC TTGTAACGCTG | 25 |
| lipoprotein promoter | CATGGCGCCCCATCAAAAAAAT ATTCTCAACATAAAAAACTTTG TGTAATACTTGTAACGCTG | 26 |

Optionally, the terminator is an rrnC terminator. Preferable, terminator sequences are recited in Table 5.

TABLE 5

| Amber Suppressor Terminator Sequence | Sequence | SEQ ID NO: |
|---|---|---|
| rrnC terminator | GATCCTTAGCGAAAGCTAAGGA TTTTTTTTAC | 27 |
| rrnC terminator | GATCCTTAGCGAAAGCTAAGGA TTTTTTTTTT | 28 |

Bacterial and BTP delivery is more attractive than viral delivery because they are more accessible to genetic manipulation, which allows the production of vector strains specifically tailored to certain applications. In one embodiment of the invention, the methods of the invention are used to create bacteria and BTPs that cause RNAi in a tissue specific manner.

Liberation of the siRNA encoding plasmid or the one or more siRNAs from the intracellular bacteria or BTPs occurs through active mechanisms. One mechanism involves the type III export system in *S. typhimurium*, a specialized multiprotein complex spanning the bacterial or BTP cell membrane whose functions include secretion of virulence factors to the outside of the cell to allow signaling towards the target cell, but which can also be used to deliver antigens into target cells (Rüssmann H. *Int J Med Microbiol*, 293: 107-12 (2003)), or through bacterial lysis and liberation of bacterial or BTP contents into the cytoplasm. The lysis of intracellular bacteria or BTPs is triggered through various mechanisms, including addition of an intracellularly active antibiotic (tetracycline), naturally through bacterial metabolic attenuation (auxotrophy), or through a lysis regulation system or bacterial suicide system comprising a bacterial regulator, promoter and sensor that is sensitive to the environment, e.g., the pH, magnesium concentration, phosphate concentration, ferric ion concentration, osmolarity, anaerobic conditions, nutritional deficiency and general stress of the target cell or the host phagosome. When the bacteria or BTP lysis regulation system senses one or more of the above environmental conditions, bacterial or BTP lysis is triggered by one or more mechanisms including but not limited to antimicrobial proteins, bacteriophage lysins and autolysins expressed by the bacteria or BTP, either naturally or through modification, or through pore-forming proteins expressed by the bacteria or BTPs, either naturally or through modification, e.g., genetic modification, which break the phagosomes containing the bacteria or BTPs and liberate the siRNA-encoding plasmid or the one or more siRNAs.

The regulator of the lysis regulation system may be selected from the group that includes but is not limited to OmpR, ArcA, PhoP, PhoB, Fur, RstA, EvgA and RpoS. Preferable, lysis regulator sequences are recited in Table 6.

TABLE 6

| Lysis Regulation System Regulator Sequence | Sequence | SEQ ID NO: |
|---|---|---|
| OmpR regulator | ATGCAAGAGAACTACAAGATTC TGGTGGTCGATGACGACATGCG CCTGCGTGCGCTGCTGGAACGT TATCTCACCGAACAAGGCTTCC AGGTTCGAAGCGTCGCTAATGC AGAACAGATGGATCGCCTGCTG ACTCGTGAATCTTTCCATCTTA TGGTACTGGATTTAATGTTACC TGGTGAAGATGGCTTGTCGATT TGCCGACGTCTTCGTAGTCAGA GCAACCCGATGCCGATCATTAT GGTGACGGCGAAAGGGGAAGAA GTGGACCGTATCGTAGGCCTGG AGATTGGCGCTGACGACTACAT TCCAAAACCGTTTAACCCGCGT GAACTGCTGGCCCGTATCCGTG CGGTGCTGCGTCGTCAGGCGAA CGAACTGCCAGGCGCACCGTCA CAGGAAGAGGCGGTAATTGCTT TCGGTAAGTTCAAACTTAACCT CGGTACGCGCGAAATGTTCCGC GAAGACGAGCCGATGCCGCTCA CCAGCGGTGAGTTTGCGGTACT GAAGGCACTGGTCAGCCATCCG CGTGAGCCGCTCTCCCGCGATA AGCTGATGAACCTTGCCCGTGG TCGTGAATATTCCGCAATGGAA CGCTCCATCGACGTGCAGATTT CGCGTCTGCGCCGCATGGTGGA AGAAGATCCAGCGCATCCGCGT TACATTCAGACCGTCTGGGGTC TGGGCTACGTCTTTGTACCGGA CGGCTCTAAAGCATGA | 29 |
| PhoP regulator | ATGCGCGTACTGGTTGTTGAAG ACAATGCGTTGTTACGTCACCA CCTTAAAGTTCAGATTCAGGAT GCTGGTCATCAGGTCGATGACG CAGAAGATGCCAAAGAAGCCGA TTATTATCTCAATGAACATATA CCGGATATTGCGATTGTCGATC TCGGATTGCCAGACGAGGACGG TCTGTCACTGATTCGCCGCTGG CGTAGCAACGATGTTTCACTGC CGATTCTGGTATTAACCGCCCG TGAAAGCTGGCAGGACAAAGTC GAAGTATTAAGTGCCGGTGCTG ATGATTATGTGACTAAACCGTT TCATATTGAAGAGGTGATGGCG CGAATGCAGGCATTAATGCGGC GTAATAGCGGTCTGGCTTCACA GGTCATTTCGCTCCCCCCGTTT CAGGTTGATCTCTCTCGCCGTG AATTATCTATTAATGACGAAGT GATCAAACTGACCGCGTTCGAA TACACTATTATGGAAACGTTGA TACGCAATAATGGCAAAGTGGT CAGCAAAGATTCGTTAATGCTC CAACTCTATCCGGATGCGGAGC TGCGGGAAAGCCATACCATTGA TGTACTGATGGGACGTCTGCGC AAAAAAATTCAGGCACAATATC CCCAAGAAGTGATTACCACCGT TCGCGGCCAGGGCTATCTGTTC GAATTGCGCTGA | 30 |

The promoter of the lysis regulation system may be selected from the group that includes but is not limited to ompF, ompC, fadB, phoPQ, mgtA, mgrB, psiB, phnD, Ptrp, sodA, sodB, sltA, sltB, asr, csgD, emrKY, yhiUV, acrAB, mdfA and tolC. Preferable, lysis regulation system promoter sequences are recited in Table 7.

TABLE 7

| Lysis Regulation System Promoter Sequence | Sequence | SEQ ID NO: |
|---|---|---|
| ompF promoter | GATCATCCTGTTACGGAATATT ACATTGCAACATTTACGCGCAA AAACTAATCCGCATTCTTATTG CGGATTAGTTTTTTCTTAGCTA ATAGCACAATTTTCATACTATT TTTTGGCATTCTGGATGTCTGA AAGAAGATTTTGTGCCAGGTCG ATAAAGTTTCCATCAGAAACAA AATTTCCGTTTAGTTAATTTAA ATATAAGGAAATCATATAAATA GATTAAAATTGCTGTAAATATC ATCACGTCTCTATGGAAATATG ACGGTGTTCACAAAGTTCCTTA AATTTTACTTTTGGTTACATAT TTTTTCTTTTTGAAACCAAATC TTTATCTTTGTAGCACTTTCAC GGTAGCGAAACGTTAGTTTGAA TGGAAAGATGCCTGCA | 31 |
| ompC promoter | TTTAAAAAAGTTCCGTAAAATT CATATTTTGAAACATCTATGTA GATAACTGTAACATCTTAAAAG TTTTAGTATCATATTCGTGTTG GATTATTCTGTATTTTTGCGGA GAATGGACTTGCCGACTGGTTA ATGAGGGTTAACCAGTAAGCAG TGGCATAAAAAAGCAATAAAGG CATATAACAGAGGGTTAATAAC | 32 |
| fadB promoter | AGTGATTCCATTTTTTACCCTT CTGTTTTTTTGACCTTAAGTCT CCGCATCTTAGCACATCGTTCA TCCAGAGCGTGATTTCTGCCGA GCGTGATCAGATCGGCATTTCT TTAATCTTTTGTTTGCATATTT TTAACACAAAATACACACTTCG ACTCATCTGGTACGACCAGATC ACCTTGCGGATTCAGGAGACTG AC | 33 |
| phoPQ promoter | GAGCTATCACGATGGTTGATGA GCTGAAATAAACCTCGTATCAG TGCCGGATGGCGATGCTGTCCG GCCTGCTTATTAAGATTATCCG CTTTTTATTTTTTCACTTTACC TCCCCTCCCCGCTGGTTTATTT AATGTTTACCCCCATAACCACA TAATCGCGTTACACTATTTTAA TAATTAAGACAGGGAGAAATAA AA | 34 |
| mgtA promoter | GCTTCAACACGCTCGCGGGTGA GCTGGCTCACGCCGCTTTCGTT ATTCAGCACCCGGGAAACTGTA GATTTCCCCACGCCGCTTAAGC GCGCGATATCTTTGATGGTCAG CCGATTTTGCATCCTGTTGTCC TGTAACGTGTTGTTTAATTATT TGAGCCTAACGTTACCCGTGCA TTCAGCAATGGGTAAAGTCTGG TTTATCGTTGGTTTAGTTGTCA GCAGGTATTATATCGCCA | 35 |
| Ptrp promoter | GAGCTGTTGACAATTAATCATC GAACTAGTTAACTAGTACGCAA GTTCACGTAAAAAGGGTATCTA GAATTCT | 36 |

The sensor of the lysis regulation system may be selected from the group that includes but is not limited to EnvZ, ArcB, PhoQ, PhoR, RstB and EvgS. Preferable, lysis regulation system sensor sequences are recited in Table 8.

TABLE 8

| Lysis Regulation System Sensor Sequence | Sequence | SEQ ID NO: |
|---|---|---|
| EnvZ sensor | ATGAGGCGATTGCGCTTCTCGC CACGAAGTTCATTTGCCCGTAC GTTATTGCTCATCGTCACCTTG CTGTTCGCCAGCCTGGTGACGA CTTATCTGGTGGTGCTGAACTT CGCGATTTTGCCGAGCCTCCAG CAGTTTAATAAAGTCCTCGCGT ACGAAGTGCGTATGTTGATGAC CGACAAACTGCAACTGGAGGAC GGCACGCAGTTGGTTGTGCCTC CCGCTTTCCGTCGGGAGATCTA CCGTGAGCTGGGGATCTCTCTC TACTCCAACGAGGCTGCCGAAG AGGCAGGTCTGCGTTGGGCGCA ACACTATGAATTCTTAAGCCAT CAGATGGCGCAGCAACTGGGCG GCCCGACGGAAGTGCGCGTTGA GGTCAACAAAAGTTCGCCTGTC GTCTGGCTGAAAACCTGGCTGT CGCCCAATATCTGGGTACGCGT GCCGCTGACCGAAATTCATCAG GGCGATTTCTCTCCGCTGTTCC GCTATACGCTGGCGATTATGCT ATTGGCGATAGGCGGGCGTGG CTGTTTATTCGTATCCAGAACC GACCGTTGGTCGATCTCGAACA CGCAGCCTTGCAGGTTGGTAAA GGGATTATTCCGCCGCCGCTGC GTGAGTATGGCGCTTCGGAGGT GCGTTCCGTTACCCGTGCCTTT AACCATATGGCGGCTGGTGTTA AGCAACTGGCGGATGACCGCAC GCTGCTGATGGCGGGGTAAGT CACGACTTGCGCACGCCGCTGA CGCGTATTCGCCTGGCGACTGA GATGATGAGCGAGCAGGATGGC TATCTGGCAGAATCGATCAATA AAGATATCGAAGAGTGCAACGC CATCATTGAGCAGTTTATCGAC TACCTGCGCACCGGGCAGGAGA TGCCGATGGAAATGGCGGATCT TAATGCAGTACTCGGTGAGGTG ATTGCTGCCGAAAGTGGCTATG AGCGGGAAATTGAAACCGCGCT TTACCCCGGCAGCATTGAAGTG AAAATGCACCCGCTGTCGATCA AACGCGCGGTGGCGAATATGGT GGTCAACGCCGCCCGTTATGGC AATGGCTGGATCAAAGTCAGCA GCGGAACGGAGCCGAATCGCGC CTGGTTCCAGGTGGAAGATGAC GGTCCGGGAATTGCGCCGGAAC AACGTAAGCACCTGTTCCAGCC GTTTGTCCGCGGCGACAGTGCG CGCACCATTAGCGGCACGGGAT TAGGGCTGGCAATTGTGCAGCG TATCGTGGATAACCATAACGGG ATGCTGGAGCTTGGCACCAGCG AGCGGGGCGGGCTTTCCATTCG CGCCTGGCTGCCAGTGCCGGTA ACGCGGGCGCAGGGCACGACAA AAGAAGGGTAA | 37 |
| PhoQ sensor | ATGAAAAAATTACTGCGTCTTT TTTTCCCGCTCTCGCTGCGGGT ACGTTTTCTGTTGGCAACGGCA GCGGTAGTACTGGTGCTTTCGC TTGCCTACGGAATGGTCGCGCT GATCGGTTATAGCGTCAGTTTC GATAAAACTACGTTTCGGCTGT TACGTGGCGAGAGCAATCTGTT CTATACCCTTGCGAAGTGGGAA AACAATAAGTTGCATGTCGAGT TACCCGAAAATATCGACAAGCA AAGCCCCACCATGACGCTAATT TATGATGAGAACGGGCAGCTTT | 38 |

TABLE 8-continued

| Lysis Regulation System Sensor Sequence | Sequence | SEQ ID NO: |
|---|---|---|
| | TATGGGCGCAACGTGACGTGCC | |
| | CTGGCTGATGAAGATGATCCAG | |
| | CCTGACTGGCTGAAATCGAATG | |
| | GTTTTCATGAAATTGAAGCGGA | |
| | TGTTAACGATACCAGCCTCTTG | |
| | CTGAGTGGAGATCATTCGATAC | |
| | AGCAACAGTTGCAGGAAGTGCG | |
| | GGAAGATGATGACGAOGCGGAG | |
| | ATGACCCACTCGGTGGCAGTAA | |
| | ACGTCTACCCGGCAACATCGCG | |
| | GATGCCAAAATTAACCATTGTG | |
| | GTGGTGGATACCATTCCGGTGG | |
| | AGCTAAAAAGTTCCTATATGGT | |
| | CTGGAGCTGGTTTATCTATGTG | |
| | CTCTCAGCCAATCTGCTGTTAG | |
| | TGATCCCGCTGCTGTGGGTCGC | |
| | CGCCTGGTGGAGTTTACGCCCC | |
| | ATCGAAGCCCTGGCAAAAGAAG | |
| | TCCGCGAACTGGAAGAACATAA | |
| | CCGCGAATTGCTCAATCCAGCC | |
| | ACAACGCGAGAACTGACCAGTC | |
| | TGGTACGAAACCTGAACCGATT | |
| | GTTAAAAAGTGAACGCGAACGT | |
| | TACGACAAATACCGTACGACGC | |
| | TCACCGACCTGACCCATAGTCT | |
| | GAAAACGCCACTGGCGGTGCTG | |
| | CAAAGTACGCTGCGTTCTCTGC | |
| | GTAGTGAAAAGATGAGCGTCAG | |
| | TGATGCTGAGCCGGTAATGCTG | |
| | GAGCAAATCAGCCGCATTTCAC | |
| | AGCAAATTGGCTACTACCTGCA | |
| | TCGTGCCAGTATGCGCGGCGGG | |
| | ACATTGCTCAGCCGCGAGCTGC | |
| | ATCCGGTCGCCCCACTGCTGGA | |
| | CAATCTCACCTCAGCGCTGAAC | |
| | AAAGTGTATCAACGCAAAGGGG | |
| | TCAATATCTCTCTCGATATTTC | |
| | GCCAGAGATCAGCTTTGTCGGT | |
| | GAGCAGAACGATTTTGTCGAGG | |
| | TGATGGGCAACGTGCTGGATAA | |
| | TGCCTGTAAATATTGCCTCGAG | |
| | TTTGTCGAAATTTCTGCAAGGC | |
| | AAACCGACGAGCATCTCTATAT | |
| | TGTGGTCGAGGATGATGGCCCC | |
| | GGTATTCCATTAAGCAAGCGAG | |
| | AGGTCATTTTCGACCGTGGTCA | |
| | ACGGGTTGATACTTTACGCCCT | |
| | GGGCAAGGTGTAGGGCTGGCGG | |
| | TAGCCCGCGAAATCACCGAGCA | |
| | ATATGAGGGTAAAATCGTCGCC | |
| | GGAGAGAGCATGCTGGGCGGTG | |
| | CGCGGATGGAGGTGATTTTTGG | |
| | TCGCCAGCATTCTGCGCCGAAA | |
| | GATGAATAA | |

The lysis regulation system may comprise any combination of one or more of the above regulators, promoters and sensors.

In one example of this embodiment, the lysis regulation system comprises OmpR as the regulator, ompF as the promoter and EnvZ as the sensor and the stimulus is reduced osmolarity. In another example of this embodiment, the lysis regulation system comprises OmpR as the regulator, ompC as the promoter and EnvZ as the sensor and the stimulus is reduced osmolarity.

In another example of this embodiment, the lysis regulation system comprises the ArcA as the regulator, fad as the promoter and Arc B as the sensor and the stimulus is anaerobic conditions.

In another example of this embodiment, the lysis regulation system comprises PhoP as the regulator, phoPQ as the promoter and PhoQ as the sensor and the stimulus is reduced magnesium concentration. In another example of this embodiment, the lysis regulation system comprises PhoP as the regulator, mgtA as the promoter and PhoQ as the sensor and the stimulus is reduced magnesium concentration. In another example of this embodiment, the lysis regulation system comprises PhoP as the regulator, mgrB as the promoter and PhoQ as the sensor and the stimulus is reduced magnesium concentration.

In another example of this embodiment, the lysis regulation system comprises PhoB as the regulator, psiB as the promoter and PhoR as the sensor and the stimulus is reduced phosphate concentration. In another example of this embodiment, the lysis regulation system comprises PhoB as the regulator, phnD as the promoter and PhoR as the sensor and the stimulus is reduced phosphate concentration. In another example of this embodiment, the lysis regulation system comprises RstA as the regulator, asr as the promoter and RstB as the sensor. In another example of this embodiment, the lysis regulation system comprises RstA as the regulator, csgD as the promoter and RstB as the sensor.

In another example of this embodiment, the lysis regulation system comprises EvgA as the regulator, emrKY as the promoter and EvgS as the sensor. In another example of this embodiment, the lysis regulation system comprises EvgA as the regulator, yhiUV as the promoter and EvgS as the sensor. In another example of this embodiment, the lysis regulation system comprises EvgA as the regulator, acrAB as the promoter and EvgS as the sensor. In another example of this embodiment, the lysis regulation system comprises EvgA as the regulator, mdfA as the promoter and EvgS as the sensor. In another example of this embodiment, the lysis regulation system comprises EvgA as the regulator, tolC as the promoter and EvgS as the sensor.

In another example of this embodiment, the lysis regulation system comprises Fur as the regulator in combination with a promoter selected from the group comprising sodA, sodB, sltA or sltB.

The antimicrobial protein may be selected from the group that includes but is not limited to α-and β-defensins, protegrins, cathelicidins (e.g., indolicidin and bactenecins), granulysin, lysozyme, lactoferrin, azurocidin, elastase, bactericidal permeability inducing peptide (BPI), adrenomedullin, brevinin, histatins and hepcidin. Additional antimicrobial proteins are disclosed in the following, each of which is incorporated herein by reference in its entirety: Devine, D. A. et al., *Current Pharmaceutical Design*, 8, 703-714 (2002); Jack R. W., et al., *Microbiological Reviews*, 59 (2), 171-200 (June 1995).

Optionally, the antimicrobial protein is an α-defensin, β-defensin, or protegrin. Preferable, antimicrobial protein sequences are recited in Table 9.

TABLE 9

| Antimicrobial Protein Sequence | Sequence | SEQ ID NO: |
|---|---|---|
| α-defensin-1 protein | CTATAGAAGACCTGGGACAGAG GACTGCTGTCTGCCCTCTCTGG TCACCCTGCCTAGCTAGAGGAT CTGTGACCCCAGCCATGAGGAC CCTCGCCATCCTTGCTGCCATT CTCCTGGTGGCCCTGCAGGCCC AGGCTGAGCCACTCCAGGCAAG AGCTGATGAGGTTGCTGCAGCC CCGGAGCAGATTGCAGCGGACA TCCCAGAAGTGGTTGTTTCCCT TGCATGGGACGAAAGCTTGGCT CCAAAGCATCCAGGCTCAAGGA | 39 |

TABLE 9-continued

| Antimicrobial Protein Sequence | Sequence | SEQ ID NO: |
|---|---|---|
| | AAAACATGGCCTGCTATTGCAG AATACCAGCGTGCATTGCAGGA GAACGTCGCTATGGAACCTGCA TCTACCAGGGAAGACTCTGGGC ATTCTGCTGCTGAGCTTGCAGA AAAAGAAAAATGAGCTCAAAAT TTGCTTTGAGAGCTACAGGGAA TTGCTATTACTCCTGTACCTTC TGCTCAATTTCCTTTCCTCATC CCAAATAAATGCCTTGGTACAA GAAAAG | |
| α-defensin-3 protein | CCTTGCTATAGAAGACCTGGGA CAGAGGACTGCTGTCTGCCCTC TCTGGTCACCCTGCCTAGCTAG AGGATCTGTGACCCCAGCCATG AGGACCCTCGCCATCCTTGCTG CCATTCTCCTGGTGGCCCTGCA GGCCCAGGCTGAGCCACTCCAG GCAAGAGCTGATGAGGTTGCTG CAGCCCCGGAGCAGATTGCAGC GGACATCCCAGAGTGGTTGTT TCCCTTGCATGGGACGAAAGCT TGGCTCCAAAGCATCCAGGCTC AAGGAAAAACATGGACTGCTAT TGCAGAATACCAGCGTGCATTG CAGGAGAACGTCGCTATGGAAC CTGCATCTACCAGGGAAGACTC TGGGCATTCTGCTGCTGAGCTT GCAGAAAAAAATGAGCTC AAAATTTGCTTTGAGAGCTACA GGGAATTGCTATTACTCCTGTA CCTTCTGCTCAATTTCCTTTCC TCATCTCAAATAAATGCCTTGT TAC | 40 |
| α-defensin-4 protein | GTCTGCCCTCTCTGCTCGCCCT GCCTAGCTTGAGGATCTGTCAC CCCAGCCATGAGGATTATCGCC CTCCTCGCTGCTATTCTCTTGG TAGCCCTCCAGGTCCGGCAGG CCCACTCCAGGCAAGAGGTGAT GAGGCTCCAGGCCAGGAGCAGC GTGGGCCAGAAGACCAGGACAT ATCTATTTCCTTTGCATGGGAT AAAAGCTCTGCTCTTCAGGTTT CAGGCTCAACAAGGGGCATGGT CTGCTCTTGCAGATTAGTATTC TGCCGGCGAACAGAACTTCGTG TTGGGAACTGCCTCATTGGTGG TGTGAGTTTCACATACTGCTGC ACGCGTGTCGATTAACGTTCTG CTGTCCAAGAGAATGTCATGCT GGGAACGCCATCATCGGTGGTG TTAGCTTCACATGCTTCTGCAG CTGAGCTTGCAGAATAGAGAAA AATGAGCTCATAATTTGCTTTG AGAGCTACAGGAAATGGTTGTT TCTCCTATACTTTGTCCTTAAC ATCTTTCTTGATCCTAAATATA TATCTCGTAACAAG | 41 |
| α-defensin-5 protein | ATATCCACTCCTGCTCTCCCTC CTGCAGGTGACCCCAGCCATGA GGACCATCGCCATCCTTGCTGC CATTCTCCTGGTGGCCCTGCAG GCCCAGGCTGAGTCACTCCAGG AAAGAGCTGATGAGGCTACAAC CCAGAAGCAGTCTGGGGAAGAC AACCAGGACCTTGCTATCTCCT TTGCAGGAAATGGACTCTCTGC TCTTAGAACCTCAGGTTCTGCA GCAAGAGCCACCTGCTATTGCC GAACCGGCCGTTGTGCTACCCG TGAGTCCCTCTCCGGGGTGTGT GAAATCAGTGGCCGCCTCTACA GACTCTGCTGTCGCTGAGCTTC | 42 |

| Antimicrobial Protein Sequence | Sequence | SEQ ID NO: |
|---|---|---|
| | CTAGATAGAAACCAAAGCAGTG CAAGATTCAGTTCAAGGTCCTG AAAAAAGAAAAACATTTTACTC TGTGTACCTTGTGTCTTTCTAA ATTTCTCTCTCCAAAATAAAGT TCAAGCATT | |
| α-defensin-6 protein | ACACATCTGCTCCTGCTCTCTC TCCTCCAGCGACCCTAGCCATG AGAACCCTCACCATCCTCACTG CTGTTCTCCTCGTGGCCCTCCA GGCCAAGGCTGAGCCACTCCAA GCTGAGGATGATCCACTGCAGG CAAAAGCTTATGAGGCTGATGC CCAGGAGCAGCGTGGGCAAAT GACCAGGACTTTGCCGTCTCCT TTGCAGAGGATGCAAGCTCAAG TCTTAGAGCTTTGGGCTCAACA AGGGCTTTCACTTGCCATTGCA GAAGGTCCTGTTATTCAACAGA ATATTCCTATGGGACCTGCACT GTCATGGGTATTAACCACAGAT TCTGCTGCCTCTGAGGGATGAG AACAGAGAGAAATATATTCATA ATTTACTTTATGACCTAGAAGG AAACTGTCGTGTGTCCCATACA TTGCCATCAACTTTGTTTCCTC ATCTCAAATAAAGTCCTTTCAG CAAAAAAAAAAA | 43 |
| β-defensin-1 protein | TCCCTTCAGTTCCGTCGACGAG GTTGTGCAATCCACCAGTCTTA TAAATACAGTGACGCTCCAGCC TCTGGAAGCCTCTGTCAGCTCA GCCTCCAAAGGAGCCAGCGTCT CCCCAGTTCCTGAAATCCTGGG TGTTGCTGCCAGTCGCCATGA GAACTTCCTACCTTCTGCTGTT TACTCTCTGCTTACTTTTGTCT GAGATGGCCTCAGGTGGTAACT TTCTCACAGGCCTTGCCACAG ATCTGATCATTACAATTGCGTC AGCAGTGGAGGGCAATGTCTCT ATTCTGCCTGCCCGATCTTTAC CAAAATTCAAGGCACCTGTTAC AGAGGGAAGGCCAAGTGCTGCA AGTGAGCTGGGAGTGACCAGAA GAAATGACGCAGAAGTGAAATG AACTTTTTATAAGCATTCTTTT AATAAAGGAAAATTGCTTTGA AGTATACCTCCTTTGGGCCAAA AAAAAAAAAAAAAAAAAAAA | 44 |
| β-defensin-3 protein | TGAGTCTCAGCGTGGGGTGAAG CCTAGCAGCTATGAGGATCCAT TATCTTCTGTTTGCTTTGCTCT TCCTGTTTTTGGTGCCTGTCCC AGGTCATGGAGGAATCATAAAC ACATTACAGAAATATTATTGCA GAGTCAGAGGCGGCCGGTGTGC TGTGCTCAGCTGCCTTCCAAAG GAGGAACAGATCGGCAAGTGCT CGACGCGTGGCCGAAATGCTG CCGAAGAAAGAAATAAAAACCC TGAAACATGACGAGAGTGTTGT AAAGTGTGGAAATGCCTTCTTA AAGTTTATAAAAGTAAAATCAA ATTACATTTTTTTTTCAAAAAA AAAAAA | 45 |
| β-defensin-4 protein | AGACTCAGCTCCTGGTGAAGCT CCCAGCCATCAGCCATGAGGGT CTTGTATCTCCTCTTCTCGTTC CTCTTCATATTCCTGATGCCTC TTCCAGGTGTTTTTGGTGGTAT AGGCGATCCTGTTACCTGCCTT AAGAGTGGAGCCATATGTCATC | 46 |

TABLE 9-continued

| Antimicrobial Protein Sequence | Sequence | SEQ ID NO: |
|---|---|---|
| | CAGTCTTTTGCCCTAGAAGGTA TAAACAAATTGGCACCTGTGGT CTCCCTGGAACAAAATGCTGCA AAAAGCCATGAGGAGGCCAAGA AGCTGCTGGCTGATGCGGAT TCAGAAAGGGCTCCCTCATCAG AGACGTGCGACATGTAAACCAA ATTAAACTATGGTGTCCAAAGA TACGCA | |
| protegrin-1 protein | ATGGAGACCCAGAGAGCCAGCC TGTGCCTGGGGCGCTGGTCACT GTGGCTTCTGCTGCTGGCACTC GTGGTGCCCTCGGCCAGCGCCC AGGCCCTCAGCTACAGGGAGGC CGTGCTTCGTGCTGTGGATCGC CTCAACGAGCAGTCCTCGGAAG CTAATCTCTACCGCCTCCTGGA GCTGGACCAGCCGCCCAAGGCC GACGAGGACCCGGGCACCCCGA AACCTGTGAGCTTCACGGTGAA GGAGACTGTGTGTCCCAGGCCG ACCCGGCAGCCCCCGGAGCTGT GTGACTTCAAGGAGAACGGGCG GGTGAAACAGTGTGTGGGGACA GTCACCCTGGATCAGATCAAGG ACCCGCTCGACATCACCTGCAA TGAGGTTCAAGGTGTCAGGGGA GGTCGCCTGTGCTATTGTAGGC GTAGGTTCTGCGTCTGTGTCGG ACGAGGATGACGGTTGCGACGG CAGGCTTTCCCTCCCCCAATTT TCCCGGGGCCAGGTTTCCGTCC CCCAATTTTTCCGCCTCCACCT TTCCGGCCCGCACCATTCGGTC CACCAAGGTTCCCTGGTAGACG GTGAAGGATTTGCAGGCAACTC ACCCAGAAGGCCTTTCGGTACA TTAAAATCCCAGCAAGGAGACC TAAGCATCTGCTTTGCCCAGGC CCGCATCTGTCAAATAAATTCT TGTGAAACC | 47 |
| protegrin-3 protein | ATGGAGACCCAGAGAGCCAGCC TGTGCCTGGGGCGCTGGTCACT GTGGCTTCTGCTGCTGGCACTC GTGGTGCCCTCGGCCAGCGCCC AGGCCCTCAGCTACAGGGAGGC CGTGCTTCGTGCTGTGGATCGC CTCAACGAGCAGTCCTCGGAAG CTAATCTCTACCGCCTCCTGGA GCTGGACCAGCCGCCCAAGGCC GACGAGGACCCGGGCACCCCGA AACCTGTGAGCTTCACGGTGAA GGAGACTGTGTGTCCCAGGCCG ACCCGGCAGCCCCCGGAGCTGT GTGACTTCAAGGAGAACGGGCG GGTGAAACAGTGTGTGGGGACA GTCACCCTGGATCAGATCAAGG ACCCGCTCGACATCACCTGCAA TGAGGTTCAAGGTGTCAGGGGA GGTGGCCTGTGCTATTGTAGGC GTAGGTTCTGCGTCTGTGTCGG ACGAGGATGACGGTTGCGACGG CAGGCTTTCCCTCCCCCAATTT TCCCGGGGCCAGGTTTCCGTCC CCCAATTTTTCCGCCTCCACCT TTCCGGCCCGCACCATTCGGTC CACCAAGGTTCCCTGGTAGACG GTGAAGGATTTGCAGGCAACTC ACCCAGAAGGCCTTTCGGTACA TTAAAATCCCAGCAAGGAGACC TAAGCATCTGCTTTGCCCAGGC CCGCATCTGTCAAATAAATTCT TGTGAAACC | 48 |
| protegrin-4 protein | ATGGAGACCCAGAGAGCCAGCC TGTGCCTGGGGCGCTGGTCACT GTGGCTTCTGCTGCTGGCACTC GTGGTGCCCTCGGCCAGCGCCC AGGCCCTCAGCTACAGGGAGGC CGTGCTTCGTGCTGTGGATCGC CTCAACGAGCAGTCCTCGGAAG CTAATCTCTACCGCCTCCTGGA GCTGGACCAGCCGCCCAAGGCC GACGAGGACCCGGGCACCCCGA AACCTGTGAGCTTCACGGTGAA GGAGACTGTGTGTCCCAGGCCG ACCCGGCAGCCCCCGGAGCTGT GTGACTTCAAGGAGAACGGGCG GGTGAAACAGTGTGTGGGGACA GTCACCCTGGATCAGATCAAGG ACCCGCTCGACATCACCTGCAA TGAGGTTCAAGGTGTCAGGGGA GGTCGCCTGTGCTATTGTAGGG GTTGGATCTGCTTCTGTGTCGG ACGAGGATGACGGTTGCGACGG CAGGCTTTCCCTCCCCCAATTT TCCCGGGGCCAGGTTTCCGTCC CCCAATTTTTCCGCCTCCACCT TTCCGGCCCGCACCATTCGGTC CACCAAGGTTCCCTGGTAGACG GTGAAGGATTTGCAGGCAACTC ACCCAGAAGGCCTTTCGGCACA TTAAAATCCCAGCAAGGAGACC TAAGCATCTGCTTTGCCCAGGC CCGCATCTGTCAAATAAATTCT TGTGAAACC | 49 |

The bacteriophase lysin may be selected from the group that includes but is not limited to holins and endolysins or lysins (e.g., lysozyme, amidase and transglycoslate). Additional lysins are disclosed in the following, each of which is incorporated herein by reference in its entirety: Kloos D.-U., et al., *Journal of Bacteriology*, 176 (23), 7352-7361 (December 1994); Jain V., et al., *Infection and Immunity*, 68 (2), 986-989 (February 2000); Srividhya K. V., et al., *J. Biosci.*, 32, 979-990 (2007); Young R. V., *Microbiological Reviews*, 56 (3), 430-481 (September 1992).

The autolysin may be selected from the group that includes but is not limited to peptidoglycan hydrolases, amidases (e.g., N-acetylmuramyl-L-alanine amidases), transglycosylases, endopeptidases and glucosaminidases. Additional autolysins are disclosed in the following, each of which is incorporated herein by reference in its entirety: Heidrich C., et al., *Molecular Microbiology*, 41 (1), 167-178 (2001); Kitano K., et al., *Journal of Bacteriology*, 167 (3), 759-765 (September 1986); Lommatzsch J., et al., *Journal of Bacteriology*, 179 (17), 5465-5470 (September 1997); Oshida T., et al., *PNAS*, 92, 285-289 (January 1995); Lenz L. L., et al., *PNAS*, 100 (21), 12432-12437 (Oct. 14, 2003); Ramadurai L., et al., *Journal of Bacteriology*, 179 (11), 3625-3631 (June 1997); Kraft A. R., et al., *Journal of Bacteriology*, 180 (12), 3441-3447 (July 1998); Dijkstra A. J., et al., *FEBS Letters*, 366, 115-118 (1995); Huard C., et al., *Microbiology*, 149, 695-705 (2003).

In one aspect of the invention, the control exerted by the lysis regulation system may further be enhanced by bacterial or BTP strain-specific regulation. In one aspect of this embodiment, the strain-specific regulation is attenuation caused by deletion of a nutritional gene. The nutritional gene may be selected from the group that includes but is not limited to dapA, aroA and guaBA. In one example of this embodiment, dapA attenuation results in deficiency in the biosynthesis of lysine and peptidoglycan. In this particular embodiment, transcription of genes including but not limited to lysC may be activated by mechanisms such as transcriptional induction, antitermination and riboswitch. In another example of this embodiment, aroA attenuation results in deficiency in aromatic amino acids and derepression of one or more genes including but not limited to aroF, aroG and aroH by regulators such as TrpR and TyrR. In another example of this embodiment, guaBA attenuation results in derepression of one or more genes that are repressed by PurR.

In addition to the lysis regulation system and strain-specific regulation, the bacteria or BTP may further contain an inducible system that includes but is not limited to a Tet-on expression system to facilitate bacterial or BTP lysis at a time desired by the clinician. Upon administration of tetracycline, which activates the Tet-on promoter, the bacteria or BTP express a protein that triggers lysis of the bacteria or BTP. In one example of this embodiment, the protein expressed under the Tet-on expression system is selected from the group that includes but is not limited to defensins and protegrins.

Figure 30:
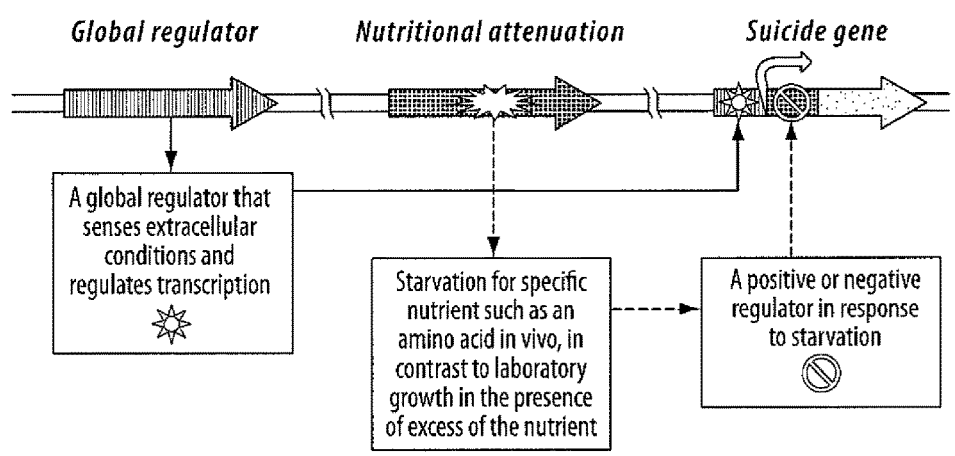
FIG. 30 is a schematic showing a lysis regulation system in combination with strain-specific nutritional attenuation.
Figure 31:
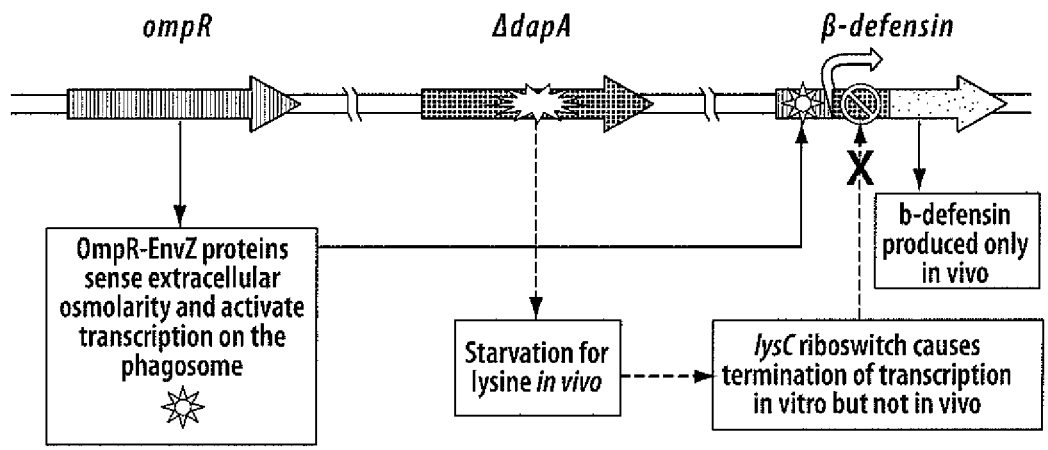
FIG. 31 is a schematic showing three cassettes in the combination lysis regulation system/nutritional attenuation system.

The present invention also provides a lysis regulation system in combination with strain-specific attenuation (e.g., nutritional attenuation). As shown in FIG. 30, a global regulator can sense an extracellular condition and regulate transcription, starvation for specific nutrient such as an amino acid in vivo, in contrast to laboratory growth in the presence of excess of the nutrient and a positive or negative regulator in response to starvation. In the schematic shown in FIG. 31 there can be three cassettes, any of which may be place on either the bacterial chromosome or on a plasmid.

Figure 32:
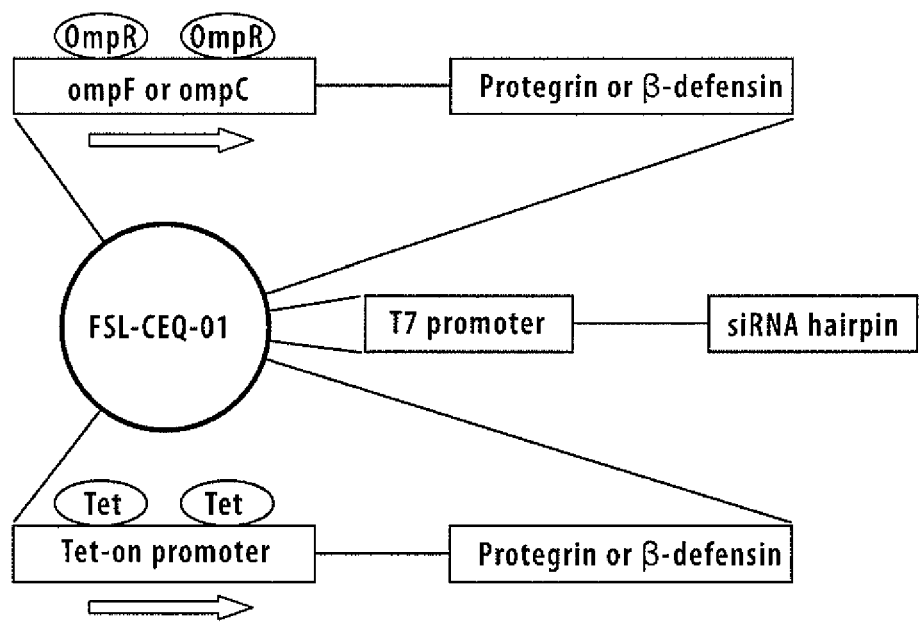
FIG. 32 is a schematic showing a lysis regulation system in combination with a Tet-on expression system.

As described, the present invention provides a plasmid containing a lysis regulation system comprising OmpR as the regulator, ompF or ompC as the promoter and protegrin or β-defensin as the antimicrobial protein, in combination with a Tet-on expression system, which provides two levels of control of bacterial lysis. This embodiment is illustrated in FIG. 32.

In another aspect of the invention, the DNA insert comprises one or more of the following constructs, each of which contains an HPV target sequence, a hairpin sequence and BamHI and SalI restriction sites to facilitate incorporation into the hairpin RNA expression cassette of the TRIP plasmid as shown in Table 10.

introducing at least one invasive bacterium, or at least one bacterial therapeutic particle (BTP), containing one or more siRNAs or one or more DNA molecules encoding one or more siRNAs to the mammalian cells, where the expressed siRNAs interfere with at least one mRNA of a gene of interest thereby regulating gene expression.

The invention provides a method for delivering RNA to any type of target cell. As used herein, the term "target cell" refers to a cell that can be invaded by a bacterium, i.e., a cell that has the necessary surface receptor for recognition by the bacterium.

Preferred target cells are eukaryotic cells. Even more preferred target cells are animal cells. "Animal cells" are defined as nucleated, non-chloroplast containing cells derived from or present in multicellular organisms whose taxanomic position lies within the kingdom animalia. The cells may be present in the intact animal, a primary cell culture, explant culture or a transformed cell line. The particular tissue source of the cells is not critical to the present invention.

The recipient animal cells employed in the present invention are not critical thereto and include cells present in or derived from all organisms within the kingdom animalia, such as those of the families mammalia, pisces, avian, reptilia.

Preferred animal cells are mammalian cells, such as humans, bovine, ovine, porcine, feline, canine, goat, equine, and primate cells. The most preferred mammalian cells are human cells. The cells can be in vivo, in vitro or ex vivo.

In some embodiments of the invention, the cell is a cervical epithelial cell, a rectal epithelial cell or a pharyngeal epithelial cell, macrophage, gastrointestinal epithelial cell, skin cell, melanocyte, keratinocyte, hair follicle, colon cancer cell, an ovarian cancer cell, a bladder cancer cell, a pharyngeal cancer cell, a rectal cancer cell, a prostate cancer cell, a breast cancer cell, a lung cancer cell, a renal cancer cell, a pancreatic cancer cell, or a hematologic cancer cell such as a lymphoma or leukemia cell. In one aspect of this embodiment, the colon cancer cell is an SW 480 cell. In another aspect of this embodiment, the pancreatic cancer cell is a CAPAN-1 cell.

In a preferred embodiment, the target cell is in a mucosal surface. Certain enteric pathogens, e.g., *E. coli, Shigella, Listeria*, and *Salmonella*, are naturally adapted for this application, as these organisms possess the ability to attach to and invade host mucosal surfaces (Kreig et al. supra).

TABLE 10

| HPV Target Sequence Construct | | | | |
|---|---|---|---|---|
| BamHI | sense (19 bp) | loop | antisense (21 bp) | SalI |
| 5'-GATCC | TAGGTATTTGAATTTGCAT | TTCAAGAGA | ATGCAAATTCAAATACCTTTT | G-3' (SEQ ID NO: 50) |
| 3'-G | ATCCATAAACTTAAACGTA | AAGTTCTCT | TACGTTTAAGTTTATGGAAAA | CAGCT-5' (SEQ ID NO: 51) |

4. Cell and Gene Targets

The present invention also provides methods of using the various bacterium, BTP and vectors provided in the invention. For example, the present invention provides methods of delivering one or more siRNAs to mammalian cells. The methods include introducing at least one invasive bacterium, or at least one bacterial therapeutic particle (BTP), containing one or more siRNAs or one or more DNA molecules encoding one or more siRNAs to the mammalian cells.

The present invention also provides methods of regulating gene expression in mammalian cells. The method includes Therefore, in the present invention, such bacteria can deliver RNA molecules or RNA-encoding DNA to cells in the host mucosal compartment.

Although certain types of bacteria may have a certain tropism, i.e., preferred target cells, delivery of RNA or RNA-encoding DNA to a certain type of cell can be achieved by choosing a bacterium which has a tropism for the desired cell type or which is modified such as to be able to invade the desired cell type. Thus, e.g., a bacterium could be genetically engineered to mimic mucosal tissue tropism and invasive properties, as discussed above, to thereby allow said bacteria to invade mucosal tissue, and deliver RNA or RNA-encoding DNA to cells in those sites.

Bacteria can also be targeted to other types of cells. For example, bacteria can be targeted to erythrocytes of humans and primates by modifying bacteria to express on their surface either, or both of, the Plasmodium vivax reticulocyte binding proteins-1 and -2, which bind specifically to erythrocytes in humans and primates (Galinski et al. Cell, 69:1213-1226 (1992)). In another embodiment, bacteria are modified to have on their surface asialoorosomucoid, which is a ligand for the asilogycoprotein receptor on hepatocytes (Wu et al. J. Biol. Chem., 263:14621-14624 (1988)). In yet another embodiment, bacteria are coated with insulin-poly-L-lysine, which has been shown to target plasmid uptake to cells with an insulin receptor (Rosenkranz et al. Expt. Cell Res., 199:323-329 (1992)). Also within the scope of the invention are bacteria modified to have on their surface p60 of *Listeria monocytogenes*, which allows for tropism for hepatocytes (Hess et al. Infect. Immun., 63:2047-2053 (1995)), or a 60 kD surface protein from *Trypanosoma cruzi* which causes specific binding to the mammalian extracellular matrix by binding to heparin, heparin sulfate and collagen (Ortega-Barria et al. Cell, 67:411-421 (1991)).

Yet in another embodiment, a cell can be modified to become a target cell of a bacterium for delivery of RNA. Accordingly, a cell can be modified to express a surface antigen that is recognized by a bacterium for its entry into the cell, i.e., a receptor of an invasion factor. The cell can be modified either by introducing into the cell a nucleic acid encoding a receptor of an invasion factor, such that the surface antigen is expressed in the desired conditions. Alternatively, the cell can be coated with a receptor of an invasion factor. Receptors of invasion factors include proteins belonging to the integrin receptor superfamily. A list of the type of integrin receptors recognized by various bacteria and other microorganisms can be found, e.g., in Isberg and Tran Van Nhieu (1994) Ann. Rev. Genet. 27:395. Nucleotide sequences for the integrin subunits can be found, e.g., in GenBank, publicly available on the internet.

As set forth above, yet other target cells include fish, avian, and reptilian cells. Examples of bacteria that are naturally invasive for fish, avian, and reptilian cells are set forth below.

Examples of bacteria that can naturally access the cytoplasm of fish cells include, but are not limited to, *Aeromonas salminocida* (ATCC No. 33658) and *Aeromonas schuberii* (ATCC No. 43700). Attenuated bacteria are preferably used in the invention, and include *A. salmonicidia* vapA (Gustafson et al. J. Mol. Biol., 237:452-463 (1994)) or *A. salmonicidia* aromatic-dependent mutant (Vaughan et al. Infect. Immun., 61:2172-2181 (1993)).

Examples of bacteria that can naturally access the cytoplasm of avian cells include, but are not restricted to, *Salmonella galinarum* (ATCC No. 9184), *Salmonella enteriditis* (ATCC No. 4931) and *Salmonella typhimurium* (ATCC No. 6994). Attenuated bacteria are preferred to the invention and include attenuated *Salmonella* strains such as *S. galinarum* cya crp mutant (Curtiss et al. (1987) supra) or *S. enteritidis* aroA aromatic-dependent mutant CVL30 (Cooper et al. Infect. Immun., 62:4739-4746 (1994)).

Examples of bacteria that can naturally access the cytoplasm of reptilian cells include, but are not restricted to, *Salmonella typhimurium* (ATCC No. 6994). Attenuated bacteria are preferable to the invention and include, attenuated strains such as *S. typhimuirum* aromatic-dependent mutant (Hormaeche et al. supra).

The invention also provides for delivery of RNA to other eukaryotic cells, e.g., plant cells, so long as there are microorganisms that are capable of invading such cells, either naturally or after having been modified to become invasive. Examples of microorganisms which can invade plant cells include *Agrobacterium tumerfacium*, which uses a pilus-like structure which binds to the plant cell via specific receptors, and then through a process that resembles bacterial conjugation, delivers at least some of its content to the plant cell.

Set forth below are examples of cell lines to which RNA can be delivered according to the method of this invention.

Examples of human cell lines include but are not limited to ATCC Nos. CCL 62, CCL 159, HTB 151, HTB 22, CCL 2, CRL 1634, CRL 8155, HTB 61, and HTB104.

Examples of bovine cell lines include ATCC Nos. CRL 6021, CRL 1733, CRL 6033, CRL 6023, CCL 44 and CRL 1390.

Examples of ovine cells lines include ATCC Nos. CRL 6540, CRL 6538, CRL 6548 and CRL 6546.

Examples of porcine cell lines include ATCC Nos. CL 184, CRL 6492, and CRL 1746.

Examples of feline cell lines include CRL 6077, CRL 6113, CRL 6140, CRL 6164, CCL 94, CCL 150, CRL 6075 and CRL 6123.

Examples of buffalo cell lines include CCL 40 and CRL 6072.

Examples of canine cells include ATCC Nos. CRL 6213, CCL 34, CRL 6202, CRL 6225, CRL 6215, CRL 6203 and CRL 6575.

Examples of goat derived cell lines include ATCC No. CCL 73 and ATCC No. CRL 6270.

Examples of horse derived cell lines include ATCC Nos. CCL 57 and CRL 6583.

Examples of deer cell lines include ATCC Nos. CRL 6193-6196.

Examples of primate derived cell lines include those from chimpanzee's such as ATCC Nos. CRL 6312, CRL 6304, and CRL 1868; monkey cell lines such as ATCC Nos. CRL 1576, CCL 26, and CCL 161; orangautan cell line ATCC No. CRL 1850; and gorilla cell line ATCC No. CRL 1854.

The invention also provides methods of regulating the expression of one or more genes. Preferably, regulating the expression of one or more genes means decreasing or lessening the expression of the gene and/or decreasing or lessening the activity of the gene and its corresponding gene product.

In one embodiment, the expressed siRNAs direct the multienzyme complex RISC (RNA-induced silencing complex) of the cell to interact with the mRNAs to be regulated. This complex degrades or sequesters the mRNA. This causes the expression of the gene to be decreased or inhibited.

In some embodiments, the gene is an animal gene. Preferred animal genes are mammalian genes, such as humans, bovine, ovine, porcine, feline, canine, goat, equine, and primate genes. The most preferred mammalian genes are human cells.

The gene to be regulated can be a viral gene, anti-inflammatory gene, obesity gene or autoimmmune disease or disorder gene. In some embodiments, more than one gene can be regulated from a single plasmid or vector.

In preferred embodiments, the gene can be, but is not limited to, ras, β-catenin, one or more HPV oncogenes, APC, HER-2, MDR-1, MRP-2, FATP4, SGLUT-1, GLUT-2, GLUT-5, apobec-1, MTP, IL-6, IL-6R, IL-7, IL-12, IL-13, IL-13 Ra-1, IL-18, p38/JNK MAP kinase, p65/NF-κB, CCL20 (MIP-3α), Claudin-2, Chitinase 3-like 1, apoA-IV, MHC class I and MHC class II. In one aspect of this embodiment, the ras is k-Ras. In another aspect of this embodiment, the HPV oncogene is E6 or E7.

Preferable β-catenin target gene sequences are recited in Table 11. The sequences in Table 11 are cross-species target sequences as they are capable of silencing the beta-catenin gene (CTNNB1) in human, mouse, rat, dog and monkey.

TABLE 11

| β-catenin target gene sequences | SEQ ID NO: |
|---|---|
| AGCCAATGGCTTGGAATGAGA | 52 |
| ATCAGCTGGCCTGGTTTGATA | 53 |
| CTGTGAACTTGCTCAGGACAA | 54 |
| AGCAATCAGCTGGCCTGGTTT | 55 |
| CCTCTGTGAACTTGCTCAGGA | 56 |
| TTCCGAATGTCTGAGGACAAG | 57 |
| CCAATGGCTTGGAATGAGACT | 58 |
| GGTGCTGACTATCCAGTTGAT | 59 |
| CAATCAGCTGGCCTGGTTTGA | 60 |
| CACCCTGGTGCTGACTATCCA | 61 |
| CACCACCCTGGTGCTGACTAT | 62 |
| TGCTTTATTCTCCCATTGAAA | 63 |
| CTGGTGCTGACTATCCAGTTG | 64 |
| TCTGTGCTCTTCGTCATCTGA | 65 |
| TGCCATCTGTGCTCTTCGTCA | 66 |
| TGGTGCTGACTATCCAGTTGA | 67 |
| CCTGGTGCTGACTATCCAGTT | 68 |
| ACCCTGGTGCTGACTATCCAG | 69 |
| GAGCCTGCCATCTGTGCTCTT | 70 |
| CTGGTTTGATACTGACCTGTA | 71 |
| TGGTTTGATACTGACCTGTAA | 72 |
| TCGAGGAGTAACAATACAAAT | 73 |
| ACCATGCAGAATACAAATGAT | 74 |
| AGGAGTAACAATACAAATGGA | 75 |
| GTCGAGGAGTAACAATACAAA | 76 |
| TTGTTGTAACCTGCTGTGATA | 77 |
| GAGTAATGGTGTAGAACACTA | 78 |
| AGTAATGGTGTAGAACACTAA | 79 |
| CACACTAACCAAGCTGAGTTT | 80 |
| TTTGGTCGAGGAGTAACAATA | 81 |
| TACCATTCCATTGTTTGTGCA | 82 |
| TAGGGTAAATCAGTAAGAGGT | 83 |
| CTAACCAAGCTGAGTTTCCTA | 84 |
| TGGTCGAGGAGTAACAATACA | 85 |

TABLE 11-continued

| β-catenin target gene sequences | SEQ ID NO: |
|---|---|
| CTGGCCTGGTTTGATACTGAC | 86 |
| TAACCTCACTTGCAATAATTA | 87 |
| ATCCCACTGGCCTCTGATAAA | 88 |
| GACCACAAGCAGAGTGCTGAA | 89 |
| CACAAGCAGAGTGCTGAAGGT | 90 |
| CTAACCTCACTTGCAATAATT | 91 |
| AGCTGATATTGATGGACAG | 92 |

Preferable HPV target gene sequences are recited in Table 12. The sequences in Table 12 are target sequences as they are capable of silencing the HPV E6 oncogene.

TABLE 12

| HPV target gene sequences | SEQ ID NO: |
|---|---|
| CGGTGCCAGAAACCGTTGAATCC | 93 |
| CACTGCAAGACATAGAAATAACC | 94 |
| AGGTGCCTGCGGTGCCAGAAACC | 95 |
| GCGGTGCCAGAAACCGTTGAATC | 96 |
| TCACTGCAAGACATAGAAATAAC | 97 |
| CCCATGCTGCATGCCATAAATGT | 98 |
| ATGCTGCATGCCATAAATGTATA | 99 |
| GTGGTGTATAGAGACAGTATACC | 100 |
| GCGCGCTTTGAGGATCCAACACG | 101 |
| CTGCGGTGCCAGAAACCGTTGAA | 102 |
| CCCCATGCTGCATGCCATAAATG | 103 |
| ACCCCATGCTGCATGCCATAAAT | 104 |
| AACACTGGGTTATACAATTTATT | 105 |
| ACGACGCAGAGAAACACAAGTAT | 106 |
| AAGGTGCCTGCGGTGCCAGAAAC | 107 |
| GGTGCCTGCGGTGCCAGAAACCG | 108 |
| CATGCTGCATGCCATAAATGTAT | 109 |
| GACGCAGAGAAACACAAGTATAA | 110 |
| TTCACTGCAAGACATAGAAATAA | 111 |
| GGTGCCAGAAACCGTTGAATCCA | 112 |
| TGGCGCGCTTTGAGGATCCAACA | 113 |
| TGTGGTGTATAGAGACAGTATAC | 114 |
| GTGCCTGCGGTGCCAGAAACCGT | 115 |
| CTGCATGCCATAAATGTATAGAT | 116 |
| GACTCCAACGACGCAGAGAAACA | 117 |
| CTGGGCACTATAGAGGCCAGTGC | 118 |
| TGCTGCATGCCATAAATGTATAG | 119 |

TABLE 12-continued

| HPV target gene sequences | SEQ ID NO: |
|---|---|
| GTGCCAGAAACCGTTGAATCCAG | 120 |
| TTACAGAGGTATTTGAATTTGCA | 121 |
| GAGGCCAGTGCCATTCGTGCTGC | 122 |

Additional preferable HPV target gene sequences are recited in Table 13. The sequences in Table 13 are target sequences as they are capable of silencing the HPV E7 oncogene.

TABLE 13

| HPV target gene sequences | SEQ ID NO: |
|---|---|
| ATTCCGGTTGACCTTCTATGTCA | 123 |
| GATGGAGTTAATCATCAACATTT | 124 |
| AAGCCAGAATTGAGCTAGTAGTA | 125 |
| CATGGACCTAAGGCAACATTGCA | 126 |
| AACCACAACGTCACACAATGTTG | 127 |
| ATGGACCTAAGGCAACATTGCAA | 128 |
| TAAGCGACTCAGAGGAAGAAAAC | 129 |
| GAAGCCAGAATTGAGCTAGTAGT | 130 |
| GAGCCGAACCACAACGTCACACA | 131 |
| ACGTCACACAATGTTGTGTATGT | 132 |
| GAACCACAACGTCACACAATGTT | 133 |
| AGGCAACATTGCAAGACATTGTA | 134 |
| AAGACATTGTATTGCATTTAGAG | 135 |
| TAAGGCAACATTGCAAGACATTG | 136 |
| CCAGCCCGACGAGCCGAACCACA | 137 |
| AAGCTCAGCAGACGACCTTCGAG | 138 |
| GCCCGACGAGCCGAACCACAACG | 139 |
| TTCCGGTTGACCTTCTATGTCAC | 140 |
| TGCATGGACCTAAGGCAACATTG | 141 |
| TTCCAGCAGCTGTTTCTGAACAC | 142 |
| AACACCCTGTCCTTTGTGTGTCC | 143 |
| CTTCTATGTCACGAGCAATTAAG | 144 |
| ACGAGCCGAACCACAACGTCACA | 145 |
| TTGAGCTAGTAGTAGAAAGCTCA | 146 |
| CAGCAGACGACCTTCGAGCATTC | 147 |
| AGCCAGAATTGAGCTAGTAGTAG | 148 |
| GTCACACAATGTTGTGTATGTGT | 149 |
| CCGACGAGCCGAACCACAACGTC | 150 |
| AATTCCGGTTGACCTTCTATGTC | 151 |
| ATTCCAGCAGCTGTTTCTGAACA | 152 |

Additional preferable HPV target gene sequences are recited in Table 14. The sequences in Table 14 are target sequences shared by both HPV E6 and E7.

TABLE 14

| HPV target gene sequences | SEQ ID NO: |
|---|---|
| TAGGTATTTGAATTTGCAT | 153 |
| GAGGTATTTGAATTTGCAT | 154 |

A preferable MDR-1 target gene sequence is recited in Table 15. The sequence in Table 15 is capable of silencing the MDR-1 gene in human.

TABLE 15

| MDR-1 target gene sequences | SEQ ID NO: |
|---|---|
| ATGTTGTCTGGACAAGCACT | 155 |

A preferable k-Ras target gene sequence is recited in Table 16. The sequence in Table 16 is capable of silencing the k-Ras gene in human.

TABLE 16

| k-Ras target gene sequences | SEQ ID NO: |
|---|---|
| GTTGGAGCTGTTGGCGTAG | 156 |

Preferable IL-6R target gene sequence are recited in Table 17. The sequences in Table 17 are capable of silencing IL-6R in human.

TABLE 17

| IL-6R target gene sequences | SEQ ID NO: |
|---|---|
| CTCCTGGAACTCATCTTTCTA | 157 |
| GCTCTCCTGCTTCCGGAAGAG | 158 |
| CTCCACGACTCTGGAAACTAT | 159 |
| CAGAAGTTCTCCTGCCAGTTA | 160 |
| CCGGAAGACAATGCCACTGTT | 161 |
| CTGAACGGTCAAAGACATTCA | 162 |
| CACAACATGGATGGTCAAGGA | 163 |
| ATGCAGGCACTTACTACTAAT | 164 |
| ATCGGGCTGAACGGTCAAAGA | 165 |
| AGCTCTCCTGCTTCCGGAAGA | 166 |
| CAGCTCTCCTGCTTCCGGAAG | 167 |
| CAGGCACTTACTACTAATAAA | 168 |
| CACTTGCTGGTGGATGTTCCC | 169 |
| AACGGTCAAAGACATTCACAA | 170 |
| TGCACAAGCTGCACCCTCAGG | 171 |

Additional referable IL-6R target gene sequences are recited in Table 18. The sequences in Table 18 are capable of silencing the IL-6R gene in mouse.

TABLE 18

| IL-6R target gene sequences | SEQ ID NO: |
|---|---|
| ATCCTGGAGGGTGACAAAGTA | 172 |
| TGGGTCTGACAATACCGTAAA | 173 |
| AACGAAGCGTTTCACAGCTTA | 174 |
| CCGCTGTTTCCTATAACAGAA | 175 |
| ACGAAGCGTTTCACAGCTTAA | 176 |
| CTGCTGTGAAAGGGAAATTTA | 177 |
| AACCTTGTGGTATCAGCCATA | 178 |
| CACAGTGTGGTGCTTAGATTA | 179 |
| CAGCTTCGATACCGACCTGTA | 180 |
| CAGTGTGGTGCTTAGATTAAA | 181 |
| CCCGGCAGGAATCCTCTGGAA | 182 |
| CCCGCTGTTTCCTATAACAGA | 183 |
| AACCACGAGGATCAGTACGAA | 184 |
| ACCTGCCGTCTTACTGAACTA | 185 |
| ACCACGAGGATCAGTACGAAA | 186 |
| ACAGCTTGTGATGACTGAATA | 187 |
| AGGATCAGTACGAAAGTTCTA | 188 |
| AACCCGCTGTTTCCTATAACA | 189 |
| CAGTACGAAAGTTCTACAGAA | 190 |
| TACGCGAGTGACAATTTCTCA | 191 |
| ACGAAAGTTCTACAGAAGCAA | 192 |
| CAGGCACTTACTACTAATAAA | 193 |
| CACTTGCTGGTGGATGTTCCC | 194 |
| AACGGTCAAAGACATTCACAA | 195 |
| TGCACAAGCTGCACCCTCAGG | 196 |

Preferable IL-7 target gene sequences are recited in Table 19. The sequences in Table 19 are capable of silencing the IL-7 gene in human.

TABLE 19

| IL-7 target gene sequences | SEQ ID NO: |
|---|---|
| TAAGAGAGTCATAAACCTTAA | 197 |
| AACAAGGTCCAAGATACCTAA | 198 |
| AAGATTGAACCTGCAGACCAA | 199 |
| AAGAGATTTCAAGAGATTTAA | 200 |
| AAGCGCAAAGTAGAAACTGAA | 201 |
| TAGCATCATCTGATTGTGATA | 202 |
| TAAGATAATAATATATGTTTA | 203 |
| ATGGTCAGCATCGATCAATTA | 204 |
| TTGCCTGAATAATGAATTTAA | 205 |

TABLE 19-continued

| IL-7 target gene sequences | SEQ ID NO: |
|---|---|
| ATCTGTGATGCTAATAAGGAA | 206 |
| AACAAACTATTTCTTATATAT | 207 |
| AACATTTATCAATCAGTATAA | 208 |
| ATCAATCAGTATAATTCTGTA | 209 |
| AAGGTATCAGTTGCAATAATA | 210 |

Additional preferable IL-7 target gene sequences are recited in Table 20. The sequences in Table 20 are capable of silencing the IL-7 gene in mouse.

TABLE 20

| IL-7 target gene sequences | SEQ ID NO: |
|---|---|
| CGGATCCTACGGAAGTTATGG | 211 |
| GACCATGTTCCATGTTTCTTT | 212 |
| AACCTAAATGACCTTTATTAA | 213 |
| CAGGAGACTAGGACCCTATAA | 214 |
| TAGGGTCTTATTCGTATCTAA | 215 |
| ATGAGCCAATATGCTTAATTA | 216 |
| GCCAATATGCTTAATTAGAAA | 217 |
| CAGCATCGATGAATTGGACAA | 218 |
| TTGCCTGAATAATGAATTTAA | 219 |
| CTGATAGTAATTGCCCGAATA | 220 |
| AAGGGTTTGCTTGTACTGAAT | 221 |
| AACATGTATGTGATGATACAA | 222 |
| TTGCAACATGTAATAATTTAA | 223 |
| AAGAGACTACTGAGAGAAATA | 224 |
| AAGAATCTACTGGTTCATATA | 225 |
| TGCCGTCAGCATATACATATA | 226 |
| AGGGCTCACGGTGATGGATAA | 227 |

Additional preferable IL-7 target gene sequences are recited in Table 21. The sequences in Table 21 are cross species sequences as they are capable of silencing the IL-7 gene in human and mouse.

TABLE 21

| IL-7 target gene sequences | SEQ ID NO: |
|---|---|
| CGCCTCCCGCAGACCATGTTC | 228 |
| TCCGTGCTGCTCGCAAGTTGA | 229 |
| GCCTCCCGCAGACCATGTTCC | 230 |
| CCTCCCGCAGACCATGTTCCA | 231 |
| CTCCCGCAGACCATGTTCCAT | 232 |
| TCCCGCAGACCATGTTCCATG | 233 |
| CCCGCAGACCATGTTCCATGT | 234 |

TABLE 21-continued

| IL-7 target gene sequences | SEQ ID NO: |
|---|---|
| CCGCAGACCATGTTCCATGTT | 235 |
| CGCAGACCATGTTCCATGTTT | 236 |
| GCAGACCATGTTCCATGTTTC | 237 |
| CAGACCATGTTCCATGTTTCT | 238 |
| AGACCATGTTCCATGTTTCTT | 239 |

Preferable IL-13Ra-1 target gene sequences are recited in Table 22. The sequences in Table 22 are capable of silencing the IL-13Ra-1 gene in human.

TABLE 22

| IL-13Ra-1 target gene sequences | SEQ ID NO: |
|---|---|
| AACCTGATCCTCCACATATTA | 240 |
| CCTGATCCTCCACATATTAAA | 241 |
| AGAAATGTTTGGAGACCAGAA | 242 |
| CAAATAATGGTCAAGGATAAT | 243 |
| TTCCTGATCCTGGCAAGATTT | 244 |
| TAAAGAAATGTTTGGAGACCA | 245 |
| ATGTTTGGAGACCAGAATGAT | 246 |
| CTCCAATTCCTGATCCTGGCA | 247 |

Additional preferable IL-13Ra-1 target gene sequences are recited in Table 23. The sequences in Table 23 are capable of silencing the IL-13Ra-1 gene in mouse.

TABLE 23

| IL-13Ra-1 target gene sequences | SEQ ID NO: |
|---|---|
| CAAGAAGACTCTAATGATGTA | 248 |
| CACAGTCAGAGTAAGAGTCAA | 249 |
| ACCCAGGGTATCATAGTTCTA | 250 |
| CTGCTTTGAAATTTCCAGAAA | 251 |
| ATCATAGTTCTAAGAATGAAA | 252 |
| AAGGCTTAAGATCATTATATT | 253 |
| AACTACTTATAAGAAAGTAAA | 254 |
| CACAGAACATCTAGCAAACAA | 255 |
| CTCGTTCTTGTTCAATCCTAA | 256 |
| AACTTGTAGGTTCACATATTA | 257 |
| AACCATTTCTGCAAATTTAAA | 258 |
| CTCAGTGTAGTGCCAATGAAA | 259 |
| CAGGCCTTAGGGACTCATAAA | 260 |
| AAGTATGACATCTATGAGAAA | 261 |

TABLE 23-continued

| IL-13Ra-1 target gene sequences | SEQ ID NO: |
|---|---|
| GTGGAGGTCAATAATACTCAA | 262 |
| CAGAGTATAGGTAAGGAGCAA | 263 |

A preferable IL-18 target gene sequence is recited in Table 24. The sequence in Table 24 is capable of silencing the IL-18 gene in human.

TABLE 24

| IL-18 target gene sequences | SEQ ID NO: |
|---|---|
| TTGAATGACCAAGTTCTCTTC | 264 |

Additional preferable IL-18 target gene sequences are recited in Table 25. The sequences in Table 25 are capable of silencing the IL-18 gene in mouse.

TABLE 25

| IL-18 target gene sequences | SEQ ID NO: |
|---|---|
| CTCTCTGTGAAGGATAGTAAA | 265 |
| CCGCAGTAATACGGAATATAA | 266 |
| CAAGGAAATGATGTTTATTGA | 267 |
| CAGACTGATAATATACATGTA | 268 |
| TTGGCCGACTTCACTGTACAA | 269 |
| CCAGACCAGACTGATAATATA | 270 |
| AAGATGGAGTTTGAATCTTCA | 271 |
| ACGCTTTACTTTATACCTGAA | 272 |
| TACAACCGCAGTAATACGGAA | 273 |
| CTGCATGATTTATAGAGTAAA | 274 |
| CCCGAGGCTGCATGATTTATA | 275 |
| CACGCTTTACTTTATACCTGA | 276 |
| CGCCTGTATTTCCATAACAGA | 277 |
| CGCAGTAATACGGAATATAAA | 278 |
| TACATGTACAAAGACAGTGAA | 279 |
| CAGGCCTGACATCTTCTGCAA | 280 |
| TTCGAGGATATGACTGATATT | 281 |
| CTGTATTTCCATAACAGAATA | 282 |
| GAGGATATGACTGATATTGAT | 283 |
| CAAGTTCTCTTCGTTGACAAA | 284 |
| CACTAACTTACATCAAAGTTA | 285 |
| ACCGCAGTAATACGGAATATA | 286 |
| CTCTCACTAACTTACATCAAA | 287 |

Preferable CCL20 target gene sequences are recited in Table 26. The sequences in Table 26 are capable of silencing the CCL20 gene in human.

TABLE 26

| CCL20 target gene sequences | SEQ ID NO: |
|---|---|
| ATCATCTTTCACACAAAGAAA | 288 |
| AACAGACTTGGGTGAAATATA | 289 |
| ATGGAATTGGACATAGCCCAA | 290 |
| GAGGGTTTAGTGCTTATCTAA | 291 |
| CTCACTGGACTTGTCCAATTA | 292 |
| ATCATAGTTTGCTTTGTTTAA | 293 |
| TTGTTTAAGCATCACATTAAA | 294 |
| AAGCATCACATTAAAGTTAAA | 295 |
| CCCAAAGAACTGGGTACTCAA | 296 |
| CACATTAAAGTTAAACTGTAT | 297 |
| CAGATCTGTTCTTTGAGCTAA | 298 |
| TTGGTTTAGTGCAAAGTATAA | 299 |
| CAGACCGTATTCTTCATCCTA | 300 |
| AACATTAATAAGACAAATATT | 301 |
| GACCGTATTCTTCATCCTAAA | 302 |

Additional referable CCL20 target gene sequences are recited in Table 27. The sequences in Table 27 are capable of silencing the CCL20 gene in mouse.

TABLE 27

| CCL20 target gene sequences | SEQ ID NO: |
|---|---|
| AAGCTTGTGACATTAATGCTA | 303 |
| CAATAAGCTATTGTAAAGATA | 304 |
| ATCATCTTTCACACGAAGAAA | 305 |
| AGCTATTGTAAAGATATTTAA | 306 |
| CAGCCTAAGAGTCAAGAAGAT | 307 |
| CCCAGTGGACTTGTCAATGGA | 308 |
| ATGAAGTTGATTCATATTGCA | 309 |
| AAGTTGATTCATATTGCATCA | 310 |
| TCACATTAGAGTTAAGTTGTA | 311 |
| CACATTAGAGTTAAGTTGTAT | 312 |
| TATGTTATTTATAGATCTGAA | 313 |
| ATGTTTAGCTATTTAATGTTA | 314 |
| TTAGTGGAAGGATTAATATTA | 315 |
| ACCCAGCACTGAGTACATCAA | 316 |
| TATGTTAAGGGAATAGTTTA | 317 |

Additional preferable CCL20 target gene sequences are recited in Table 28. The sequences in Table 28 are cross-species target sequences as they are capable of silencing the CCL20 gene in human and mouse.

TABLE 28

| CCL20 target gene sequences | SEQ ID NO: |
|---|---|
| ATGAAGTTGATTCATATTGCA | 318 |
| TGAAGTTGATTCATATTGCAT | 319 |
| GAAGTTGATTCATATTGCATC | 320 |
| AAGTTGATTCATATTGCATCA | 321 |
| AGTTGATTCATATTGCATCAT | 322 |
| GTTGATTCATATTGCATCATA | 323 |
| TTGATTCATATTGCATCATAG | 324 |
| TGATTCATATTGCATCATAGT | 325 |
| TCAATGCTATCATCTTTCACA | 326 |
| CAATGCTATCATCTTTCACAC | 327 |
| TAATGAAGTTGATTCATATTG | 328 |
| AATGAAGTTGATTCATATTGC | 329 |

Preferable CCL20 target gene sequences are recited in Table 29. The sequences in Table 29 are capable of silencing the CCL20 gene in human.

TABLE 29

| Claudin-2 target gene sequences | SEQ ID NO: |
|---|---|
| AGCATGAAATTTGAGATTGGA | 330 |
| TACAGAGCCTCTGAAAGACCA | 331 |
| CACTACAGAGCCTCTGAAAGA | 332 |
| CTGACAGCATGAAATTTGAGA | 333 |
| ATCTCTGTGGTGGGCATGAGA | 334 |
| CATGAAATTTGAGATTGGAGA | 335 |
| TCTGGCTGAGGTTGGCTCTTA | 336 |
| GTGGGCTACATCCTAGGCCTT | 337 |

Additional preferable CCL20 target gene sequences are recited in Table 30. The sequences in Table 30 are capable of silencing the CCL20 gene in mouse.

TABLE 30

| Claudin-2 target gene sequences | SEQ ID NO: |
|---|---|
| CAGCTTCCTGCTAAACCACAA | 338 |
| CAAGAGTGAGTTCAACTCATA | 339 |
| CTGGTTCCTGACAGCATGAAA | 340 |
| TGGCTGGGACTATATATATAA | 341 |
| GAGGGCAATTGCTATATCTTA | 342 |
| CAGCAGCCAAACGACAAGCAA | 343 |
| CAAGGGTTTCCTTAAGGACAA | 344 |
| CAGATACTTGTAAGGAGGAAA | 345 |
| AAGAAATGGATTAGTCAGTAA | 346 |

TABLE 30-continued

| Claudin-2 target gene sequences | SEQ ID NO: |
|---|---|
| AAGGAAAGCACAAGAAGCCAA | 347 |
| CTGGCTGAGGTTGGCTCTTAA | 348 |
| AACCTGGGATCTAAAGAAACA | 349 |
| AAGGGCTTGGGTATCAAAGAA | 350 |
| CAGGCTCCGAAGATACTTCTA | 351 |
| CCCAATATATAAATTGCCTAA | 352 |
| CTGACCCAGCTTCCTGCTAAA | 353 |

Preferable Chitinase-3 target gene sequences are recited in Table 31. The sequences in Table 31 are capable of silencing the Chitinase-3 gene in human.

TABLE 31

| Chitinase-3 target gene sequences | SEQ ID NO: |
|---|---|
| ACCCACATCATCTACAGCTTT | 354 |
| CATCATCTACAGCTTTGCCAA | 355 |
| CAGCTGGTCCCAGTACCGGGA | 356 |
| CACCAAGGAGGCAGGGACCCT | 357 |
| CCGGTTCACCAAGGAGGCAGG | 358 |
| AGCTGGTCCCAGTACCGGGAA | 359 |
| CAGGCCGGTTCACCAAGGAGG | 360 |
| GGCCGGTTCACCAAGGAGGCA | 361 |

Additional preferable Chitinase-3 target gene sequences are recited in Table 32. The sequences in Table 32 are capable of silencing the Chitinase-3 gene in mouse.

TABLE 32

| Chitinase-3 target gene sequences | SEQ ID NO: |
|---|---|
| TAGGTTTGACAGATACAGCAA | 362 |
| AACCCTGTTAAGGAATGCAAA | 363 |
| ATCAAGTAGGCAAATATCTTA | 364 |
| CGCAGCTTTGTCAGCAGGAAA | 365 |
| TTGGATCAAGTAGGCAAATAT | 366 |
| TTGAGGGACCATACTAATTAT | 367 |
| GAGGACAAGGAGAGTGTCAAA | 368 |
| TGCGTACAAGCTGGTCTGCTA | 369 |
| CAGGAGTTTAATCTCTTGCAA | 370 |
| ATCAAGGAACTGAATGCGGAA | 371 |
| CACCCTGATCAAGGAACTGAA | 372 |
| CACTTGGATCAAGTAGGCAAA | 373 |
| CAGGATTGAGGGACCATACTA | 374 |
| AACTATGACAAGCTGAATAAA | 375 |

TABLE 32-continued

| Chitinase-3 target gene sequences | SEQ ID NO: |
|---|---|
| ATGCAAATTCTCAGACTCTAA | 376 |
| ATCCTTCCCTTAGGAACTTAA | 377 |

5. Treatment of Diseases and Disorders

The present invention also provides methods of treating or preventing a disease or disorder in a mammal. The methods include regulating the expression of at least one gene in a cell known to cause a disease or disorder by introducing to the cells of the mammal at least one invasive bacterium, or at least one bacterial therapeutic particle (BTP), containing one or more siRNAs or one or more DNA molecules encoding one or more siRNAs, where the expressed siRNAs interfere with the mRNA of the gene known to cause the disease or disorder of interest.

The RNAi methods of the invention, including BMGS and tkRNAi are used to treat any disease or disorder for which gene expression regulation would be beneficial. This method is effected by silencing or knocking down (decreasing) genes involved with one or more diseases and disorders.

The gene to be regulated to treat or prevent a disease or disorder of interest, can be, but is not limited to, ras, β-catenin, one or more HPV oncogenes, APC, HER-2, MDR-1, MRP-2, FATP4, SGLUT-1, GLUT-2, GLUT-5, apobec-1, MTP, IL-6, IL-6R, IL-7, IL-12, IL-13, IL-13 Ra-1, IL-18, p38/JNK MAP kinase, p65/NF-κB, CCL20 (MIP-3α), Claudin-2, Chitinase 3-like 1, apoA-IV, MHC class I and MHC class II. In one aspect of this embodiment, the ras is k-Ras. In another aspect of this embodiment, the HPV oncogene is E6 or E7.

Preferably, the present invention provides methods of treating or preventing cancer or a cell proliferation disorder, viral disease, an inflammatory disease or disorder, a metabolic disease or disorder, an autoimmune disease or disorder, or a disease, disorder or cosmetic concern in the skin or hair in a mammal by regulating the expression of a gene or several genes known to be associated with the onset, propagation or prolongation of the disease or disorder by introducing a bacterium or BTP to the cell. The bacterium or BTP contain one or more siRNAs or one or more DNA molecules encoding one or more siRNAs, where the expressed siRNAs interfere with the mRNA of the gene known to cause, propagate or prolong the disease or disorder of interest.

In some preferred embodiments, the viral disease can be, but is not limited to, hepatitis B, hepatitis C, Human Papilloma Virus (HPV) infection or epithelial dysplasia or cancer caused by HPV infection or HPV induced transformation, including cervical cancer, rectal cancer and pharyngeal cancer.

In some preferred embodiments, the inflammatory disease or disorder can be, but is not limited to, inflammatory bowel disease, Crohn's disease, ulcerative colitis, an allergy, rheumatoid arthritis.

In some preferred embodiments, the autoimmmune disease or disorder can be, but is not limited to, celiac disease.

In some preferred embodiments, the disease, disorder or cosmetic concern can be, but is not limited to, psoriasis, eczema, albinism, balding or gray hair.

The mammal can be any mammal including, but not limited to, human, bovine, ovine, porcine, feline, canine, goat, equine, or primate. Preferably, the mammal is a human.

The terms "treating" and "treatment" as used herein refer to the administration of an agent or formulation (e.g., bacterium and/or BTP containing an siRNA or a DNA encoding for an siRNA) to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage.

The terms "preventing" and "prevention" refer to the administration of an agent or composition to a clinically asymptomatic individual who is susceptible to a particular adverse condition, disorder, or disease, and thus relates to the prevention of the occurrence of symptoms and/or their underlying cause.

6. Pharmaceutical Compositions and Modes of Administration

In a preferred embodiment of the invention, the invasive bacteria or BTPs containing the RNA molecules, and/or DNA encoding such, are introduced into an animal by intravenous, intramuscular, intradermal, intraperitoneally, peroral, intranasal, intraocular, intrarectal, intravaginal, intraosseous, oral, immersion and intraurethral inoculation routes.

The amount of the invasive bacteria or BTPs of the present invention to be administered to a subject will vary depending on the species of the subject, as well as the disease or condition that is being treated. Generally, the dosage employed will be about $10^3$ to $10^{11}$ viable organisms, preferably about $10^5$ to $10^9$ viable organisms per subject.

The invasive bacteria or BTPs of the present invention are generally administered along with a pharmaceutically acceptable carrier and/or diluent. The particular pharmaceutically acceptable carrier an/or diluent employed is not critical to the present invention. Examples of diluents include a phosphate buffered saline, buffer for buffering against gastric acid in the stomach, such as citrate buffer (pH 7.0) containing sucrose, bicarbonate buffer (pH 7.0) alone (Levine et al. J. Clin. Invest., 79:888-902 (1987); and Black et al J. Infect. Dis., 155:1260-1265 (1987)), or bicarbonate buffer (pH 7.0) containing ascorbic acid, lactose, and optionally aspartame (Levine et al. Lancet, II:467-470 (1988)). Examples of carriers include proteins, e.g., as found in skim milk, sugars, e.g., sucrose, or polyvinylpyrrolidone. Typically these carriers would be used at a concentration of about 0.1-30% (w/v) but preferably at a range of 1-10% (w/v).

Set forth below are other pharmaceutically acceptable carriers or diluents which may be used for delivery specific routes. Any such carrier or diluent can be used for administration of the bacteria of the invention, so long as the bacteria or BTPs are still capable of invading a target cell. In vitro or in vivo tests for invasiveness can be performed to determine appropriate diluents and carriers. The compositions of the invention can be formulated for a variety of types of administration, including systemic and topical or localized administration. Lyophilized forms are also included, so long as the bacteria are invasive upon contact with a target cell or upon administration to the subject. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the composition, e.g., bacteria or BTPs, of the invention can be formulated in liquid solutions, preferably in physiologically compatible buffers such as Hank's solution or Ringer's solution.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner.

For administration by inhalation, the pharmaceutical compositions for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the composition, e.g., bacteria, and a suitable powder base such as lactose or starch.

The pharmaceutical compositions may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The pharmaceutical compositions may also be formulated in rectal, intravaginal or intraurethral compositions such as suppositories or retention enemas, e.g., containing conventional suppository bases such as cocoa butter or other glycerides.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the bacteria of the invention are formulated into ointments, salves, gels, or creams as generally known in the art, so long as the bacteria are still invasive upon contact with a target cell.

The compositions may, if desired, be presented in a pack or dispenser device and/or a kit that may contain one or more unit dosage forms containing the active ingredient. The pack may for example comprise metal or plastic foil, such as a blister pack. The pack or dispenser device may be accompanied by instructions for administration.

The invasive bacteria or BTPs containing the RNA or RNA-encoding DNA to be introduced can be used to infect animal cells that are cultured in vitro, such as cells obtained from a subject. These in vitro-infected cells can then be introduced into animals, e.g., the subject from which the cells were obtained initially, intravenously, intramuscularly, intradermally, or intraperitoneally, or by any inoculation route that allows the cells to enter the host tissue. When delivering RNA to individual cells, the dosage of viable organisms administered will be at a multiplicity of infection ranging from about 0.1 to $10^6$, preferably about $10^2$ to $10^4$ bacteria per cell.

In yet another embodiment of the present invention, bacteria can also deliver RNA molecules encoding proteins to cells, e.g., animal cells, from which the proteins can later be harvested or purified. For example, a protein can be produced in a tissue culture cell.

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The present invention is further illustrated by the following examples that should not be construed as limiting in any way. The contents of all cited references including literature references, issued patents, published patent applications as cited throughout this application are hereby expressly incorporated by reference. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

The following non-limiting examples are merely illustrative of the preferred embodiments of the present invention, and are not to be construed as limiting the invention.

EXAMPLES

Example 1

Knockdown of β-Catenin and k-Ras

Previous studies have demonstrated the powerful nature of the siRNA knockdown technology disclosed herein. For example, in vitro and in vivo knockdown of beta catenin and k-ras utilizing bacterial delivery is described in PCT Publication No. WO 06/066048, which is incorporated herein by reference in its entirety.

Example 2

TRIP with Multiple shRNA Expression Cassettes

The TRIP described herein, and described in further detail in PCT Publication No. WO 06/066048, can be modified to produce a plasmid which allows targeting of multiple genes simultaneously or multiple sequences within one gene simultaneously. For example, TRIP with multiple hairpin expression cassettes to produce shRNA can target different sequences in a given gene, or target multiple genes through a simultaneous bacterial treatment.

The TRIP plasmid can incorporate multiple (up to ten) cloning sites to express different shRNA constructs (FIG. 1). The purpose of such a plasmid will be to allow silencing of various genes through a single therapeutic bacterium which will be empowered by the Multiple-expression cassette-TRIP (mec-TRIP) to synthesize short hairpin RNA against a variety of targets simultaneously.

These different hairpins can either be expressed competitively at high levels through the use of an identical high level promoter (such as T7 promoter or a different high level bacterial promoter), or they can be expressed at different levels through the use of promoters with different levels of activity, this will depend on the intended use of the plasmid and the desired relative silencing levels of the target gene.

This mec-TRIP could be useful to treat complex diseases as described herein (e.g. inflammatory diseases, or cancer), through the simultaneous silencing(targeting) of multiple targets as described herein (e.g. multiple oncogenes, such as k-ras and beta-catenin in the case of colon cancer, or HER-2 and MDR-1 in breast cancer, or other combinations).

Example 3

Operator Repressor Titration System

The TRIP system (bacteria and plasmid) have been modified to include the ORT (Operator Repressor Titration) system from Cobra Biomanufacturing (Keele, UK). This adaptation helps to maintain the plasmid in suitable strains in the absence of selective antibiotics. The bacterial carrier strain has been modified accordingly to allow for the ORT system to function (deletion of the DAP gene and replacement with an ORT-controlled DAP gene expression system). The plasmid has been modified to remove the antibiotic selection sequences to support the ORT system. Further changes have been introduced to the bacterial genome, including for example, (a) deletion of the aroA gene (in some CEQ strains) to make the bacteria more susceptible to nutrient shortage, particularly in the intracellular compartment where they will die due to lack of nutrients; (b) insertion of T7RNApolymerase gene into the chromosome and or (c) integration of a shRNA expression cassette under T7 promoter into the chromosome.

Figure 2:
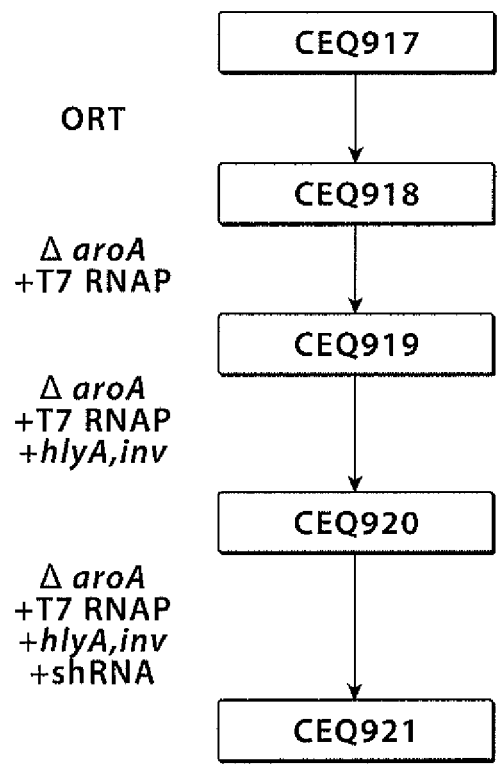
FIG. 2 is a schematic showing the TRIP system (bacteria and plasmid) modified with the Operator Repressor Titration (ORT) system.

FIG. 2 shows development examples of bacterial strains. Further strains developed include, but are not limited to, CEQ922 (CEQ919 without aroA deletion), CEQ923 (CEQ920 without aroA deletion), CEQ924 (CEQ921 without aroA deletion).

Example 4

Intestinal Tract Gene Delivery

*S. typhimurium* was investigated to determine if it could be used as a vector for RNAi delivery into the epithelial cells lining the intestinal tract. Mice were treated orally with a single dose of $10^8$ SL 7207 and sacrificed at various time points after administration. SL7207 were then stained using the *Salmonella* specific antibody. 2 h after treatment, numerous SL7207 could be seen invading the intestinal epithelial layer (*Salmonella* stained red), suggesting that oral administration of SL7207 may be a useful tool to deliver payloads to the intestinal and colonic mucosa. In a follow up experiment, mice were treated with SL7207 harboring a GFP expression plasmid (pEGFPC1, Invitrogen). At 24 h after a single treatment, a small percentage (approximately 1%) of cells was clearly found to express GFP.

Figure 3:
FIG. 3 is a photograph showing cellular staining of the intestinal epithelial layer demonstrating efficient invasion and plasmid delivery by *S. typhimurium*.

FIG. 3 shows the efficient invasion and plasmid delivery into the intestinal mucosa by *S. typhimurium*. SL7207 were stained using red fluorescent antibody 6 h after oral administration. Intact SL7207 and fragments of SL7207 were seen in epithelial cells as well as underlying cells of the lamina propria (top left/right). SL7207 successfully deliver expressed DNA into the intestinal mucosa: intestinal mucosal cells expressing GFP after treatment with SL7207 carrying a eukaryotic expression plasmid for GFP (pEGFP-C1) (lower left). For fluorescence microscopy, SL7207 were stained with red fluorescent antibody and nuclei were counterstained with Hoechst 37111.

To test whether SL7207 could be used for the delivery of RNAi to target genes in the intestinal tract, GFP transgenic mice (4 per group) were treated with *S. typhimurium* harboring a shRNA expression plasmid directed against GFP (SL-siGFP) or a shRNA expression plasmid directed against k-RAS (SL-siRAS). $10^8$ c.f.u. was given three times weekly for two weeks by oral gavage. Colonic tissues were subsequently reviewed with fluorescent microscopy (data not shown) and stained analyzed after immunhistochemistry staining for GFP expression using a specific antibody (Living Colors®, Invitrogen). There was a significant reduction in the overall GFP expression level and significant reduction in the number of GFP expressing crypts in the SL-siGFP treated animals compared with the SL-siRAS treated animals (33.9% vs 50%, p<0.05), suggesting that this method could be useful to deliver therapeutic RNAi into the colonic epithelium.

Figure 4:
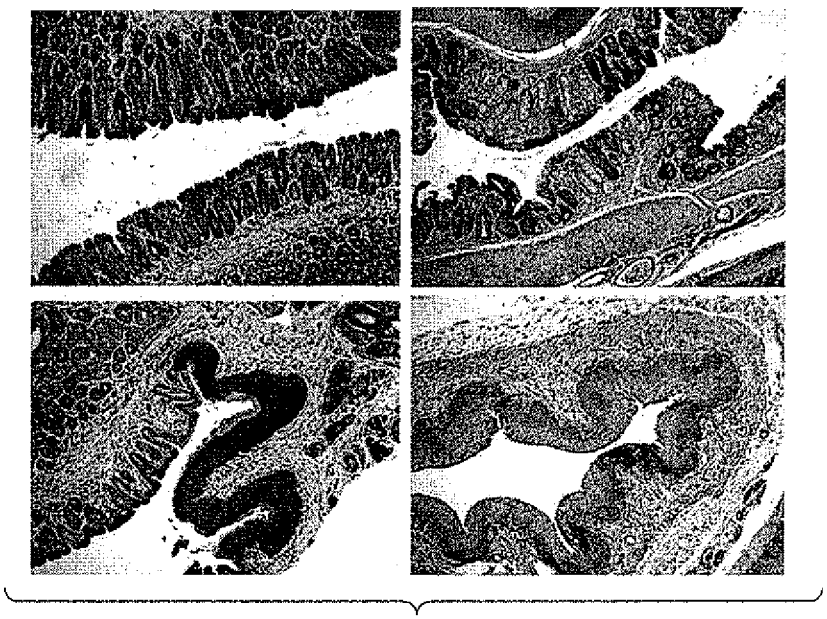
FIG. 4 is a photograph showing that bacteria-mediated RNA interference reduces target gene expression in the gastrointestinal epithelium.

FIG. 4 shows that bacteria-mediated RNA interference reduces target gene expression in the gastrointestinal epithelium. After treatment with SL7207 carrying expression plasmids targeting GFP (SL-siGFP, right bottom panel), colon tissues showed lower levels of GFP expression, and fewer colonic crypts were stained positive for GFP compared with animals treated with SL-siRAS (left bottom panel). Slides were stained with GFP-specific antibody.

Example 5

Construction of CEQ503 Bacterial Strain

Derivation and Description of CEQ 503 (Strain CEQ201 (pNJSZ))

CEQ503 consists of a combination of an attenuated *E. coli* strain (CEQ201) with a specially engineered TRIP plasmid (pNJSZ). The plasmid confers the abilities required to induce tkRNAi (in this case: invasiveness, escape from the entry vesicle, expression of short hairpin RNA). Strain Description of CEQ503 (pNJSZ):

1. Genotype: *Escherichia coli* CEQ201 [glnV44(AS), LAM⁻, rfbC1, endA1, spoT1, thi-1, hsdR17, $(r_k^- m_k^+)$, creC510 ΔdapA, ΔrecA].
2. Derivation of CEQ201

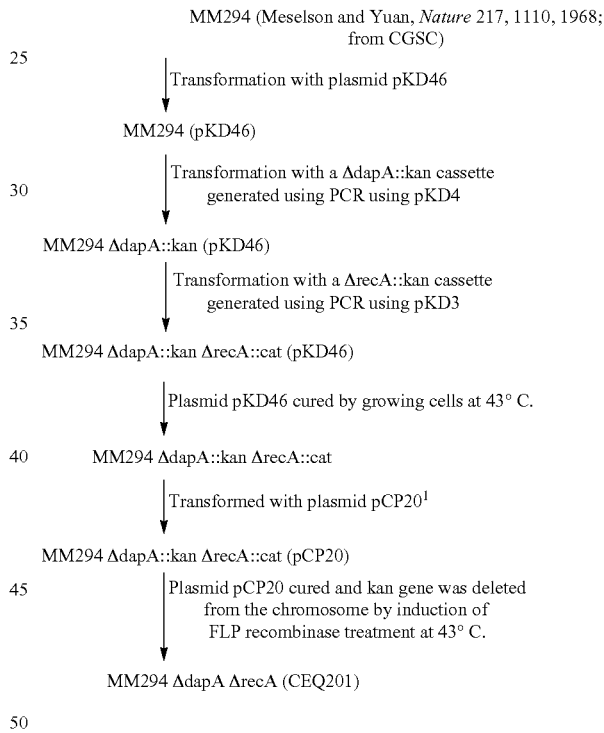

Figure 5:
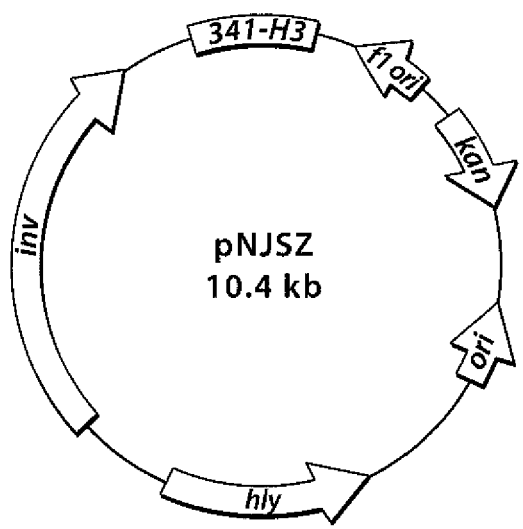
FIG. 5 is a schematic showing pNJSZ plasmid construct.

3. Plasmid: pNJSZ, shown schematically in FIG. 5, is a 10.4 kb plasmid that confers kanamycin resistance to our bacterial strain (CEQ503). This plasmid contains two genes, hly and inv, and the H3 hairpin sequence: ggatc-cAGGAGTAACAATACAAATGGATTCAAGAGATC-CATTTGTATTGTTACTCCTTTgt cgac (SEQ ID NO:380), which includes BamHI and SalI restriction sites. To verify the presence of this plasmid, PCRs are performed to verify chromosomal deletion of dapA, and minipreps and/or PCR are performed to confirm inv, hly and 341-H3 on the plasmid.
4. Nutritional Requirements: Althea Media Broth or LB, Miller (Luria-Bertani) broth (Amresco; cat. no.: J106-2KG) and 50 μg/ml of DL-Δ;ε-Diaminopemilic acid (DAP) (SIGMA; cat. no.: D1377-10G).
5. Growth Conditions: 37° C.

Example 6

BTP Production

BTPs or minicells containing a suitable plasmid such as TRIP have been engineered for delivery of tkRNAi. These cells will express invasin or Opa to enable entry into mammalian cells and listeriolysin will allow lysis of phagosome following minicell degradation/lysis. Additionally, a method for manufacturing minicells has been developed that utilizes a suicide construct for killing intact cells to aid in the purification of minicells. Such suicide plasmids have been described in the literature (Kloos et al., (1994) J. Bacteriol. 176, 7352-61; Jain and Mekalanos, (2000) Infect. Immun 68, 986-989). Summarily, the lambda S and R genes that code for holing and lysozyme are placed under regulation of an inducible promoter on the bacterial chromosome. When induced, they will lyse intact cells but not minicells since minicells lack chromosomes. A number of different types of regulators such as lad, araC, lambda cI857 and rhaS-rhaR can be used for development of an inducible suicide gene construct. Similarly, a number of different types of suicide genes, including *E. coli* autolysis genes and antimicrobial small peptides, can be used in a similar scheme. Purification is enhanced by treatments or mutations that induce filamentation (see, for example, Ward and Lutkenhaus, (1985) Cell 42, 941-949; Bi and Lutkenhaus, 1992). Initial purification involves low speed centrifugation to separate intact cells and retain minicells in the supernatant. This can be followed by density gradient purification or filtration (for example, Shull et al., (1971) J. Bacteriol. 106, 626-633).

Any cell death-triggering gene, also known as a suicide gene, including but not limited to genes encoding antimicrobial proteins, bacteriophage lysins or autolysins can be used in this method for obtaining BTPs from a mixture containing BTPs and bacteria. Suicide genes can kill live bacteria by mechanisms that include but are not limited to cell lysis, or by the destruction, degradation or poisoning of cellular components such as chromosomal DNA or filament components. Any inducible promoter may be used in conjunction with this system. In one embodiment of this invention, the suicide genes are integrated within the chromosome, thereby limiting their presence only in intact bacterial cells as BTPs or minicells will not incorporate these genes because they do not harbor chromosomal DNA.

Figure 6:
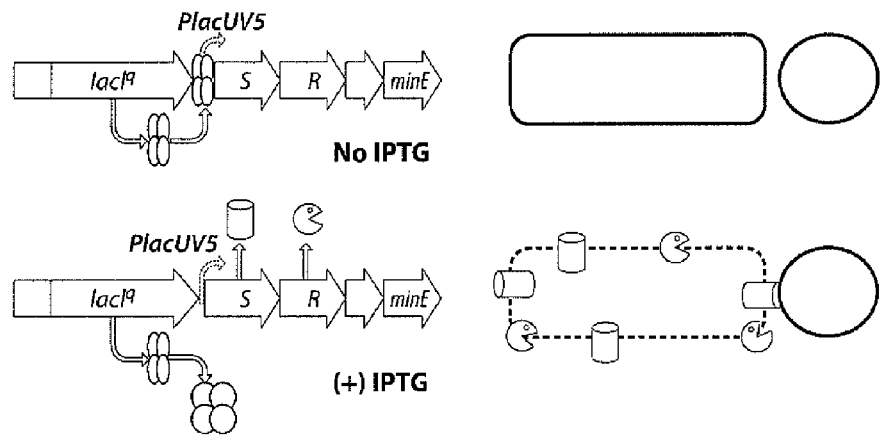
FIG. 6 is a schematic showing the use of lamba S and R genes to kill intact bacteria.

As shown in FIG. 6, induction of suicide genes will lyse intact bacterial cells. The lambda S and R genes (suicide genes) are put under the control of $P_{lacUV5}$ (inducible promoter). The leaky basal activity is repressed by a "super-repressor" coded by $lacI^q$ gene on a $P_{gapA}$ (strong promoter). This cassette is put at the minCD locus.

Example 7 siRNA Inhibition of Human Papillomavirus (HPV) Oncogenes

Experimental Procedures

Cell Culture: Hela cells were cultured in Minimum Essential Medium (MEM, ATCC No. 30-2003) with 10% FBS supplemented with antibiotics: 100 U/ml penicillin G, 10 µg/ml streptomycin (Sigma).

Bacterial Culture: Plasmids were transformed into BL21 (DE3) strain (Invitrogen). Bacteria were grown at 37° C. in LB Broth containing 100 µg/ml ampicillin. Bacterial cell density (in CFU/ml) was calculated using $OD_{600}$ measurement. For cell infection, overnight cultures were inoculated into fresh medium for another 2-3 h growth until the optical density at 600 nm [OD600] reached 0.6. Invasion Assay: For bacterial invasion, Hela cells were plated in 6-well dishes at 200,000 cells/well and allowed to incubate overnight in 2 ml complete growth medium. The bacterial cells were grown to mid-exponential phase with optical density at 600 nm [OD600] 0.6 in LB Broth with Ampicillin, and then centrifuged at 3,400 rpm for 10 minutes at 4° C. Bacterial pellets were resuspended in MEM without serum or the antibiotics and the bacteria were added to the cells at an MOI of 1:1000, 1:500, 1:250, 1:125, or 1:62.5 and allowed to invade the Hela cells for 2 hours at 37° C. in 5% CO2. The cells were washed 4 times with MEM containing 10% FBS and penicillin-streptomycin (100 IU of penicillin and 100 µg of streptomycin per ml). Cells were incubated in fresh complete medium for further 48 hours at 37° C. in 5% CO2 and total RNA was then isolated by the Qiagen RNeasy system with on-column DNAse digestion or by TRIZOL extraction method.

siRNA Transfection: One day before the transfection, cells were plated in complete growth medium without antibiotics so that the cells will be 30-50% confluent at the time of transfection. Diluted various concentrations of siRNA from a stock of 20 µM in 175 µl of Opti-MEM. Mixed 4 µl of Oligofectamine separately in 15 µl of Opti-MEM. Mixed gently and incubated for 5-10 min at room temperature. Combined the diluted siRNA with diluted oligofectamine and incubated for 15-20 min at room temperature. While the complexes were being formed, removed the growth medium from the cells and added 800 µl of medium without serum to each well containing cells. Added the 200 µl of siRNA/oligofectamine complexes to the cells and incubated at 37° C. for 4 h. Added 1 ml of growth medium containing 3× the normal concentration of serum without removing the transfection mixture. Gene silencing was assayed at 48 h.

RT-PCR: Quantitative real-time reverse transcription PCR (RT-PCR) was performed with the TaqMan RT-PCR master Mix Reagents Kit (Applied Biosystems) using the following primers and a probe set for detection of HPV18E6E7 transcripts:

```
Forward Primer:
                                 (SEQ ID NO: 381)
5'-CTGATCTGTGCACGGAACTGA-3' (148-168)

Reverse Primer:
                                 (SEQ ID NO: 382)
5'-TGTCTAAGTTTTTCTGCTGGATTCA-3'(439-463)

Probe:
                                 (SEQ ID NO: 383)
5'-TTGGAACTTACAGAGGTGCCTGCGC-3' (219-233 and 416-425)
```

The probe was labeled at the 5' end with a reporter fluorescent dye, FAM and at the 3' end with fluorescent dye quencher TAMRA. GAPDH was used to detect human GAPDH transcripts for the normalization.

```
HPVsHRNA sequences:
H1 (working sequence)
                                 (SEQ ID NO: 384)
5'- ggATCCTAGGTATTTGAATTTGCATTTCAAGAGAATGCAAATTCAA ATACCTTTTgTCgAC
```

(SEQ ID NO: 385)
5'- GTCGACAAAAGGTATTTGAATTTGCATTCTCTTGAAATGCAAATTC

AAATACCTAGGATCC

H2 (ineffective sequence)
(SEQ ID NO: 386)
5'-ggATCCTCAGAAAAACTTAGACACCTTCAAGAGAGGTGTCTAAGTTT TTCTGTTTgTCgAC (SEQ ID NO: 387)
5'- GTCGACAAACAGAAAAACTTAGACACCTCTCTTGAAGGTGTCTAAG

TTTTTCTGAGGATCC

Western Blot: Hela cells were lysed using 1× Cell lysis Buffer (Cell Signaling Technology, Cat No. 9803). For electrophoresis, 50 μg of total protein in 2× loading buffer was loaded to each well of a 12% SDS-PAGE gel. After transferring the blot was blocked and probed with primary antibody at 2 h followed by incubation with HRP-conjugated secondary antibody before detection by ECL. All primary antibodies were used at 1/1000 dilution except HPV18E7 antibody at 1/250. Anti-Human pRb antibody: BD Pharmingen (Cat No. 554136), Sec Ab: HRP-anti Mouse HPV18E7: Santa Cruz (Cat No. sc-1590), Sec Ab: donkey anti-goat IgG-HRP Cat no. sc 2020
p53: Santa Cruz (Cat No. sc-126), Sec Ab: HRP-anti Mouse
p21: Santa Cruz (Cat No. sc-397), Sec Ab: HRP-anti Rabbit
c-Myc: Cell Signaling Technology (Cat No. 9402), Sec Ab: HRP-anti Rabbit Colony Formation Assay: Hela cells were harvested after bacterial invasion for 2 h. The cells in either control treated or HPV shRNA treated cells were washed 3× times with complete MEM and one time with PBS. The cells were then trypsinized and counted. 500 cells from each treatment were added to a single well of a six well plate containing 2 ml of complete growth medium. The cells were allowed to grow for 10 days following which the colonies were fixed with GEIMSA stain.

MTT Assay: Hela cells were harvested after bacterial invasion for 2 h. The cells in either control treated or HPV shRNA treated cells were washed 3× times with complete MEM and one time with PBS. The cells were then trypsinized and counted. 5000 cells from each treatment were added to a single well of a 96 well plate in 100 μl of complete growth medium in triplicates. The cells were incubated at 37° C. for 48-72 h following which 10 μl of 0.5 mg/ml MTT was added to each well. The plate was further incubated at 37° C. for 3 h, the medium was aspirated off from the wells and after incubation, 100 μl of MTT solubilization solution [10% Triton X-100 in acidic isoproponal (0.1 N HCl)] was added to each well to stop the reaction. The absorbance was read at 570 nm on the plate reader.

Results

In this example, the suppressive effect of a short hairpin RNA directed towards HPV 18 E6 and E7 oncogenes was investigated. The short hairpin RNA was delivered by infecting human cervical cancer cells (Hela) with bacterial strains that produce the short hairpin RNA. The shRNA expression cassette contained 19 nucleotide (nt) of the target sequence followed by the loop sequence (TTCAAGAGA) (SEQ ID NO:388) and the reverse complement to the 19 nt. For the 19 nt, two shRNA sequences published in Cancer Gene Therapy (2006) 13, 1023-1032, were used to measure siRNA delivery and gene silencing efficiency, oligofectamine reagent in a 6 well format was used. Briefly, Hela cells were plated at a cell density of about 40% confluence in antibiotic free medium. On the next day, siRNA was added to 6 well plates at varying concentrations of 50, 100, 200 nM. The control siRNA was added at a single concentration of 100 nM.

Figure 7:
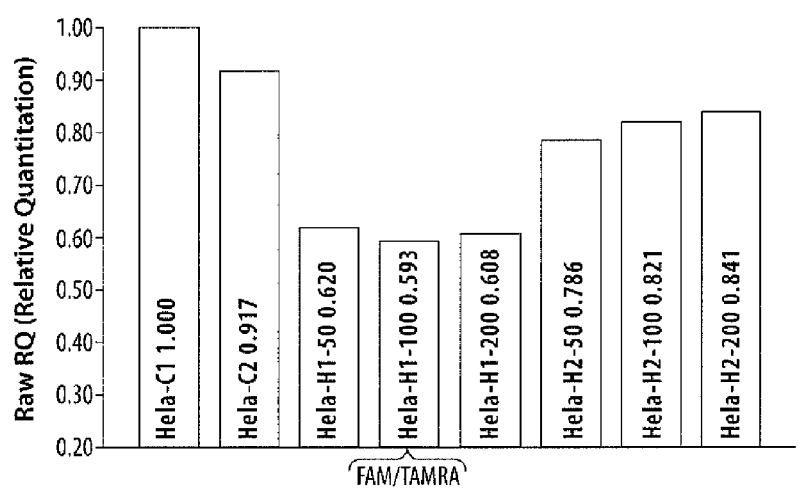
FIG. 7 is a bar graph showing a reduction in HPV oncogene expression with bacterial delivered siRNA.

As shown in FIG. 7, the oligofectamine transfection method resulted in a decrease in E6 mRNA in Hela cells with respect to the control siRNA. The siRNA (H1) showed up to about 40% of reduction in E6 mRNA. The knockdown response was not dose dependent.

Next, the hairpin of the siRNA (H1) was cloned into the TRIP vector. In order to determine if gene silencing could be achieved through the transkingdom system, the shRNA in human cervical cancer cells (Hela) was tested in an invasion assay. Briefly, Hela cells were plated in a six-well plate at $2 \times 10^5$ cells/well, allowed to grow overnight and incubated the next day for 2 h at different MOIs with bacteria (E. coli) engineered to produce the hairpin RNA. The bacteria were washed off with medium containing 10% FBS and Pen Strep four times and the mammalian cells were further incubated for an additional 48 h in the complete medium. RNA or protein was isolated from the bacteria.

Figure 8:
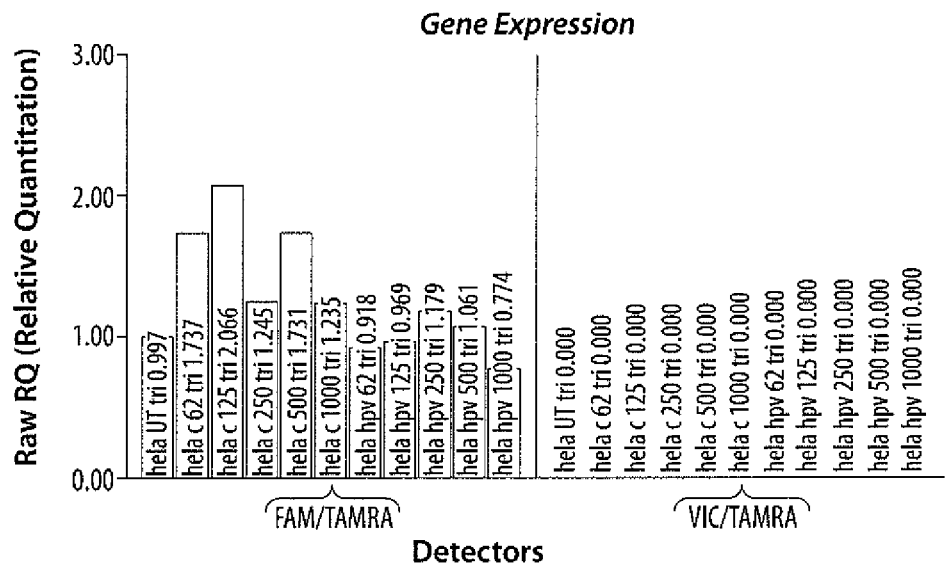
FIG. 8 is a bar graph showing a reduction in HPV oncogene expression with bacterial delivered siRNA.
Figure 9:
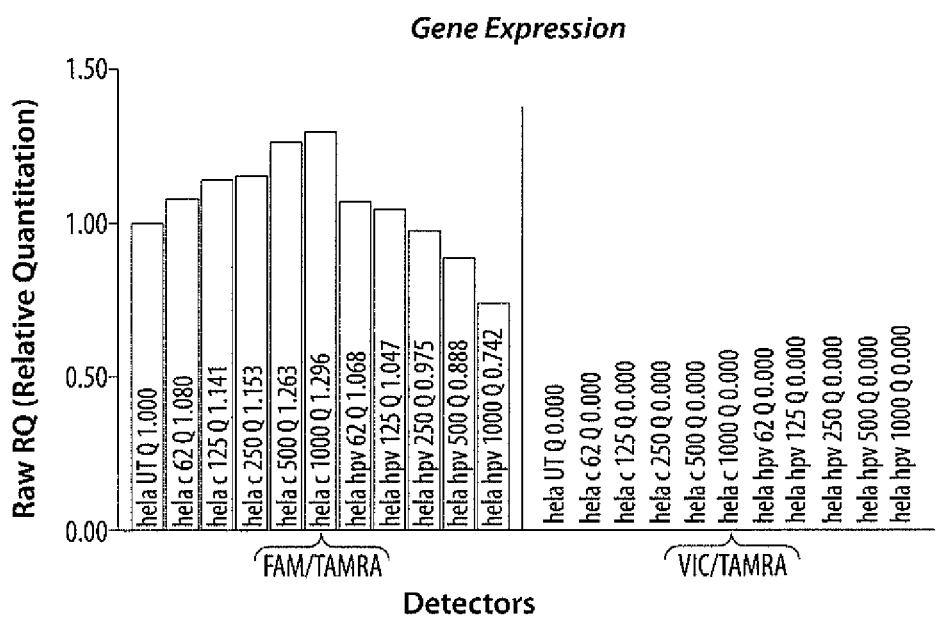
FIG. 9 is a bar graph showing a reduction in HPV oncogene expression with bacterial delivered siRNA.

FIG. 8 and FIG. 9 demonstrate that siRNA downregulates HPV E6 expression in Hela cells. Cells were plated in six well plates and allowed to grow to a confluence of 40% (about 40,000 cells). Oligofectamine/siRNA transfection complexes were prepared in Opti-MEM serum-free medium by mixing 4 μl of oligofectamine with siRNAs (final concentration in 185 μl of medium is 50, 100, 200 nM). 48 hours post-transfection cells were harvested and analyzed by real-time RT-PCR for both target and GAPDH mRNA levels. Data were normalized against the GAPDH signal. Two different negative control siRNAs were used at a single concentration of 200 nM.

Figure 10:
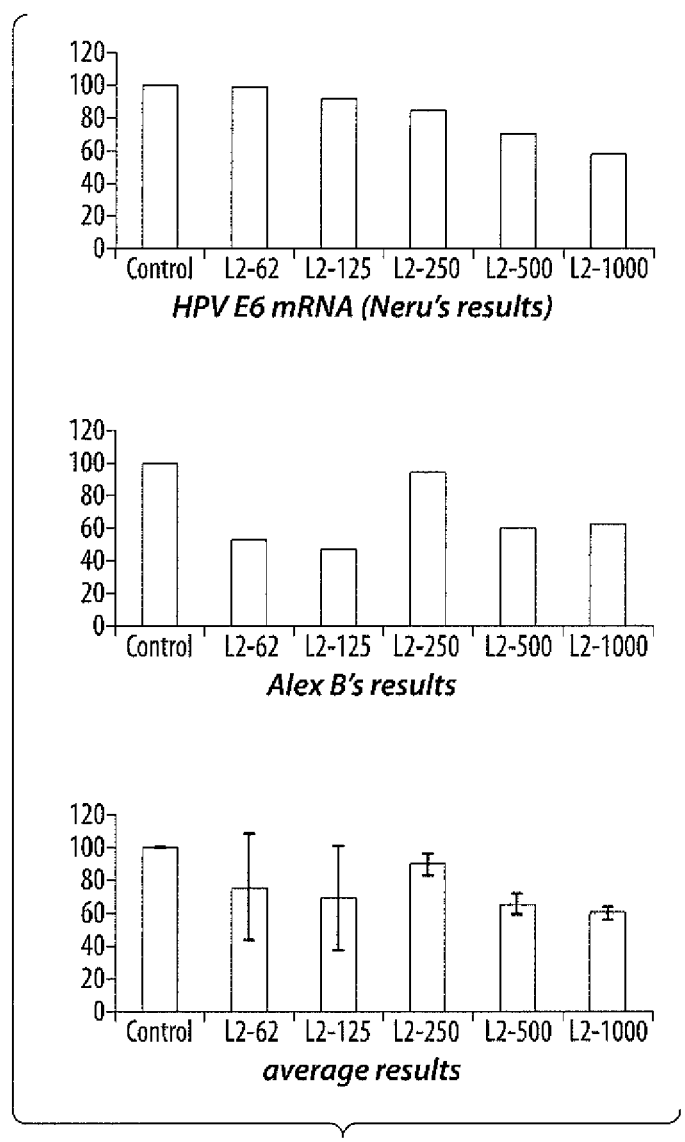
FIG. 10, Panels A-C, are a series of bar graphs showing real time PCR results following invasion of Hela cells with various siRNAs.

FIG. 10, Panels A-C show real time PCR results following invasion assay of Hela cells. Hela cells were incubated for 2 h with shRNA-expressing BL21(DE3) at different multiplicities of infection (MOI). Forty-eight hours post-infection the cells were harvested and analyzed by real-time RT-PCR for both target and GAPDH mRNA levels. Data were normalized against the GAPDH signal. These data were then further normalized to untreated control cells.

Figure 11:
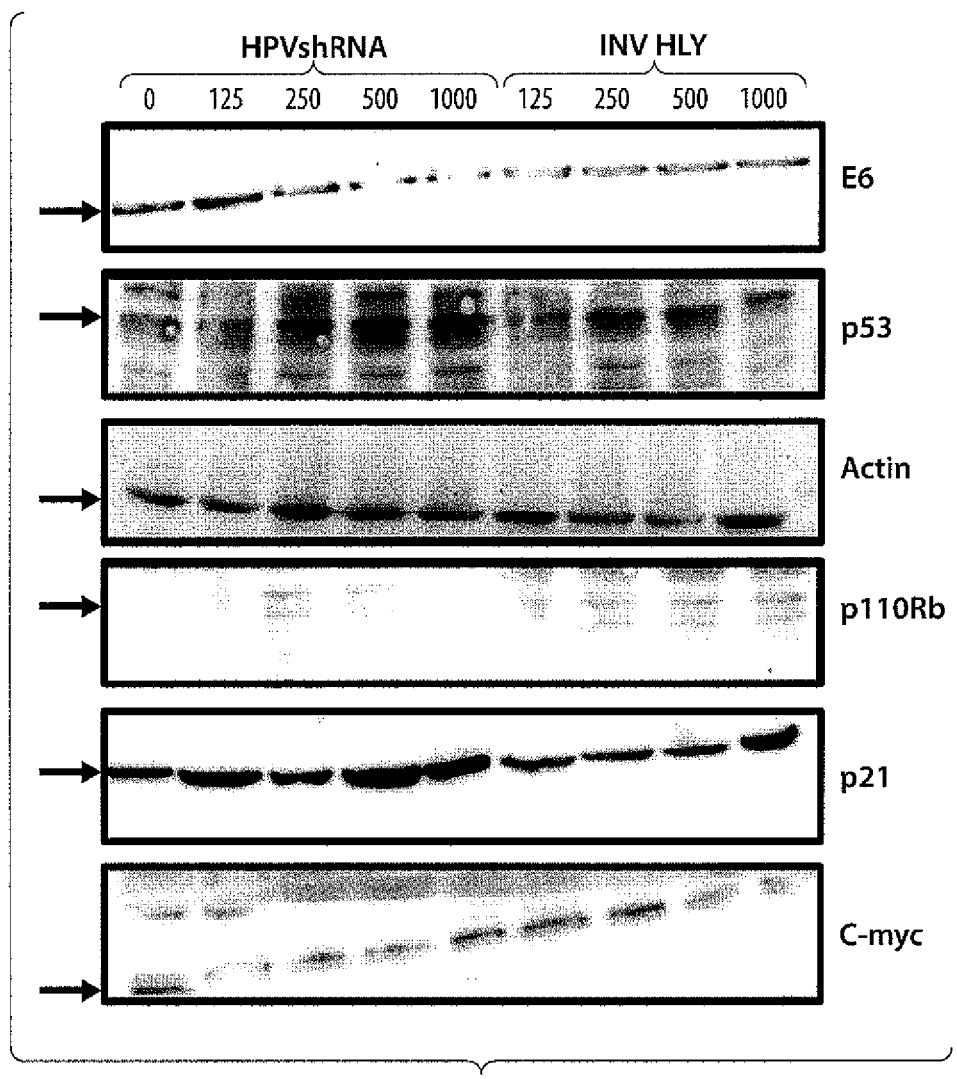
FIG. 11 is a photograph of an immunoblot showing the effects of downregulation of HPV E6 and E7 genes on tumor suppressor pathways and other downstream targets.

FIG. 11 shows the effects of downregulation of HPV E6 and E7 genes on tumor suppressor pathways and other downstream targets. Hela cells were incubated for 2 h with shRNA-expressing BL21(DE3) at different multiplicities of infection (MOI). Forty-eight hours post-infection cells were harvested and analyzed by western blotting. 50 μg of protein was loaded in each lane and resolved by gel electrophoresis, transferred to a membrane and probed with antibodies specific for HPV 18 E7, p53, actin, p110Rb, p21 and c-myc as indicated.

Figure 12:
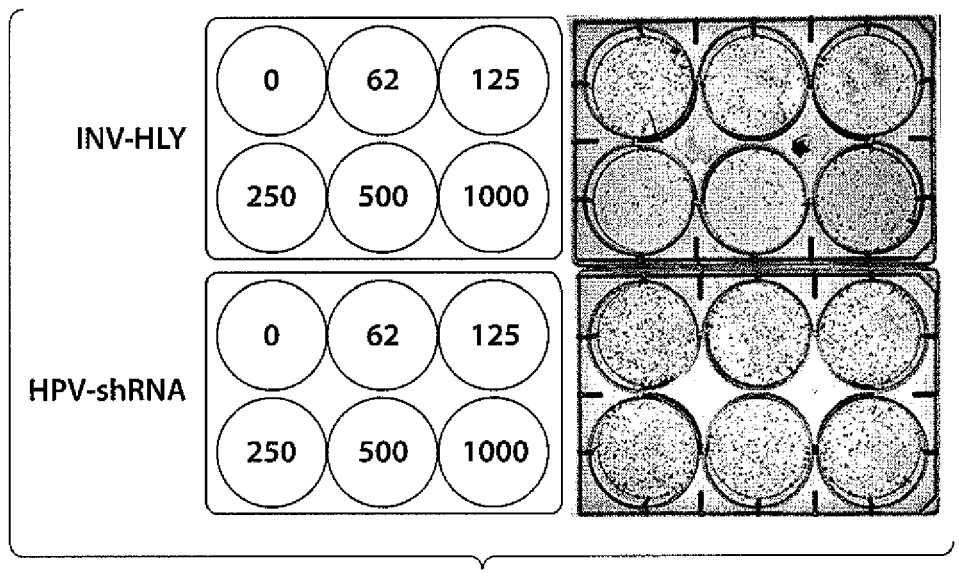
FIG. 12 is a photograph of a colony forming assay showing infection at different multiplicities of infection (MOI).
Figure 13:
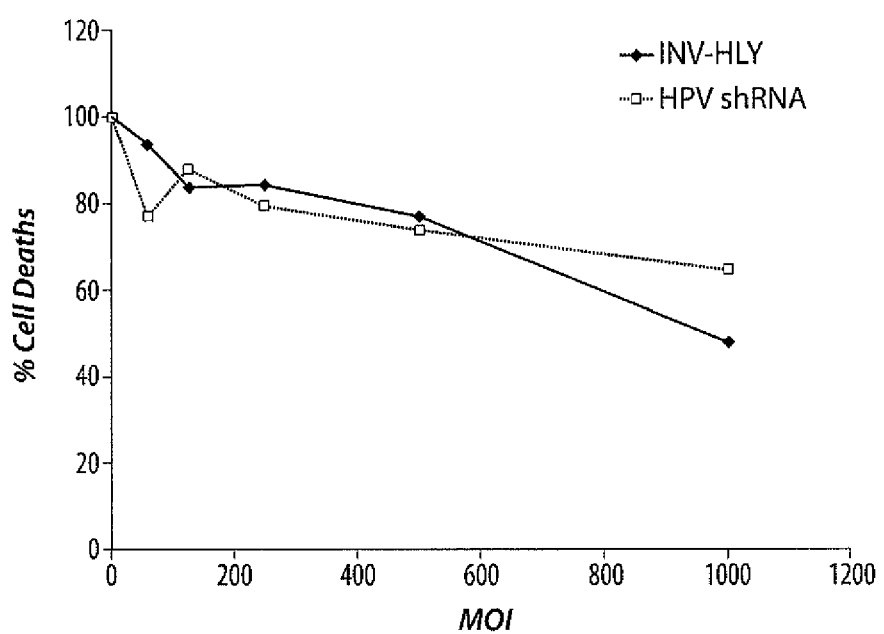
FIG. 13 is a line graph of a MTT assay showing infection at different multiplicities of infection (MOI).

FIGS. 12 and 13 show a colony formation and MTT assay, respectively. Hela cells were incubated for 2 h with shRNA-expressing BL21(DE3) at different multiplicities of infection (MOI). 2 h post-infection cells were washed trypsinized and counted and an equal number of cells for each MOI was added to a well of a six well plate (For CFA: added 500 cells to each well of a 6 well plate, for MTT added 5000 cells in each well of a 96 well plate). For colony formation, the cells were allowed to grow for 10 days and stained with Geimsa, MTT assay was analyzed at 72 h post plating.

Figure 14:
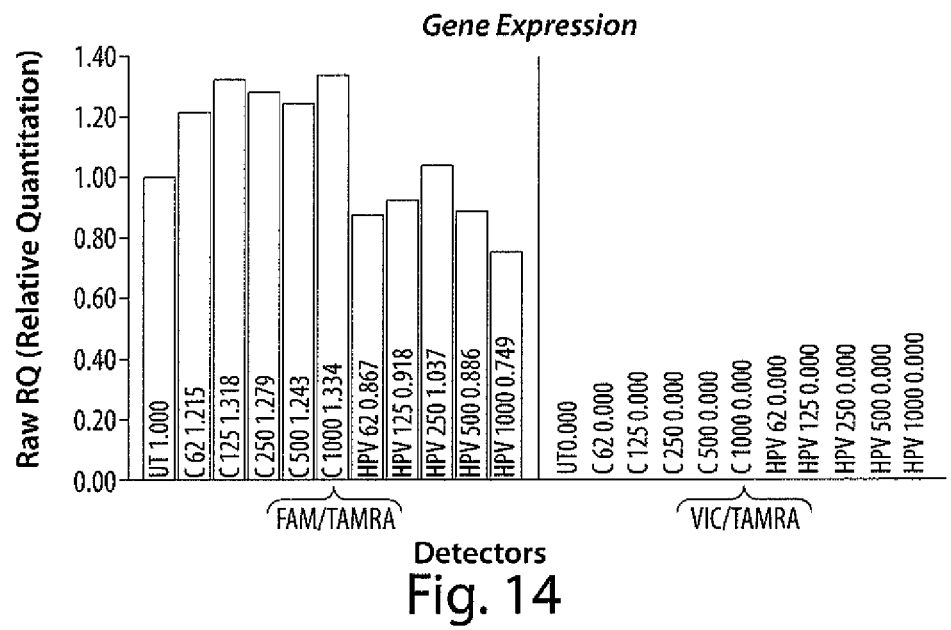
FIG. 14 is a bar graph showing real time PCR results following invasion of Hela cells with various siRNAs FIG. 15, Panels A-C, are a series of bar graphs showing real time PCR results following invasion of Hela cells with various siRNAs.
Figure 15:
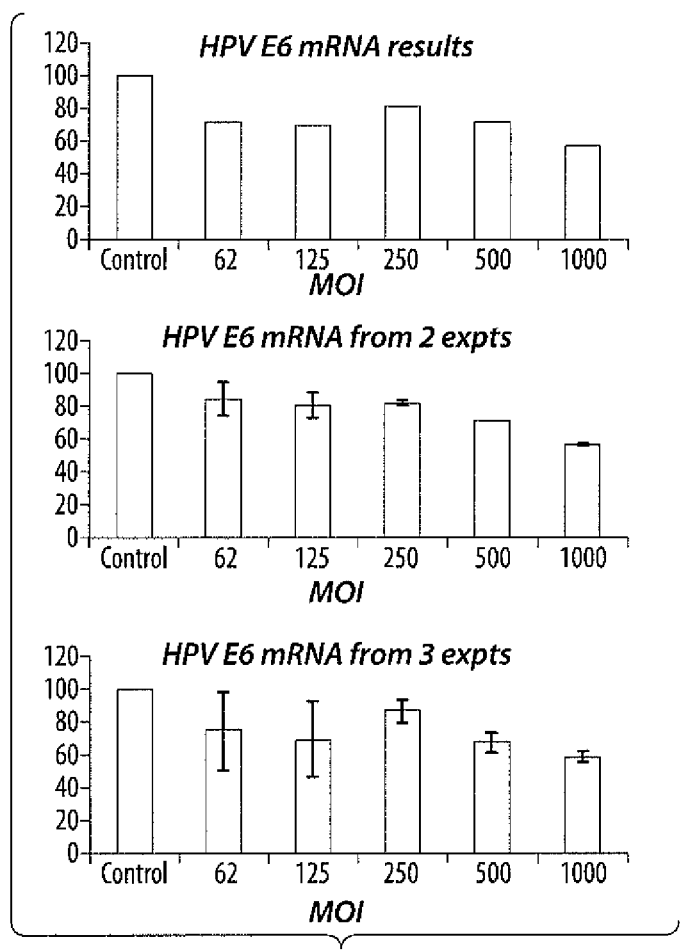

FIGS. 14 and 15 show real time PCR results following invasion assay of Hela cells. Hela cells were incubated for 2 h with shRNA-expressing BL21(DE3) at different multiplicities of infection (MOI). Forty-eight hours post-infection cells were harvested and analyzed by real-time RT-PCR for both target and GAPDH mRNA levels. Data were normalized against the GAPDH signal. These data were then further normalized to untreated control cells.

Figure 16:
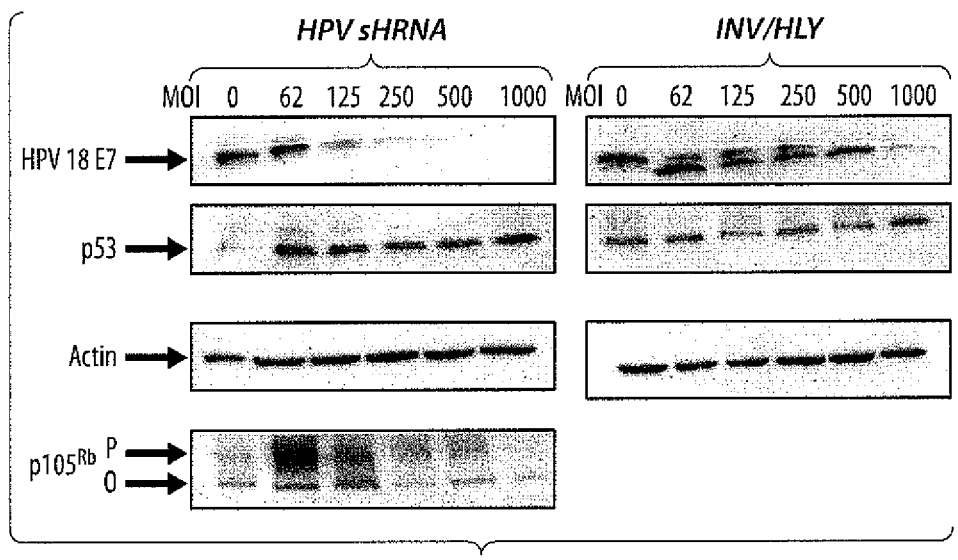
FIG. 16 is a photograph of an immunoblot showing the effects of downregulation of HPV E6 and E7 genes on tumor suppressor pathways and other downstream targets.

FIG. 16 shows the effects of downregulation of HPV E6 and E7 genes on tumor suppressor pathways and other downstream targets. Hela cells were incubated for 2 h with shRNA-expressing BL21(DE3) at different multiplicities of infection (MOI). Forty-eight hours post-infection cells were harvested and analyzed by western blotting. 50 μg of protein was loaded in each lane and resolved by gel electrophoresis, transferred to a membrane and probed with antibodies specific for HPV 18 E7, p53, actin, p110Rb as indicated.

Figure 17:
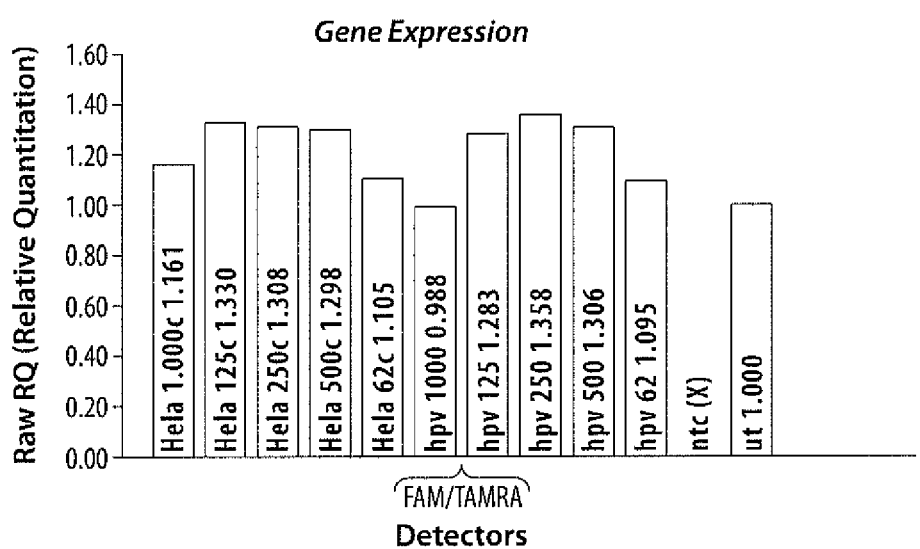
FIG. 17 is a bar graph showing real time PCR results following invasion assay of Hela cells with a frozen aliquot of negative sHRNA control and HPV sHRNA in BL21.

FIG. 17 shows real time PCR results following invasion assay of Hela cells with a frozen aliquot of negative sHRNA control and HPV sHRNA in BL21 (DE3). Hela cells were incubated for 2 h with shRNA-expressing BL21(DE3) at different multiplicities of infection (MOI). Forty-eight hours post-infection cells were harvested and analyzed by real-time RT-PCR for both target and GAPDH mRNA levels. Data were normalized against the GAPDH signal. These data were then further normalized to untreated control cells.

Figure 18:
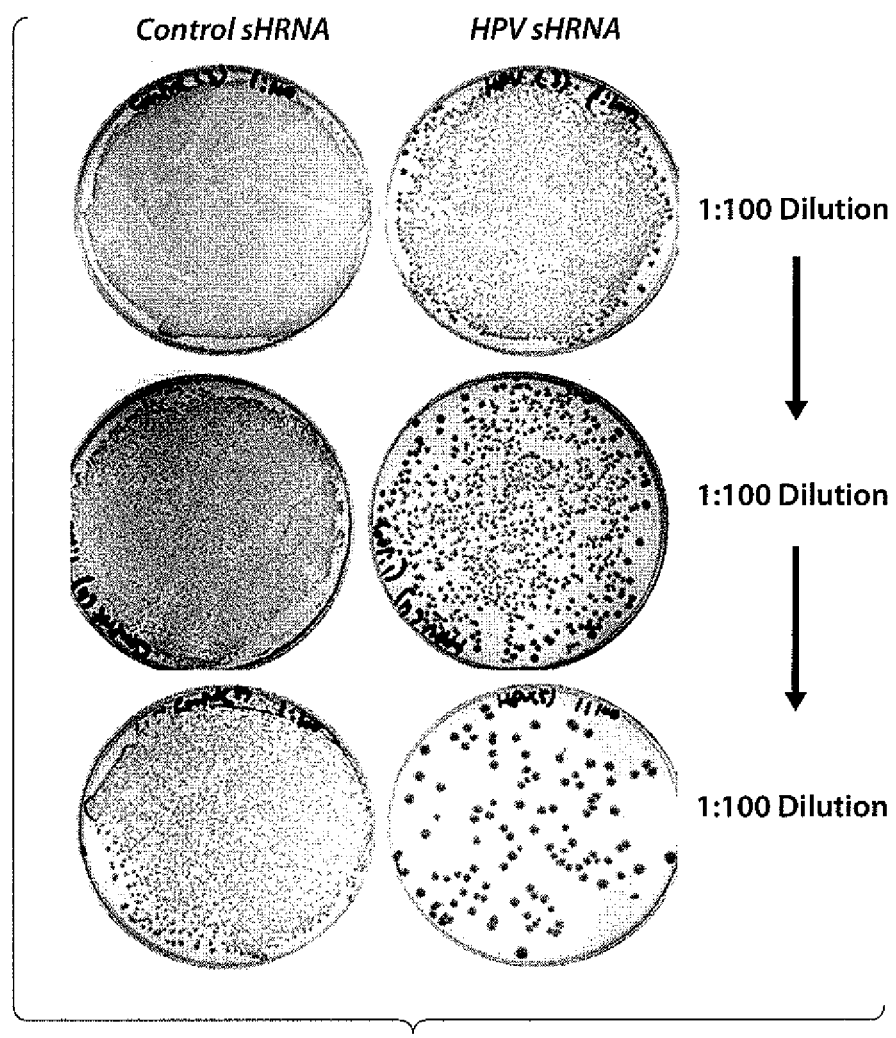
FIG. 18 is a photograph showing the plating efficiency of frozen aliquots of negative sHRNA control and HPV sHRNA in BL21.

FIG. 18 shows the plating efficiency of frozen aliquots of negative sHRNA control and HPV sHRNA in BL21 (DE3). The frozen bacteria were thawed and resuspended to a final concentration of 3.38×10$^8$ cells/ml. Invasion assay was performed with this concentration taking 2 mls of 3.38×10$^8$ cells/ml as an MOI of 1000. Some stock control bacteria or HPV bacteria were serially diluted (1:100) and plated on LB plates to assess for the number and viability of bacteria treated cells at 48 h. Gene silencing was analyzed either by quantitative real-time PCR using the ΔΔCt relative quantitation method or by western blot analysis. HPVE6 mRNA levels were normalized to an endogenous control, GAPDH. The final data were further normalized to the RNA from the untreated cells. For Protein analysis, cell lysates were prepared in Cell Lysis Buffer (Cell Signaling Technology) and the protein concentration was determined using a BCA kit from BioRad. For electrophoresis, the protein expression was normalized to Actin loading control.

Example 8

Knockdown of HPV E6 Gene Assessed by Western Blotting with HPV 18 E7 Antibody

Hela cells were incubated for 2 h with shRNA-expressing BL21(DE3) (HPVH1 construct below) at different multiplicities of infection (MOI). Forty-eight hours post-infection cells were harvested and analyzed by western blotting. The HPV E6 specific knockdown was compared with a negative shRNA control. Briefly, 50 μg of protein was loaded in each lane and resolved by gel electrophoresis, transferred to a membrane and probed with antibodies specific for HPV 18 E7, and actin as indicated.

```
HPVH 1
                                        (SEQ ID NO: 389)
5'-GATCC TAGGTATTTGAATTTGCAT TTCAAGAGA

ATGCAAATTCAAATACCTTTT G-3'
```

```
                          -continued
                                        (SEQ ID NO: 390)
3'-G ATCCATAAACTTAAACGTA AAGTTCTCT

TACGTTTAAGTTTATGGAAAA CAGCT-5'
```

Figure 19:
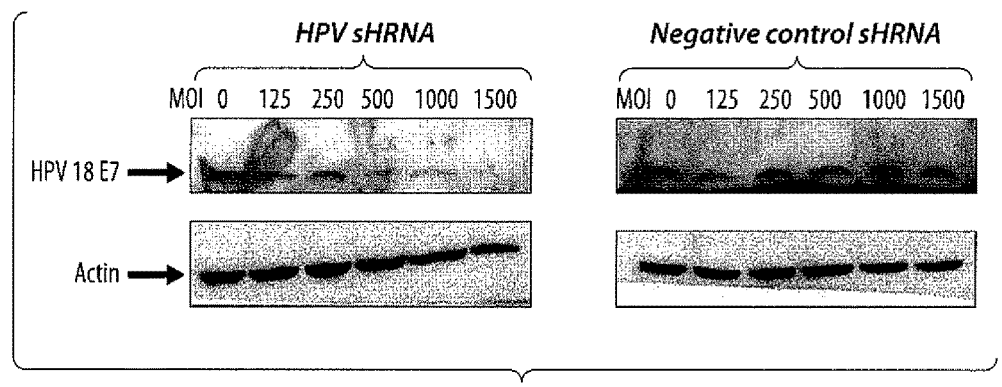
FIG. 19 is a photograph of an immunoblot showing the knockdown of HPV E6 gene assessed by western blotting with HPV 18 E7 antibody.

FIG. 19 shows the knockdown of HPV E6 gene assessed by western blotting with HPV 18 E7 antibody. Hela cells were incubated for 2 h with shRNA-expressing BL21 (DE3) at different multiplicities of infection (MOI). Forty-eight hours post-infection cells were harvested and analyzed by western blotting. The HPV E6 specific knockdown was compared with a negative sHRNA control. Briefly, 50 μg of protein was loaded in each lane and resolved by gel electrophoresis, transferred to a membrane and probed with antibodies specific for HPV 18 E7 and actin as indicated.

Example 9

Inhibition of CCL20 Expression in CMT93 Cells

One confluent T-175 flask of CMT93 cells was trypsinized in 10 mls until the cells detached. Trypsin was inactivated by addition of 30 mls of DMEM (10% FCS, pen/strep) and the cells thoroughly mixed by pipetting. From this solution, 8 mls was transferred into a sterile 50 ml tube and 32 mLs of DMEM 10% added. Cells were well mixed and 250 uLs added to each well of a 48 well plate and incubated overnight at 37 C resulting in adherent cells that were approximately 70% confluent the following morning. The next day, siRNA transfection complexes were created by the following method.

Sequences were ordered from Qiagen as pre-annealed siRNA duplexes. Each well was resuspended in 250 ul of siRNA buffer (from Qiagen) to give a stock concentration of 20 uM. The plate was then placed in a water bath at 95 C for 5 minutes and then allowed to slowly cool to resuspend the duplexes and break apart aggregates. The suspended duplexes were then used in transfection experiments described in standard protocols. The formulation is per well of a 48 well plate containing 250 uL of media; each screen was performed in biological triplicate so the solution was made for 4 wells; 3 for transfection and 1 extra.

0.3 uL of the appropriate siRNA (from a 20 uM stock solution) were diluted to 47 uL with serum/antibiotic free media and mixed. To this solution was added 3 uL of HiPerfect transfection reagent (Qiagen) followed by brief vortexing and incubation at room temperature for 20 minutes. 50 uLs of the complex containing mixture was added to each of 3 wells in a 48 well plate containing CMT93 cells. Transfection was for 24 hours at 37 C at which time the media was removed and replaced with 400 uLs of DMEM/10% FCS containing 10Ong/mL of LPS for 2 hours. Following stimulation, the cells were washed and RNA isolated for qRT-PCR according the Qiagen Quantitech method (see manufacturer's protocol) for 50 cycles.

Figure 20:
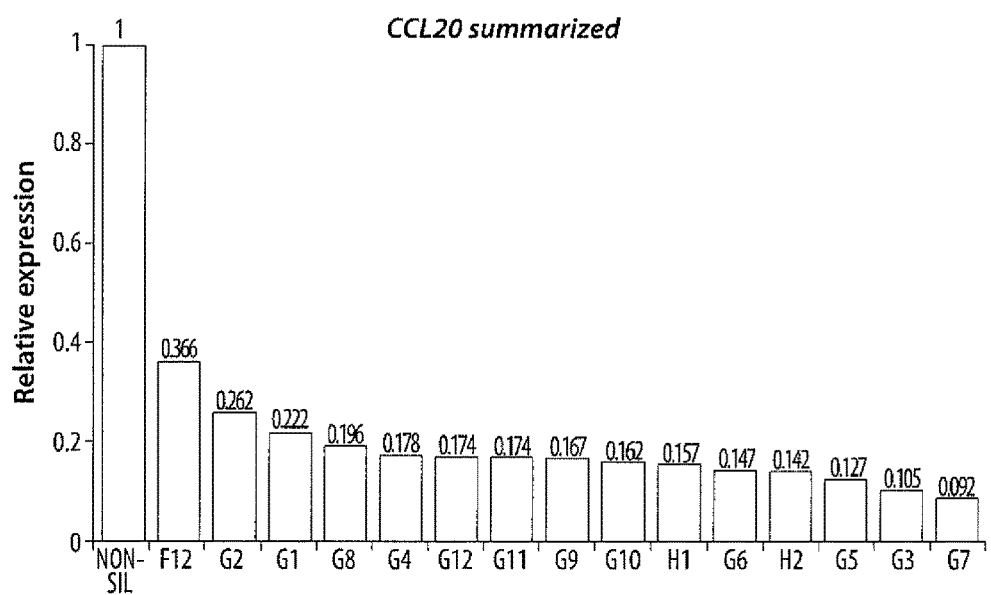
FIG. 20 is a bar graph showing the knockdown of CCL20 expression with the various siRNA sequences in CMT93 cells.

FIG. 20 shows the knockdown of CCL20 expression with the various siRNA sequences in CMT93 cells. The siRNA sequences tested are listed below:

| Well | siRNA sense 5'→3' | SEQ ID NO: | siRNA antisense 5'→3' | SEQ ID NO: |
|---|---|---|---|---|
| G1 | GCUUGUGACAUUAAUGCUAtt | 391 | UAGCAUUAAUGUCACAAGCtt | 392 |
| H1 | AUAAGCUAUUGUAAAGAUAtt | 393 | UAUCUUUACAAUAGCUUAUtg | 394 |
| G2 | CAUCUUUCACACGAAGAAAtt | 395 | UUUCUUCGUGUGAAAGAUGat | 396 |
| H2 | CUAUUGUAAAGAUAUUUAAtt | 397 | UUAAAUAUCUUUACAAUAGct | 398 |
| G3 | GCCUAAGAGUCAAGAAGAUtt | 399 | AUCUUCUUGACUCUUAGGCtg | 400 |
| G4 | CAGUGGACUUGUCAAUGGAtt | 401 | UCCAUUGACAAGUCCACUGgg | 402 |
| G5 | GAAGUUGAUUCAUAUUGCAtt | 403 | UGCAAUAUGAAUCAACUUCat | 404 |
| G6 | GUUGAUUCAUAUUGCAUCAtt | 405 | UGAUGCAAUAUGAAUCAACtt | 406 |
| G7 | ACAUUAGAGUUAAGUUGUAtt | 407 | UACAACUUAACUCUAAUGUga | 408 |
| G8 | CAUUAGAGUUAAGUUGUAUtt | 409 | AUACAACUUAACUCUAAUGtg | 410 |
| G9 | UGUUAUUUAUAGAUCUGAAtt | 411 | UUCAGAUCUAUAAAUAACAta | 412 |
| G10 | GUUUAGCUAUUUAAUGUUAtt | 413 | UAACAUUAAAUAGCUAAACat | 414 |
| G11 | AGUGGAAGGAUUAAUAUUAtt | 415 | UAAUAUUAAUCCUUCCACUaa | 416 |
| F12 | CCAGCACUGAGUACAUCAAtt | 417 | UUGAUGUACUCAGUGCUGGgt | 418 |
| G12 | UGUUUAAGGGAAUAGUUUAtt | 419 | UAAACUAUUCCCUUAAACAta | 420 |

Example 10

Inhibition of Expression of Claudin-2 in CMT93 Cells

One confluent T-175 flask of CMT93 cells was trypsinized in 10 mls until the cells detached. Trypsin was inactivated by addition of 30 mls of DMEM (10% FCS, pen/strep) and the cells thoroughly mixed by pipetting. From this solution, 8 mls was transferred into a sterile 50 ml tube and 32 mLs of DMEM 10% added. Cells were well mixed and 250 uL added to each well of a 48 well plate and incubated overnight at 37 C resulting in adherent cells that were approximately 70% confluent the following morning. The next day, siRNA transfection complexes were created by the following method:

Sequences were ordered from Qiagen as pre-annealed siRNA duplexes. Each well was resuspended in 250 ul of siRNA buffer (from Qiagen) to give a stock concentration of 20 uM. The plate was then placed in a water bath at 95 C for 5 minutes and then allowed to slowly cool to resuspend the duplexes and break apart aggregates. The suspended duplexes were then used in transfection experiments described in standard protocols. The formulation is per well of a 48 well plate containing 250 uL of media; each screen was performed in biological triplicate so the solution was made for 4 wells; 3 for transfection and 1 extra.

0.3 uL of the appropriate siRNA (from a 20 uM stock solution) to 47 uL of serum/antibiotic free media and mixed. To this solution was added 3 uL of HiPerfect transfection reagent (Qiagen) followed by brief vortexing and incubation at room temperature for 20 minutes. 50 uLs of the complex containing mixture was added to each of 3 wells in a 48 well plate containing CMT93 cells. Transfection was for 24 or 48 hours at 37 C at which time the cells were washed and RNA isolated for qRT-PCR according the Qiagen Quantitech method (see manufacturer's protocol) for 50 cycles.

Figure 21:
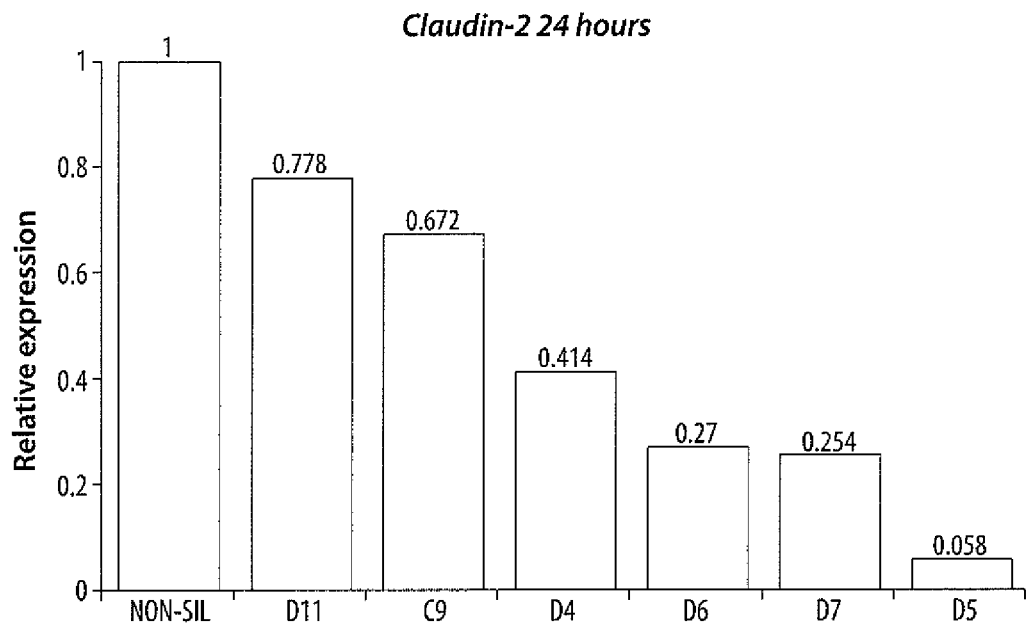
FIG. 21 is a bar graph showing the knockdown of Claudin-2 expression with the various siRNA sequences in CMT93 cells post 24 hr transfection.

FIG. 21 shows the knockdown of Claudin-2 expression with the various siRNA sequences in CMT93 cells post 24 hr transfection. The siRNA sequences tested are listed below:

| Well | siRNA sense 5'→3' | SEQ ID NO: | siRNA antisense 5'→3' | SEQ ID NO: |
|---|---|---|---|---|
| D4 | GCUGGGACUAUAUAUAUAAtt | 421 | UUAUAUAUAUAGUCCCAGCca | 422 |
| D5 | GGGCAAUUGCUAUAUCUUAtt | 423 | UAAGAUAUAGCAAUUGCCCtc | 424 |
| D6 | GCAGCCAAACGACAAGCAAtt | 425 | UUGCUUGUCGUUUGGCUGCtg | 426 |
| D7 | AGGGUUUCCUUAAGGACAAtt | 427 | UUGUCCUUAAGGAAACCCUtg | 428 |
| C9 | GAAAUGGAUUAGUCAGUAAtt | 429 | UUACUGACUAAUCCAUUUCtt | 430 |
| D11 | GGCUCCGAAGAUACUUCUAtt | 431 | UAGAAGUAUCUUCGGAGCCtg | 432 |

Example 11

Inhibition of Expression of IL6-Ra in CMT93 Cells

One confluent T-175 flask of CMT93 cells was trypsinized in 10 mls until the cells detached. Trypsin was inactivated by addition of 30 mls of DMEM (10% FCS, pen/strep) and the cells thoroughly mixed by pipetting. From this solution, 8 mls was transferred into a sterile 50 ml tube and 32 mLs of DMEM 10% added. Cells were well mixed and 250 uLs added to each well of a 48 well plate and incubated overnight at 37 C resulting in adherent cells that were approximately 70% confluent the following morning. The next day, siRNA transfection complexes were created by the following method:

Sequences were ordered from Qiagen as pre-annealed siRNA duplexes. Each well was resuspended in 250 ul of siRNA buffer (from Qiagen) to give a stock concentration of 20 uM. The plate was then placed in a water bath at 95 C for 5 minutes and then allowed to slowly cool to resuspend the duplexes and break apart aggregates. The suspended duplexes were then used in transfection experiments described in standard protocols. The formulation is per well of a 48 well plate containing 250 uL of media; each screen was performed in biological triplicate so the solution was made for 4 wells; 3 for transfection and 1 extra.

0.3 uL of the appropriate siRNA (from a 20 uM stock solution) to 47 uL of serum/antibiotic free media and mixed. To this solution was added 3 uL of HiPerfect transfection reagent (Qiagen) followed by brief vortexing and incubation at room temperature for 20 minutes. 50 uLs of the complex containing mixture was added to each of 3 wells in a 48 well plate containing CMT93 cells. Transfection was for 24, 48 or 72 hours at 37 C at which time the cells were washed and RNA isolated for qRT-PCR according the Qiagen Quantitech method (see manufacturer's protocol) for 40 cycles.

Figure 22:
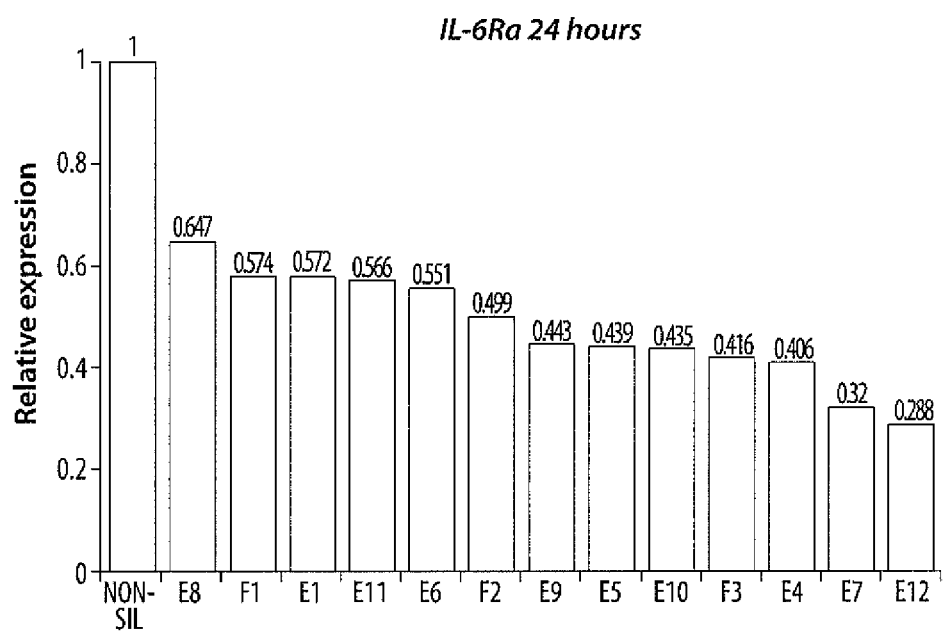
FIG. 22 is a bar graph showing the knockdown of IL6-RA expression with the various siRNA sequences in CMT93 cells post 24 hr transfection.

FIG. 22 shows the knockdown of IL6-RA expression with the various siRNA sequences in CMT93 cells post 24 hr transfection. The siRNA sequences tested are listed below:

Example 12

Inhibition of Expression of IL13-Ra1 in CMT93 Cells

One confluent T-175 flask of CMT93 cells was trypsinized in 10 mls until the cells detached. Trypsin was inactivated by addition of 30 mls of DMEM (10% FCS, pen/strep) and the cells thoroughly mixed by pipetting. From this solution, 8 mls was transferred into a sterile 50 ml tube and 32 mLs of DMEM 10% added. Cells were well mixed and 250 uLs added to each well of a 48 well plate and incubated overnight at 37 C resulting in adherent cells that were approximately 70% confluent the following morning. The next day, siRNA transfection complexes were created by the following method:

Sequences were ordered from Qiagen as pre-annealed siRNA duplexes. Each well was resuspended in 250 ul of siRNA buffer (from Qiagen) to give a stock concentration of 20 uM. The plate was then placed in a water bath at 95 C for 5 minutes and then allowed to slowly cool to resuspend the duplexes and break apart aggregates. The suspended duplexes were then used in transfection experiments described in standard protocols. The formulation is per well of a 48 well plate containing 250 uL of media; each screen was performed in biological triplicate so the solution was made for 4 wells; 3 for transfection and 1 extra.

0.3 uL of the appropriate siRNA (from a 20 uM stock solution) to 47 uL of serum/antibiotic free media and mixed. To this solution was added 3 uL of HiPerfect transfection reagent (Qiagen) followed by brief vortexing and incubation at room temperature for 20 minutes. 50 uLs of the complex containing mixture was added to each of 3 wells in a 48 well plate containing CMT93 cells. Transfection was for 24 or 72 hours at 37 C at which time the cells were washed and RNA isolated for qRT-PCR according the Qiagen Quantitech method (see manufacturer's protocol) for 40 cycles.

Figure 23:
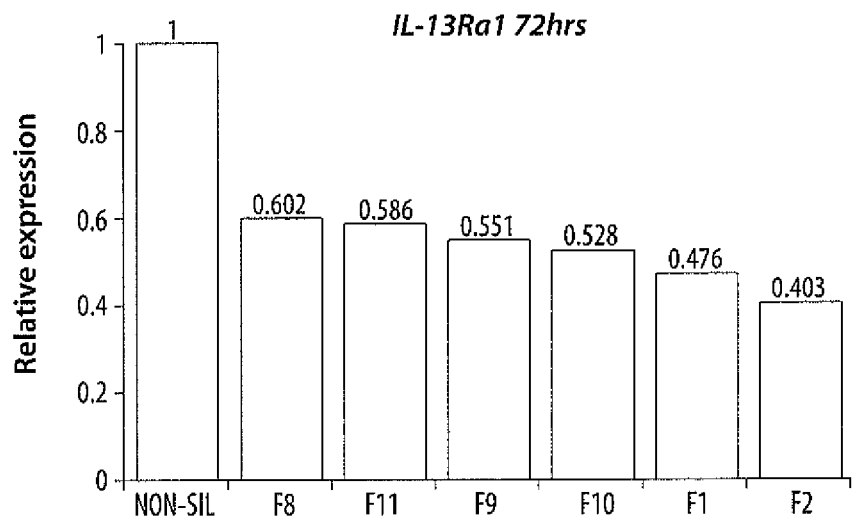
FIG. 23 is a bar graph showing the knockdown of IL13-RA1 expression with the various siRNA sequences in CMT93 cells post 24 hr transfection.

FIG. 23 shows the knockdown of IL13-RA1 expression with the various siRNA sequences in CMT93 cells post 24 hr transfection. The siRNA sequences tested are listed below:

| Well | siRNA sense 5'→3' | SEQ ID NO: | siRNA antisense 5'→3' | SEQ ID NO: |
|------|-------------------|------------|------------------------|------------|
| E1   | CCUGGAGGGUGACAAAGUAtt | 433 | UACUUUGUCACCCUCCAGGat | 434 |
| F1   | GGUCUGACAAUACCGUAAAtt | 435 | UUUACGGUAUUGUCAGACCca | 436 |
| F2   | GCUGUUUCCUAUAACAGAAtt | 437 | UUCUGUUAUAGGAAACAGCgg | 438 |
| F3   | GCUGUGAAAGGGAAAUUUAtt | 439 | UAAAUUUCCCUUUCACAGCag | 440 |
| E4   | CCUUGUGGUAUCAGCCAUAtt | 441 | UAUGGCUGAUACCACAAGGtt | 442 |
| E5   | GCUUCGAUACCGACCUGUAtt | 443 | UACAGGUCGGUAUCGAAGCtg | 444 |
| E6   | CGGCAGGAAUCCUCUGGAAtt | 445 | UUCCAGAGGAUUCCUGCCGgg | 446 |
| E7   | CCACGAGGAUCAGUACGAAtt | 447 | UUCGUACUGAUCCUCGUGGtt | 448 |
| E8   | CACGAGGAUCAGUACGAAAtt | 449 | UUUCGUACUGAUCCUCGUGgt | 450 |
| E9   | GAUCAGUACGAAAGUUCUAtt | 451 | UAGAACUUUCGUACUGAUCct | 452 |
| E10  | GUACGAAAGUUCUACAGAAtt | 453 | UUCUGUAGAACUUUCGUACtg | 454 |
| E11  | GAAAGUUCUACAGAAGCAAtt | 455 | UUGCUUCUGUAGAACUUUCgt | 456 |
| E12  | GGGUCUGACAAUACCGUAAtt | 457 | UUACGGUAUUGUCAGACCCag | 458 |

| Well | siRNA sense 5'→3' | SEQ ID NO: | siRNA antisense 5'→3' | SEQ ID NO: |
|---|---|---|---|---|
| F1 | AGAAGACUCUAAUGAUGUAtt | 459 | UACAUCAUUAGAGUCUUCUtg | 460 |
| F2 | CAGUCAGAGUAAGAGUCAAtt | 461 | UUGACUCUUACUCUGACUGtg | 462 |
| F8 | CAGAACAUCUAGCAAACAAtt | 463 | UUGUUUGCUAGAUGUUCUGtg | 464 |
| F9 | CUUGUAGGUUCACAUAUUAtt | 465 | UAAUAUGUGAACCUACAAGtt | 466 |
| F10 | CAGUGUAGUGCCAAUGAAAtt | 467 | UUUCAUUGGCACUACACUGag | 468 |
| F11 | GUAUGACAUCUAUGAGAAAtt | 469 | UUUCUCAUAGAUGUCAUACtt | 470 |

Example 13

Inhibition of Expression of IL-18 in CMT93 Cells

One confluent T-175 flask of CMT93 cells was trypsinized in 10 mls until the cells detached. Trypsin was inactivated by addition of 30 mls of DMEM (10% FCS, pen/strep) and the cells thoroughly mixed by pipetting. From this solution, 8 mls was transferred into a sterile 50 ml tube and 32 mLs of DMEM 10% added. Cells were well mixed and 250 uLs added to each well of a 48 well plate and incubated overnight at 37 C resulting in adherent cells that were approximately 70% confluent the following morning. The next day, siRNA transfection complexes were created by the following method:

Sequences were ordered from Qiagen as pre-annealed siRNA duplexes. Each well was resuspended in 250 ul of siRNA buffer (from Qiagen) to give a stock concentration of 20 uM. The plate was then placed in a water bath at 95 C for 5 minutes and then allowed to slowly cool to resuspend the duplexes and break apart aggregates. The suspended duplexes were then used in transfection experiments described in standard protocols. The formulation is per well of a 48 well plate containing 250 uL of media; each screen was performed in biological triplicate so the solution was made for 4 wells; 3 for transfection and 1 extra.

0.3 uL of the appropriate siRNA (from a 20 uM stock solution) to 47 uL of serum/antibiotic free media and mixed. To this solution was added 3 uL of Lipofectamine RNAiMAX transfection reagent (Invitrogen) followed by brief vortexing and incubation at room temperature for 20 minutes. 50 uLs of the complex containing mixture was added to each of 3 wells in a 48 well plate containing CMT93 cells. Transfection was for 24 hours at 37 C at which time the cells were washed and RNA isolated for qRT-PCR according the Qiagen Quantitech method (see manufacturer's protocol) for 40 cycles.

Figure 24:
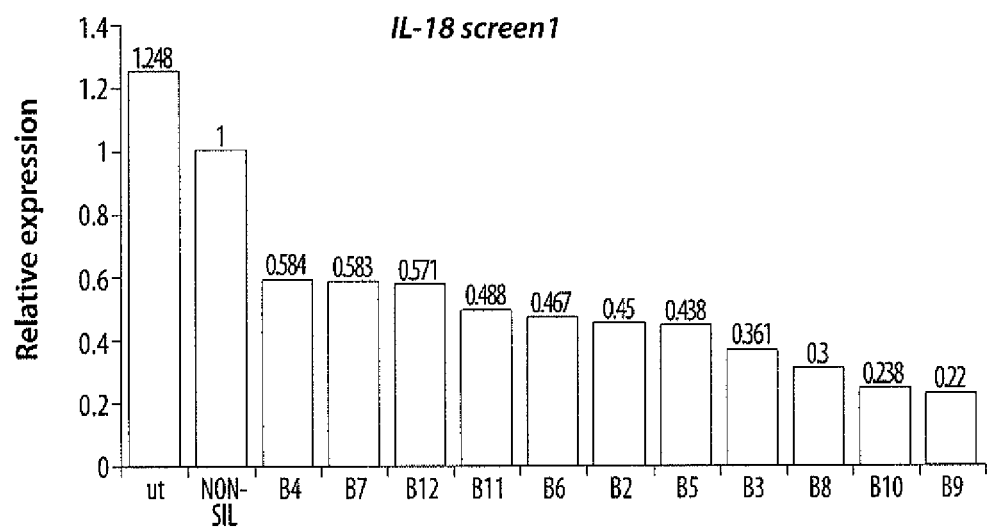
FIG. 24 is a bar graph showing the knockdown of IL18 expression with the various siRNA sequences in CMT93 cells post 24 hr transfection.

FIG. 24 shows the knockdown of IL18 expression with the various siRNA sequences in CMT93 cells post 24 hr transfection. The siRNA sequences tested are listed below:

| Well | siRNA sense 5'→3' | SEQ ID NO: | siRNA antisense 5'→3' | SEQ ID NO: |
|---|---|---|---|---|
| B2 | AGGAAAUGAUGUUUAUUGAtt | 471 | UCAAUAAACAUCAUUUCCUtg | 472 |
| B3 | GGCCGACUUCACUGUACAAtt | 473 | UUGUACAGUGAAGUCGGCCaa | 474 |
| B4 | GAUGGAGUUUGAAUCUUCAtt | 475 | UGAAGAUUCAAACUCCAUCtt | 476 |
| B5 | CAACCGCAGUAAUACGGAAtt | 477 | UUCCGUAUUACUGCGGUUGta | 478 |
| B6 | CGAGGCUGCAUGAUUUAUAtt | 479 | UAUAAAUCAUGCAGCCUCGgg | 480 |
| B7 | CCUGUAUUUCCAUAACAGAtt | 481 | UCUGUUAUGGAAAUACAGGcg | 482 |
| B8 | CAUGUACAAAGACAGUGAAtt | 483 | UUCACUGUCUUUGUACAUGta | 484 |
| B9 | CGAGGAUAUGACUGAUAUUtt | 485 | AAUAUCAGUCAUAUCCUCGaa | 486 |
| B10 | GGAUAUGACUGAUAUUGAUtt | 487 | AUCAAUAUCAGUCAUAUCCtc | 488 |
| B11 | CUAACUUACAUCAAAGUUAtt | 489 | UAACUUUGAUGUAAGUUAGtg | 490 |
| B12 | CUCACUAACUUACAUCAAAtt | 491 | UUUGAUGUAAGUUAGUGAGag | 492 |

Example 14

Inhibition of Expression of IL-7 in CMT93 Cells

One confluent T-175 flask of CMT93 cells was trypsinized in 10 mls until the cells detached. Trypsin was inactivated by addition of 30 mls of DMEM (10% FCS, pen/strep) and the cells thoroughly mixed by pipetting. From this solution, 8 mls was transferred into a sterile 50 ml tube and 32 mLs of DMEM 10% added. Cells were well mixed and 250 uLs added to each well of a 48 well plate and incubated overnight at 37 C resulting in adherent cells that were approximately 70% confluent the following morning. The next day, siRNA transfection complexes were created by the following method:

Sequences were ordered from Qiagen as pre-annealed siRNA duplexes. Each well was resuspended in 250 ul of siRNA buffer (from Qiagen) to give a stock concentration of 20 uM. The plate was then placed in a water bath at 95 C for 5 minutes and then allowed to slowly cool to resuspend the duplexes and break apart aggregates. The suspended duplexes were then used in transfection experiments described in standard protocols. The formulation is per well of a 48 well plate containing 250 uL of media; each screen was performed in biological triplicate so the solution was made for 4 wells; 3 for transfection and 1 extra.

0.3 uL of the appropriate siRNA (from a 20 uM stock solution) to 47 uL of serum/antibiotic free media and mixed. To this solution was added 3 uL of Lipofectamine RNAiMAX transfection reagent (Invitrogen) followed by brief vortexing and incubation at room temperature for 20 minutes.

50 uLs of the complex containing mixture was added to each of 3 wells in a 48 well plate containing CMT93 cells. Transfection was for 24 hours at 37 C at which time the cells were washed and RNA isolated for qRT-PCR according the Qiagen Quantitech method (see manufacturer's protocol) for 40 cycles.

Figure 25:
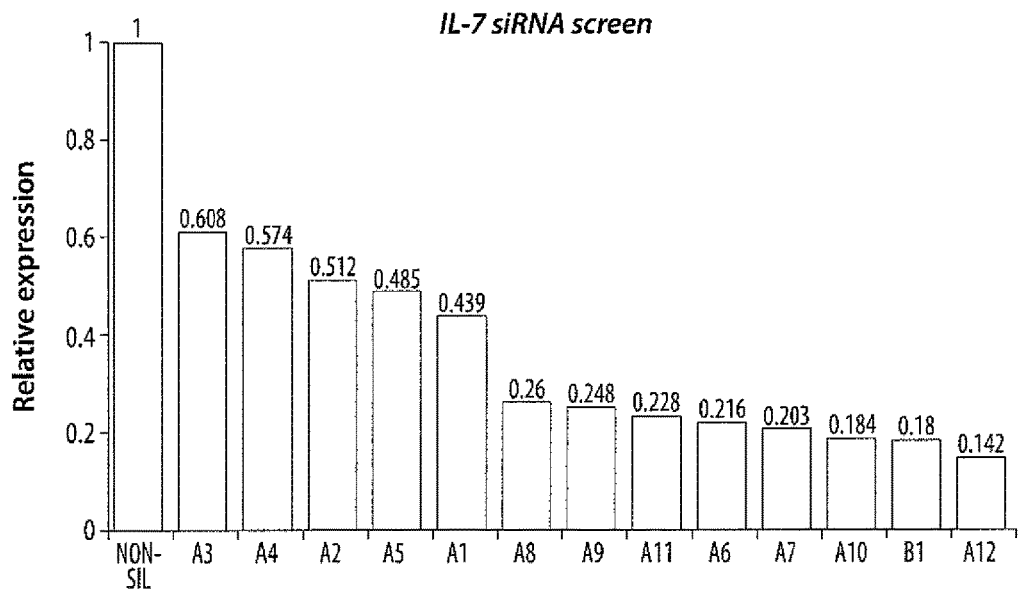
FIG. 25 is a bar graph showing the knockdown of IL-7 expression with the various siRNA sequences in CMT93 cells post 24 hr transfection.

FIG. 25 shows the knockdown of IL-7 expression with the various siRNA sequences in CMT93 cells post 24 hr transfection. The siRNA sequences tested are listed below:

| Well | siRNA sense 5'→3' | SEQ ID NO: | siRNA antisense 5'→3' | SEQ ID NO: |
|---|---|---|---|---|
| A1 | GAUCCUACGGAAGUUAUGGtt | 493 | CCAUAACUUCCGUAGGAUCcg | 494 |
| B1 | CCAUGUUCCAUGUUUCUUUtt | 495 | AAAGAAACAUGGAACAUGGtc | 496 |
| A2 | CCUCCCGCAGACCAUGUUCtt | 497 | GAACAUGGUCUGCGGGAGGcg | 498 |
| A3 | CUCCCGCAGACCAUGUUCCtt | 499 | GGAACAUGGUCUGCGGGAGgc | 500 |
| A4 | UCCCGCAGACCAUGUUCCAtt | 501 | UGGAACAUGGUCUGCGGGAgg | 502 |
| A5 | cCCGCAGACCAUGUUCCAUtt | 503 | AUGGAACAUGGUCUGCGGGag | 504 |
| A6 | CCGCAGACCAUGUUCCAUGtt | 505 | CAUGGAACAUGGUCUGCGGga | 506 |
| A7 | CGCAGACCAUGUUCCAUGUtt | 507 | ACAUGGAACAUGGUCUGCGgg | 508 |
| A10 | AGACCAUGUUCCAUGUUUCtt | 509 | GAAACAUGGAACAUGGUCUgc | 510 |
| A12 | ACCAUGUUCCAUGUUUCUUtt | 511 | AAGAAACAUGGAACAUGGUct | 512 |

Example 15

Inhibition of Expression of Chitinase3-like-1 (CH13L1) Expression in CMT93 Cells In a 1.7 ml microcentrifuge tube, 2.4 µl of 20 µM double-stranded RNA solution (from Qiagen) was diluted into 394 µL Opti-MEM serum-free medium (Invitrogen) containing 1 µl Lipofectamine RNAiMAX (Invitrogen), mixed, and incubated 10 min at room temperature to enable the formation of transfection complexes. 100 µl of this mixture was added to each of three wells of a 24-well tissue culture dish, on top of which CMT-93 cells were plated in a 500 µl volume, resulting in a final volume of 600 µl per well and a final RNA concentration of 20 nM. After 24 h transfection, 0.1 µg/ml lipopolysaccharide (LPS) (Sigma) was added to each well and cells were incubated for a further 24 h to stimulate CHI3L1 production, after which cells were washed in PBS and harvested for RNA extraction. CMT-93 cells were prepared for transfection as follows. 1 confluent T-175 flask of CMT93 cells was trypsinized in 10 mls until the cells detached. Trypsin was inactivated by addition of 30 mls of DMEM (10% FBS) and the cells thoroughly mixed by pipetting. From this solution, 10 mls was transferred into a sterile 50 ml tube and 40 mLs of DMEM 10% FBS added. Cells were well mixed and 500 µLs added to each well of a 24-well plate. This concentration of cells resulted in approximately 70% confluency after 24 h of growth.

Figure 26:
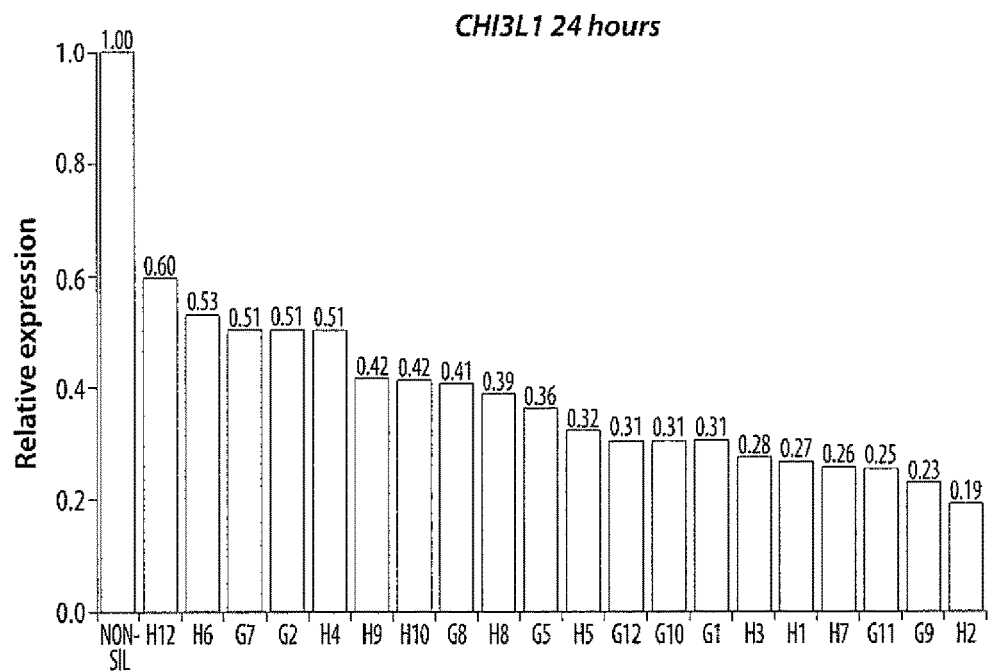
FIG. 26 is a bar graph showing the knockdown of CH13L1 expression with the various siRNA sequences in CMT93 cells post 24 hr transfection.

FIG. 26 shows the knockdown of CH13L1 expression with the various siRNA sequences in CMT93 cells post 24 hr transfection. The siRNA sequences tested are listed below:

| Well | siRNA sense 5'→3' | SEQ ID NO: | siRNA antisense 5'→3' | SEQ ID NO: |
|---|---|---|---|---|
| G1 | CCACAUCAUCUACAGCUUUtt | 513 | AAAGCUGUAGAUGAUGUGGgt | 514 |
| H1 | GGUUUGACAGAUACAGCAAtt | 515 | UUGCUGUAUCUGUCAAACCta | 516 |
| G2 | UCAUCUACAGCUUUGCCAAtt | 517 | UUGGCAAAGCUGUAGAUGAtg | 518 |
| H2 | ccCUGUUAAGGAAUGCAAAtt | 519 | UUUGCAUUCCUUAACAGGGtt | 520 |
| H3 | CAAGUAGGCAAAUAUCUUAtt | 521 | UAAGAUAUUUGCCUACUUGat | 522 |
| H4 | CAGCUUUGUCAGCAGGAAAtt | 523 | UUUCCUGCUGACAAAGCUGcg | 524 |
| G5 | GGUUCACCAAGGAGGCAGGtt | 525 | CCUGCCUCCUUGGUGAACCgg | 526 |
| H5 | GGAUCAAGUAGGCAAAUAUtt | 527 | AUAUUUGCCUACUUGAUCCaa | 528 |
| H6 | GAGGGACCAUACUAAUUAUtt | 529 | AUAAUUAGUAUGGUCCCUCaa | 530 |
| G7 | GGCCGGUUCACCAAGGAGGtt | 531 | CCUCCUUGGUGAACCGGCCtg | 532 |
| H7 | GGACAAGGAGAGUGUCAAAtt | 533 | UUUGACACUCUCCUUGUCCtc | 534 |
| G8 | CCGGUUCACCAAGGAGGCAtt | 535 | UGCCUCCUUGGUGAACCGGcc | 536 |
| H8 | CGUACAAGCUGGUCUGCUAtt | 537 | UAGCAGACCAGCUUGUACGca | 538 |
| G9 | GGAGUUUAAUCUCUUGCAAtt | 539 | UUGCAAGAGAUUAAACUCCtg | 540 |
| H9 | CAAGGAACUGAAUGCGAAtt | 541 | UUCCGCAUUCAGUUCCUUGat | 542 |
| G10 | CCCUGAUCAAGGAACUGAAtt | 543 | UUCAGUUCCUUGAUCAGGGtg | 544 |
| H10 | CUUGGAUCAAGUAGGCAAAtt | 545 | UUUGCCUACUUGAUCCAAGtg | 546 |
| G11 | GGAUUGAGGGACCAUACUAtt | 547 | UAGUAUGGUCCCUCAAUCCtg | 548 |
| G12 | GCAAAUUCUCAGACUCUAAtt | 549 | UUUAGAGUCUGAGAAUUUGCat | 550 |
| H12 | ccuuccCUUAGGAACUUAAtt | 551 | UUAAGUUCCUAAGGGAAGGat | 552 |

Example 16

Construction of CEQ200

CEQ200 has the following genotype: glnV44(AS), LAM⁻, rfbC1, endA1, spoT1, thi-1, hsdR17, ($r_k^-m_k^+$), creC510 ΔdapA. The MM294 has the following genotype: glnV44(AS), LAM⁻, rfbC1, endA1, spoT1, thi-1, hsdR17, ($r_k^-m_k^+$),creC510. We purchased the plasmids from CGSC (see Datsenko et al., (2000) Proc. Natl. Acad. Sci. USA 97,6640-6645).

Derivation of CEQ200

MM294 (from CGSC)
↓ Transformation with plasmid pKD46
MM294 (pKD46)
↓ Transformation with a ΔdapA::kan cassette generated using PCR using pKD4
MM294 ΔdapA::kan (pKD46)
↓ Plasmid pKD46 cured by growing cells at 43° C.
MM294 ΔdapA::kan
↓ Transformed with plasmid pCP20
MM294 ΔdapA::kan (pCP20)
↓ Plasmid pCP20 cured and kan gene was deleted by induction of FLP recombinase treatment at 43° C.
CEQ200

Example 17

Construction of CEQ201

CEQ201 has the following genotype: CEQ200 [glnV44(AS), LAM⁻, rfbC1, endA1, spoT1, thi-1, hsdR17, ($r_k^-m_k^+$), creC510 ΔdapA ΔrecA. The MM294 has the following genotype: glnV44(AS), LAM⁻, rfbC1, endA1, spoT1, thi-1, hsdR17, ($r_k^-m_k^+$),creC510. We purchased the plasmids from CGSC (see Datsenko et al., (2000) Proc. Natl. Acad. Sci. USA 97,6640-6645).

73
Derivation of CEQ200

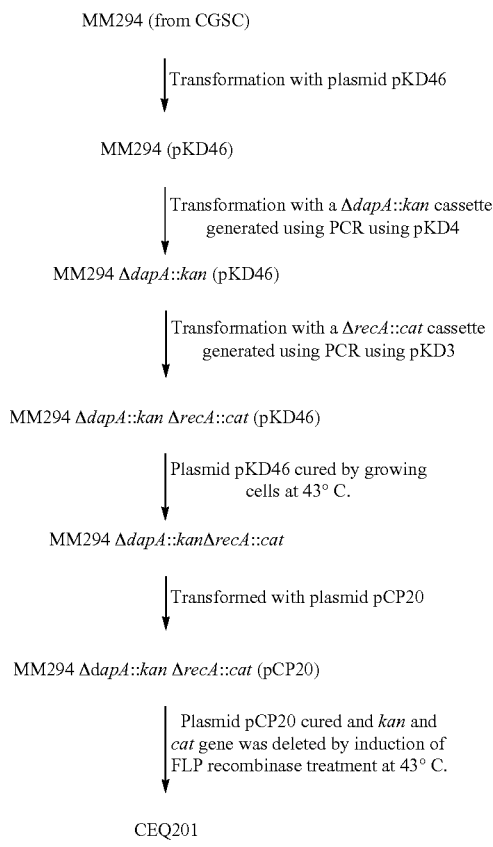

Example 18

Construction of BTPs (CEQ210) by deletion of minC and/or minD Genes from MM294

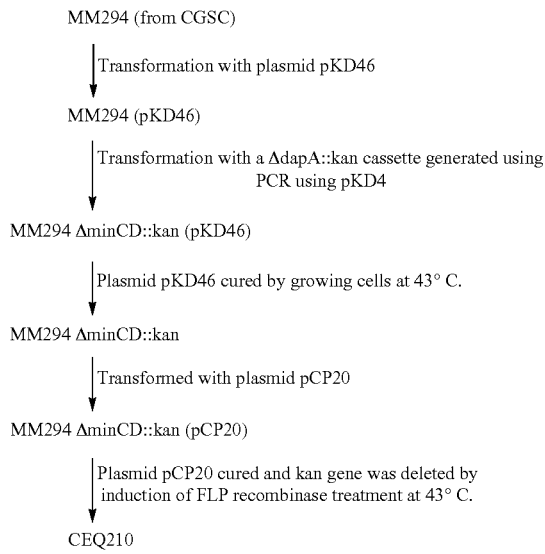

74
Example 19

Illustration of the pMBV40, pMBV43 and pMBV44 Plasmids

The pMBV40, pMBV43 and pMBV44 plasmids may be used as final or intermediary plasmid in the tkRNA system and may be constructed as follows: pUC19 digested with restriction enzyme PvuII. Resultant ~2.4 kb fragment was ligated with a ~200 bp DNA fragment generated by annealing 5 oligonucleotides with each other. The oligonucleotides have the following names and sequences:

OHTOP1:
(SEQ ID NO: 553)
GACTTCATATACCCAAGCTTGGAAAATTTTTTTTAAAAAAGTCTTGACAC

TTTATGCTTCCGGCTCGTATAATGGATCCAGGAGTAACAATACAAATGGA

OHTOP2:
(SEQ ID NO: 554)
TTCAAGAGATCCATTTGTATTGTTACTCCTTTTTTTTTTGTCGACGATC

CTTAGCGAAAGCTAAGGATTTTTTTTTACTCGAGCGGATTACTACATAC

OHBOT1:
(SEQ ID NO: 555)
GTATGTAGTAATCCGCTCGAGTAAAAAAAAAATCCTTAGCTTTCGCTAAG

GATCGTCGACAAAAAAAAAA

OHBOT2:
(SEQ ID NO: 556)
AGGAGTAACAATACAAATGGATCTCTTGAATCCATTTGTATTGTTACTCC

TGGATCCATT

OHBOT3:
(SEQ ID NO: 557)
ATACGAGCCGGAAGCATAAAGTGTCAAGACTTTTTTAAAAAAAATTTTCC

AAGCTTGGGTATATGAAGTC

↓

Ligation mix was transformed in *E. coli* and Ampicillin resistant transformants were selected. Plasmid DNA from a transformant that had the expected DNA sequence of the insert and restriction map was named pMBV38.

↓ pMBV38 was digested with NdeI and blunt end ligated with a ~ 6 kb fragment generated by BamHI-SalI digestion of the plasmid pKSII-inv-hly The predicted sequence of pKSII-inv-hly is as follows:

(SEQ ID NO: 558)
```
CTAAATTGTAAGCGTTAATATTTTGTTAAAATTCGCGTTAAATTTTTGTTAAATCAGCTCATTTTTTAACCAA
TAGGCCGAAATCGGCAAAATCCCTTATAAATCAAAAGAATAGACCGAGATAGGGTTGAGTGTTGTTCCAGTTT
GGAACAAGAGTCCACTATTAAAGAACGTGGACTCCAACGTCAAAGGGCGAAAAACCGTCTATCAGGGCGATGG
CCCACTACGTGAACCATCACCCTAATCAAGTTTTTTGGGGTCGAGGTGCCGTAAAGCACTAAATCGGAACCCT
AAAGGGAGCCCCCGATTTAGAGCTTGACGGGGAAAGCCGGCGAACGTGGCGAGAAAGGAAGGGAAGAAAGCGA
AAGGAGCGGGCGCTAGGGCGCTGGCAAGTGTAGCGGTCACGCTGCGCGTAACCACCACACCCGCCGCGCTTAA
TGCGCCGCTACAGGGCGCGTCCCATTCGCCATTCAGGCTGCGCAACTGTTGGGAAGGGCGATCGGTGCGGGCC
TCTTCGCTATTACGCCAGCTGGCGAAAGGGGGATGTGCTGCAAGGCGATTAAGTTGGGTAACGCCAGGGTTTT
CCCAGTCACGACGTTGTAAAACGACGGCCAGTGAGCGCGCGTAATACGACTCACTATAGGGCGAATTGGAGCT
CCACCGCGGTGGCGGCCGCTCTAGAACTAGTGGATCCCCCGGGCTGCAGCTGGGCCGTAAGATCGGCATTTAA
TCGCGACAATCCTTTTAAAAAAACAGCGCCGCTCAATTAACCTGAGCGGCGTTGTTCTTCTGGACGTTTGCTA
CTTATGGGGCGAGTCTAGGATTGCCGGACTCCCATTCGCGCCCCAAATAATCAGCTCATTAAACTGTTCTTAT
TGCTATCTGTTATCTGGTTATATTGACAGCGCACAGAGCGGGAACGCCAAGTATGCAGGCCCTGGTTGCAGTG
CGCCTGTGTCCATATTCATGGTTTCAAAATCCGTGCTGGTCTTTTTGACCCAATATTCACCAGATTGCCAATC
AGAACTATACGCGGTCAAGCTCCCCCACTCGCCCCACAATGTCCCGTCAGGCGCACGCGTTCCGTTGGTTGCA
CGTGAGGATTCAAGAACCGCAGACATATCTGAACCTTGGCATTGTCTGCTGGCCTCGAGACTGGATACCAGCG
ATCTGCCGCCATCGTATATCCACCGATTTGGGTAGAACCGATAACTCACCGAATAACTTGGGAATTTTTTACT
TTTCGCCGTCACAGCCACTTCGCTATAGGTTTGGTAGGTAATCGTCACCTGACCCTGATCGTTAACCGATACA
TTGGGTGTGAATGACGACGACCACTCATACTGAGTATTATTAGCAACATCGTTATCCATCTGTAACTGGAATG
TGGCGTTTTTAAAGATCGTTTTCGGGAACCCTTTATCCGTAGCGAAATTTTGCCCGTTAACCAGAATACCGGT
CAGCGTAGGTACCGGGAATAGGGATATTTTTTCTGCAATGTACTCAGTATCAGGGTATCAACCTGCGGCGTG
ATTGTGACATCACCGACACTATTCCCAACCACCGTCGCGGTATAGCTATCTGGCTGCTCGGTAATGGGGCTAA
TACTCACCGGCACACCGTTTTGAGTAAAACTCAAGCCCTGCATCCCACTGATAAAATGGCCATTCTTATCGAC
AGGGACAAAGGATAATGTGGAACTCATCGTGCCATCAGCCAAGATATCCGGTGTGGAGACGGTGAAACTGGAG
CGGCCAGCATCTGGAATAGGATCTGCCGTGAAATTAACCGTCACACTCGGCACACTGAACGCAGCCCCATCCA
CTTTCACCGTTACTGTTGCTACCCCCAACGTGGTACTGGTCAATGGTGCGCTATAAGTGCCGTCATTGTGATC
CGTGATAACGCCCATATTGCCTAAGGTTGTGTCAAAAGCCACATTCGCGCCAGCCTGCGGGTCCCCATAGGTA
TCCTTCAACTCCAACGTGATGGTTGAAGCCATTAGACCATCAGCGATGATAGATGTCGGTACCGCAGCCAGAG
TGGATTTATCCGCCGCGATAGTACCCTTAACAAAGTGGGTATCAACACTTTGCCGTTGCCCCTCCACTTCTGC
TGTGACTACCGTCACGCCATCTGTCGTATTGGTTAATGCAATGCGCGCGACGCCATTTGCATCTGTCTTTTCC
GTGATTTTATTCGGTAGCGCACCATTATTGGTGGTTATCACCACCTCCTGCCCGGCTAAGGGTTTCCCCTCAA
AATCAGCAACGGTGAACTCAACGGTGATTGCAGTTTTCCCATTAGCCGGTGCGCCATCACCAATGACGGCCGC
CGTTAATGTCAACTGAGGCTGCTGAACGGTGACGCTCAATGTGAATGAGTTAGATCGGTTTCCTTGGTGATCA
ACCGCGAGCGCACTAAGCGAATAAAAGTTGGCTGTCAGGTCGTCCGTTACCCGACTCACTTGTGCTGTGCGTT
TATAAGGCGGTAAAACCAAGTTGAATTGTGTGGTACTCAGTGGTGTTAATGTGCCGCCAGCGGCAATCAGTTC
GGCATCACTCCAGACAATTTCCCTTACAGCAGATGCCCCTTGTACTTGTGCGTTCACCTGATAAACCTGACCC
GGCAGGCCGGAGATAGTTGCTGGCGATAATGTCAGTTTAACCACCTGCTGTTTCTGATACTCCAACACGATAT
TATTGTTACGATCGACAAGGTTATAGCGGCTCTCCGCCAGTAGACGTGTTCCTGCCACCGCTGAAGGGCTAAG
TTGCGACTGAAAACTCTCGCCCAGGCGATAGTTCATTTGGAGGTTCCACTGTGTTTCATGCTTACTGCTTTTC
```

-continued

```
CCCATACGCTGATCTACCCCGACAGTGAGTAGAGGCACGGGGGTGTAATTGATCCCGGCAGTCACGGCATAAG
GGTTGCGTTGCAGATTATCTTTACCAAATAAAGCAACACGCTCACCGGTGTATTGCTCATACATCAACTTCCC
CCCCAGTTGTGGGAGTGCAGGTAAATAAGCATTCGCGCGCAAATCCCCCCCAGTGGCTGGGCGCTCTTTATAG
TCGGAGAAATCACGCGACGAGTGCCATCCATTGAGGCGAAAATACCCATTGGCAGCCAACTGTAAATAATCGG
TCCAGGCCTCGGCACCAAGACCGATACGGTGGTTGTGGCCGGTCAAATCATTATCATAAAAAGTATTAAGTCC
GTACAGCCAACCGTTCTCCAATGTACGTATCCCGACGCCAAGGTTAAGTGTGTTGCGGCTGTCTTTATTGCGA
ATACCTAACTGACTAAAAAAGAGGAATGAAGCAGAGTCATACCAAGGAGCCAGCCAATCAAGAGAGCTTTCTT
TTAGCGAAAAATTTTTGTCAAAATTCAGATTAACTTGAGCCGTACCGAATCGATTTAACCACTGTTTGATTTC
TTGATTAACCGCATCGCCCACCATTGAGTGAGCAACATCAGATGCCCTGCCTGATGCAGCTAACCTGGCCCCG
GTGCTTATCATCTTATTCACCGCTTCAGTCTCCTGCTCCTTATTGGCGCGATCTATTATTGCAGCATTTCTTT
CTGTATCCGATGCGGAAAAGGGATTGATTGAACTCTCCATTTCATTATTAGGATGGAGATTTTCAAATGCAGA
TGAAGAGACAGAATAAGGCTGGACCTGTTGCGGTGCGTTAGCATCATATTTTTCTGAAGCCCCAGCCATGAAC
ATTCCACATATCAAAAGATACAAATAACTATTCGTGAAATAATATTAAATGAATTATTTTATTAAAATACA
TAGACATTCCCGCATTCCTTATCAAGAGAAACTCACTGATTGGCTGGAAAACCATCATAATTTAAATGAAATA
AAGCATACCTGTCATACGTCAAACTGCATGTGCGTTGGCTGTGCTCAACAACTTGAGTTATTTGAGGTATAAC
TGGCCACAAACGAGCATTTGAAATCACCTTGACCATTAATTAAAGATGCAATAGTTGAAAGTGAAACTTGTTT
TCTAATTTAGTAAAGACATTAAGAGGATAGCACTTTTTTAAAAAACCAGACTGGGCAGATTAAAAATATTCAA
AATATATAATAAAACAGTCTATACCATACAGCGATAGAATTGATTTATTGTAACTAAGCAGGTGAGAATATCA
AAAAAAACAAAAATACAAATGAACTATTATCATATAAATAATATCAATTAGAATAAGCCCCCTTCATTTGAT
GTTGTCAGTTGTCTGCTGCGGTTTTTATTTCTACTTTCAGTCTGAAGTGTTACTCCGCAATATCCGCATTAAT
CCTGATGGTTGCCTTGATGACTGCAGGAATTCGATCCCTCCTTTGATTAGTATATTCCTATCTTAAAGTGACT
TTTATGTTGAGGCATTAACATTTGTTAACGACGATAAAGGGACAGCAGGACTAGAATAAAGCTATAAAGCAAG
CATATAATATTGCGTTTCATCTTTAGAAGCGAATTTCGCCAATATTATAATTATCAAAAGAGAGGGGTGGCAA
ACGGTATTTGGCATTATTAGGTTAAAAAATGTAGAAGGAGAGTGAAACCCATGAAAAAAATAATGCTAGTTTT
TATTACACTTATATTAGTTAGTCTACCAATTGCGCAACAAACTGAAGCAAAGGATGCATCTGCATTCAATAAA
GAAAATTCAATTTCATCCATGGCACCACCAGCATCTCCGCCTGCAAGTCCTAAGACGCCAATCGAAAAGAAAC
ACGCGGATGAAATCGATAAGTATATACAAGGATTGGATTACAATAAAAACAATGTATTAGTATACCACGGAGA
TGCAGTGACAAATGTGCCGCCAAGAAAAGGTTACAAAGATGGAAATGAATATATTGTTGTGGAGAAAAAGAAG
AAATCCATCAATCAAAATAATGCAGACATTCAAGTTGTGAATGCAATTTCGAGCCTAACCTATCCAGGTGCTC
TCGTAAAAGCGAATTCGGAATTAGTAGAAAATCAACCAGATGTTCTCCCTGTAAAACGTGATTCATTAACACT
CAGCATTGATTTGCCAGGTATGACTAATCAAGACAATAAAATCGTTGTAAAAAATGCCACTAAATCAAACGTT
AACAACGCAGTAAATACATTAGTGGAAAGATGGAATGAAAAATATGCTCAAGCTTATCCAAATGTAAGTGCAA
AAATTGATTATGATGACGAAATGGCTTACAGTGAATCACAATTAATTGCGAAATTTGGTACAGCATTTAAAGC
TGTAAATAATAGCTTGAATGTAAACTTCGGCGCAATCAGTGAAGGGAAAATGCAAGAAGAAGTCATTAGTTTT
AAACAAATTTACTATAACGTGAATGTTAATGAACCTACAAGACCTTCCAGATTTTTCGGCAAAGCTGTTACTA
AAGAGCAGTTGCAAGCGCTTGGAGTGAATGCAGAAAATCCTCCTGCATATATCTCAAGTGTGGCGTATGGCCG
TCAAGTTTATTTGAAATTATCAACTAATTCCCATAGTACTAAAGTAAAAGCTGCTTTTGATGCTGCCGTAAGC
GGAAAATCTGTCTCAGGTGATGTAGAACTAACAAATATCATCAAAAATTCTTCCTTCAAAGCCGTAATTTACG
GAGGTTCCGCAAAAGATGAAGTTCAAATCATCGACGGCAACCTCGGAGACTTACGCGATATTTTGAAAAAGG
CGCTACTTTTAATCGAGAAACACCAGGAGTTCCCATTGCTTATACAACAAACTTCCTAAAAGACAATGAATTA
GCTGTTATTAAAAACAACTCAGAATATATTGAAACAACTTCAAAAGCTTATACAGATGGAAAAATTAACATCG
```

```
ATCACTCTGGAGGATACGTTGCTCAATTCAACATTTCTTGGGATGAAGTAAATTATGATCCTGAAGGTAACGA

AATTGTTCAACATAAAAACTGGAGCGAAAACAATAAAAGCAAGCTAGCTCATTTCACATCGTCCATCTATTTG

CCAGGTAACGCGAGAAATATTAATGTTTACGCTAAAGAATGCACTGGTTTAGCTTGGGAATGGTGGAGAACGG

TAATTGATGACCGGAACTTACCACTTGTGAAAAATAGAAATATCTCCATCTGGGCACCACGCTTTATCCGAA

ATATAGTAATAAAGTAGATAATCCAATCGAATAATTGTAAAAGTAATAAAAAATTAAGAATAAAACCGCTTAA

CACACACGAAAAAATAAGCTTGTTTTGCACTCTTCGTAAATTATTTTGTGAAGAATGTAGAAACAGGCTTATT

TTTTAATTTTTTTAGAAGAATTAACAAATGTAAAAGAATATCTGACTGTTTATCCATATAATATAAGCATATC

CCAAAGTTTAAGCCACCTATAGTTTCTACTGCAAAACGTATAATTTAGTTCCCACATATACTAAAAAACGTGT

CCTTAACTCTCTCTGTCAGATTAGTTGTAGGTGGCTTAAACTTAGTTTTACGAATTAAAAAGGAGCGGTGAAA

TGAAAAGTAAACTTATTTGTATCATCATGGTAATAGCTTTTCAGGCTCATTTCACTATGACGGTAAAAGCAGA

TTCTGTCGGGGAAGAAAAACTTCAAAATAATACACAAGCCAAAAAGACCCCTGCTGATTTAAAAGCTTATCAA

GCTTATCGATACCGTCGACCTCGAGGGGGGGCCCGGTACCCAGCTTTTGTTCCCTTTAGTGAGGGTTAATTGC

GCGCTTGGCGTAATCATGGTCATAGCTGTTTCCTGTGTGAAATTGTTATCCGCTCACAATTCCACACAACATA

CGAGCCGGAAGCATAAAGTGTAAAGCCTGGGGTGCCTAATGAGTGAGCTAACTCACATTAATTGCGTTGCGCT

CACTGCCCGCTTTCCAGTCGGGAAACCTGTCGTGCCAGCTGCATTAATGAATCGGCCAACGCGCGGGGAGAGG

CGGTTTGCGTATTGGGCGCTCTTCCGCTTCCTCGCTCACTGACTCGCTGCGCTCGGTCGTTCGGCTGCGGCGA

GCGGTATCAGCTCACTCAAAGGCGGTAATACGGTTATCCACAGAATCAGGGGATAACGCAGGAAAGAACATGT

GAGCAAAAGGCCAGCAAAAGGCCAGGAACCGTAAAAAGGCCGCGTTGCTGGCGTTTTTCCATAGGCTCCGCCC

CCCTGACGAGCATCACAAAAATCGACGCTCAAGTCAGAGGTGGCGAAACCCGACAGGACTATAAAGATACCAG

GCGTTTCCCCCTGGAAGCTCCCTCGTGCGCTCTCCTGTTCCGACCCTGCCGCTTACCGGATACCTGTCCGCCT

TTCTCCCTTCGGGAAGCGTGGCGCTTTCTCATAGCTCACGCTGTAGGTATCTCAGTTCGGTGTAGGTCGTTCG

CTCCAAGCTGGGCTGTGTGCACGAACCCCCCGTTCAGCCCGACCGCTGCGCCTTATCCGGTAACTATCGTCTT

GAGTCCAACCCGGTAAGACACGACTTATCGCCACTGGCAGCAGCCACTGGTAACAGGATTAGCAGAGCGAGGT

ATGTAGGCGGTGCTACAGAGTTCTTGAAGTGGTGGCCTAACTACGGCTACACTAGAAGGACAGTATTTGGTAT

CTGCGCTCTGCTGAAGCCAGTTACCTTCGGAAAAAGAGTTGGTAGCTCTTGATCCGGCAAACAAACCACCGCT

GGTAGCGGTGGTTTTTTTGTTTGCAAGCAGCAGATTACGCGCAGAAAAAAAGGATCTCAAGAAGATCCTTTGA

TCTTTTCTACGGGGTCTGACGCTCAGTGGAACGAAAACTCACGTTAAGGGATTTTGGTCATGAGATTATCAAA

AAGGATCTTCACCTAGATCCTTTTAAATTAAAAATGAAGTTTTAAATCAATCTAAAGTATATATGAGTAAACT

TGGTCTGACAGTTACCAATGCTTAATCAGTGAGGCACCTATCTCAGCGATCTGTCTATTTCGTTCATCCATAG

TTGCCTGACTCCCCGTCGTGTAGATAACTACGATACGGGAGGGCTTACCATCTGGCCCCAGTGCTGCAATGAT

ACCGCGAGACCCACGCTCACCGGCTCCAGATTTATCAGCAATAAACCAGCCAGCCGGAAGGGCCGAGCGCAGA

AGTGGTCCTGCAACTTTATCCGCCTCCATCCAGTCTATTAATTGTTGCCGGGAAGCTAGAGTAAGTAGTTCGC

CAGTTAATAGTTTGCGCAACGTTGTTGCCATTGCTACAGGCATCGTGGTGTCACGCTCGTCGTTTGGTATGGC

TTCATTCAGCTCCGGTTCCCAACGATCAAGGCGAGTTACATGATCCCCCATGTTGTGCAAAAAAGCGGTTAGC

TCCTTCGGTCCTCCGATCGTTGTCAGAAGTAAGTTGGCCGCAGTGTTATCACTCATGGTTATGGCAGCACTGC

ATAATTCTCTTACTGTCATGCCATCCGTAAGATGCTTTTCTGTGACTGGTGAGTACTCAACCAAGTCATTCTG

AGAATAGTGTATGCGGCGACCGAGTTGCTCTTGCCCGGCGTCAATACGGGATAATACCGCGCCACATAGCAGA

ACTTTAAAAGTGCTCATCATTGGAAAACGTTCTTCGGGGCGAAAACTCTCAAGGATCTTACCGCTGTTGAGAT

CCAGTTCGATGTAACCCACTCGTGCACCCAACTGATCTTCAGCATCTTTTACTTTCACCAGCGTTTCTGGGTG

AGCAAAAACAGGAAGGCAAAATGCCGCAAAAAAGGGAATAAGGGCGACACGGAAATGTTGAATACTCATACTC
```

-continued

TTCCTTTTTCAATATTATTGAAGCATTTATCAGGGTTATTGTCTCATGAGCGGATACATATTTGAATGTATTT

AGAAAAATAAACAAATAGGGGTTCCGCGCACATTTCCCCGAAAAGTGCCAC

Ligation mix was transformed in *E. coli* and Ampicillin resistant transformants were selected. Plasmid DNA from a transformant that had insertion of inv and hly genes was named pMBV40.

↓ pMBV40 was digested with BspHI and the resultant 7.4 kb DNA fragment was ligated with a PCR fragment containing kan gene generated using plasmid pKD4 (purchased from CGSC (see Datsenko et al., (2000) Proc. Natl. Acad. Sci. USA 97, 6640-6645) as the template.

↓

Figure 27:
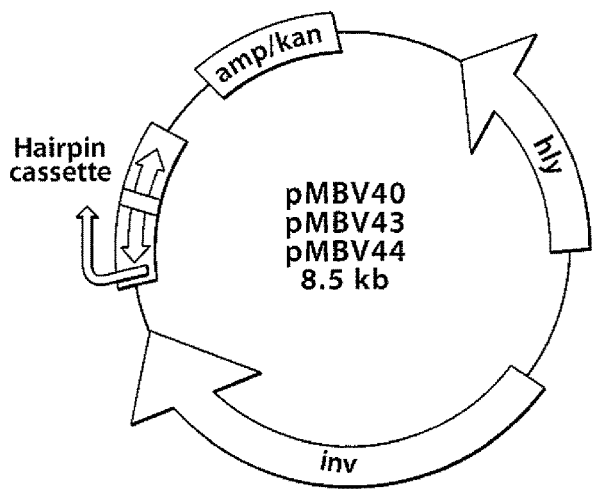
FIG. 27 is a schematic of the pMBV40 or pMBV43 or pMBV44 plasmids.

Ligation mix was transformed in *E. coli* and Kanamycin resistant transformants were selected. They were screened restriction mapping. They two different orientation of kan gene. The plasmids having clockwise and anticlockwise orientation of open reading frame of kan gene were called pMBV43 and pMBV44, respectively As shown in FIG. 27, the pMBV40 (amp selected having H3 hairpin) or pMBV43 and pMBV44 (kan selected having H3 hairpin) plasmids, are followed by the respective sequences.

pMBV40

(SEQ ID NO: 559)

TCGCGCGTTTCGGTGATGACGGTGAAAACCTCTGACACATGCAGCTCCCGGAGACGGTCACAGCTTGTCTGTAAG

CGGATGCCGGGAGCAGACAAGCCCGTCAGGGCGCGTCAGCGGGTGTTGGCGGGTGTCGGGGCTGGCTTAACTATG

CGGCATCAGAGCAGATTGTACTGAGAGTGCACCATATCGACGGTATCGATAAGCTTGATAAGCTTTTAAATCAGC

AGGGGTCTTTTGGCTTGTGTATTATTTTGAAGTTTTTCTTCCCCGACAGAATCTGCTTTTACCGTCATAGTGAA

ATGAGCCTGAAAAGCTATTACCATGATGATACAAATAAGTTTACTTTTCATTTCACCGCTCCTTTTTAATTCGTA

AAACTAAGTTTAAGCCACCTACAACTAATCTGACAGAGAGAGTTAAGGACACGTTTTTAGTATATGTGGGAACT

AAATTATACGTTTTGCAGTAGAAACTATAGGTGGCTTAAACTTTGGGATATGCTTATATTATATGGATAAACAGT

CAGATATTCTTTTACATTTGTTAATTCTTCTAAAAAAATTAAAAAATAAGCCTGTTTCTACATTCTTCACAAAAT

AATTTACGAAGAGTGCAAAACAAGCTTATTTTTCGTGTGTGTTAAGCGGTTTTATTCTTAATTTTTTATTACTT

TTACAATTATTCGATTGGATTATCTACTTTATTACTATATTTCGGATAAAGCGTGGTGCCCCAGATGGAGATATT

TCTATTTTTCACAAGTGGTAAGTTCCGGTCATCAATTACCGTTCTCCACCATTCCCAAGCTAAACCAGTGCATTC

TTTAGCGTAAACATTAATATTTCTCGCGTTACCTGGCAAATAGATGGACGATGTGAAATGAGCTAGCTTGCTTTT

ATTGTTTTCGCTCCAGTTTTTATGTTGAACAATTTCGTTACCTTCAGGATCATAATTTACTTCATCCCAAGAAAT

GTTGAATTGAGCAACGTATCCTCCAGAGTGATCGATGTTAATTTTTCCATCTGTATAAGCTTTTGAAGTTGTTTC

AATATATTCTGAGTTGTTTTTAATAACAGCTAATTCATTGTCTTTTAGGAAGTTTGTTGTATAAGCAATGGGAAC

TCCTGGTGTTTCTCGATTAAAAGTAGCGCCTTTTTTCAAAATATCGCGTAAGTCTCCGAGGTTGCCGTCGATGAT

TTGAACTTCATCTTTTGCGGAACCTCCGTAAATTACGGCTTTGAAGGAAGAATTTTTGATGATATTTGTTAGTTC

TACATCACCTGAGACAGATTTTCCGCTTACGGCAGCATCAAAAGCAGCTTTTACTTTAGTACTATGGGAATTAGT

TGATAATTTCAAATAAACTTGACGGCCATACGCCACACTTGAGATATATGCAGGAGGATTTTCTGCATTCACTCC

AAGCGCTTGCAACTGCTCTTTAGTAACAGCTTTGCCGAAAAATCTGGAAGGTCTTGTAGGTTCATTAACATTCAC

GTTATAGTAAATTTGTTTAAAACTAATGACTTCTTCTTGCATTTTCCCTTCACTGATTGCGCCGAAGTTTACATT

CAAGCTATTATTTACAGCTTTAAATGCTGTACCAAATTTCGCAATTAATTGTGATTCACTGTAAGCCATTTCGTC

ATCATAATCAATTTTTGCACTTACATTTGGATAAGCTTGAGCATATTTTCATTCCATCTTTCCACTAATGTATT

TACTGCGTTGTTAACGTTTGATTTAGTGGCATTTTTTACAACGATTTTATTGTCTTGATTAGTCATACCTGGCAA

ATCAATGCTGAGTGTTAATGAATCACGTTTTACAGGGAGAACATCTGGTTGATTTTCTACTAATTCCGAATTCGC

TTTTACGAGAGCACCTGGATAGGTTAGGCTCGAAATTGCATTCACAACTTGAATGTCTGCATTATTTTGATTGAT

-continued

```
GGATTTCTTCTTTTTCTCCACAACAATATATTCATTTCCATCTTTGTAACCTTTTCTTGGCGGCACATTTGTCAC

TGCATCTCCGTGGTATACTAATACATTGTTTTTATTGTAATCCAATCCTTGTATATACTTATCGATTTCATCCGC

GTGTTTCTTTTCGATTGGCGTCTTAGGACTTGCAGGCGGAGATGCTGGTGGTGCCATGGATGAAATTGAATTTTC

TTTATTGAATGCAGATGCATCCTTTGCTTCAGTTTGTTGCGCAATTGGTAGACTAACTAATATAAGTGTAATAAA

AACTAGCATTATTTTTTTCATGGGTTTCACTCTCCTTCTACATTTTTTAACCTAATAATGCCAAATACCGTTTGC

CACCCCTCTCTTTTGATAATTATAATATTGGCGAAATTCGCTTCTAAAGATGAAACGCAATATTATATGCTTGCT

TTATAGCTTTATTCTAGTCCTGCTGTCCCTTTATCGTCGTTAACAAATGTTAATGCCTCAACATAAAAGTCACTT

TAAGATAGGAATATACTAATCAAAGGAGGGATCGAATTCCTGCAGTCATCAAGGCAACCATCAGGATTAATGCGG

ATATTGCGGAGTAACACTTCAGACTGAAAGTAGAAATAAAAACCGCAGCAGACAACTGACAACATCAAATGAAGG

GGGCTTATTCTAATTGATATTATTTATATGATAATAGTTCATTTTGTATTTTTGTTTTTTTTGATATTCTCACCT

GCTTAGTTACAATAAATCAATTCTATCGCTGTATGGTATAGACTGTTTTATTATATATTTTGAATATTTTTAATC

TGCCCAGTCTGGTTTTTTAAAAAAGTGCTATCCTCTTAATGTCTTTACTAAATTAGAAAACAAGTTTCACTTTCA

ACTATTGCATCTTTAATTAATGGTCAAGGTGATTTCAAATGCTCGTTTGTGGCCAGTTATACCTCAAATAACTCA

AGTTGTTGAGCACAGCCAACGCACATGCAGTTTGACGTATGACAGGTATGCTTTATTTCATTTAAATTATGATGG

TTTTCCAGCCAATCAGTGAGTTTCTCTTGATAAGGAATGCGGGAATGTCTATGTATTTAATAAAATAATTTCAT

TTAATATTATTTCACGAATAGTTATTTGTATCTTTTTGATATGTGGAATGTTCATGGCTGGGGCTTCAGAAAAAT

ATGATGCTAACGCACCGCAACAGGTCCAGCCTTATTCTGTCTCTTCATCTGCATTTGAAAATCTCCATCCTAATA

ATGAAATGGAGAGTTCAATCAATCCCTTTTCCGCATCGGATACAGAAAGAAATGCTGCAATAATAGATCGCGCCA

ATAAGGAGCAGGAGACTGAAGCGGTGAATAAGATGATAAGCACCGGGGCCAGGTTAGCTGCATCAGGCAGGGCAT

CTGATGTTGCTCACTCAATGGTGGGCGATGCGGTTAATCAAGAAATCAAACAGTGGTTAAATCGATTCGGTACGG

CTCAAGTTAATCTGAATTTTGACAAAAATTTTTCGCTAAAAGAAAGCTCTCTTGATTGGCTGGCTCCTTGGTATG

ACTCTGCTTCATTCCTCTTTTTTAGTCAGTTAGGTATTCGCAATAAAGACAGCCGCAACACACTTAACCTTGGCG

TCGGGATACGTACATTGGAGAACGGTTGGCTGTACGGACTTAATACTTTTTATGATAATGATTTGACCGGCCACA

ACCACCGTATCGGTCTTGGTGCCGAGGCCTGGACCGATTATTTACAGTTGGCTGCCAATGGGTATTTTCGCCTCA

ATGGATGGCACTCGTCGCGTGATTTCTCCGACTATAAAGAGGGCCCAGCCACTGGGGGGATTTGCGCGCGAATG

CTTATTTACCTGCACTCCCACAACTGGGGGGGAAGTTGATGTATGAGCAATACACCGGTGAGCGTGTTGCTTTAT

TTGGTAAAGATAATCTGCAACGCAACCCTTATGCCGTGACTGCCGGGATCAATTACACCCCCGTGCCTCTACTCA

CTGTCGGGGTAGATCAGCGTATGGGGAAAAGCAGTAAGCATGAAACACAGTGGAACCTCCAAATGAACTATCGCC

TGGGCGAGAGTTTTCAGTCGCAACTTAGCCCTTCAGCGGTGGCAGGAACACGTCTACTGGCGGAGAGCCGCTATA

ACCTTGTCGATCGTAACAATAATATCGTGTTGGAGTATCAGAAACAGCAGGTGGTTAAACTGACATTATCGCCAG

CAACTATCTCCGGCCTGCCGGGTCAGGTTTATCAGGTGAACGCACAAGTACAAGGGGCATCTGCTGTAAGGGAAA

TTCTCTGGAGTGATGCCGAACTGATTGCCGCTGGCGGCACATTAACACCACTGAGTACCACACAATTCAACTTGG

TTTTACCGCCTTATAAACGCACAGCACAAGTGAGTCGGGTAACGGACGACCTGACAGCCAACTTTTATTCGCTTA

GTGCGCTCGCGGTTGATCACCAAGGAAACCGATCTAACTCATTCACATTGAGCGTCACCGTTCAGCAGCCTCAGT

TGACATTAACGGCGGCCGTCATTGGTGATGGCGCACCGGCTAATGGGAAAACTGCAATCACCGTTGAGTTCACCG

TTGCTGATTTTGAGGGGAAACCCTTAGCCGGGCAGGAGGTGGTGATAACCACCAATAATGGTGCGCTACCGAATA

AAATCACGGAAAAGACAGATGCAAATGGCGTCGCGCGCATTGCATTAACCAATACGACAGATGGCGTGACGGTAG

TCACAGCAGAAGTGGAGGGGCAACGGCAAAGTGTTGATACCCACTTTGTTAAGGGTACTATCGCGGCGGATAAAT

CCACTCTGGCTGCGGTACCGACATCTATCATCGCTGATGGTCTAATGGCTTCAACCATCACGTTGGAGTTGAAGG

ATACCTATGGGACCCGCAGGCTGGCGCGAATGTGGCTTTTGACACAACCTTAGGCAATATGGGCGTTATCACGG
```

-continued
```
ATCACAATGACGGCACTTATAGCGCACCATTGACCAGTACCACGTTGGGGGTAGCAACAGTAACGGTGAAAGTGG
ATGGGGCTGCGTTCAGTGTGCCGAGTGTGACGGTTAATTTCACGGCAGATCCTATTCCAGATGCTGGCCGCTCCA
GTTTCACCGTCTCCACACCGGATATCTTGGCTGATGGCACGATGAGTTCCACATTATCCTTTGTCCCTGTCGATA
AGAATGGCCATTTTATCAGTGGGATGCAGGGCTTGAGTTTTACTCAAAACGGTGTGCCGGTGAGTATTAGCCCCA
TTACCGAGCAGCCAGATAGCTATACCGCGACGGTGGTTGGGAATAGTGTCGGTGATGTCACAATCACGCCGCAGG
TTGATACCCTGATACTGAGTACATTGCAGAAAAAAATATCCCTATTCCCGGTACCTACGCTGACCGGTATTCTGG
TTAACGGGCAAAATTTCGCTACGGATAAAGGGTTCCCGAAAACGATCTTTAAAAACGCCACATTCCAGTTACAGA
TGGATAACGATGTTGCTAATAATACTCAGTATGAGTGGTCGTCGTCATTCACACCCAATGTATCGGTTAACGATC
AGGGTCAGGTGACGATTACCTACCAAACCTATAGCGAAGTGGCTGTGACGGCGAAAAGTAAAAAATTCCCAAGTT
ATTCGGTGAGTTATCGGTTCTACCCAAATCGGTGGATATACGATGGCGGCAGATCGCTGGTATCCAGTCTCGAGG
CCAGCAGACAATGCCAAGGTTCAGATATGTCTGCGGTTCTTGAATCCTCACGTGCAACCAACGGAACGCGTGCGC
CTGACGGGACATTGTGGGGCGAGTGGGGGAGCTTGACCGCGTATAGTTCTGATTGGCAATCTGGTGAATATTGGG
TCAAAAAGACCAGCACGGATTTTGAAACCATGAATATGGACACAGGCGCACTGCAACCAGGGCCTGCATACTTGG
CGTTCCCGCTCTGTGCGCTGTCAATATAACCAGATAACAGATAGCAATAAGAACAGTTTAATGAGCTGATTATTT
GGGGCGCGAATGGGAGTCCGGCAATCCTAGACTCGCCCCATAAGTAGCAAACGTCCAGAAGAACAACGCCGCTCA
GGTTAATTGAGCGGCGCTGTTTTTTTAAAAGGATTGTCGCGATTAAATGCCGATCTTACGGCCCAGCTGCAGCCC
GGGGGATCTATGCGGTGTGAAATACCGCACAGATGCGTAAGGAGAAAATACCGGATCAGGCGCCATTCGGCATTC
AGGCTGCGCAACTGTTGGGAAGGGCGATCGGTGCGGGCCTCTTCGCTATTACGCCAGGACTTCATATACCCAAGC
TTGGAAAATTTTTTTAAAAAAGTCTTGACACTTTATGCTTCCGGCTCGTATAATGGATCCAGGAGTAACAATAC
AAATGGATTCAAGAGATCCATTTGTATTGTTACTCCTTTTTTTTTTGTCGACGATCCTTAGCGAAAGCTAAGGA
TTTTTTTTTACTCGAGCGGATTACTACATACCTGCATTAATGAATCGGCCAACGCGCGGGGAGAGGCGGTTTGC
GTATTGGGCGCTCTTCCGCTTCCTCGCTCACTGACTCGCTGCGCTCGGTCGTTCGGCTGCGGCGAGCGGTATCAG
CTCACTCAAAGGCGGTAATACGGTTATCCACAGAATCAGGGGATAACGCAGGAAAGAACATGTGAGCAAAAGGCC
AGCAAAAGGCCAGGAACCGTAAAAAGGCCGCGTTGCTGGCGTTTTTCCATAGGCTCCGCCCCCCTGACGAGCATC
ACAAAAATCGACGCTCAAGTCAGAGGTGGCGAAACCCGACAGGACTATAAAGATACCAGGCGTTTCCCCCTGGAA
GCTCCCTCGTGGGCTCTCCTGTTCCGACCCTGCCGCTTACCGGATACCTGTCCGCCTTTCTCCCTTCGGGAAGCG
TGGCGCTTTCTCATAGCTCACGCTGTAGGTATCTCAGTTCGGTGTAGGTCGTTCGCTCCAAGCTGGGCTGTGTGC
ACGAACCCCCCGTTCAGCCCGACCGCTGCGCCTTATCCGGTAACTATCGTCTTGAGTCCAACCCGGTAAGACACG
ACTTATCGCCACTGGCAGCAGCCACTGGTAACAGGATTAGCAGAGCGAGGTATGTAGGCGGTGCTACAGAGTTCT
TGAAGTGGTGGCCTAACTACGGCTACACTAGAAGGACAGTATTTGGTATCTGCGCTCTGCTGAAGCCAGTTACCT
TCGGAAAAAGAGTTGGTAGCTCTTGATCCGGCAAACAAACCACCGCTGGTAGCGGTGGTTTTTTTGTTTGCAAGC
AGCAGATTACGCGCAGAAAAAAAGGATCTCAAGAAGATCCTTTGATCTTTTCTACGGGGTCTGACGCTCAGTGGA
ACGAAAACTCACGTTAAGGGATTTTGGTCATGAGATTATCAAAAAGGATCTTCACCTAGATCCTTTTAAATTAAA
AATGAAGTTTTAAATCAATCTAAAGTATATATGAGTAAACTTGGTCTGACAGTTACCAATGCTTAATCAGTGAGG
CACCTATCTCAGCGATCTGTCTATTTCGTTCATCCATAGTTGCCTGACTCCCCGTCGTGTAGATAACTACGATAC
GGGAGGGCTTACCATCTGGCCCCAGTGCTGCAATGATACCGCGAGACCCACGCTCACCGGCTCCAGATTTATCAG
CAATAAACCAGCCAGCCGGAAGGGCCGAGCGCAGAAGTGGTCCTGCAACTTTATCCGCCTCCATCCAGTCTATTA
ATTGTTGCCGGGAAGCTAGAGTAAGTAGTTCGCCAGTTAATAGTTTGCGCAACGTTGTTGCCATTGCTACAGGCA
TCGTGGTGTCACGCTCGTCGTTTGGTATGGCTTCATTCAGCTCCGGTTCCCAACGATCAAGGCGAGTTACATGAT
CCCCCATGTTGTGCAAAAAAGCGGTTAGCTCCTTCGGTCCTCCGATCGTTGTCAGAAGTAAGTTGGCCGCAGTGT
TATCACTCATGGTTATGGCAGCACTGCATAATTCTCTTACTGTCATGCCATCCGTAAGATGCTTTTCTGTGACTG
```

-continued

```
GTGAGTACTCAACCAAGTCATTCTGAGAATAGTGTATGCGGCGACCGAGTTGCTCTTGCCCGGCGTCAATACGGG

ATAATACCGCGCCACATAGCAGAACTTTAAAAGTGCTCATCATTGGAAAACGTTCTTCGGGGCGAAAACTCTCAA

GGATCTTACCGCTGTTGAGATCCAGTTCGATGTAACCCACTCGTGCACCCAACTGATCTTCAGCATCTTTTACTT

TCACCAGCGTTTCTGGGTGAGCAAAAACAGGAAGGCAAAATGCCGCAAAAAAGGGAATAAGGGCGACACGGAAAT

GTTGAATACTCATACTCTTCCTTTTTCAATATTATTGAAGCATTTATCAGGGTTATTGTCTCATGAGCGGATACA

TATTTGAATGTATTTAGAAAAATAAACAAATAGGGGTTCCGCGCACATTTCCCCGAAAAGTGCCACCTGACGTCT

AAGAAACCATTATTATCATGACATTAACCTATAAAAATAGGCGTATCACGAGGCCCTTTCGTC
``` pMBV43

(SEQ ID NO: 560)
```
TCGCGCGTTTCGGTGATGACGGTGAAAACCTCTGACACATGCAGCTCCCGGAGACGGTCACAGCTTGTCTGTAAG

CGGATGCCGGGAGCAGACAAGCCCGTCAGGGCGCGTCAGCGGGTGTTGGCGGGTGTCGGGGCTGGCTTAACTATG

CGGCATCAGAGCAGATTGTACTGAGAGTGCACCATATCGACGGTATCGATAAGCTTGATAAGCTTTTAAATCAGC

AGGGGTCTTTTTGGCTTGTGTATTATTTTGAAGTTTTTCTTCCCCGACAGAATCTGCTTTTACCGTCATAGTGAA

ATGAGCCTGAAAAGCTATTACCATGATGATACAAATAAGTTTACTTTTCATTTCACCGCTCCTTTTTAATTCGTA

AAACTAAGTTTAAGCCACCTACAACTAATCTGACAGAGAGAGTTAAGGACACGTTTTTTAGTATATGTGGGAACT

AAATTATACGTTTTGCAGTAGAAACTATAGGTGGCTTAAACTTTGGGATATGCTTATATTATATGGATAAACAGT

CAGATATTCTTTTACATTTGTTAATTCTTCTAAAAAAATTAAAAAAATAAGCCTGTTTCTACATTCTTCACAAAAT

AATTTACGAAGAGTGCAAAACAAGCTTATTTTTTCGTGTGTGTTAAGCGGTTTTATTCTTAATTTTTTATTACTT

TTACAATTATTCGATTGGATTATCTACTTTATTACTATATTTCGGATAAAGCGTGGTGCCCCAGATGGAGATATT

TCTATTTTTCACAAGTGGTAAGTTCCGGTCATCAATTACCGTTCTCCACCATTCCCAAGCTAAACCAGTGCATTC

TTTAGCGTAAACATTAATATTTCTCGCGTTACCTGGCAAATAGATGGACGATGTGAAATGAGCTAGCTTGCTTTT

ATTGTTTTCGCTCCAGTTTTTATGTTGAACAATTTCGTTACCTTCAGGATCATAATTTACTTCATCCCAAGAAAT

GTTGAATTGAGCAACGTATCCTCCAGAGTGATCGATGTTAATTTTTCCATCTGTATAAGCTTTTGAAGTTGTTTC

AATATATTCTGAGTTGTTTTTAATAACAGCTAATTCATTGTCTTTTAGGAAGTTTGTTGTATAAGCAATGGGAAC

TCCTGGTGTTTCTCGATTAAAAGTAGCGCCTTTTTTCAAAATATCGCGTAAGTCTCCGAGGTTGCCGTCGATGAT

TTGAACTTCATCTTTTGCGGAACCTCCGTAAATTACGGCTTTGAAGGAAGAATTTTTGATGATATTTGTTAGTTC

TACATCACCTGAGACAGATTTTCCGCTTACGGCAGCATCAAAAGCAGCTTTTACTTTAGTACTATGGGAATTAGT

TGATAATTTCAAATAAACTTGACGGCCATACGCCACACTTGAGATATATGCAGGAGGATTTTCTGCATTCACTCC

AAGCGCTTGCAACTGCTCTTTAGTAACAGCTTTGCCGAAAAATCTGGAAGGTCTTGTAGGTTCATTAACATTCAC

GTTATAGTAAATTTGTTTAAAACTAATGACTTCTTCTTGCATTTTCCCTTCACTGATTGCGCCGAAGTTTACATT

CAAGCTATTATTTACAGCTTTAAATGCTGTACCAAATTTCGCAATTAATTGTGATTCACTGTAAGCCATTTCGTC

ATCATAATCAATTTTTGCACTTACATTTGGATAAGCTTGAGCATATTTTTCATTCCATCTTTCCACTAATGTATT

TACTGCGTTGTTAACGTTTGATTTAGTGGCATTTTTTACAACGATTTTATTGTCTTGATTAGTCATACCTGGCAA

ATCAATGCTGAGTGTTAATGAATCACGTTTTACAGGGAGAACATCTGGTTGATTTTCTACTAATTCCGAATTCGC

TTTTACGAGAGCACCTGGATAGGTTAGGCTCGAAATTGCATTCACAACTTGAATGTCTGCATTATTTTGATTGAT

GGATTTCTTCTTTTTCTCCACAACAATATATTCATTTCCATCTTTGTAACCTTTTCTTGGCGGCACATTTGTCAC

TGCATCTCCGTGGTATACTAATACATTGTTTTTATTGTAATCCAATCCTTGTATATACTTATCGATTTCATCCGC

GTGTTTCTTTTCGATTGGCGTCTTAGGACTTGCAGGCGGAGATGCTGGTGGTGCCATGGATGAAATTGAATTTTC

TTTATTGAATGCAGATGCATCCTTTGCTTCAGTTTGTTGCGCAATTGGTAGACTAACTAATATAAGTGTAATAAA

AACTAGCATTATTTTTTTCATGGGTTTCACTCTCCTTCTACATTTTTTAACCTAATAATGCCAAATACCGTTTGC

CACCCCTCTCTTTTGATAATTATAATATTGGCGAAATTCGCTTCTAAAGATGAAACGCAATATTATATGCTTGCT
```

-continued
TTATAGCTTTATTCTAGTCCTGCTGTCCCTTTATCGTCGTTAACAAATGTTAATGCCTCAACATAAAAGTCACTT

TAAGATAGGAATATACTAATCAAAGGAGGGATCGAATTCCTGCAGTCATCAAGGCAACCATCAGGATTAATGCGG

ATATTGCGGAGTAACACTTCAGACTGAAAGTAGAAATAAAAACCGCAGCAGACAACTGACAACATCAAATGAAGG

GGGCTTATTCTAATTGATATTATTTATATGATAATAGTTCATTTTGTATTTTTGTTTTTTTTGATATTCTCACCT

GCTTAGTTACAATAAATCAATTCTATCGCTGTATGGTATAGACTGTTTTATTATATATTTTGAATATTTTTAATC

TGCCCAGTCTGGTTTTTTAAAAAAGTGCTATCCTCTTAATGTCTTTACTAAATTAGAAAACAAGTTTCACTTTCA

ACTATTGCATCTTTAATTAATGGTCAAGGTGATTTCAAATGCTCGTTTGTGGCCAGTTATACCTCAAATAACTCA

AGTTGTTGAGCACAGCCAACGCACATGCAGTTTGACGTATGACAGGTATGCTTTATTTCATTTAAATTATGATGG

TTTTCCAGCCAATCAGTGAGTTTCTCTTGATAAGGAATGCGGGAATGTCTATGTATTTTAATAAAATAATTTCAT

TTAATATTATTTCACGAATAGTTATTTGTATCTTTTTGATATGTGGAATGTTCATGGCTGGGGCTTCAGAAAAAT

ATGATGCTAACGCACCGCAACAGGTCCAGCCTTATTCTGTCTCTTCATCTGCATTTGAAAATCTCCATCCTAATA

ATGAAATGGAGAGTTCAATCAATCCCTTTTCCGCATCGGATACAGAAAGAAATGCTGCAATAATAGATCGCGCCA

ATAAGGAGCAGGAGACTGAAGCGGTGAATAAGATGATAAGCACCGGGGCCAGGTTAGCTGCATCAGGCAGGGCAT

CTGATGTTGCTCACTCAATGGTGGGCGATGCGGTTAATCAAGAAATCAAACAGTGGTTAAATCGATTCGGTACGG

CTCAAGTTAATCTGAATTTTGACAAAAATTTTTCGCTAAAAGAAAGCTCTCTTGATTGGCTGGCTCCTTGGTATG

ACTCTGCTTCATTCCTCTTTTTTAGTCAGTTAGGTATTCGCAATAAAGACAGCCGCAACACACTTAACCTTGGCG

TCGGGATACGTACATTGGAGAACGGTTGGCTGTACGGACTTAATACTTTTTATGATAATGATTTGACCGGCCACA

ACCACCGTATCGGTCTTGGTGCCGAGGCCTGGACCGATTATTTACAGTTGGCTGCCAATGGGTATTTTCGCCTCA

ATGGATGGCACTCGTCGCGTGATTTCTCCGACTATAAAGAGCGCCCAGCCACTGGGGGGGATTTGCGCGCGAATG

CTTATTTACCTGCACTCCCACAACTGGGGGGGAAGTTGATGTATGAGCAATACACCGGTGAGCGTGTTGCTTTAT

TTGGTAAAGATAATCTGCAACGCAACCCTTATGCCGTGACTGCCGGGATCAATTACACCCCCGTGCCTCTACTCA

CTGTCGGGGTAGATCAGCGTATGGGGAAAAGCAGTAAGCATGAAACACAGTGGAACCTCCAAATGAACTATCGCC

TGGGCGAGAGTTTTCAGTCGCAACTTAGCCCTTCAGCGGTGGCAGGAACACGTCTACTGGCGGAGAGCCGCTATA

ACCTTGTCGATCGTAACAATAATATCGTGTTGGAGTATCAGAAACAGCAGGTGGTTAAACTGACATTATCGCCAG

CAACTATCTCCGGCCTGCCGGGTCAGGTTTATCAGGTGAACGCACAAGTACAAGGGGCATCTGCTGTAAGGGAAA

TTGTCTGGAGTGATGCCGAACTGATTGCCGCTGGCGGCACATTAACACCACTGAGTACCACACAATTCAACTTGG

TTTTACCGCCTTATAAACGCACAGCACAAGTGAGTCGGGTAACGGACGACCTGACAGCCAACTTTTATTCGCTTA

GTGCGCTCGCGGTTGATCACCAAGGAAACCGATCTAACTCATTCACATTGAGCGTCACCGTTCAGCAGCCTCAGT

TGACATTAACGGCGGCCGTCATTGGTGATGGCGCACCGGCTAATGGGAAAACTGCAATCACCGTTGAGTTCACCG

TTGCTGATTTTGAGGGGAAACCCTTAGCCGGGCAGGAGGTGGTGATAACCACCAATAATGGTGCGCTACCGAATA

AAATCACGGAAAAGACAGATGCAAATGGCGTCGCGCGCATTGCATTAACCAATACGACAGATGGCGTGACGGTAG

TCACAGCAGAAGTGGAGGGGCAACGGCAAAGTGTTGATACCCACTTTGTTAAGGGTACTATCGCGGCGGATAAAT

CCACTCTGGCTGCGGTACCGACATCTATCATCGCTGATGGTCTAATGGCTTCAACCATCACGTTGGAGTTGAAGG

ATACCTATGGGACCCGCAGGCTGGCGCGAATGTGGCTTTTGACACAACCTTAGGCAATATGGGCGTTATCACGG

ATCACAATGACGGCACTTATAGCGCACCATTGACCAGTACCACGTTGGGGGTAGCAACAGTAACGGTGAAAGTGG

ATGGGCTGCGTTCAGTGTGCCGAGTGTGACGGTTAATTTCACGGCAGATCCTATTCCAGATGCTGGCCGCTCCA

GTTTCACCGTCTCCACACCGGATATCTTGGCTGATGGCACGATGAGTTCCACATTATCCTTTGTCCCTGTCGATA

AGAATGGCCATTTTATCAGTGGGATGCAGGGCTTGAGTTTTACTCAAAACGGTGTGCCGGTGAGTATTAGCCCCA

TTACCGAGCAGCCAGATAGCTATACCGCGACGGTGGTTGGGAATAGTGTCGGTGATGTCACAATCACGCCGCAGG

TTGATACCCTGATACTGAGTACATTGCAGAAAAAAATATCCCTATTCCCGGTACCTACGCTGACCGGTATTCTGG

TTAACGGGCAAAATTTCGCTACGGATAAAGGGTTCCCGAAAACGATCTTTAAAAACGCCACATTCCAGTTACAGA

-continued

```
TGGATAACGATGTTGCTAATAATACTCAGTATGAGTGGTCGTCGTCATTCACACCCAATGTATCGGTTAACGATC

AGGGTCAGGTGACGATTACCTACCAAACCTATAGCGAAGTGGCTGTGACGGCGAAAAGTAAAAAATTCCCAAGTT

ATTCGGTGAGTTATCGGTTCTACCCAAATCGGTGGATATACGATGGCGGCAGATCGCTGGTATCCAGTCTCGAGG

CCAGCAGACAATGCCAAGGTTCAGATATGTCTGCGGTTCTTGAATCCTCACGTGCAACCAACGGAACGCGTGCGC

CTGACGGGACATTGTGGGGCGAGTGGGGGAGCTTGACCGCGTATAGTTCTGATTGGCAATCTGGTGAATATTGGG

TCAAAAAGACCAGCACGGATTTTGAAACCATGAATATGGACACAGGCGCACTGCAACCAGGGCCTGCATACTTGG

CGTTCCCGCTCTGTGCGCTGTCAATATAACCAGATAACAGATAGCAATAAGAACAGTTTAATGAGCTGATTATTT

GGGGCGCGAATGGGAGTCCGGCAATCCTAGACTCGCCCCATAAGTAGCAAACGTCCAGAAGAACAACGCCGCTCA

GGTTAATTGAGCGGCGCTGTTTTTTTAAAAGGATTGTCGCGATTAAATGCCGATCTTACGGCCCAGCTGCAGCCC

GGGGGATCTATGCGGTGTGAAATACCGCACAGATGCGTAAGGAGAAAATACCGCATCAGGCGCCATTCGCCATTC

AGGCTGCGCAACTGTTGGGAAGGGCGATCGGTGCGGGCCTCTTCGCTATTACGCCAGGACTTCATATACCCAAGC

TTGGAAAATTTTTTTAAAAAAGTCTTGACACTTTATGCTTCCGGCTCGTATAATGGATCCAGGAGTAACAATAC

AAATGGATTCAAGAGATCCATTTGTATTGTTACTCCTTTTTTTTTTGTCGACGATCCTTAGCGAAAGCTAAGGA

TTTTTTTTTACTCGAGCGGATTACTACATACCTGCATTAATGAATCGGCCAACGCGCGGGGAGAGGCGGTTTGC

GTATTGGGCGCTCTTCCGCTTCCTCGCTCACTGACTCGCTGCGCTCGGTCGTTCGGCTGCGGCGAGCGGTATCAG

CTCACTCAAAGGCGGTAATACGGTTATCCACAGAATCAGGGGATAACGCAGGAAAGAACATGTGAGCAAAAGGCC

AGCAAAAGGCCAGGAACCGTAAAAAGGCCGCGTTGCTGGCGTTTTTCCATAGGCTCCGCCCCCCTGACGAGCATC

ACAAAAATCGACGCTCAAGTCAGAGGTGGCGAAACCCGACAGGACTATAAAGATACCAGGCGTTTCCCCCTGGAA

GCTCCCTCGTGCGCTCTCCTGTTCCGACCCTGCCGCTTACCGGATACCTGTCCGCCTTTCTCCCTTCGGGAAGCG

TGGCGCTTTCTCATAGCTCACGCTGTAGGTATCTCAGTTCGGTGTAGGTCGTTCGCTCCAAGCTGGGCTGTGTGC

ACGAACCCCCCGTTCAGCCCGACCGCTGCGCCTTATCCGGTAACTATCGTCTTGAGTCCAACCCGGTAAGACACG

ACTTATCGCCACTGGCAGCAGCCACTGGTAACAGGATTAGCAGAGCGAGGTATGTAGGCGGTGCTACAGAGTTCT

TGAAGTGGTGGCCTAACTACGGCTACACTAGAAGGACAGTATTTGGTATCTGCGCTCTGCTGAAGCCAGTTACCT

TCGGAAAAAGAGTTGGTAGCTCTTGATCCGGCAAACAAACCACCGCTGGTAGCGGTGGTTTTTTTGTTTGCAAGC

AGCAGATTACGCGCAGAAAAAAAGGATCTCAAGAAGATCCTTTGATCTTTTCTACGGGGTCTGACGCTCAGTGGA

ACGAAAACTCACGTTAAGGGATTTTGGTCATGATCTGGTAAGGTTGGGAAGCCCTGCAAAGTAAACTGGATGGCT

TTCTTGCCGCCAAGGATCTGATGGCGCAGGGGATCAAGATCTGATCAAGAGACAGGATGAGGATCGTTTCGCATG

ATTGAACAAGATGGATTGCACGCAGGTTCTCCGGCCGCTTGGGTGGAGAGGCTATTCGGCTATGACTGGGCACAA

CAGACAATCGGCTGCTCTGATGCCGCCGTGTTCCGGCTGTCAGCGCAGGGGCGCCCGGTTCTTTTTGTCAAGACC

GACCTGTCCGGTGCCCTGAATGAACTGCAGGACGAGGCAGCGCGGCTATCGTGGCTGGCCACGACGGGCGTTCCT

TGCGCAGCTGTGCTCGACGTTGTCACTGAAGCGGGAAGGGACTGGCTGCTATTGGGCGAAGTGCCGGGGCAGGAT

CTCCTGTCATCTCACCTTGCTCCTGCCGAGAAAGTATCCATCATGGCTGATGCAATGCGGCGGCTGCATACGCTT

GATCCGGCTACCTGCCCATTCGACCACCAAGCGAAACATCGCATCGAGCGAGCACGTACTCGGATGGAAGCCGGT

CTTGTCGATCAGGATGATCTGGACGAAGAGCATCAGGGGCTCGCGCCAGCCGAACTGTTCGCCAGGCTCAAGGCG

CGCATGCCCGACGGCGAGGATCTCGTCGTGACCCATGGCGATGCCTGCTTGCCGAATATCATGGTGGAAAATGGC

CGCTTTTCTGGATTCATCGACTGTGGCCGGCTGGGTGTGGCGGACCGCTATCAGGACATAGCGTTGGCTACCCGT

GATATTGCTGAAGAGCTTGGCGGCGAATGGGCTGACCGCTTCCTCGTGCTTTACGGTATCGCCGCTCCCGATTCG

CAGCGCATCGCCTTCTATCGCCTTCTTGACGAGTTCTTCTGAGCGGGACTCTGGGGTTCGAAATGACCGACCAAG

CGACGCCCAACCTGCCATCACGAGATTTCGATTCCACCGCCGCCTTCTATGAAATCATGACATTAACCTATAAAA
```

ATAGGCGTATCACGAGGCCCTTTCGTC pMBV44

(SEQ ID NO: 561)

TCGCGCGTTTCGGTGATGACGGTGAAAACCTCTGACACATGCAGCTCCCGGAGACGGTCACAGCTTGTCTGTAAG

CGGATGCCGGGAGCAGACAAGCCCGTCAGGGCGCGTCAGCGGGTGTTGGCGGGTGTCGGGGCTGGCTTAACTATG

CGGCATCAGAGCAGATTGTACTGAGAGTGCACCATATCGACGGTATCGATAAGCTTGATAAGCTTTTAAATCAGC

AGGGGTCTTTTTGGCTTGTGTATTATTTTGAAGTTTTTCTTCCCCGACAGAATCTGCTTTTACCGTCATAGTGAA

ATGAGCCTGAAAAGCTATTACCATGATGATACAAATAAGTTTACTTTTCATTTCACCGCTCCTTTTTAATTCGTA

AAACTAAGTTTAAGCCACCTACAACTAATCTGACAGAGAGAGTTAAGGACACGTTTTTTAGTATATGTGGGAACT

AAATTATACGTTTTGCAGTAGAAACTATAGGTGGCTTAAACTTTGGGATATGCTTATATTATATGGATAAACAGT

CAGATATTCTTTTACATTTGTTAATTCTTCTAAAAAAATTAAAAAAATAAGCCTGTTTCTACATTCTTCACAAAAT

AATTTACGAAGAGTGCAAAACAAGCTTATTTTTTCGTGTGTGTTAAGCGGTTTTATTCTTAATTTTTTATTACTT

TTACAATTATTCGATTGGATTATCTACTTTATTACTATATTTCGGATAAAGCGTGGTGCCCCAGATGGAGATATT

TCTATTTTTCACAAGTGGTAAGTTCCGGTCATCAATTACCGTTCTCCACCATTCCCAAGCTAAACCAGTGCATTC

TTTAGCGTAAACATTAATATTTCTCGCGTTACCTGGCAAATAGATGGACGATGTGAAATGAGCTAGCTTGCTTTT

ATTGTTTTCGCTCCAGTTTTTATGTTGAACAATTTCGTTACCTTCAGGATCATAATTTACTTCATCCCAAGAAAT

GTTGAATTGAGCAACGTATCCTCCAGAGTGATCGATGTTAATTTTTCCATCTGTATAAGCTTTTGAAGTTGTTTC

AATATATTCTGAGTTGTTTTTAATAACAGCTAATTCATTGTCTTTTAGGAAGTTTGTTGTATAAGCAATGGGAAC

TCCTGGTGTTTCTCGATTAAAAGTAGCGCCTTTTTTCAAAATATCGCGTAAGTCTCCGAGGTTGCCGTCGATGAT

TTGAACTTCATCTTTTGCGGAACCTCCGTAAATTACGGCTTTGAAGGAAGAATTTTTGATGATATTTGTTAGTTC

TACATCACCTGAGACAGATTTTCCGCTTACGGCAGCATCAAAAGCAGCTTTTACTTTAGTACTATGGGAATTAGT

TGATAATTTCAAATAAACTTGACGGCCATACGCCACACTTGAGATATATGCAGGAGGATTTTCTGCATTCACTCC

AAGCGCTTGCAACTGCTCTTTAGTAACAGCTTTGCCGAAAAATCTGGAAGGTCTTGTAGGTTCATTAACATTCAC

GTTATAGTAAATTTGTTTAAAACTAATGACTTCTTCTTGCATTTTCCCTTCACTGATTGCGCCGAAGTTTACATT

CAAGCTATTATTTACAGCTTTAAATGCTGTACCAAATTTCGCAATTAATTGTGATTCACTGTAAGCCATTTCGTC

ATCATAATCAATTTTTGCACTTACATTTGGATAAGCTTGAGCATATTTTTCATTCCATCTTTCCACTAATGTATT

TACTGCGTTGTTAACGTTTGATTTAGTGGCATTTTTTACAACGATTTTATTGTCTTGATTAGTCATACCTGGCAA

ATCAATGCTGAGTGTTAATGAATCACGTTTTACAGGGAGAACATCTGGTTGATTTTCTACTAATTCCGAATTCGC

TTTTACGAGAGCACCTGGATAGGTTAGGCTCGAAATTGCATTCACAACTTGAATGTCTGCATTATTTTGATTGAT

GGATTTCTTCTTTTTCTCCACAACAATATATTCATTTCCATCTTTGTAACCTTTTCTTGGCGGCACATTTGTCAC

TGCATCTCCGTGGTATACTAATACATTGTTTTTATTGTAATCCAATCCTTGTATATACTTATCGATTTCATCCGC

GTGTTTCTTTTCGATTGGCGTCTTAGGACTTGCAGGCGGAGATGCTGGTGGTGCCATGGATGAAATTGAATTTTC

TTTATTGAATGCAGATGCATCCTTTGCTTCAGTTTGTTGCGCAATTGGTAGACTAACTAATATAAGTGTAATAAA

AACTAGCATTATTTTTTTCATGGGTTTCACTCTCCTTCTACATTTTTAACCTAATAATGCCAAATACCGTTTGC

CACCCCTCTCTTTTGATAATTATAATATTGGCGAAATTCGCTTCTAAAGATGAAACGCAATATTATATGCTTGCT

TTATAGCTTTATTCTAGTCCTGCTGTCCCTTTATCGTCGTTAACAAATGTTAATGCCTCAACATAAAAGTCACTT

TAAGATAGGAATATACTAATCAAAGGAGGGATCGAATTCCTGCAGTCATCAAGGCAACCATCAGGATTAATGCGG

ATATTGCGGAGTAACACTTCAGACTGAAAGTAGAAATAAAAACCGCAGCAGACAACTGACAACATCAAATGAAGG

GGGCTTATTCTAATTGATATTATTTATATGATAATAGTTCATTTTGTATTTTTGTTTTTTTGATATTCTCACCT

GCTTAGTTACAATAAATCAATTCTATCGCTGTATGGTATAGACTGTTTTATTATATATTTTGAATATTTTTAATC

TGCCCAGTCTGGTTTTTTAAAAAAGTGCTATCCTCTTAATGTCTTTACTAAATTAGAAAACAAGTTTCACTTTCA

-continued

```
ACTATTGCATCTTTAATTAATGGTCAAGGTGATTTCAAATGCTCGTTTGTGGCCAGTTATACCTCAAATAACTCA
AGTTGTTGAGCACAGCCAACGCACATGCAGTTTGACGTATGACAGGTATGCTTTATTTCATTTAAATTATGATGG
TTTTCCAGCCAATCAGTGAGTTTCTCTTGATAAGGAATGCGGGAATGTCTATGTATTTTAATAAAATAATTTCAT
TTAATATTATTTCACGAATAGTTATTTGTATCTTTTTGTATATGTGGAATGTTCATGGCTGGGGCTTCAGAAAAAT
ATGATGCTAACGCACCGCAACAGGTCCAGCCTTATTCTGTCTCTTCATCTGCATTTGAAAATCTCCATCCTAATA
ATGAAATGGAGAGTTCAATCAATCCCTTTTCCGCATCGGATACAGAAAGAAATGCTGCAATAATAGATCGCGCCA
ATAAGGAGCAGGAGACTGAAGCGGTGAATAAGATGATAAGCACCGGGGCCAGGTTAGCTGCATCAGGCAGGGCAT
CTGATGTTGCTCACTCAATGGTGGGCGATGCGGTTAATCAAGAAATCAAACAGTGGTTAAATCGATTCGGTACGG
CTCAAGTTAATCTGAATTTTGACAAAAATTTTTCGCTAAAAGAAAGCTCTCTTGATTGGCTGGCTCCTTGGTATG
ACTCTGCTTCATTCCTCTTTTTTAGTCAGTTAGGTATTCGCAATAAAGACAGCCGCAACACACTTAACCTTGGCG
TCGGGATACGTACATTGGAGAACGGTTGGCTGTACGGACTTAATACTTTTTATGATAATGATTTGACCGGCCACA
ACCACCGTATCGGTCTTGGTGCCGAGGCCTGGACCGATTATTTACAGTTGGCTGCCAATGGGTATTTTCGCCTCA
ATGGATGGCACTCGTCGCGTGATTTCTCCGACTATAAAGAGCGCCCAGCCACTGGGGGGATTTGCGCGCGAATG
CTTATTTACCTGCACTCCCACAACTGGGGGGGAAGTTGATGTATGAGCAATACACCGGTGAGCGTGTTGCTTTAT
TTGGTAAAGATAATCTGCAACGCAACCCTTATGCCGTGACTGCCGGGATCAATTACACCCCCGTGCCTCTACTCA
CTGTCGGGGTAGATCAGCGTATGGGGAAAAGCAGTAAGCATGAAACACAGTGGAACCTCCAAATGAACTATCGCC
TGGGCGAGAGTTTTCAGTCGCAACTTAGCCCTTCAGCGGTGGCAGGAACACGTCTACTGGCGGAGAGCCGCTATA
ACCTTGTCGATCGTAACAATAATATCGTGTTGGAGTATCAGAAACAGCAGGTGGTTAAACTGACATTATCGCCAG
CAACTATCTCCGGCCTGCCGGGTCAGGTTTATCAGGTGAACGCACAAGTACAAGGGGCATCTGCTGTAAGGGAAA
TTGTCTGGAGTGATGCCGAACTGATTGCCGCTGGCGGCACATTAACACCACTGAGTACCACACAATTCAACTTGG
TTTTACCGCCTTATAAACGCACAGCACAAGTGAGTCGGGTAACGGACGACCTGACAGCCAACTTTTATTCGCTTA
GTGCGCTCGCGGTTGATCACCAAGGAAACCGATCTAACTCATTCACATTGAGCGTCACCGTTCAGCAGCCTCAGT
TGACATTAACGGCGGCCGTCATTGGTGATGGCGCACCGGCTAATGGGAAAACTGCAATCACCGTTGAGTTCACCG
TTGCTGATTTTGAGGGGAAACCCTTAGCCGGGCAGGAGGTGGTGATAACCACCAATAATGGTGCGCTACCGAATA
AAATCACGGAAAAGACAGATGCAAATGGCGTCGCGCGCATTGCATTAACCAATACGACAGATGGCGTGACGGTAG
TCACAGCAGAAGTGGAGGGGCAACGGCAAAGTGTTGATACCCACTTTGTTAAGGGTACTATCGCGGCGGATAAAT
CCACTCTGGCTGCGGTACCGACATCTATCATCGCTGATGGTCTAATGGCTTCAACCATCACGTTGGAGTTGAAGG
ATACCTATGGGGACCCGCAGGCTGGCGCGAATGTGGCTTTTGACACAACCTTAGGCAATATGGGCGTTATCACGG
ATCACAATGACGGCACTTATAGCGCACCATTGACCAGTACCACGTTGGGGGTAGCAACAGTAACGGTGAAAGTGG
ATGGGGCTGCGTTCAGTGTGCCGAGTGTGACGGTTAATTTCACGGCAGATCCTATTCCAGATGCTGGCCGCTCCA
GTTTCACCGTCTCCACACCGGATATCTTGGCTGATGGCACGATGAGTTCCACATTATCCTTTGTCCCTGTCGATA
AGAATGGCCATTTTATCAGTGGGATGCAGGGCTTGAGTTTTACTCAAAACGGTGTGCCGGTGAGTATTAGCCCCA
TTACCGAGCAGCCAGATAGCTATACCGCGACGGTGGTTGGGAATAGTGTCGGTGATGTCACAATCACGCCGCAGG
TTGATACCCTGATACTGAGTACATTGCAGAAAAAAATATCCCTATTCCCGGTACCTACGCTGACCGGTATTCTGG
TTAACGGGCAAAATTTCGCTACGGATAAAGGGTTCCCGAAAACGATCTTTAAAAACGCCACATTCCAGTTACAGA
TGGATAACGATGTTGCTAATAATACTCAGTATGAGTGGTCGTCGTCATTCACACCCAATGTATCGGTTAACGATC
AGGGTCAGGTGACGATTACCTACCAAACCTATAGCGAAGTGGCTGTGACGGCGAAAGTAAAAAATTCCCAAGTT
ATTCGGTGAGTTATCGGTTCTACCCAAATCGGTGGATATACGATGGCGGCAGATCGCTGGTATCCAGTCTCGAGG
CCAGCAGACAATGCCAAGGTTCAGATATGTCTGCGGTTCTTGAATCCTCACGTGCAACCAACGGAACGCGTGCGC
CTGACGGGACATTGTGGGCGAGTGGGGGAGCTTGACCGCGTATAGTTCTGATTGGCAATCTGGTGAATATTGGG
TCAAAAAGACCAGCACGGATTTTGAAACCATGAATATGGACACAGGCGCACTGCAACCAGGGCCTGCATACTTGG
```

-continued

```
CGTTCCCGCTCTGTGCGCTGTCAATATAACCAGATAACAGATAGCAATAAGAACAGTTTAATGAGCTGATTATTT
GGGGCGCGAATGGGAGTCCGGCAATCCTAGACTCGCCCCATAAGTAGCAAACGTCCAGAAGAACAACGCCGCTCA
GGTTAATTGAGCGGCGCTGTTTTTTTAAAAGGATTGTCGCGATTAAATGCCGATCTTACGGCCCAGCTGCAGCCC
GGGGGATCTATGCGGTGTGAAATACCGCACAGATGCGTAAGGAGAAAATACCGCATCAGGCGCCATTCGCCATTC
AGGCTGCGCAACTGTTGGGAAGGGCGATCGGTGCGGGCCTCTTCGCTATTACGCCAGGACTTCATATACCCAAGC
TTGGAAAATTTTTTTTAAAAAAGTCTTGACACTTTATGCTTCCGGCTCGTATAATGGATCCAGGAGTAACAATAC
AAATGGATTCAAGAGATCCATTTGTATTGTTACTCCTTTTTTTTTTTGTCGACGATCCTTAGCGAAAGCTAAGGA
TTTTTTTTTTACTCGAGCGGATTACTACATACCTGCATTAATGAATCGGCCAACGCGCGGGGAGAGGCGGTTTGC
GTATTGGGCGCTCTTCCGCTTCCTCGCTCACTGACTCGCTGCGCTCGGTCGTTCGGCTGCGGCGAGCGGTATCAG
CTCACTCAAAGGCGGTAATACGGTTATCCACAGAATCAGGGGATAACGCAGGAAAGAACATGTGAGCAAAAGGCC
AGCAAAAGGCCAGGAACCGTAAAAAGGCCGCGTTGCTGGCGTTTTTCCATAGGCTCCGCCCCCCTGACGAGCATC
ACAAAAATCGACGCTCAAGTCAGAGGTGGCGAAACCCGACAGGACTATAAAGATACCAGGCGTTTCCCCCTGGAA
GCTCCCTCGTGCGCTCTCCTGTTCCGACCCTGCCGCTTACCGGATACCTGTCCGCCTTTCTCCCTTCGGGAAGCG
TGGCGCTTTCTCATAGCTCACGCTGTAGGTATCTCAGTTCGGTGTAGGTCGTTCGCTCCAAGCTGGGCTGTGTGC
ACGAACCCCCCGTTCAGCCCGACCGCTGCGCCTTATCCGGTAACTATCGTCTTGAGTCCAACCCGGTAAGACACG
ACTTATCGCCACTGGCAGCAGCCACTGGTAACAGGATTAGCAGAGCGAGGTATGTAGGCGGTGCTACAGAGTTCT
TGAAGTGGTGGCCTAACTACGGCTACACTAGAAGGACAGTATTTGGTATCTGCGCTCTGCTGAAGCCAGTTACCT
TCGGAAAAAGAGTTGGTAGCTCTTGATCCGGCAAACAAACCACCGCTGGTAGCGGTGGTTTTTTTGTTTGCAAGC
AGCAGATTACGCGCAGAAAAAAAGGATCTCAAGAAGATCCTTTGATCTTTTCTACGGGGTCTGACGCTCAGTGGA
ACGAAAACTCACGTTAAGGGATTTTGGTCATGATTTCATAGAAGGCGGCGGTGGAATCGAAATCTCGTGATGGCA
GGTTGGGCGTCGCTTGGTCGGTCATTTCGAACCCCAGAGTCCCGCTCAGAAGAACTCGTCAAGAAGGCGATAGAA
GGCGATGCGCTGCGAATCGGGAGCGGCGATACCGTAAAGCACGAGGAAGCGGTCAGCCCATTCGCCGCCAAGCTC
TTCAGCAATATCACGGGTAGCCAACGCTATGTCCTGATAGCGGTCCGCCACACCCAGCCGGCCACAGTCGATGAA
TCCAGAAAAGCGGCCATTTTCCACCATGATATTCGGCAAGCAGGCATCGCCATGGGTCACGACGAGATCCTCGCC
GTCGGGCATGCGCGCCTTGAGCCTGGCGAACAGTTCGGCTGGCGCGAGCCCCTGATGCTCTTCGTCCAGATCATC
CTGATCGACAAGACCGGCTTCCATCCGAGTACGTGCTCGCTCGATGCGATGTTTCGCTTGGTGGTCGAATGGGCA
GGTAGCCGGATCAAGCGTATGCAGCCGCCGCATTGCATCAGCCATGATGGATACTTTCTCGGCAGGAGCAAGGTG
AGATGACAGGAGATCCTGCCCCGGCACTTCGCCCAATAGCAGCCAGTCCCTTCCCGCTTCAGTGACAACGTCGAG
CACAGCTGCGCAAGGAACGCCCGTCGTGGCCAGCCACGATAGCCGCGCTGCCTCGTCCTGCAGTTCATTCAGGGC
ACCGGACAGGTCGGTCTTGACAAAAAGAACCGGGCGCCCCTGCGCTGACAGCCGGAACACGGCGGCATCAGAGCA
GCCGATTGTCTGTTGTGCCCAGTCATAGCCGAATAGCCTCTCCACCCAAGCGGCCGGAGAACCTGCGTGCAATCC
ATCTTGTTCAATCATGCGAAACGATCCTCATCCTGTCTCTTGATCAGATCTTGATCCCCTGCGCCATCAGATCCT
TGGCGGCAAGAAAGCCATCCAGTTTACTTTGCAGGGCTTCCCAACCTTACCAGATCATGACATTAACCTATAAAA
ATAGGCGTATCACGAGGCCCTTTCGTC
```

Example 23

Construction of pNJSZc Plasmid pNJSZ is a 10.4 kb plasmid that confers the abilities required to induce tkRNAi. It contains two genes, inv and hly, that allows bacteria to invade mammalian cells and to escape from the entry vacuole. Expression of the short hairpin RNA is different between the original Trip plasmid and pNJSZ. In pNJSZ, expression of shRNA is under the control of a constitutive bacterial promoter which allows for continuous expression. This is different from the original Trip plasmid, which has an ITPG inducible promoter, which controls the expression of the shRNA. Moreover, pNJSZ and the original Trip plasmid contain different antibiotic resistant genes. pNJSZ has the kanamycin resistance gene, whereas the original Trip plasmid has the ampicillin resistance gene. pNJSZc was constructed from pNJSZ by removing any regions of pNJSZ that were not required for its maintenance or abilities to induce tkRNAi.

Figure 28:
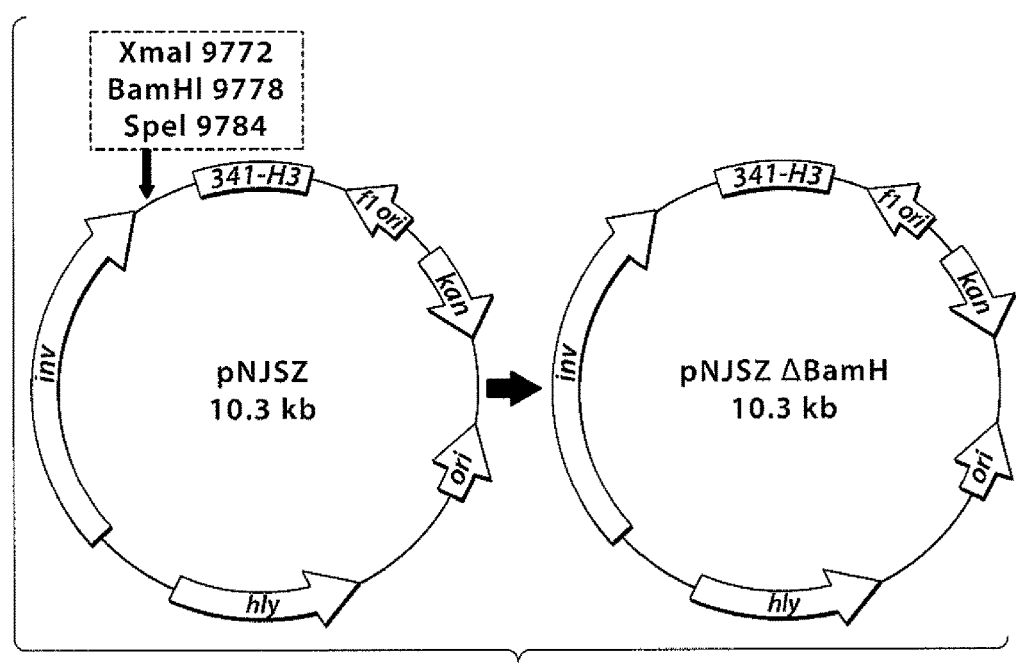
FIG. 28 is a schematic of the pNJSZ ΔBamH1 plasmid.

Step 1 as shown in FIG. 28: Removed an extra BamH1 site at 9778 by digesting pNJSZ with both SpeI (9784) and XmaI (9772), T4 DNA polymerase filled-in these two sites and then allowed the plasmid to self ligate, creating pNJSZ ΔBamH1.

Figure 29:
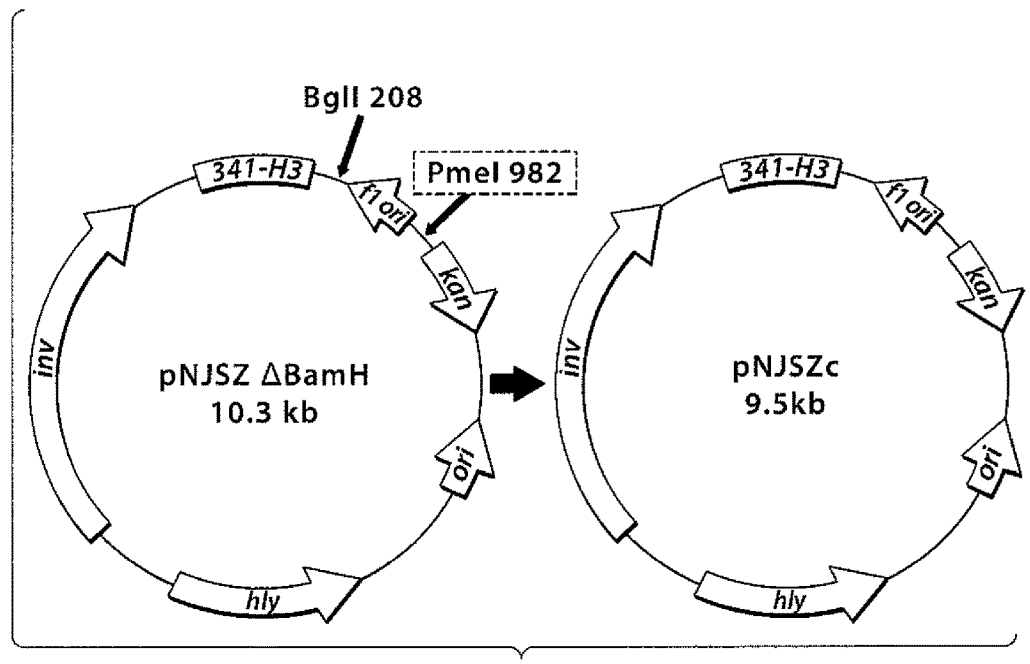
FIG. 29 is a schematic of the pNJSZ pNJSZc plasmid.

Step 2 as shown in FIG. 29: Removed both an extra SalI site at 972 and the f1 origin of replication by digesting pNJSZ ΔBamH1 with BglI (208) and PmeI (982), T4 DNA polymerase filled-in these two sites and allowed the plasmid to self ligate, creating pNJSZc.

The pNJSZc DNA sequence is as follows:

(SEQ ID NO: 562)

```
GGCCGCTCGAGCATGCATCTAGAGGGCCCAATTCGCCCTATAGTGAGTCGTATTACAATTCACTGGCCGTCGTTT
TACAACGTCGTGACTGGGAAAACCCTGGCGTTACCCAACTTAATCGCCTTGCAGCACATCCCCCTTTCGCCAGCT
GGCGTAATAGCGAAGAGGCCCGCACCGATCGCCCTTCCCAACAGTTGCGCAGCCTGAAAAACCGCGCCATGGTGT
GTAGGCTGGAGCTGCTTCGAAGTTCCTATACTTTCTAGAGAATAGGAACTTCGGAATAGGAACTTCAAGATCCCC
CACGCTGCCGCAAGCACTCAGGGCGCAAGGGCTGCTAAAGGAAACGGAACACGTAGAAAGCCAGTCCGCAGAAAC
GGTGCTGACCCCGGATGAATGTCAGCTACTGGGCTATCTGGACAAGGGAAAACGCAAGCGCAAAGAGAAAGCAGG
TAGCTTGCAGTGGGCTTACATGGCGATAGCTAGACTGGGCGGTTTTATGGACAGCAAGCGAACCGGAATTGCCAG
CTGGGGCGCCCTCTGGTAAGGTTGGGAAGCCCTGCAAAGTAAACTGGATGGCTTTCTTGCCGCCAAGGATCTGAT
GGCGCAGGGGATCAAGATCTGATCAAGAGACAGGATGAGGATCGTTTCGCATGATTGAACAAGATGGATTGCACG
CAGGTTCTCCGGCCGCTTGGGTGGAGAGGCTATTCGGCTATGACTGGGCACAACAGACAATCGGCTGCTCTGATG
CCGCCGTGTTCCGGCTGTCAGCGCAGGGGCGCCCGGTTCTTTTTGTCAAGACCGACCTGTCCGGTGCCCTGAATG
AACTGCAGGACGAGGCAGCGCGGCTATCGTGGCTGGCCACGACGGGCGTTCCTTGCGCAGCTGTGCTCGACGTTG
TCACTGAAGCGGGAAGGGACTGGCTGCTATTGGGCGAAGTGCCGGGGCAGGATCTCCTGTCATCTCACCTTGCTC
CTGCCGAGAAAGTATCCATCATGGCTGATGCAATGCGGCGGCTGCATACGCTTGATCCGGCTACCTGCCCATTCG
ACCACCAAGCGAAACATCGCATCGAGCGAGCACGTACTCGGATGGAAGCCGGTCTTGTCGATCAGGATGATCTGG
ACGAAGAGCATCAGGGGCTCGCGCCAGCCGAACTGTTCGCCAGGCTCAAGGCGCGCATGCCCGACGGCGAGGATC
TCGTCGTGACCCATGGCGATGCCTGCTTGCCGAATATCATGGTGGAAAATGGCCGCTTTTCTGGATTCATCGACT
GTGGCCGGCTGGGTGTGGCGGACCGCTATCAGGACATAGCGTTGGCTACCCGTGATATTGCTGAAGAGCTTGGCG
GCGAGTGGGCTGACCGCTTCCTCGTGCTTTACGGTATCGCCGCTCCCGATTCGCAGCGCATCGCCTTCTATCGCC
TTCTTGACGAGTTCTTCTGAGCGGGACTCTGGGGTTCGAAATGACCGACCAAGCGACGCCCAACCTGCCATCACG
AGATTTCGATTCCACCGCCGCCTTCTATGAAAGGTTGGGCTTCGGAATCGTTTTCCGGGACGCCGGCTGGATGAT
CCTCCAGCGCGGGGATCTCATGCTGGAGTTCTTCGCCCACCCCAGCTTCAAAAGCGCTCTGAAGTTCCTATACTT
TCTAGAGAATAGGAACTTCGGAATAGGAACTAAGGAGGATATTCATATGGACCATGGCGCGGCATGCAAGCTCGG
TATCATTGCAGCACTGGGGCCAGATGGTAAGCCCTCCCGTATCGTAGTTATCTACACGACGGGGAGTCAGGCAAC
TATGGATGAACGAAATAGACAGATCGCTGAGATAGGTGCCTCACTGATTAAGCATTGGTAACTGTCAGACCAAGT
TTACTCATATATACTTTAGATTGATTTAAAACTTCATTTTTAATTTAAAAGGATCTAGGTGAAGATCCTTTTTGA
TAATCTCATGACCAAAATCCCTTAACGTGAGTTTTCGTTCCACTGAGCGTCAGACCCCGTAGAAAAGATCAAAGG
ATCTTCTTGAGATCCTTTTTTTCTGCGCGTAATCTGCTGCTTGCAAACAAAAAAACCACCGCTACCAGCGGTGGT
TTGTTTGCCGGATCAAGAGCTACCAACTCTTTTTCCGAAGGTAACTGGCTTCAGCAGAGCGCAGATACCAAATAC
TGTTCTTCTAGTGTAGCCGTAGTTAGGCCACCACTTCAAGAACTCTGTAGCACCGCCTACATACCTCGCTCTGCT
AATCCTGTTACCAGTGGCTGCTGCCAGTGGCGATAAGTCGTGTCTTACCGGGTTGGACTCAAGACGATAGTTACC
GGATAAGGCGCAGCGGTCGGGCTGAACGGGGGGTTCGTGCACACAGCCCAGCTTGGAGCGAACGACCTACACCGA
ACTGAGATACCTACAGCGTGAGCTATGAGAAAGCGCCACGCTTCCCGAAGGGAGAAAGGCGGACAGGTATCCGGT
AAGCGGCAGGGTCGGAACAGGAGAGCGCACGAGGGAGCTTCCAGGGGGAAACGCCTGGTATCTTTATAGTCCTGT
CGGGTTTCGCCACCTCTGACTTGAGCGTCGATTTTTGTGATGCTCGTCAGGGGGGCGGAGCCTATGGAAAAACGC
```

-continued

```
CAGCAACGCGGCCTTTTTACGGTTCCTGGCCTTTTGCTGGCCTTTTGCTCACATGTTCTTTCCTGCGTTATCCCC
TGATTCTGTGGATAACCGTATTACCGCCTTTGAGTGAGCTGATACCGCTCGCCGCAGCCGAACGACCGAGCGCAG
CGAGTCAGTGAGCGAGGAAGCGGAAGAGCGCCCAATACGCAAACCGCCTCTCCCCGCGCGTTGGCCGATTCATTA
ATGCAGCTGGCACGACAGTATCGATAAGCTTGATAAGCTTTTAAATCAGCAGGGGTCTTTTTGGCTTGTGTATTA
TTTTGAAGTTTTTCTTCCCCGACAGAATCTGCTTTTACCGTCATAGTGAAATGAGCCTGAAAAGCTATTACCATG
ATGATACAAATAAGTTTACTTTTCATTTCACCGCTCCTTTTTAATTCGTAAAACTAAGTTTAAGCCACCTACAAC
TAATCTGACAGAGAGAGTTAAGGACACGTTTTTTAGTATATGTGGGAACTAAATTATACGTTTTGCAGTAGAAAC
TATAGGTGGCTTAAACTTTGGGATATGCTTATATTATATGGATAAACAGTCAGATATTCTTTTACATTTGTTAAT
TCTTCTAAAAAAATTAAAAAATAAGCCTGTTTCTACATTCTTCACAAAATAATTTACGAAGAGTGCAAAACAAGC
TTATTTTTCGTGTGTGTTAAGCGGTTTTATTCTTAATTTTTTATTACTTTTACAATTATTCGATTGGATTATCT
ACTTTATTACTATATTTCGGATAAAGCGTGGTGCCCCAGATGGAGATATTTCTATTTTTCACAAGTGGTAAGTTC
CGGTCATCAATTACCGTTCTCCACCATTCCCAAGCTAAACCAGTGCATTCTTTAGCGTAAACATTAATATTTCTC
GCGTTACCTGGCAAATAGATGGACGATGTGAAATGAGCTAGCTTGCTTTTATTGTTTTCGCTCCAGTTTTTATGT
TGAACAATTTCGTTACCTTCAGGATCATAATTTACTTCATCCCAAGAAATGTTGAATTGAGCAACGTATCCTCCA
GAGTGATCGATGTTAATTTTTCCATCTGTATAAGCTTTTGAAGTTGTTTCAATATATTCTGAGTTGTTTTTAATA
ACAGCTAATTCATTGTCTTTTAGGAAGTTTGTTGTATAAGCAATGGGAACTCCTGGTGTTTCTCGATTAAAAGTA
GCGCCTTTTTTCAAAATATCGCGTAAGTCTCCGAGGTTGCCGTCGATGATTTGAACTTCATCTTTTGCGGAACCT
CCGTAAATTACGGCTTTGAAGGAAGAATTTTTGATGATATTTGTTAGTTCTACATCACCTGAGACAGATTTTCCG
CTTACGGCAGCATCAAAAGCAGCTTTTACTTTAGTACTATGGGAATTAGTTGATAATTTCAAATAAACTTGACGG
CCATACGCCACACTTGAGATATATGGAGGAGGATTTTCTGCATTCACTCCAAGCGCTTCCAACTGCTCTTTAGTA
ACAGCTTTGCCGAAAAATCTGGAAGGTCTTGTAGGTTCATTAACATTCACGTTATAGTAAATTTGTTTAAAACTA
ATGACTTCTTCTTGCATTTTCCCTTCACTGATTGCGCCGAAGTTTACATTCAAGCTATTATTTACAGCTTTAAAT
GCTGTACCAAATTTCGCAATTAATTGTGATTCACTGTAAGCCATTTCGTCATCATAATCAATTTTTGCACTTACA
TTTGGATAAGCTTGAGCATATTTTTCATTCCATCTTTCCACTAATGTATTTACTGCGTTGTTAACGTTTGATTTA
GTGGCATTTTTTACAACGATTTTATTGTCTTGATTAGTCATACCTGGCAAATCAATGCTGAGTGTTAATGAATCA
CGTTTTACAGGGAGAACATCTGGTTGATTTTCTACTAATTCCGAATTGCTTTTACGAGAGCACCTGGATAGGTT
AGGCTCGAAATTGCATTCACAACTTGAATGTCTGCATTATTTTGATTGATGGATTTCTTCTTTTTCTCCACAACA
ATATATTCATTTCCATCTTTGTAACCTTTTCTTGGCGGCACATTTGTCACTGCATCTCCGTGGTATACTAATACA
TTGTTTTTATTGTAATCCAATCCTTGTATATACTTATCGATTTCATCCGCGTGTTTCTTTTCGATTGGCGTCTTA
GGACTTGCAGGCGGAGATGCTGGTGGTGCCATGGATGAAATTGAATTTTCTTTATTGAATGCAGATGCATCCTTT
GCTTCAGTTTCTTGCCCAATTGGTAGACTAACTAATATAAGTGTAATAAAACTAGCATTATTTTTTTCATGGGT
TTCACTCTCCTTCTACATTTTTTAACCTAATAATGCCAAATACCGTTTGCCACCCCTCTCTTTTGATAATTATAA
TATTGGCGAAATTCGCTTCTAAAGATGAAACGCAATATTATATGCTTGCTTTATAGCTTTATTCTAGTCCTGCTG
TCCCTTTATCGTCGTTAACAAATGTTAATGCCTCAACATAAAGTCACTTTAAGATAGGAATATACTAATCAAAG
GAGGGATCGAATTCCTGCAGTCATCAAGGCAACCATCAGGATTAATGCGGATATTGCGGAGTAACACTTCAGACT
GAAAGTAGAAATAAAAACCGCAGCAGACAACTGACAACATCAAATGAAGGGGGCTTATTCTAATTGATATTATTT
ATATGATAATAGTTCATTTTGTATTTTGTTTTTTTGATATTCTCACCTGCTTAGTTACAATAAATCAATTCTATC
GCTGTATGGTATAGACTGTTTTATTATATATTTTGAATATTTTTAATCTGCCCAGTCTGGTTTTTTAAAAAAGTG
CTATCCTCTTAATGTCTTTACTAAATTAGAAAACAAGTTTCACTTTCAACTATTGCATCTTTAATTAATGGTCAA
GGTGATTTCAAATGCTCGTTTGTGGCCAGTTATACCTCAAATAACTCAAGTTGTTGAGCACAGCCAACGCACATG
CAGTTTGACGTATGACAGGTATGCTTTATTTCATTTAAATTATGATGGTTTTCCAGCCAATCAGTGAGTTTCTCT
```

-continued

```
TGATAAGGAATCCGGGAATGTCTATGTATTTTAATAAAATAATTTCATTTAATATTATTTCACGAATAGTTATTT

GTATCTTTTTGATATGTGGAATGTTCATGGCTGGGGCTTCAGAAAAATATGATGCTAACGCACCGCAACAGGTCC

AGCCTTATTCTGTCTCTTCATCTGCATTTGAAAATCTCCATCCTAATAATGAAATGGAGAGTTCAATCAATCCCT

TTTCCGCATCGGATACAGAAAGAAATGCTGCAATAATAGATCGCGCCAATAAGGAGCAGGAGACTGAAGCGGTGA

ATAAGATGATAAGCACCGGGGCCAGGTTAGCTGCATCAGGCAGGGCATCTGATGTTGCTCACTCAATGGTGGGCG

ATGCGGTTAATCAAGAAATCAAACAGTGGTTAAATCGATTCGGTACGGCTCAAGTTAATCTGAATTTTGACAAAA

ATTTTTCGCTAAAAGAAAGCTCTCTTGATTGGCTGGCTCCTTGGTATGACTCTGCTTCATTCCTCTTTTTTAGTC

AGTTAGGTATTCGCAATAAAGACAGCCGCAACACACTTAACCTTGGCGTGGGGATACGTACATTGGAGAACGGTT

GGCTGTACGGACTTAATACTTTTTATGATAATGATTTGACCGGCCACAACCACCGTATCGGTCTTGGTGCCGAGG

CCTGGACCGATTATTTACAGTTGGCTGCCAATGGGTATTTTCGCCTCAATGGATGGCACTCGTCGCGTGATTTCT

CCGACTATAAAGAGCGCCCAGCCACTGGGGGGATTTGCGCGCGAATGCTTATTTACCTGCACTCCCACAACTGG

GGGGGAAGTTGATGTATGAGCAATACACCGGTGAGCGTGTTGCTTTATTTGGTAAAGATAATCTGCAACGCAACC

CTTATGCCGTGACTGCCGGGATCAATTACACCCCCGTGCCTCTACTCACTGTCGGGGTAGATCAGCGTATGGGGA

AAAGCAGTAAGCATGAAACACAGTGGAACCTCCAAATGAACTATCGCCTGGGCGAGAGTTTTCAGTCGCAACTTA

GCCCTTCAGCGGTGGCAGGAACACGTCTACTGGCGGAGAGCCGCTATAACCTTGTCGATCGTAACAATAATATCG

TGTTGGAGTATCAGAAACAGCAGGTGGTTAAACTGACATTATCGCCAGCAACTATCTCCGGCCTGCCGGGTCAGG

TTTATCAGGTGAACGCACAAGTACAAGGGGCATCTGCTGTAAGGGAAATTGTCTGGAGTGATGCCGAACTGATTG

CCGCTGGCGGCACATTAACACCACTGAGTACCACACAATTCAACTTGGTTTTACCGCCTTATAAACGCACAGCAC

AAGTGAGTCGGGTAACGGACGACCTGACAGCCAACTTTTATTCGCTTAGTGCGCTCGCGGTTGATCACCAAGGAA

ACCGATCTAACTCATTCACATTGAGCGTCACCGTTCAGCAGCCTCAGTTGACATTAACGGCGGCCGTCATTGGTG

ATGGCGCACCGGCTAATGGGAAAACTGCAATCACCGTTGAGTTCACCGTTGCTGATTTTGAGGGGAAACCCTTAG

CCGGGCAGGAGGTGGTGATAACCACCAATAATGGTGCGCTACCGAATAAAATCACGGAAAAGACAGATGCAAATG

GCGTCGCGCGCATTGCATTAACCAATACGACAGATGGCGTGACGGTAGTCACAGCAGAAGTGGAGGGGCAACGGC

AAAGTGTTGATACCCACTTTGTTAAGGGTACTATCGCGGCGGATAAATCCACTCTGGCTGCGGTACCGACATCTA

TCATCGCTGATGGTCTAATGGCTTCAACCATCACGTTGGAGTTGAAGGATACCTATGGGACCCGCAGGCTGGCG

CGAATGTGGCTTTTGACACAACCTTAGGCAATATGGGCGTTATCACGGATCACAATGACGGCACTTATAGCGCAC

CATTGACCAGTACCACGTTGGGGGTAGCAACAGTAACGGTGAAAGTGGATGGGGCTGCGTTCAGTGTGCCGAGTG

TGACGGTTAATTTCACGGCAGATCCTATTCCAGATGCTGGCCGCTCCAGTTTCACCGTCTCCACACCGGATATCT

TGGCTGATGGCACGATGAGTTCCACATTATCCTTTGTCCCTGTCGATAAGAATGGCCATTTTATCAGTGGGATGC

AGGGCTTGAGTTTTACTCAAAACGGTGTGCCGGTGAGTATTAGCCCCATTACCGAGCAGCCAGATAGCTATACCG

CGACGGTGGTTGGGAATAGTGTCGGTGATGTCACAATCACGCCGCAGGTTGATACCCTGATACTGAGTACATTGC

AGAAAAAAATATCCCTATTCCCGGTACCTACGCTGACCGGTATTCTGGTTAACGGGCAAAATTTCGCTACGGATA

AAGGGTTCCCGAAAACGATCTTTAAAAACGCCACATTCCAGTTACAGATGGATAACGATGTTGCTAATAATACTC

AGTATGAGTGGTCGTCGTCATTCACACCCAATGTATCGGTTAACGATCAGGGTCAGGTGACGATTACCTACCAAA

CCTATAGCGAAGTGGCTGTGACGGCGAAAAGTAAAAAATTCCCAAGTTATTCGGTGAGTTATCGGTTCTACCCAA

ATCGGTGGATATACGATGGCGGCAGATCGCTGGTATCCAGTCTCGAGGCCAGCAGACAATGCCAAGGTTCAGATA

TGTCTGCGGTTCTTGAATCCTCACGTGCAACCAACGGAACGCGTGCGCCTGACGGGACATTGTGGGGCGAGTGGG

GGAGCTTGACCGCGTATAGTTCTGATTGGCAATCTGGTGAATATTGGGTCAAAAAGACCAGCACGGATTTTGAAA

CCATGAATATGGACACAGGCGCACTGCAACCAGGGCCTGCATACTTGGCGTTCCCGCTCTGTGCGCTGTCAATAT

AACCAGATAACAGATAGCAATAAGAACAGTTTAATGAGCTGATTATTTGGGGCGCGAATGGGAGTCCGGCAATCC
```

```
TAGACTCGCCCCATAAGTAGCAAACGTCCAGAGAACAACGCCGCTCAGGTTAATTGAGCGGCGTTGTTTTTTTAA

AAGGATTTGTCGCGATAAGCGTGAGCTGGCGTTAAATGCCGATCTTACGGCCCAGCTGCAGCCCGGCTAGTAACG

GCCGCCAGTGTGCTGGAATTCGCCCTTAATCGGCATCATTCACCAAGCTTGCCAGGCGACTGTCTTCAATATTAC

AGCCGCAACTACTGACATGGCGGGTGATGGTGTTCACTATTCCAGGGCGATCGGCACCCAACGCAGTGATCACCA

GATAATGTTGCGATGACAGTGTCAAACTGGTTATTCCTTCAAGGGGTGAGTTGTTCTTAAGCATGCCGGTTTGCT

GTAAAGTTTAGGGAGATTTGATGGCTTACTCTGTTCAAAAGTCGCGCCTGGCAAAGGTTGCGGGTGTTTCGCTTG

TTTTATTACTCGCTGCCTGTAGTTCTGACTCACGCTATAAGCGTCAGGTCAGTGGTGATGAAGCCTACCTGGAAG

CGCCATGGCATGCAAGGGCGAATTCTGCAGATATCCATCACACTGGCGGCCCTAGACCAGGCTTTACACTTTATG

CTTCCGGCTCGTATAATGTGTGGAAGGATCCAGGAGTAACAATACAAATGGATTCAAGAGATCCATTTGTATTGT

TACTCCTTTGTCGACTGGACAGTTCAAGAGACTGTCCATCAATATCAGCTTTGTCACAAACCCCGCCACCGGCGG

GGTTTTTTTCTGCTCTAGGGCCGCTCGAGCATGCATCTAGAGGGCCCAATTCGCCCTATAGTGAGTCGTATTACA

ATTCACTGGCCGTCGTTTTACAACGTCGTGACTGGGAAAACCCTGGCGTTACCCAACTTAATCGCCTTGCAGCAC

ATCCCCCTTTCGCCAGCTGGCGTAATAGCGAAGAGGCCCGCACCGATCGCCCTTCCCAACAGTTGCGCAGCCTGA

AAAACCGCGCCATGGTGTGTAGGCTGGAGCTGCTTCGAAGTTCCTATACTTTCTAGAGAATAGGAACTTCGGAAT

AGGAACTTCAAGATCCCCCACGCTGCCGCAAGCACTCAGGGCGCAAGGGCTGCTAAAGGAAACGGAACACGTAGA

AAGCCAGTCCGCAGAAACGGTGCTGACCCCGGATGAATGTCAGCTACTGGGCTATCTGGACAAGGGAAAACGCAA

GCGCAAAGAGAAAGCAGGTAGCTTGCAGTGGGCTTACATGGCGATAGCTAGACTGGGCGGTTTTATGGACAGCAA

GCGAACCGGAATTGCCAGCTGGGGCGCCCTCTGGTAAGGTTGGGAAGCCCTGCAAAGTAAACTGGATGGCTTTCT

TGCCGCCAAGGATCTGATGGCGCAGGGGATCAAGATCTGATCAAGAGACAGGATGAGGATCGTTTCGCATGATTG

AACAAGATGGATTGCACGCAGGTTCTCCGGCCGCTTGGGTGGAGAGGCTATTCGGCTATGACTGGGCACAACAGA

CAATCGGCTGCTCTGATGCCGCCGTGTTCCGGCTGTCAGCGCAGGGGCGCCCGGTTCTTTTTGTCAAGACCGACC

TGTCCGGTGCCCTGAATGAACTGCAGGACGAGGCAGCGCGGCTATCGTGGCTGGCCACGACGGGCGTTCCTTGCG

CAGCTGTGCTCGACGTTGTCACTGAAGCGGGAAGGGACTGGCTGCTATTGGGCGAAGTGCCGGGGCAGGATCTCC

TGTCATCTCACCTTGCTCCTGCCGAGAAAGTATCCATCATGGCTGATGCAATGCGGCGGCTGCATACGCTTGATC

CGGCTACCTGCCCATTCGACCACCAAGCGAAACATCGCATCGAGCGAGCACGTACTCGGATGGAAGCCGGTCTTG

TCGATCAGGATGATCTGGACGAAGAGCATCAGGGGCTCGCGCCAGCCGAACTGTTCGCCAGGCTCAAGGCGCGCA

TGCCCGACGGCGAGGATCTCGTCGTGACCCATGGCGATGCCTGCTTGCCGAATATCATGGTGGAAAATGGCCGCT

TTTCTGGATTCATCGACTGTGGCCGGCTGGGTGTGGCGGACCGCTATCAGGACATAGCGTTGGCTACCCGTGATA

TTGCTGAAGAGCTTGGCGGCGAGTGGGCTGACCGCTTCCTCGTGCTTTACGGTATCGCCGCTCCCGATTCGCAGC

GCATCGCCTTCTATCGCCTTCTTGACGAGTTCTTCTGAGCGGGACTCTGGGGTTCGAAATGACCGACCAAGCGAC

GCCCAACCTGCCATCACGAGATTTCGATTCCACCGCCGCCTTCTATGAAAGGTTGGGCTTCGGAATCGTTTTCCG

GGACGCCGGCTGGATGATCCTCCAGCGCGGGGATCTCATGCTGGAGTTCTTCGCCCACCCCAGCTTCAAAAGCGC

TCTGAAGTTCCTATACTTTCTAGAGAATAGGAACTTCGGAATAGGAACTAAGGAGGATATTCATATGGACCATGG

CGCGGCATGCAAGCTCGGTATCATTGCAGCACTGGGGCCAGATGGTAAGCCCTCCCGTATCGTAGTTATCTACAC

GACGGGGAGTCAGGCAACTATGGATGAACGAAATAGACAGATCGCTGAGATAGGTGCCTCACTGATTAAGCATTG

GTAACTGTCAGACCAAGTTTACTCATATATACTTTAGATTGATTTAAAACTTCATTTTTAATTTAAAAGGATCTA

GGTGAAGATCCTTTTTGATAATCTCATGACCAAAATCCCTTAACGTGAGTTTTCGTTCCACTGAGCGTCAGACCC

CGTAGAAAAGATCAAGGATCTTCTTGAGATCCTTTTTTTCTGCGCGTAATCTGCTGCTTGCAAACAAAAAAACC

ACCGCTACCAGCGGTGGTTTGTTTGCCGGATCAAGAGCTACCAACTCTTTTTCCGAAGGTAACTGGCTTCAGCAG

AGCGCAGATACCAAATACTGTTCTTCTAGTGTAGCCGTAGTTAGGCCACCACTTCAAGAACTCTGTAGCACCGCC

TACATACCTCGCTCTGCTAATCCTGTTACCAGTGGCTGCTGCCAGTGGCGATAAGTCGTGTCTTACCGGGTTGGA
```

```
CTCAAGACGATAGTTACCGGATAAGGCGCAGCGGTCGGGCTGAACGGGGGGTTCGTGCACACAGCCCAGCTTGGA

GCGAACGACCTACACCGAACTGAGATACCTACAGCGTGAGCTATGAGAAAGCGCCACGCTTCCCGAAGGGAGAAA

GGCGGACAGGTATCCGGTAAGCGGCAGGGTCGGAACAGGAGAGCGCACGAGGGAGCTTCCAGGGGGAAACGCCTG

GTATCTTTATAGTCCTGTCGGGTTTCGCCACCTCTGACTTGAGCGTCGATTTTTGTGATGCTCGTCAGGGGGCG

GAGCCTATGGAAAAACGCCAGCAACGCGGCCTTTTTACGGTTCCTGGCCTTTTGCTGGCCTTTTGCTCACATGTT

CTTTCCTGCGTTATCCCCTGATTCTGTGGATAACCGTATTACCGCCTTTGAGTGAGCTGATACCGCTCGCCGCAG

CCGAACGACCGAGCGCAGCGAGTCAGTGAGCGAGGAAGCGGAAGAGCGCCCAATACGCAAACCGCCTCTCCCCGC

GCGTTGGCCGATTCATTAATGCAGCTGGCACGACAGTATCGATAAGCTTGATAAGCTTTTAAATCAGCAGGGGTC

TTTTTGGCTTGTGTATTATTTTGAAGTTTTTCTTCCCCGACAGAATCTGCTTTTACCGTCATAGTGAAATGAGCC

TGAAAAGCTATTACCATGATGATACAAATAAGTTTACTTTTCATTTCACCGCTCCTTTTTAATTCGTAAAACTAA

GTTTAAGCCACCTACAACTAATCTGACAGAGAGAGTTAAGGACACGTTTTTTAGTATATGTGGGAACTAAATTAT

ACGTTTTGCAGTAGAAACTATAGGTGGCTTAAACTTTGGGATATGCTTATATTATATGGATAAACAGTCAGATAT

TCTTTTACATTTGTTAATTCTTCTAAAAAAATTAAAAAATAAGCCTGTTTCTACATTCTTCACAAAATAATTTAC

GAAGAGTGCAAAACAAGCTTATTTTTTCGTGTGTGTTAAGCGGTTTTATTCTTAATTTTTTATTACTTTTACAAT

TATTCGATTGGATTATCTACTTTATTACTATATTTCGGATAAAGCGTGGTGCCCCAGATGGAGATATTTCTATTT

TTCACAAGTGGTAAGTTCCGGTCATCAATTACCGTTCTCCACCATTCCCAAGCTAAACCAGTGCATTCTTTAGCG

TAAACATTAATATTTCTCGCGTTACCTGGCAAATAGATGGACGATGTGAAATGAGCTAGCTTGCTTTTATTGTTT

TCGCTCCAGTTTTTATGTTGAACAATTTCGTTACCTTCAGGATCATAATTTACTTCATCCCAAGAAATGTTGAAT

TGAGCAACGTATCCTCCAGAGTGATCGATGTTAATTTTTCCATCTGTATAAGCTTTTGAAGTTGTTTCAATATAT

TCTGAGTTGTTTTTAATAACAGCTAATTCATTGTCTTTTAGGAAGTTTGTTGTATAAGCAATGGGAACTCCTGGT

GTTTCTCGATTAAAAGTAGCGCCTTTTTTCAAAATATCGCGTAAGTCTCCGAGGTTGCCGTCGATGATTTGAACT

TCATCTTTTGCGGAACCTCCGTAAATTACGGCTTTGAAGGAAGAATTTTTGATGATATTTGTTAGTTCTACATCA

CCTGAGACAGATTTTCCGCTTACGGCAGCATCAAAAGCAGCTTTTACTTTAGTACTATGGGAATTAGTTGATAAT

TTCAAATAAACTTGACGGCCATACGCCACACTTGAGATATATGCAGGAGGATTTTCTGCATTCACTCCAAGCGCT

TGCAACTGCTCTTTAGTAACAGCTTTGCCGAAAAATCTGGAAGGTCTTGTAGGTTCATTAACATTCACGTTATAG

TAAATTTGTTTAAAACTAATGACTTCTTCTTGCATTTTCCCTTCACTGATTGCGCCGAAGTTTACATTCAAGCTA

TTATTTACAGCTTTAAATGCTGTACCAAATTTCGCAATTAATTGTGATTCACTGTAAGCCATTTCGTCATCATAA

TCAATTTTTGCACTTACATTTGGATAAGCTTGAGCATATTTTTCATTCCATCTTTCCACTAATGTATTTACTGCG

TTGTTAACGTTTGATTTAGTGGCATTTTTTACAACGATTTTATTGTCTTGATTAGTCATACCTGGCAAATCAATG

CTGAGTGTTAATGAATCACGTTTTACAGGGAGAACATCTGGTTGATTTTCTACTAATTCCGAATTCGCTTTTACG

AGAGCACCTGGATAGGTTAGGCTCGAATTGCATTCACAACTTGAATGTCTGCATTATTTTGATTGATGGATTTC

TTCTTTTTCTCCACAACAATATATTCATTTCCATCTTTGTAACCTTTTCTTGGCGGCACATTTGTCACTGCATCT

CCGTGGTATACTAATACATTGTTTTTATTGTAATCCAATCCTTGTATATACTTATCGATTTCATCCGCGTGTTTC

TTTTCGATTGGCGTCTTAGGACTTGCAGGCGGAGATGCTGGTGGTGCCATGGATGAAATTGAATTTTCTTTATTG

AATGCAGATGCATCCTTTGCTTCAGTTTGTTGCGCAATTGGTAGACTAACTAATATAAGTGTAATAAAAACTAGC

ATTATTTTTTCATGGGTTTCACTCTCCTTCTACATTTTTAACCTAATAATGCCAAATACCGTTTGCCACCCCT

CTCTTTTGATAATTATAATATTGGCGAAATTCGCTTCTAAAGATGAAACGCAATATTATATGCTTGCTTTATAGC

TTTATTCTAGTCCTGCTGTCCCTTTATCGTCGTTAACAAATGTTAATGCCTCAACATAAAAGTCACTTTAAGATA

GGAATATACTAATCAAAGGAGGGATCGAATTCCTGCAGTCATCAAGGCAACCATCAGGATTAATGCGGATATTGC

GGAGTAACACTTCAGACTGAAAGTAGAAATAAAAACCGCAGCAGACAACTGACAACATCAAATGAAGGGGCTTA
```

-continued

```
TTCTAATTGATATTATTTATATGATAATAGTTCATTTTGTATTTTGTTTTTTGATATTCTCACCTGCTTAGTTA

CAATAAATCAATTCTATCGCTGTATGGTATAGACTGTTTTATTATATATTTTGAATATTTTTAATCTGCCCAGTC

TGGTTTTTTAAAAAAGTGCTATCCTCTTAATGTCTTTACTAAATTAGAAAACAAGTTTCACTTTCAACTATTGCA

TCTTTAATTAATGGTCAAGGTGATTTCAAATGCTCGTTTGTGGCCAGTTATACCTCAAATAACTCAAGTTGTTGA

GCACAGCCAACGCACATGCAGTTTGACGTATGACAGGTATGCTTTATTTCATTTAAATTATGATGGTTTTCCAGC

CAATCAGTGAGTTTCTCTTGATAAGGAATGCGGGAATGTCTATGTATTTTAATAAAATAATTTCATTTAATATTA

TTTCACGAATAGTTATTTGTATCTTTTTGATATGTGGAATGTTCATGGCTGGGGCTTCAGAAAAATATGATGCTA

ACGCACCGCAACAGGTCCAGCCTTATTCTGTCTCTTCATCTGCATTTGAAAATCTCCATCCTAATAATGAAATGG

AGAGTTCAATCAATCCCTTTTCCGCATCGGATACAGAAAGAAATGCTGCAATAATAGATCGCGCCAATAAGGAGC

AGGAGACTGAAGCGGTGAATAAGATGATAAGCACCGGGGCCAGGTTAGCTGCATCAGGCAGGGCATCTGATGTTG

CTCACTCAATGGTGGGCGATGCGGTTAATCAAGAAATCAAACAGTGGTTAAATCGATTCGGTACGGCTCAAGTTA

ATCTGAATTTTGACAAAAATTTTTCGCTAAAAGAAAGCTCTCTTGATTGGCTGGCTCCTTGGTATGACTCTGCTT

CATTCCTCTTTTTTAGTCAGTTAGGTATTCGCAATAAAGACAGCCGCAACACACTTAACCTTGGCGTCGGGATAC

GTACATTGGAGAACGGTTGGCTGTACGGACTTAATACTTTTTATGATAATGATTTGACCGGCCACAACCACCGTA

TCGGTCTTGGTGCCGAGGCCTGGACCGATTATTTACAGTTGGCTGCCAATGGGTATTTTCGCCTCAATGGATGGC

ACTCGTCGCGTGATTTCTCCGACTATAAAGAGCGCCCAGCCACTGGGGGGATTTGCGCGCGAATGCTTATTTAC

CTGCACTCCCACAACTGGGGGGAAGTTGATGTATGAGCAATACACCGGTGAGCGTGTTGCTTTATTTGGTAAAG

ATAATCTGCAACGCAACCCTTATGCCGTGACTGCCGGGATCAATTACACCCCCGTGCCTCTACTCACTGTCGGGG

TAGATCAGCGTATGGGGAAAAGCAGTAAGCATGAAACACAGTGGAACCTCCAAATGAACTATCGCCTGGGCGAGA

GTTTTCAGTCGCAACTTAGCCCTTCAGCGGTGGCAGGAACACGTCTACTGGCGGAGAGCCGCTATAACCTTGTCG

ATCGTAACAATAATATCGTGTTGGAGTATCAGAAACAGCAGGTGGTTAAACTGACATTATCGCCAGCAACTATCT

CCGGCCTGCCGGGTCAGGTTTATCAGGTGAACGCACAAGTACAAGGGGCATCTGCTGTAAGGGAAATTGTCTGGA

GTGATGCCGAACTGATTGCCGCTGGCGGCACATTAACACCACTGAGTACCACACAATTCAACTTGGTTTTACCGC

CTTATAAACGCACAGCACAAGTGAGTCGGGTAACGGACGACCTGACAGCCAACTTTTATTCGCTTAGTGCGCTCG

CGGTTGATCACCAAGGAAACCGATCTAACTCATTCACATTGAGCGTCACCGTTCAGCAGCCTCAGTTGACATTAA

CGGCGGCCGTCATTGGTGATGGCGCACCGGCTAATGGGAAAACTGCAATCACCGTTGAGTTCACCGTTGCTGATT

TTGAGGGGAAACCCTTAGCCGGGCAGGAGGTGGTGATAACCACCAATAATGGTGCGCTACCGAATAAAATCACGG

AAAAGACAGATGCAAATGGCGTCGCGCGCATTGCATTAACCAATACGACAGATGGCGTGACGGTAGTCACAGCAG

AAGTGGAGGGGCAACGGCAAAGTGTTGATACCCACTTTGTTAAGGGTACTATCGCGGCGGATAAATCCACTCTGG

CTGCGGTACCGACATCTATCATCGCTGATGGTCTAATGGCTTCAACCATCACGTTGGAGTTGAAGGATACCTATG

GGGACCCGCAGGCTGGCGCGAATGTGGCTTTTGACACAACCTTAGGCAATATGGGCGTTATCACGGATCACAATG

ACGGCACTTATAGCGCACCATTGACCAGTACCACGTTGGGGGTAGCAACAGTAACGGTGAAAGTGGATGGGGCTG

CGTTCAGTGTGCCGAGTGTGACGGTTAATTTCACGGCAGATCCTATTCCAGATGCTGGCCGCTCCAGTTTCACCG

TCTCCACACCGGATATCTTGGCTGATGGCACGATGAGTTCCACATTATCCTTTGTCCCTGTCGATAAGAATGGCC

ATTTTATCAGTGGGATGCAGGGCTTGAGTTTTACTCAAAACGGTGTGCCGGTGAGTATTAGCCCCATTACCGAGC

AGCCAGATAGCTATACCGCGACGGTGGTTGGGAATAGTGTCGGTGATGTCACAATCACGCCGCAGGTTGATACCC

TGATACTGAGTACATTGCAGAAAAAAATATCCCTATTCCCGGTACCTACGCTGACCGGTATTCTGGTTAACGGGC

AAAATTTCGCTACGGATAAAGGGTTCCCGAAAACGATCTTTAAAAACGCCACATTCCAGTTACAGATGGATAACG

ATGTTGCTAATAATACTCAGTATGAGTGGTCGTCGTCATTCACACCCAATGTATCGGTTAACGATCAGGGTCAGG

TGACGATTACCTACCAAACCTATAGCGAAGTGGCTGTGACGGCGAAAAGTAAAAAATTCCCAAGTTATTCGGTGA

GTTATCGGTTCTACCCAAATCGGTGGATATACGATGGCGGCAGATCGCTGGTATCCAGTCTCGAGGCCAGCAGAC
```

-continued

AATGCCAAGGTTCAGATATGTCTGCGGTTCTTGAATCCTCACGTGCAACCAACGGAACGCGTGCGCCTGACGGGA

CATTGTGGGGCGAGTGGGGGAGCTTGACCGCGTATAGTTCTGATTGGCAATCTGGTGAATATTGGGTCAAAAGA

CCAGCACGGATTTTGAAACCATGAATATGGACACAGGCGCACTGCAACCAGGGCCTGCATACTTGGCGTTCCCGC

TCTGTGCGCTGTCAATATAACCAGATAACAGATAGCAATAAGAACAGTTTAATGAGCTGATTATTTGGGGCGCGA

ATGGGAGTCCGGCAATCCTAGACTCGCCCCATAAGTAGCAAACGTCCAGAGAACAACGCCGCTCAGGTTAATTGA

GCGGCGTTGTTTTTTAAAAGGATTTGTCGCGATAAGCGTGAGCTGGCGTTAAATGCCGATCTTACGGCCCAGCT

GCAGCCCGGCTAGTAACGGCCGCCAGTGTGCTGGAATTCGCCCTTAATCGGCATCATTCACCAAGCTTGCCAGGC

GACTGTCTTCAATATTACAGCCGCAACTACTGACATGGCGGGTGATGGTGTTCACTATTCCAGGGCGATCGGCAC

CCAACGCAGTGATCACCAGATAATGTTGCGATGACAGTGTCAAACTGGTTATTCCTTCAAGGGGTGAGTTGTTCT

TAAGCATGCCGGTTTGCTGTAAAGTTTAGGGAGATTTGATGGCTTACTCTGTTCAAAAGTCGCGCCTGGCAAAGG

TTGCGGGTGTTTCGCTTGTTTTATTACTCGCTGCCTGTAGTTCTGACTCACGCTATAAGCGTCAGGTCAGTGGTG

ATGAAGCCTACCTGGAAGCGCCATGGCATGCAAGGGCGAATTCTGCAGATATCCATCACACTGGCGGCCCTAGAC

CAGGCTTTACACTTTATGCTTCCGGCTCGTATAATGTGTGGAAGGATCCAGGAGTAACAATACAAATGGATTCAA

GAGATCCATTTGTATTGTTACTCCTTTGTCGACTGGACAGTTCAAGAGACTGTCCATCAATATCAGCTTTGTCAC

AAACCCCGCCACCGGCGGGTTTTTTCTGCTCTAG

What is claimed is:

1. An invasive bacterium comprising a prokaryotic vector, said vector comprising one or more DNA molecules encoding one or more siRNAs, at least one Inv gene and at least one HlyA gene, wherein the siRNAs are targeted to a viral gene, wherein at least one of the siRNAs is SEQ ID NOs:384 and 385.

2. A prokaryotic vector comprising at least one DNA molecule encoding one or more siRNAs, at least one Inv gene, at least one HlyA gene, and at least one prokaryotic promoter, wherein the siRNAs are targeted to a viral gene, and wherein at least one of the siRNAs is SEQ ID NOs:384 and 385.

3. The invasive bacterium of claim 1, wherein said invasive bacterium is a non-pathogenic or non-virulent bacterium.

4. The invasive bacterium of claim 1, wherein said invasive bacterium is a therapeutic bacterium.

5. A composition comprising the invasive bacterium of claim 1 and a pharmaceutically acceptable carrier.

6. A eukaryotic host cell comprising the invasive bacterium of claim 1, and a pharmaceutically acceptable carrier.

7. The invasive bacterium of claim 1, wherein said invasive bacterium is attenuated.

8. The prokaryotic vector of claim 2, wherein said prokaryotic promoter is a $P_{tac}$ promoter.

9. The prokaryotic vector of claim 2, further comprising a rrnC terminator.

* * * * *